US012753241B2

(12) United States Patent
Arathoon et al.

(10) Patent No.: US 12,753,241 B2
(45) Date of Patent: Oct. 6, 2026

(54) ANTI-ABCG2 ANTIBODIES AND USES THEREOF

(71) Applicant: William Robert Arathoon Living Trust Dated August 29, 2016, Tiburon, CA (US)

(72) Inventors: William Robert Arathoon, Tiburon, CA (US); Raffaella Briante, Burlingame, CA (US); Suchismita Mohanty, San Bruno, CA (US); Paul David Ponath, San Francisco, CA (US); Richard Theolis, Santa Cruz, CA (US); Qianting Zhai, South San Francisco, CA (US); Pingping Zhang, Cupertino, CA (US)

(73) Assignee: William Robert Arathoon Living Trust Dated August 29, 2016, Tiburon, CA (US)

( * ) Notice: Subject to any disclaimer, the term of this patent is extended or adjusted under 35 U.S.C. 154(b) by 943 days.

(21) Appl. No.: 17/998,773

(22) PCT Filed: May 28, 2021

(86) PCT No.: PCT/US2021/034947

§ 371 (c)(1),
(2) Date: Nov. 14, 2022

(87) PCT Pub. No.: WO2021/247426

PCT Pub. Date: Dec. 9, 2021

(65) Prior Publication Data

US 2023/0212305 A1 Jul. 6, 2023

Related U.S. Application Data

(60) Provisional application No. 63/034,806, filed on Jun. 4, 2020.

(51) Int. Cl.

| | |
|---|---|
| ***C07K 16/28*** | (2006.01) |
| ***A61K 45/06*** | (2006.01) |
| ***C07K 16/30*** | (2006.01) |
| ***G01N 33/68*** | (2006.01) |

(52) U.S. Cl.

CPC .......... *C07K 16/2896* (2013.01); *A61K 45/06* (2013.01); *C07K 16/2863* (2013.01); *C07K 16/30* (2013.01); *G01N 33/68* (2013.01); *C07K 2317/24* (2013.01); *C07K 2317/31* (2013.01); *G01N 2333/70596* (2013.01)

(58) Field of Classification Search

CPC ........... C07K 16/2896; C07K 16/2863; C07K 16/30; C07K 2317/24; C07K 2317/31; C07K 16/18; A61K 45/06; A61K 2039/505; G01N 33/68; G01N 2333/70596; A61P 35/00

See application file for complete search history.

(56) References Cited

U.S. PATENT DOCUMENTS

| | | | |
|---|---|---|---|
| 5,959,084 A | 9/1999 | Ring et al. | |
| 6,063,621 A | 5/2000 | Deeley et al. | |
| 8,372,399 B2 | 2/2013 | Stolen | |
| 2017/0224837 A1 | 8/2017 | Chang et al. | |
| 2019/0248912 A1 | 8/2019 | Zhen | |

FOREIGN PATENT DOCUMENTS

| | | | |
|---|---|---|---|
| CN | 106432490 A | 2/2017 | |
| JP | 2004051553 A | 2/2004 | |
| JP | 2018-502062 A | 5/2016 | |
| JP | 2018-504113 A | 2/2018 | |
| WO | WO-03035685 A1 * | 5/2003 | .......... C07K 14/705 |

OTHER PUBLICATIONS

Chang et al. (2016) "Combining ABCG2 Inhibitors with IMMU-132, an Anti-Trop-2 Antibody Conjugate of SN-38, Overcomes Resistance to SN-38 in Breast and Gastric Cancers", Molecular Cancer Therapeutics, 15:8 1910-1919.

Mickisch (1992) "Monoclonal Antibody MRK16 Reverses the Multidrug Resistance of Multidrug-resistant Transgenic Mice", Cancer Research, 52:16 4427-4432.

(Sep. 6, 2009) "ABCC1 Gene—ATP Binding Cassette Subfamily C Member 1", Retrieved from:—"https://www.genecards.org/cgi-bin/carddisp.pl?gene=ABCC1&keywords=ABCC1,GENE", 27 pages.

BioLegend (Aug. 4, 2019) "Anti-MRP1 (ABCC1) Antibody (Previously Covance catalog# SIG-38760)", Catalog #907201, Version 4, 8 pages.

BioLegend (2016) "Purified anti-human/mouse MRP1 (ABCC1) Antibody", 2 pages.

Godinot et al. (Mar. 2003) "Cloning and functional characterization of the multidrug resistance-associated protein (MRP1/ABCC1) from the cynomolgus monkey", Molecular Cancer Therapeutics, vol. 2, No. 3, pp. 307-316.

Rudikoff et al. (Mar. 1982) "Single amino acid substitution altering antigen-binding specificity", Proc. Natl Acad. Sci., vol. 79, pp. 1979-1983.

(Continued)

*Primary Examiner* — Nelson B Moseley, II
*Assistant Examiner* — Josephine K Darpolor
(74) *Attorney, Agent, or Firm* — Shweta Chandra; Bozicevic, Field & Francis LLP

(57) ABSTRACT

Provided are antibodies that target the cellular efflux pump ABCG2. Also provided are pharmaceutical compositions, nucleic acids, recombinant expression vectors, cells, and kits that include or encode such antibodies. Methods of using the antibodies for detecting presence or absence of ABCG2 expression in cells, e.g., tumor cells, level of ABCG2 expression, and/or inhibiting ABCG2 function are also disclosed. In addition, multi-specific antibodies that bind to ABCG2 and a polypeptide expressed on surface of a cancer cell are provided. The polypeptide may be the efflux pump MDR1 or a cancer-associated antigen. Also provided are methods for treating a subject for a cancer that include administering to the subject an anti-ABCG2 antibody as disclosed herein or a multi-specific antibody that targets both ABCG2 and a cancer-associated antigen or MDR1.

17 Claims, 37 Drawing Sheets

Specification includes a Sequence Listing.

(56) References Cited

OTHER PUBLICATIONS

Van Dijk et al. (1989) “Bispecific antibodies reactive with the multidrug-resistance-related glycoprotein and CD3 induce lysis of multidrug-resistant tumor cells”, International Journal of Cancer, vol. 44, pp. 738-743.
Yang et al. (2015) “Target therapy of multiple myeloma by PTX-NPs and ABCG2 antibody in a mouse xenograft model”, Oncotarget, vol. 6, No. 29, pp. 27714-27724.

* cited by examiner

| Ab | EC50 |
|---|---|
| 5D3 | 8.5 |
| G2-65 | 179.7 |
| G2-248 | 124.9 |
| G2-255 | 363.3 |
| G2-302 | 18.5 |
| G2-173 | 17.1 |

| | G2-173h.1 | G2-173h.3 | G2-252 | G2-257 | G2-173h.2 | G2-302 | G2 247 | G2-302 Hv1 | h5D3 |
|---|---|---|---|---|---|---|---|---|---|
| Kd | 46.35 | 33.51 | 347.4 | 7.944 | 273.8 | 33.63 | 58.95 | 58.95 | 3.122 |

| Sample | Kd | Bmax |
|---|---|---|
| G2_629 | 16.82 | 19031 |
| G2_620 | 15.75 | 17567 |
| G2_640 | NB | 25.14 |
| G2_641 | 23.4 | 26628 |
| G2_642 | 48.49 | 19003 |
| G2_631 | 14.2 | 24826 |
| G2_636 | 16.98 | 25079 |
| H28-ctrl | NB | ~0 |
| G2_643 | NB | ~0 |
| h5D3 | 2.99 | 22813 |
| hIgG1 | NB | ~0 |

| Anti-ABCG2 Antibody | Binding KD (nM) | Efflux EC50 (nM) |
|---|---|---|
| G2.318 | 41 | 48 |
| G2.320 | 58 | 45 |
| G2.629 | 17 | 17 |
| G2.630 | 16 | 31 |
| G2.631 | 14 | 22 |
| G2.636 | 17 | 47 |
| G2.641 | 23 | 58 |

ABCG2 recombinant mAbs binding to hG2 and cG2

| | G2_748 | G2_757 | G2_758 | G2_760 | G2_767 | 5D3 |
|---|---|---|---|---|---|---|
| hG2 Kd (nM) | 0.5 | 12.4 | 17.5 | 3.4 | 31.2 | 37.7 |
| cG2 Kd (nM) | 0.5 | 73.5 | 106.6 | 2.4 | 1372.0 | 99.2 |

| | G2_748 | 5D3 |
|---|---|---|
| hG2 Kd (nM) | 0.5 | 37.7 |
| cG2 Kd (nM) | 0.5 | 99.2 |

Binding of anti-ABCG2 recombinant mAbs to hG2 and cG2- panel#1

| | G2_377 | G2_656 | G2_709 | G2_711 | G2_636 | G2_746 | G2_336 |
|---|---|---|---|---|---|---|---|
| hG2 Kd (nM) | 16.7 | 36.8 | 20.6 | 72.0 | 10.9 | 22.3 | 28.2 |
| cG2 Kd (nM) | 31.4 | 271.7 | 41.4 | 2404.0 | 62.5 | 66.4 | 410.0 |

Binding of anti-ABCG2 recombinant mAbs to hG2 and cG2-panel#2

| | G2_360 | G2_392 | G2_418 | G2_631 | G2_639 | G2_643 | G2_732 | G2_745 |
|---|---|---|---|---|---|---|---|---|
| hG2 Kd (nM) | 23.7 | 35.3 | 59.0 | 14.3 | 46.8 | 5.9 | 6.2 | 23.3 |
| cG2 Kd (nM) | 155.9 | 93.4 | 38.8 | 15.0 | 14.3 | 17.1 | 14.8 | NB |

Binding of anti-ABCG2 recombinant mAbs to hG2 and cG2- panel#3

| | G2_420 | G2_343 | G2_333 | G2_629 | G2_631 | G2_318 | 5D3 |
|---|---|---|---|---|---|---|---|
| hG2 Kd (nM) | 11.1 | 8.4 | 22.5 | 50.1 | 4.6 | 5.0 | 15.7 |
| cG2 Kd (nM) | 29.9 | 58.4 | 111.4 | 539.7 | 67.7 | 49.8 | 252.7 |

| Treat | IC50 | % of IgG |
|---|---|---|
| Topo | 1.55 | 109 |
| FTC | 0.03 | 2 |
| hIgG | 1.42 | 100 |
| 5D3 | 1.36 | 95 |
| G2-643 | 0.67 | 47 |
| G2-420 | 0.88 | 62 |
| G2-631 | 0.28 | 19 |

Xenograft study – A549 NSCLC carcinoma cells

Xenograft study - G2/KT3 bispecific antibody

G2.636.hu47 efflux inhibition and binding

| | 5D3 | G2.636. hu25 | G2.636. hu27 | G2.636. hu45 | G2.636. hu47 | G2.636. rat |
|---|---|---|---|---|---|---|
| Efflux EC50 (nM) | 8.5 | 9.7 | 8.9 | 10.7 | 11.6 | 77.6 |
| hG2 EC50 (nM) | 4.9 | 28.5 | 23.1 | 18.5 | 20.4 | 80.0 |
| cG2 EC50 (nM) | 131.4 | 87.4 | 38.8 | 65.3 | 42.6 | 340.9 |
| cG2/hG2 | 26.6 | 3.1 | 1.7 | 3.5 | 2.1 | 4.3 |

| Concentration (nM) | BA024_KT1scFv-G2.318.hu33 |
|---|---|
| hG2 EC50 (nM) | 54.31 |
| hKT1 EC50 (nM) | 11.34 |

G2-318/KT9/G2-318 (common LC) Bispecific Antibody Binding

| Ab | EC50 (nM) |
|---|---|
| G2-318KK KT9DD G2-318 | 16.3 |
| G2-318 | 18.4 |
| KT9 | NB |
| hIgG | NB |

G2-318/KT9/G2-318 (common LC) Bispecific Antibody Binding

| Ab | EC50 (nM) |
|---|---|
| G2-318KK KT9DD G2-318 | 0.71 |
| KT9 | 0.19 |
| G2-318 | NB |
| hIgG | NB |

G2-318/KT9/G2-318 (common LC) Bispecific Antibody Binding

| Ab | EC50 (nM) |
|---|---|
| G2-318KK KT9DD G2-318 | 1.6 |
| G2-318 | 37.3 |
| KT9 | 0.4 |
| hIgG | NB |

| | G2.643 | G2.643.hu36 |
|---|---|---|
| Efflux EC50 (nM) | 4.4 | 2.3 |
| hG2 EC50 (nM) | 27 | 23 |
| cG2 EC50 (nM) | 65 | 96 |
| cG2/hG2 | **2.4** | **4.2** |

ANTI-ABCG2 ANTIBODIES AND USES THEREOF

CROSS-REFERENCE TO RELATED APPLICATIONS

This application is a 371 of PCT Application No. US2021/034947, filed May 28, 2021 which claims the benefit of priority to U.S. Provisional Patent Application No. 63/034,806 filed on Jun. 4, 2020, which applications are incorporated herein by reference in their entirety.

INCORPORATION BY REFERENCE OF SEQUENCE LISTING PROVIDED AS TEXT FILE

A Sequence Listing is provided herewith as a text file, "KNJY-004_SEQ LIST_ST25.txt," created on Nov. 12, 2025 and having a size of 274,371 bytes. The contents of the text file are incorporated by reference herein in their entirety.

INTRODUCTION

Drug resistance, a well-known phenomenon that results when diseases become tolerant to pharmaceutical treatments, is a major and increasing challenge in various fields of medicine, including oncology. Although many types of cancers are initially susceptible to chemotherapy, over time they can develop resistance through these and other mechanisms, including DNA mutations and metabolic changes that promote drug inhibition, degradation and enhanced efflux.

Efflux pumps (EP) are proteins expressed by living cells and have evolved to naturally expel various compounds from the cells. Members of the ATP-binding cassette (ABC) transporter family proteins are examples of EPs that enable drug efflux. Though a transporter's structure varies from protein to protein (e.g., there are 49 known members of the ABC family in humans), they are all classified by the presence of two distinct domains—a highly conserved nucleotide binding domain and a more variable transmembrane domain. Multidrug resistance protein 1 (MDR1), encoded by the ATP Binding Cassette Subfamily B Member 1 (ABCB1) gene, was the first of these to be identified and has been studied extensively. ABCG2 expression is increased in response to treatment with certain chemotherapeutics.

EPs enable tumors to develop resistance to chemotherapeutic agents. Such resistance is frequently associated with enhanced efflux of the chemotherapeutic agent from the drug resistant cells. This chemotherapy resistance is termed multi drug resistance (MDR) when it applies to more than one chemotherapeutic agent.

As such there is a need to develop reagents that may be used for assaying for expression of EPs and/or inhibiting EPs.

SUMMARY

Provided are antibodies that target the cellular efflux pump ABCG2. Also provided are pharmaceutical compositions, nucleic acids, recombinant expression vectors, cells, and kits that include or encode such antibodies. Methods of using the antibodies for detecting presence or absence of ABCG2 expression in cells, e.g., tumor cells, level of ABCG2 expression, and/or inhibiting ABCG2 function are also disclosed. In addition, multi-specific antibodies that bind to cancer cells that overexpress ABCG2 and a tumor associated antigen (TAA) on cell surface are provided. In addition, multi-specific antibodies that bind to cancer cells that overexpress ABCG2 and the efflux pump ABCB1 are provided. Also provided are methods for treating a subject for a cancer that include administering to the subject an anti-ABCG2 antibody or a multi-specific antibody as disclosed herein.

DEFINITIONS

Figure 1A:
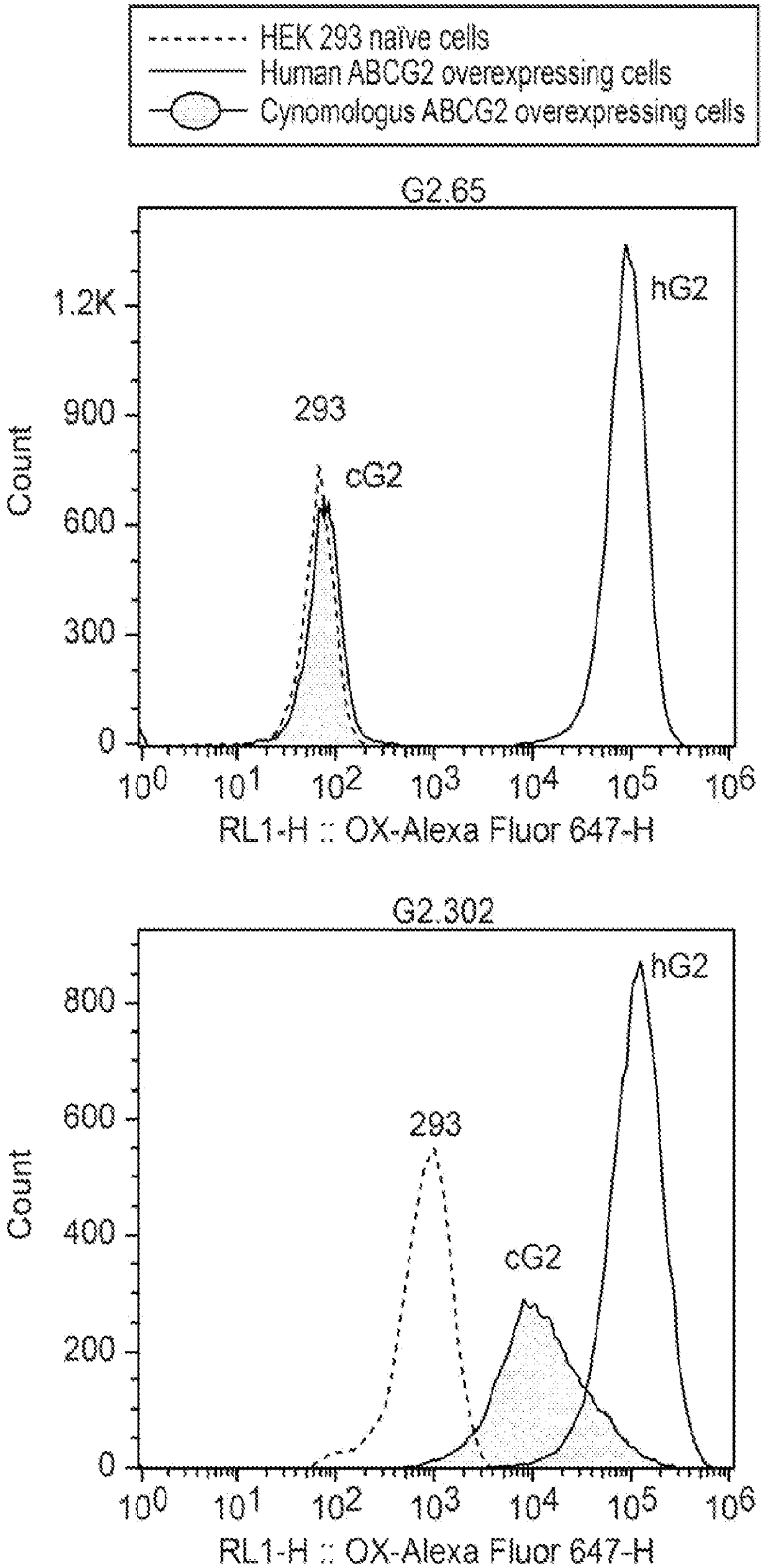
FIG. 1 depicts FACS analysis of binding of anti-ABCG2 antibodies, G2.65 and G.302, to HEK 293 naïve cells, HEK 293 cells overexpressing human ABCG2 ("hG2"), and HEK 293 cells overexpressing cynomolgus ABCG2 ("cG2").

The terms "antibody" and "immunoglobulin" include antibodies or immunoglobulins of any isotype, fragments of antibodies which retain specific binding to antigen, including, but not limited to, Fab, Fv, scFv, Fd, Fab', Fv, $F(ab')_2$, chimeric antibodies, humanized antibodies, monoclonal antibodies, single-chain antibodies, including antibodies comprising only heavy chains (e.g. VHH camelid antibodies), bispecific antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. An antibody may be monovalent or bivalent. An antibody may be conjugated to a toxic moiety, such as, a chemotherapeutic agent.

"Antibody fragments" comprise a portion of an intact antibody, for example, the antigen binding or variable region of the intact antibody. Examples of antibody fragments include Fab, Fab', $F(ab')_2$, and Fv fragments; diabodies; linear antibodies (Zapata et al., Protein Eng. 8(10): 1057-1062 (1995)); single-chain antibody molecules, including antibodies comprising only heavy chains (e.g. VHH camelid antibodies); and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an $F(ab')_2$ fragment that has two antigen combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site comprising the three CDRs of each variable domain.

The "Fab" fragment also contains the constant domain of the light chain and the first constant domain ($CH_1$) of the heavy chain. Fab fragments differ from Fab' fragments by the addition of a few residues at the carboxyl terminus of the heavy chain $CH_1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv", "sFv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains, which enables the sFv to form the desired structure for antigen binding. For a review of sFv, see *Pluckthun in The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA,* 90:6444-6448 (1993).

As used herein, the term "affinity" refers to the equilibrium constant for the reversible binding of two agents and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges. An ABCG2-specific antibody binds specifically to an epitope within a ABCG2 polypeptide. The epitope may be a linear epitope formed by a contiguous stretch of amino acids or a non-linear or a conformational epitope formed by non-contiguous stretches of amino acids. Non-specific binding would refer to binding with an affinity of less than about $10^{-7}$ M, e.g., binding with an affinity of $10^{-6}$ M, $10^{-5}$ M, $10^{-4}$ M, etc.

As used herein, the term "CDR" or "complementarity determining region" is intended to mean the non-contiguous antigen combining sites found within the variable region of both heavy and light chain polypeptides. CDRs are hypervariable regions and are interspersed with regions that are more conserved, termed "framework regions (FR)". CDRs have been described by Kabat et al., J. Biol. Chem. 252: 6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison.

TABLE 1

CDR Definitions

| | Kabat[1] | Chothia[2] | MacCallum[3] |
|---|---|---|---|
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein, the term "framework" when used in reference to an antibody variable region is intended to mean all amino acid residues outside the CDR regions within the variable region of an antibody. A variable region framework is generally a discontinuous amino acid sequence between about 100-120 amino acids in length but is intended to reference only those amino acids outside of the CDRs. As used herein, the term "framework region" is intended to mean each domain of the framework that is separated by the CDRs. A VH chain can comprise three CDRs and four FRs arranged from N-terminus to C-terminus in the following order: FR1, CDR1, FR2, CDR2, FR3, CDR3, FR4. Similarly, a VL chain can comprise three CDRs and four FRs arranged from N-terminus to C-terminus in the following order: FR1, CDR1, FR2, CDR2, FR3, CDR3, FR4.

As used herein, the term antibody encompasses a tetramer of two heavy and two light chains, wherein the heavy and light chains are interconnected by, for example, disulphide bonds. The heavy chain constant region is comprised of three domains, CH1, CH2 and CH3. The light chain constant region is comprised of one domain, CL. The variable regions of the heavy and light chains comprise binding regions that interact with antigen. The constant regions of the antibodies typically mediate the binding of the antibody to host tissues and factors, including various cells of the immune system and the first component of the complement system. The term "antibody" includes immunoglobulins of types IgA, IgG, IgE, IgD, IgM and subtypes thereof. In some embodiments, a subject antibody is an IgG isotype, e.g., IgG1.

As used herein the term "immunoglobulin" refers to a protein including one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes; and numerous immunoglobulin variable region genes. Full-length immunoglobulin light chains (about 25 kD or 214 amino acids) are encoded by a variable region gene at the N-terminus (about 110 amino acids) and a kappa or lambda constant region at the C-terminus. Full-length immunoglobulin heavy chains (about 50 kD or 446 amino acids) are encoded by a variable region gene at the N-terminus (about 116 amino acids) and one of the other aforementioned constant region genes at the C-terminus, e.g. gamma (encoding about 330 amino acids). In some embodiments, a subject antibody comprises full-length immunoglobulin heavy chain and a full-length immunoglobulin light chain.

The term "antigen-binding fragment" refers to one or more fragments of a full-length antibody that are capable of specifically binding to an antigen. Examples of binding fragments include (i) a Fab fragment (a monovalent fragment including, e.g., consisting of, the VL, VH, CL and CH1 domains; (ii) a $F(ab')_2$ fragment (a bivalent fragment comprising two Fab fragments linked by a disulfide bridge at the hinge region; (iii) a Fd fragment (including, e.g., consisting of, the VH and CH1 domains); (iv) a Fv fragment (including, e.g., consisting of, the VH and VL domains of a single arm of an antibody); (v) a dAb fragment (including, e.g., consisting of, the VH domain); (vi) an isolated CDR; (vii) a single chain Fv (scFv) (including, e.g., consisting of, the VH and VL domains of a single arm of an antibody joined by a synthetic linker using recombinant means such that the VH and VL domains pair to form a monovalent molecule); (viii) diabodies (including, e.g., consisting of, two scFvs in which the VH and VL domains are joined such that they do not pair to form a monovalent molecule; the VH of each one of the scFv pairs with the VL domain of the other scFv to form a bivalent molecule).

The term "chimeric" antibody refers to an antibody in which a portion of the heavy and/or light chain is derived from a particular source or species, while the remainder of the heavy and/or light chain is derived from a different source or species.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework (FR) which represents the most commonly occurring amino acid residues in a selection of human immunoglobulin variable light chain (VL) or variable heavy chain (VH) framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human CDRs and amino acid residues from human frameworks (FRs). At least a portion of a humanized antibody constant region is derived from a human antibody, e.g., a human IgG1 antibody. In preferred embodiments, the antibody molecules disclosed herein include a heavy chain comprising a variable heavy chain region as provided herein and a human IgG1 constant region having the amino acid sequence sequence set forth in UniProt: P01857-1, version 1. In preferred embodiments, the antibody molecules disclosed herein include a light chain comprising a variable light chain region as provided herein and a human light chain constant region. In preferred embodiments, the human light chain constant region is a human kappa light chain constant region having the amino acid set forth in UniProtKB/Swiss-Prot: P01834.2. In certain aspects, the human IgG1 heavy chain constant region present in the subject antibodies may include mutations, e.g., substitutions to modulate Fc function. For example, the LALAPG effector function mutations (L234A, L235A, and P329G) or the N297A mutation may be introduced to reduce antibody dependent cellular cytotoxicity (ADCC). The numbering of the substitutions is based on the EU numbering system. The "EU numbering system" or "EU index" is generally used when referring to a residue in an immunoglobulin heavy chain constant region (e.g., the EU index reported in Kabat et al., Sequences of Proteins of Immunological Interest, 5th Ed. Public Health Service, National Institutes of Health, Bethesda, MD. (1991)). The "EU index as in Kabat" refers to the residue numbering of the human IgG 1 EU antibody.

A "humanized form" of an antibody, e.g., a non-human antibody, refers to an antibody that has undergone humanization.

The term "epitope" refers to a region of an antigen that is recognized by the immune system, for example by antibodies, B cells, or T cells. For example, the epitope is the specific region of the antigen to which an antibody binds.

An "isolated" antibody is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In some embodiments, the antibody will be purified (1) to greater than 90%, greater than 95%, or greater than 98%, by weight of antibody as determined by the Lowry method, for example, more than 99% by weight, (2) to a degree sufficient to obtain at least 15 residues of N-terminal or internal amino acid sequence by use of a spinning cup sequenator, or (3) to homogeneity by sodium dodecyl sulfate-polyacrylamide gel electrophoresis (SDS-PAGE) under reducing or nonreducing conditions using Coomassie blue or silver stain. Isolated antibody includes the antibody in situ within recombinant cells since at least one component of the antibody's natural environment will not be present. In some instances, isolated antibody will be prepared by at least one purification step.

The term "cytotoxic agent" as used herein refers to a substance that inhibits or prevents a cellular function and/or causes cell death or destruction. A "chemotherapeutic agent," also referred to an "antineoplastic agent," can be a cytotoxic agent which is used for treating a cancer or other disease or disorder.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, including in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc.

A "therapeutically effective amount" or "efficacious amount" refers to the amount of a target-specific antibody that, when administered to a mammal or other subject for treating a disease, is sufficient to affect such treatment for the disease. The "therapeutically effective amount" will vary depending on the antibody, the disease and its severity and the age, weight, etc., of the subject to be treated.

The term "refractory", used herein, refers to a disease or condition that does not respond to treatment. With regard to cancer, "refractory cancer", as used herein, refers to cancer that does not respond to treatment. A refractory cancer may be resistant at the beginning of treatment or it may become resistant during treatment. Refractory cancer may also be called resistant cancer.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples.

Percent identity between a pair of sequences may be calculated by multiplying the number of matches in the pair by 100 and dividing by the length of the aligned region, including gaps.

Identity scoring only counts perfect matches and does not consider the degree of similarity of amino acids to one another. Only internal gaps are included in the length, not gaps at the sequence ends. Percent Identity=(Matches×100)/Length of aligned region (with gaps) The phrase "conservative amino acid substitution" refers to substitution of amino acid residues within the following groups: 1) L, I, M, V, F; 2) R, K; 3) F, Y, H, W, R; 4) G, A, T, S; 5) Q, N; and 6) D, E. Conservative amino acid substitutions may preserve the activity of the protein by replacing an amino acid(s) in the protein with an amino acid with a side chain of similar acidity, basicity, charge, polarity, or size of the side chain.

Guidance for substitutions, insertions, or deletions may be based on alignments of amino acid sequences of proteins from different species or from a consensus sequence based on a plurality of proteins having the same or similar function.

The term "vector" means any molecule or entity (e.g., nucleic acid, plasmid, bacteriophage or virus) used to transfer protein coding information into a host cell.

The term "expression vector" or "expression construct" refers to a vector that is suitable for transformation of a host cell and contains nucleic acid sequences that direct and/or control (in conjunction with the host cell) expression of one or more heterologous coding regions operatively linked thereto. An expression construct may include, but is not limited to, sequences that affect or control transcription, translation, and, if introns are present, affect RNA splicing of a coding region operably linked thereto.

The term "stimulation," refers to a primary response induced by binding of a stimulatory molecule (e.g., a TCR/CD3 complex or CAR) with its cognate ligand (or tumor antigen in the case of a CAR) thereby mediating a signal transduction event, such as, but not limited to, signal transduction via the TCR/CD3 complex or signal transduction via the appropriate NK receptor or signaling domains of the CAR. Stimulation can mediate altered expression of certain molecules.

The term "stimulatory molecule," refers to a molecule expressed by an immune cell (e.g., T cell, NK cell, B cell) that provides the cytoplasmic signaling sequence(s) that regulate activation of the immune cell in a stimulatory way for at least some aspect of the immune cell signaling pathway. In one aspect, the signal is a primary signal that is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or ITAM. Examples of an ITAM containing cytoplasmic signaling sequence that is of particular use in the invention includes, but is not limited to, those derived from CD3 zeta, common FcR gamma (FCER1G), Fc gamma RIIa, FcR beta (Fc Epsilon R1b), CD3 gamma, CD3 delta, CD3 epsilon, CD79a, CD79b, DAP10, and DAP12.

The term a "costimulatory molecule" refers to a cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are contribute to an efficient immune response. Costimulatory molecules include, but are not limited to an MHC class I molecule, BTLA and a Toll ligand receptor, as well as OX40, CD27, CD28, CDS, ICAM-1, LFA-1 (CD11a/CD18), ICOS (CD278), and 4-1BB (CD137).

The term "autologous" refers to any material derived from the same individual to whom it is later to be re-introduced into the individual.

An "intracellular signaling domain," as the term is used herein, refers to an intracellular portion of a molecule. The intracellular signaling domain generates a signal that promotes an immune effector function of the CAR containing cell, e.g., a CAR-T cell. Examples of immune effector function, e.g., in a CAR-T cell, include cytolytic activity and helper activity, including the secretion of cytokines.

"Immune effector cell," as that term is used herein, refers to a cell that is involved in an immune response, e.g., in the promotion of an immune effector response. Examples of immune effector cells include T cells, e.g., alpha/beta T cells and gamma/delta T cells, B cells, natural killer (NK) cells, natural killer T (NKT) cells, mast cells, and myeloid-derived phagocytes.

DETAILED DESCRIPTION

Provided are antibodies that bind to the cellular efflux pump ABCG2. Also provided are pharmaceutical compositions, nucleic acids, recombinant expression vectors, cells, and kits that include or encode such antibodies. Methods of using the antibodies for detecting presence or absence of ABCG2 expression in cells, e.g., tumor cells, level of ABCG2 expression, and/or inhibiting ABCG2 function are also disclosed. In addition, multi-specific antibodies, such as bispecific antibodies that bind to cancer cells that express both ABCG2 and a tumor associated antigen (TAA) on cell surface are provided. In addition, bi-specific antibodies that bind to cancer cells that express both ABCG2 and the efflux pump ABCB1 are provided. In certain aspects, the bi-specific antibodies disclosed herein bind to a cell expressing both antigens and do not detectably bind to a cell expressing only one of the antigens. Also provided are methods for treating a subject for a cancer that include administering to the subject an anti-ABCG2 antibody or a multi-specific antibody as disclosed herein.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the methods and compositions have or will be described for the sake of grammatical fluidity with functional explanations, it is to be expressly understood that the claims, unless expressly formulated under 35 U.S.C. § 112(f), are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112(f) are to be accorded full statutory equivalents under 35 U.S.C. § 112(f).

Antibodies

As summarized above, the present disclosure provides antibodies that bind a cellular efflux pump ABCG2.

ABCG2, also known as CD388 and BCRP, is an energy-dependent efflux pump responsible for decreased drug accumulation in multidrug-resistant cells that is expressed from the ATP binding cassette subfamily G member 2 (ABCG2) gene.

In some aspects, the antibodies disclosed herein bind to one or more sites on the extracellular domain of the ABCG2.

In certain aspects, the anti-ABCG2 antibodies of the present disclosure bind to human ABCG2. In certain aspects, the anti-ABCG2 antibodies of the present disclosure bind to human ABCG2 expressed on the cell surface of a human cell, e.g., cancer cell. In certain aspects, the antibodies disclosed herein bind to one or more sites on an extracellular domain (ECD) of the human ABCG2, where the ECD may include the sequence: KNDSTGIQNRAG (SEQ ID NO:1), which sequence corresponds to amino acid residue 417-428 of the human ABCG2 sequence having the Accession No. NP_004818. In certain aspects, the antibodies disclosed herein bind to one or more sites on an extracellular domain (ECD) of the human ABCG2, where the ECD may include the sequence: LKPKADAF (SEQ ID NO:2), which sequence corresponds to amino acid residue 499-506 of the human ABCG2 sequence having the Accession No. NP_004818. In certain aspects, the antibodies disclosed herein bind to one or more sites on an extracellular domain (ECD) of the human ABCG2, where the ECD may include the sequence: NLTTIASWLSWLQYFSIPRYGFTALQH-NEFLGQNFCPGLNATGNNPCNYATCTGEEYLVKQGI DLSPWGLWKNH (SEQ ID NO:3), which sequence corresponds to amino acid residue 557-630 of the human ABCG2 sequence having the Accession No. NP_004818.

Antibodies of the present disclosure may have one or more of the following properties:

i) Inhibits efflux from ABCG2;
ii) increases sensitivity of cancer cell to treatment with a chemotherapeutic agent thereby lowering the IC50 of the chemotherapeutic agent by at least a factor of 2;
iii) binds to human and cynomolgus ABCG2;
iv) is effective in in vitro cell killing assays;
v) is effective in inhibiting tumor growth even in absence of chemotherapy;
vi) binds preferentially to an ABCG2 mutant constrained in an open configuration;
vii) has an affinity for ABCG2 in a lower range such that it binds to cancer cells that express ABCG2 at a higher level as compared to non-cancer cells and binds significantly less to non-cancer cells; and
viii) binds preferentially to an ABCG2 mutant constrained in a closed configuration.

In certain aspects, the antibodies of the present disclosure may have an EC50 that is lower than that of the anti-ABCG2 antibody 5D3. As used herein, EC50 refers to the concentration of an antibody that provides half maximal response (e.g., half of the maximum fluorescence intensity). The antibodies of the present disclosure may have an EC50 of 100 nM or lower, e.g., 100 nM-4 nM, 80 nM-4 nM, 60 nM-4 nM, 40 nM-4 nM, 30 nM-4 nM, 20 nM-4 nM, 15 nM-4 nM, or 10 nM-4 nM. EC50 of a test antibody many be determined by flow cytometry or ELISA. For example, flow cytometry may involve contacting a cell expressing ABCG2 (e.g. human wild type ABCG2 or a mutant ABCG2) with the antibody in a flow cytometry buffer, where the antibody is serially diluted, and incubating at room temperature or 4° C. for a period of time sufficient for the antibody to bind to the cells (e.g. 10 min-1 hr). After incubating, the cells may optionally be washed to remove and non-specifically bound antibody and/or the cells may be contacted with a fluorescently labeled secondary antibody that specifically binds to the test antibody. After incubation, the fluorescently labeled secondary antibody may be removed and the cells washed. The washed cells may be sorted by flow cytometry and the number of cells bound to the fluorescently labeled secondary antibody counted. The concentration that provides half maximal response (e.g., half of the maximum fluorescence intensity) is measured as the EC50. In variations of the flow cytometry assay, the cell may be a 293T cell overexpressing ABCG2. In certain aspects, the antibodies of the present disclosure may have an EC50 that is higher than that of the anti-ABCG2 antibody 5D3.

In certain aspects, in addition to having one or more properties i)-viii) listed above, one or more of the anti-ABCG2 antibodies of the present disclosure may have an EC50 that is at least half of the EC50 of the anti-ABCG2 antibody 5D3. In certain aspects, in addition to having one or more properties i)-viii) listed above, one or more of the anti-ABCG2 antibodies of the present disclosure may have an EC50 that is at least twice that of the EC50 of the anti-ABCG2 antibody 5D3.

The IC50 of a test antibody may be determined by measuring inhibition of cell growth. IC50 may be measured by using the test antibody alone to determine the concentration of the antibody that produced half maximal response. The IC50 of a chemotherapeutic agent may be measured in the absence and in the presence of the test antibody to determine the effect of the antibody on the IC50 chemotherapeutic agent. The chemotherapeutic agent may be topotecan. The cell may be a cancer cell line. The cancer cell line may be N6/ADR, a doxorubicin-selected, B1-positive variant of the human acute lymphoblastic leukemia (ALL) cell line, NALM6. N6/ADR cells is also referred to as NALM6/ADR cells. Cells may be contacted with antibody alone if determining the IC50 of the antibody, wherein the antibody is tested at serial dilutions. Cells may be contacted with antibody and the chemotherapeutic agent to determine the effect of the antibody on the IC50 of the agent, where the agent is tested at serial dilutions. The cells may be incubated at 37° C. for a period of time (e.g. 24 hr-84 hr) and cell viability assessed using standard reagents and methods. The antibodies disclosed herein may increase sensitivity of cancer cell to treatment with a chemotherapeutic agent thereby lowering the IC50 of the chemotherapeutic agent by at least a factor of 5. The cancer cell may be N6/ADR. The chemotherapeutic agent may be topotecan. In certain aspects, the antibodies of the present disclosure may lower the IC50 of the chemotherapeutic agent by factor of 5 or more, e.g., factor of 6 or more, factor of 7 or more, factor of 8 or more, factor of 9 or more, or factor of 10 or more, e.g., by a factor of 5 to 10.

In certain aspects, one or more of the anti-ABCG2 antibodies disclosed herein bind to both human and cynomolgus ABCG2. This property may be utilized in determining safety of the antibody in an animal model.

In certain aspects, the anti-ABCG2 antibodies disclosed herein are specific for ABCG2 and do not show significant binding to other antigens.

In certain aspects, the in vitro cell killing activity of the presently disclosed antibodies may be superior to that observed for the 5D3 antibody. For example, the presently disclosed antibodies may have in vitro cell killing activity that is twice or more than that of the 5D3 antibody.

In certain aspects, one or more of the antibodies provided herein bind preferentially to an ABCG2 mutant constrained in an open configuration. The ABCG2 mutant may be a human or a cynomolgus ABCG2 comprising the substitution E211Q, where the numbering of the amino acid positions is with reference to human ABCG2. Such antibodies may bind to an ABCG2 mutant constrained in an open configuration with an affinity that is at least two times (e.g. 2×, 3×, 4×, 5×, 6×, 7×, 8×, 9×, 10×, or more) as compared to the wild-type ABCG2 or an ABCG2 mutant constrained in a closed configuration.

In certain aspects, one or more of the antibodies provided herein bind preferentially to an ABCG2 mutant constrained in a closed configuration. The ABCG2 mutant may be a human or a cynomolgus ABCG2 comprising the substitutions: (i) K86M and S87A; (ii) K86M, S87A, and Q126A; or (iii) K86M.S87A.Q126A.R246E, where the numbering of the amino acid positions is with reference to human ABCG2. Such antibodies may bind to an ABCG2 mutant constrained in a closed configuration with an affinity that is at least two times (e.g. 3×, 4×, 5×, 6×, 7×, 8×, 9×, 10×, or more) as compared to the wild-type ABCG2 or an ABCG2 mutant constrained in an open configuration.

In certain aspects, the antibodies provided herein are monospecific bivalent anti-ABCG2 antibodies. In certain aspects, the monospecific bivalent anti-ABCG2 antibodies of the present disclosure do not include at least one, two, three, four, five, six, seven, eight, nine, ten, eleven, or all twelve of HCDR1-3 and LCDR1-3 present in the anti-ABCG2 antibody, 5D3.

The 5D3 antibody includes a variable heavy chain having the sequence:

```
                                        (SEQ ID NO: 4)
QVQLQESGPGLVKPSQSLSLTCTVTGFSITSDYAWNWIRQFPGKKLEWM

GYINFDGGTTYNPSLRGRISITRDTSKNQFFLQLRSVTPEDTATYYCAT

FYGAKGTLDYWGQGTSVTVSS
```

and a variable light chain having the sequence:

```
                                        (SEQ ID NO: 5)
DIVLTQSPSSFSVSLGDRVTISCKASGYILNRLAWYQQKPGNAPRLLIS

GATSLETGFPSRFSGTGSGKDYTLSISSLQTEDVGTYYCQQYWSTPWTF

GGGTKLEIK.
```

The HCDRs 1-3 and LCDRs 1-3 of the 5D3 antibody defined as per Kabat nomenclature are as follows:

```
HCDR 1:
                        (SEQ ID NO: 6)
GFSITSDYAW;

HCDR 2:
                        (SEQ ID NO: 7)
GYINFDGGTTYNPSLRG;

HCDR 3:
                        (SEQ ID NO: 8)
ATFYGAKGTLDY;

LCDR 1:
                        (SEQ ID NO: 9)
KASGYILNRLA;

LCDR 2:
                       (SEQ ID NO: 10)
GATSLET;

LCDR 3:
                       (SEQ ID NO: 11)
QQYWSTPWT.
```

In some embodiments, one or more of the subject antibodies may, when bound to a cell expressing ABCG2, prevent the functioning of the cellular ABCG2 protein. Accordingly, one or more antibodies of the present disclosure may inhibit efflux by the ABCG2 protein, including e.g., where efflux is reduced by 5% or more, including e.g., 10% or more, 15% or more, 20% or more, 25% or more, 30% or more, 40% or more, 50% or more, 60% or more, 70% or more, 80% or more, or 90% or more, as compared to efflux by ABCG2 in the absence of the subject antibody. In some embodiments, the subject antibodies may, when bound to a cell expressing ABCG2 may otherwise impede the action of ABCG2 by other mechanisms, e.g., rendering ABCG2 leaky which in turn may enhance uptake of a chemotherapeutic agent and/or decrease viability of the cell.

In certain aspects, an antibody that binds to ABCG2 is provided, where the antibody competes for binding to ABCG2 with an antibody comprising heavy chain complementarity determining regions (HCDRs) and light chain CDRs (LCDRs) of the variable heavy chain (VH) region and the variable light chain (VL) region pair, respectively, of an antibody listed in Table 2. For example, in one aspect, an anti-ABCG2 antibody of the present disclosure competes for binding to ABCG2 with the G2.302 antibody listed in Table 2. In certain aspects, HCDRs 1-3 and LCDRs 1-3 are defined as per Kabat nomenclature.

In certain aspects, the antibody comprises the HCDR1, HCDR2, and HCDR3 of the VH region of the antibody listed in Table 2. In certain aspects, the HCDR1, HCDR2, and HCDR3 are defined as per Kabat nomenclature. For example, in one aspect, the anti-ABCG2 antibody of the present disclosure that competes for binding to ABCG2 with the G2.302 antibody listed in Table 2 comprises the HCDR1, HCDR2, and HCDR3 of the VH region of the G2.302 antibody.

Any suitable approach for determining whether a first antibody competes with a second antibody for binding to ABCG2 may be employed. Whether a first antibody "competes with" a second antibody for binding to a compound may be readily determined using competitive binding assays known in the art. Competing antibodies may be identified, for example, via an antibody competition assay. For example, a sample of a first antibody can be bound to a solid support. Then, a sample of a second antibody suspected of being able to compete with such first antibody is added. One of the two antibodies is labelled. If the labeled antibody and the unlabeled antibody bind to separate and discrete sites on the compound, the labeled antibody will bind to the same level whether or not the suspected competing antibody is present. However, if the sites of interaction are identical or overlapping, the unlabeled antibody will compete, and the amount of labeled antibody bound to the antigen will be lowered. If the unlabeled antibody is present in excess, very little, if any, labeled antibody will bind.

For purposes of the present disclosure, competing antibodies are those that decrease the binding of an antibody to the compound by about 30% or more, about 40% or more, about 50% or more, about 60% or more, about 70% or more, about 80% or more, about 85% or more, about 90% or more, about 95% or more, or about 99% or more. Details of procedures for carrying out such competition assays are well known in the art and can be found, for example, in Harlow and Lane, Antibodies, A Laboratory Manual, Cold Spring Harbor Laboratory Press, Cold Spring Harbor, New York, 1988, 567-569, 1988, ISBN 0-87969-314-2. Such assays can be made quantitative by using purified antibodies. A standard curve may be established by titrating one antibody against itself, i.e., the same antibody is used for both the label and the competitor. The capacity of an unlabeled competing antibody to inhibit the binding of the labeled antibody to the target epitope may be titrated. The results may be plotted, and the concentrations necessary to achieve the desired degree of binding inhibition may be compared.

In certain aspects, an antibody that specifically binds to ABCG2 comprises (i) HCDRs 1-3 and light chain CDRs (LCDRs 1-3) of a pair of variable heavy chain (VH) region and variable light chain (VL) region of an antibody listed in Table 2; (ii) HCDRs 1-3 of a VH region of an antibody listed in Table 2; or (iii) LCDRs 1-3 of a VH region of an antibody listed in Table 2. The HCDRs and the LCDRs may be defined based on the Kabat nomenclature.

In certain aspects, an antibody of the present disclosure that binds specifically to human ABCG2 comprises the HCDR1, HCDR2, and HCDR3 sequences and the LCDR1, LCDR2, and LCDR3 sequences of an antibody listed in Table 2. In addition to binding to human ABCG2, one or more of the antibodies provided herein may bind to ABCG2 from other mammalian species, such as, mouse, monkey, chimpanzee, etc. The antibodies may be raised in mouse or rat. In Table 2, the animal in which the antibody was generated is indicated. Some of the antibodies were humanized.

TABLE 2

From left to right, 1st column: Anti-ABCG2 antibody name, 2nd column: VH region, 3rd column: HCDR1, 4th column: HCDR2, 5th column: HCDR3, 6th column: VL region, 7th column: LCDR1, 8th column: LCDR2, 9th column: LCDR3.

| Antibody | Heavy Chain Variable Region | CDRH1 | CDRH2 | CDRH3 | Light Chain Variable Region | CDRL1 | CDRL2 | CDRL3 |
|---|---|---|---|---|---|---|---|---|
| G2.248 mouse | QVQLQQPGAELVKPGASVKLSCKTSGFTFSNSYISWLKQKPRQSLEWIAWIYAGTGGTNYNQKFTGKAQLTVDTSSSTAYMQLSSLTSEDSAIYYCATYGNFLYAMDNWGQGTSVTVSS (SEQ ID NO: 12) | NSYIS (SEQ ID NO: 81) | WIYAGTGGTNYNQKFTG (SEQ ID NO: 111) | YGNFLYAMDN (SEQ ID NO: 153) | DIQMKQSPASLSASVGETVTITCRASGNIHNYLAWYQQKQGKSPQLLVYNTKTLADGVPSRFSGSGSGTQYSLKINSLQPEDFGSYYCQHFWSTPWTFGGGTKLEIK (SEQ ID NO: 195) | RASGNIHNYLA (SEQ ID NO: 266) | NTKTLAD (SEQ ID NO: 302) | QHFWSTPWT (SEQ ID NO: 330) |
| G2.255 mouse | EVMLVESGGALVKPGGSLKLSCAASGFTFSNNAMSWVRQTPETRLEWVATITGGGSYTYYPDSVKGRFTISRDNARNTLYLQMSSLRSEDTATYYCASPDGNYEGVLAYWGQGTLVTVSA (SEQ ID NO: 13) | NNAMS (SEQ ID NO: 82) | TITGGGSYTYYPDSVKG (SEQ ID NO: 112) | PDGNYEGVLAY (SEQ ID NO: 154) | DIQMNQSPSSLSASLGDRVTISCSASQGISNYLNWYQQKPDGTIKLLIYYTSTLHSGVPSRFSGSGSGTDYSLTISNLEPEDIATYYCQHYSSLPWTFGGGTKLEIK (SEQ ID NO: 196) | SASQGISNYLN (SEQ ID NO: 267) | YTSTLHS (SEQ ID NO: 303) | QHYSSLPWT (SEQ ID NO: 331) |
| G2.256 mouse | EVQLQQSGPELVKPGASLKISCKTFGYSFTGYYMHWVKQSPEKSLEWIGKIVPSTGGTTYNQKFKAKATLTVDKSSFTAYMQLKSLTSEDSAVYYCAREKVYGYDVYYFDYWGQGTTLTVSS (SEQ ID NO: 14) | GYYMH (SEQ ID NO: 83) | KIVPSTGGTTYNQKFKA (SEQ ID NO: 113) | EKVYGYDVYYFDY (SEQ ID NO: 155) | DIVMSQSPATLSVTPGDRVSLSCRASQSISDYLHWYQQKSHESPRLLIKYASQSISGIPSRFSGSGSGSDFTLSINSVEPEDVGVYYCQNGHSFPWTFGGGTKLEIK (SEQ ID NO: 197) | RASQSISDYLH (SEQ ID NO: 268) | YASQSIS (SEQ ID NO: 304) | QNGHSFPWT (SEQ ID NO: 332) |
| G2.65 mouse | QGQMHQSGAELVKPGASVKLSCKTSGFTFNSGYISWLKQKPRQSLEWIAWIYAGTGISNFNQKFTGKAQLTVDTSSSTAYMQLSSLTSADSAIYFCASGARKTLDFWGQGTSVTVSS (SEQ ID NO: 15) | SGYIS (SEQ ID NO: 84) | WIYAGTGISNFNQKFTG (SEQ ID NO: 114) | GARKTLDF (SEQ ID NO: 156) | DIQMTQSSSYLSVSVGGRVTITCKASDQINYWLAWYQQKPGNAPRLLISGATSLETGVPSRFSGSGSGKDYTLSITSFQTEDVATYYCQQYWTTPYTFGGGTKVEIK (SEQ ID NO: 198) | KASDQINYWLA (SEQ ID NO: 269) | GATSLET (SEQ ID NO: 10) | QQYWTTPYT (SEQ ID NO: 333) |
| G2.173 mouse | QVQLQQSGADLVRPGASVKLSCTASGFNIKDDYVHWVKQRPEQGLEWIGRIDPANGNTRYAPKFRGKATMTADTSSNTAYLQLSSLTSADTAVYYCSPPLWVGGFAYWGQGTLVTVSS (SEQ ID NO: 16) | DDYVH (SEQ ID NO: 85) | RIDPANGNTRYAPKFRG (SEQ ID NO: 115) | PLWVGGFAY (SEQ ID NO: 157) | DVVMTQTPLSLPVSLGDQASISCRSSQSLVHSDVNTYLHWYLQRPGQSPKLLIYKVSNRFSGVPDRFSGSGSGTDFTLKISRVESEDLGIYFCSQTTHVPYTFGGGTKLEIK (SEQ ID NO: 199) | RSSQSLVHSDVNTYLH (SEQ ID NO: 270) | KVSNRFS (SEQ ID NO: 305) | SQTTHVPYT (SEQ ID NO: 334) |
| G2.173 Humanized 1 | EVQLVQSGAEVKKPGASVKVSCKASGFNIKDDYVHWVRQAPGQGLEWIGRIDPANGNTRYAPKFRGRATMTADTSISTAYMELSRLRSDDTAVYYCSPPLWVGGFAYWGQGTLVTVSS (SEQ ID NO: 17) | DDYVH (SEQ ID NO: 85) | RIDPANGNTRYAPKFRG (SEQ ID NO: 115) | PLWVGGFAY (SEQ ID NO: 157) | DVVMTQSPLSLPVTLGQPASISCRSSQSLVHSDVNTYLHWYQQRPGQSPRLLIYKVSNRFSGVPDRFSGSGSGTDFTLKISRVEAEDVGVYFCSQTTHVPYTFGGGTKLEIK (SEQ ID NO: 200) | RSSQSLVHSDVNTYLH (SEQ ID NO: 270) | KVSNRFS (SEQ ID NO: 305) | SQTTHVPYT (SEQ ID NO: 334) |

TABLE 2-continued

From left to right, 1st column: Anti-ABCG2 antibody name, 2nd column: VH region, 3rd column: HCDR1, 4th column: HCDR2, 5th column: HCDR3, 6th column: VL region, 7th column: LCDR1, 8th column: LCDR2, 9th column: LCDR3.

| Antibody | Heavy Chain Variable Region | CDRH1 | CDRH2 | CDRH3 | Light Chain Variable Region | CDRL1 | CDRL2 | CDRL3 |
|---|---|---|---|---|---|---|---|---|
| G2.173 Humanized 2 | EVQLVQSGAEVKKPGASVKVSCKASGFNIKDDYVHWVRQAPGQGLEWIGRIDPAQGNTRYAPKFRGRATMTADTSISTAYMELSRLRSDDTAVYYCSPPLWVGGFAYWGQGTLVTVSS (SEQ ID NO: 18) | DDYVH (SEQ ID NO: 85) | RIDPAQGNTRYAPKFRG (SEQ ID NO: 116) | PLWVGGFAY (SEQ ID NO: 157) | DVVMTQSPLSLPVTLGQPASISCRSSQSLVHSDVNTYLHWYQQRPGQSPRLLIYKVSNRFSGVPDRFSGSGSGTDFTLKISRVEAEDVGVYFCSQTTHVPYTFGGGTKLEIK (SEQ ID NO: 200) | RSSQSLVHSDVNTYLH (SEQ ID NO: 270) | KVSNRFS (SEQ ID NO: 305) | SQTTHVPYT (SEQ ID NO: 334) |
| G2.173 Humanized 3 | EVQLVQSGAEVKKPGASVKVSCKASGFNIKDDYVHWVRQAPGQGLEWIGRIDPASGNTRYAPKFRGRATMTADTSISTAYMELSRLRSDDTAVYYCSPPLWVGGFAYWGQGTLVTVSS (SEQ ID NO: 19) | DDYVH (SEQ ID NO: 85) | RIDPASGNTRYAPKFRG (SEQ ID NO: 117) | PLWVGGFAY (SEQ ID NO: 157) | DVVMTQSPLSLPVTLGQPASISCRSSQSLVHSDVNTYLHWYQQRPGQSPRLLIYKVSNRFSGVPDRFSGSGSGTDFTLKISRVEAEDVGVYFCSQTTHVPYTFGGGTKLEIK (SEQ ID NO: 200) | RSSQSLVHSDVNTYLH (SEQ ID NO: 270) | KVSNRFS (SEQ ID NO: 305) | SQTTHVPYT (SEQ ID NO: 334) |
| G2.302 mouse | QIQLQQSGPELVRPGASVKISCKASGYTFTDYYINWVKQRPGQGLEWIGWIYPGNVNVKYNEKFKGKATLTVDTSSSTGYMQLRSLTSEDSAVYFCARSIGLRYFDNWGQGTTLTVSS (SEQ ID NO: 20) | DYYIN (SEQ ID NO: 86) | WIYPGNVNVKYNEKFKG (SEQ ID NO: 118) | SIGLRYFDN (SEQ ID NO: 158) | EKVLTQSPAIMSASLGEKVTMSCRASSSVHYMYWHQQKSDASPRLWIYYTSNLAPGVPARFSGSGSGNFYSLTISSVEDEDGATYYCQQFTTSTWTFGGGTKLEIK (SEQ ID NO: 201) | RASSSVHYMY (SEQ ID NO: 271) | YTSNLAP (SEQ ID NO: 306) | QQFTTSTWT (SEQ ID NO: 335) |
| G2.302 Humanized | EIQLVQSGAEVKKPGASVKVSCKASGYTFTDYYINWVRQAPGQRLEWIGWIYPGNVNVKYNEKFKGRATLTVDTSASTGYMELSSLRSEDTAVYFCARSIGLRYFDNWGQGTLVTVSS (SEQ ID NO: 21) | DYYIN (SEQ ID NO: 86) | WIYPGNVNVKYNEKFKG (SEQ ID NO: 118) | SIGLRYFDN (SEQ ID NO: 158) | EKVLTQSPATLSLSPGERATLSCRASSSVHYMYWHQQKPGQSPRLWIYYTSNLAPGVPARFSGSGSGNDYTLTISSLEPEDFAVYYCQQFTTSTWTFGGGTKLEIK (SEQ ID NO: 202) | RASSSVHYMY (SEQ ID NO: 271) | YTSNLAP (SEQ ID NO: 306) | QQFTTSTWT (SEQ ID NO: 335) |
| G2.247 mouse | EVRLQQSGAELVKPGASVKLSCKTSGFTFSNSYISWLKQKPRQSLEWIAWIYAGTGGTNYNQKFTGKAQLTVDTSSSTAYMQLSSLTSEDSAIYYCATYGNFLYAMDNWGQGTSVTVSS (SEQ ID NO: 22) | NSYIS (SEQ ID NO: 81) | WIYAGTGGTNYNQKFTG (SEQ ID NO: 111) | YGNFLYAMDN (SEQ ID NO: 153) | DIVMTQSPASLSASVGETVTITCRASGNIHNYLAWYQQKQGKSPQLLVYNTKTLADGVPSRFSGSGSGTQYSLKINSLQPEDFGSYYCQHFWSTPWTFGGGTKLEIK (SEQ ID NO: 203) | RASGNIHNYLA (SEQ ID NO: 266) | NTKTLAD (SEQ ID NO: 302) | QHFWSTPWT (SEQ ID NO: 330) |
| G2.257 mouse | EVQLQQSGPELVKPGASLKISCKTFGYSFTGYYMHWVKQSPEKSLEWIGKIVPSTGGTTYNQKFKAKATLTVDKSSFTAYMQLKSLTTEDSAVYYCAREKVYGYDVYYFDYWGQGTTLTVSS (SEQ ID NO: 23) | GYYMH (SEQ ID NO: 83) | KIVPSTGGTTYNQKFKA (SEQ ID NO: 113) | EKVYGYDVYYFDY (SEQ ID NO: 155) | DIQMTQTPSSLSASLGDRVTITCSTSQGVRSYLNWYQQKPDGSVKLLIYYTSSLHSGVPSRFSGSGSGTDYSLTISNLEPEDIATYYCQQYSKLPYTFGGGTKLELK (SEQ ID NO: 204) | STSQGVRSYLN (SEQ ID NO: 272) | YTSSLHS (SEQ ID NO: 307) | QQYSKLPYT (SEQ ID NO: 336) |

TABLE 2-continued

From left to right, 1st column: Anti-ABCG2 antibody name, 2nd column: VH region, 3rd column: HCDR1, 4th column: HCDR2, 5th column: HCDR3, 6th column: VL region, 7th column: LCDR1, 8th column: LCDR2, 9th column: LCDR3.

| Antibody | Heavy Chain Variable Region | CDRH1 | CDRH2 | CDRH3 | Light Chain Variable Region | CDRL1 | CDRL2 | CDRL3 |
|---|---|---|---|---|---|---|---|---|
| G2.252 mouse | EVQLQQSGAELVKPGASVKLSCKTSGFTFSNSYISWLKQKPRQSLEWIAWIYAGTGGTNYNQKFTGKAQLTVDTSSSTAYMQLSSLTSEDSAIYYCATYGNFLYAMDYWGQGTTLTVSS (SEQ ID NO: 24) | NSYIS (SEQ ID NO: 81) | WIYAGTGGTNYNQKFTG (SEQ ID NO: 111) | YGNFLYAMDY (SEQ ID NO: 159) | EIVLTQSPASLSASVGETVTITCRASGNIHNYLAWYQQKQGKSPQLLVYNAKTLADGVPSRFSGSGSGTQYSLKINSLQPEDFGSYYCQHFWSTPWTFGGGTKLEIK (SEQ ID NO: 205) | RASGNIHNYLA (SEQ ID NO: 266) | NAKTLAD (SEQ ID NO: 308) | QHFWSTPWT (SEQ ID NO: 330) |
| G2.318 rat | EVKLLESGPGLVKPSQSLSLTCSVTGYTITSGYDWSWIRKFPGNKMEWMGYISYSGWTNYNPSLRSRISISRDTSKNQFFLQLNSVTTEDTATYYCARVRGYNPFAYWGQGTLVTVSS (SEQ ID NO: 25) | SGYDWS (SEQ ID NO: 87) | YISYSGWTNYNPSLRS (SEQ ID NO: 119) | VRGYNPFAY (SEQ ID NO: 160) | DIVMTQSPSLLSASVGDRVTLSCKAGQNINNYLAWYQQKLGEAPKLLIYNANSLQTGIPSRFSGSGSGTDFTLTISSLQPEDVATYFCQQYNSWTTFGSGTKLEIK (SEQ ID NO: 206) | KAGQNINNYLA (SEQ ID NO: 273) | NANSLQT (SEQ ID NO: 309) | QQYNSWTT (SEQ ID NO: 337) |
| G2.320 rat | EVQLEESGPGLVKPSQSLSLTCSVTGYTITSGYDWTWIRKFPGNKMEWMGYISYSGFTNYNPSLRSRISITRDTSKNQFFLQLNSVTTEDTATYYCTRTRGYNPFAYWGQGASVSSAS (SEQ ID NO: 26) | SGYDWT (SEQ ID NO: 88) | YISYSGFTNYNPSLRS (SEQ ID NO: 120) | TRGYNPFAY (SEQ ID NO: 161) | DIVMTQSPSLLSASVGDRVTLSCKAGRNINNYLAWYQQKLGKAPKLLIYNTNSLQTGIPSRFSGSGSGTDFTLTISSLQPEDVATYFCQQYNSWTTFGSGTKLEIK (SEQ ID NO: 207) | KAGRNINNYLA (SEQ ID NO: 274) | NTNSLQT (SEQ ID NO: 310) | QQYNSWTT (SEQ ID NO: 337) |
| G2.333 rat | EIQLQESGPGLVKPSQSLSLTCSVTGYTITSGYDWTWIRKFPGNKMEWMGYISYSGFTNYNPSLRSRISISRDTSKNQFFLQLNSVTTEDTATYYCARTRGYNPFPYWGQGTLVTVSS (SEQ ID NO: 27) | SGYDWT (SEQ ID NO: 88) | YISYSGFTNYNPSLRS (SEQ ID NO: 120) | TRGYNPFPY (SEQ ID NO: 162) | DIQMTQSPSLLSASVGDRVSLSCKAGRNVNNYLAWYQQKLGKPPKLLIYNSNSLQTGIPSRFSGSGSGTDFTLTISSLQPEDVATYFCQQYNSWTTFGSGTKLEIK (SEQ ID NO: 208) | KAGRNVNNYLA (SEQ ID NO: 275) | NSNSLQT (SEQ ID NO: 311) | QQYNSWTT (SEQ ID NO: 337) |
| G2.343 rat | SVQLKESGPGLVQPSQTLSLTCTVSGFSLTSNGVSWVRQPPGKGLEWIAAISSGGSTYYNSVLKSRLSISRDTSKSQVFLKMNSLQTEDTAIYFCTRDTYYGYNQIPFVYWGQGTLVTVSS (SEQ ID NO: 28) | SNGVS (SEQ ID NO: 89) | AISSGGSTYYNSVLKS (SEQ ID NO: 121) | DTYYGYNQIPFVY (SEQ ID NO: 163) | DVVLAQTPPTLSATIGQSVSISCRSSQSLLHSSGNTYLNWLLQRPGQPPQLLIYLVSRLESRVPNRFSGSGSGTDFTLKISGVEAEDLGVYYCVQSTHAPRTFGGGTKLELK (SEQ ID NO: 209) | RSSQSLLHSSGNTYLN (SEQ ID NO: 276) | LVSRLES (SEQ ID NO: 312) | VQSTHAPRT (SEQ ID NO: 338) |
| G2.346 rat | SVQWKESGPGLVQPSQTLSLTCTVSGFSLTSNGVSWVRQPPGKGLEWIAAISSGGSTYYNSGLKSRLSISRDTSKSQVFLKMNSLQTEDTAIYFCTRAGYYGYNPIWFTYWGQGTLVTVSS (SEQ ID NO: 29) | SNGVS (SEQ ID NO: 89) | AISSGGSTYYNSGLKS (SEQ ID NO: 122) | AGYYGYNPIWFTY (SEQ ID NO: 164) | DVVMTQTPPTLSATIGQSVSISCRSSQSLLHGSGNTYLNWLLQRPGQPPQILIYLVSRLESRVPKRFSGSGSGTDFTLKISGVEADDLGVYYCVQSTHAPFTFGSGTKLELK (SEQ ID NO: 210) | RSSQSLLHGSGNTYLN (SEQ ID NO: 277) | LVSRLES (SEQ ID NO: 312) | VQSTHAPFT (SEQ ID NO: 339) |

TABLE 2-continued

From left to right, 1st column: Anti-ABCG2 antibody name, 2nd column: VH region, 3rd column: HCDR1, 4th column: HCDR2, 5th column: HCDR3, 6th column: VL region, 7th column: LCDR1, 8th column: LCDR2, 9th column: LCDR3.

| Antibody | Heavy Chain Variable Region | CDRH1 | CDRH2 | CDRH3 | Light Chain Variable Region | CDRL1 | CDRL2 | CDRL3 |
|---|---|---|---|---|---|---|---|---|
| G2.348 rat | EVQLVESGPGLMQPSQTLSLTCTVSGFSLTSNGVSWVRQPPGKGLEWIATISSGGNTNYNSALKSRLSISRDTSKSQVFLKMNSLQTEDTAIYFCTRVGYYGYNPIWFAYWGQGTLVTVSS (SEQ ID NO: 30) | SNGVS (SEQ ID NO: 89) | TISSGGNTNYNSALKS (SEQ ID NO: 123) | VGYYGYNPIWFAY (SEQ ID NO: 165) | DVVMTQTPPTLSATIGHSVSISCRSSQSLFHSSGNTYLSWFLQRPGQPPQLLIYLVSRLESRVPNRFSGSGSGTDFTLKISVLEAEDLGVYYCVQTTHAPFTFGSGTKLEIK (SEQ ID NO: 211) | RSSQSLFHSSGNTYLS (SEQ ID NO: 278) | LVSRLES (SEQ ID NO: 312) | VQTTHAPFT (SEQ ID NO: 340) |
| G2.394 rat | EVQLKESGPGLVQPSQTLSLTCTVSGFSLTDYTITWVRQPPGKGLEWIAATSVGGATHYNSPLKSRLSISGDTSKSQVFLKMNSLRTEDTAMYFCVRSGYYSTYMNWGRGTMVTVSS (SEQ ID NO: 31) | DYTIT (SEQ ID NO: 90) | ATSVGGATHYNSPLKS (SEQ ID NO: 124) | SGYYSTYMN (SEQ ID NO: 166) | DVVMTQTPPTFSATIGQSVSISCRSSQSLLHSSGNTFLSWLLQRPGQPPQLLIYLVSRLEFGVPNRFSGSGSGTDFTLKISGVEAEDLGVYYCVQSTHVMNTFGAGTKLEIK (SEQ ID NO: 212) | RSSQSLLHSSGNTFLS (SEQ ID NO: 279) | LVSRLEF (SEQ ID NO: 313) | VQSTHVMNT (SEQ ID NO: 341) |
| G2. 420 rat | SVQLMESGPGLVQPSQTLSLTCTVSGFSLNSYNVNWVRQPPGKGLEWIAAISSGGSTYYNSVLKSRLSITRDTSKSQVFLKMNSLQTEDTAMYFCARSGYYSSYMNWGQGVMVTVSS (SEQ ID NO: 32) | SYNVN (SEQ ID NO: 91) | AISSGGSTYYNSVLKS (SEQ ID NO: 121) | SGYYSSYMN (SEQ ID NO: 167) | DVVMTQTPPTLSATIGQSVSISCRSSQSLLHSTGNTYLNWLLQRPGQPPQLLIYLVSRLEYGVPNRFSGSGSGTDFTLKISGVEAEDLGVYYCAQSTHALNTFGAGTKLELK (SEQ ID NO: 213) | RSSQSLLHSTGNTYLN (SEQ ID NO: 280) | LVSRLEY (SEQ ID NO: 314) | AQSTHALNT (SEQ ID NO: 342) |
| G2.629 rat | EVQLVESGGGLVQPGRSLKLSCAASGFIFSRFYMAWVRQAPTKGLEWVAYINTGGGTTYYRDSVKGRFTISRDNAKTTLYLQMDSLRSEDTATYYCTTLAAPWNYVMDAWGQGASVTVSSA (SEQ ID NO: 33) | RFYMA (SEQ ID NO: 92) | YINTGGGTTYYRDSVKG (SEQ ID NO: 125) | LAAPWNYVMDA (SEQ ID NO: 168) | DVVMTQSPSLLSASVGDRVTLTCKGSQNINNFLAWYQQKLGEAPKLLTYKTNSLHTGIPSRFSGSGSGTDYTLTISSLHSEDLATYYCYQYNNGYTFGPGTKLELK (SEQ ID NO: 214) | KGSQNINNFLA (SEQ ID NO: 281) | KTNSLHT (SEQ ID NO: 315) | YQYNNGYT (SEQ ID NO: 343) |
| G2.630 rat | EVQLVESGPGLVKPSQSLSLTCSVTGYTITSGYDWTWIRKFPGNKMEWMGYISYSGFTNYNPSLRSRISITRDTSKNQFFLQLNSVTTEDTATYYCTRTRGYNPFAYWGQGTLVTVSS (SEQ ID NO: 34) | SGYDWT (SEQ ID NO: 88) | YISYSGFTNYNPSLRS (SEQ ID NO: 120) | TRGYNPFAY (SEQ ID NO: 161) | DVVMTQSPSLLSASVGDRVTLSCKAGRNINNYLAWYQQKLGKAPKLLIYNTNSLQTGIPSRFSGSGSGTDFTLTISSLQPEDVATYFCQQYNSWTTFGSGTKLEIK (SEQ ID NO: 215) | KAGRNINNYLA (SEQ ID NO: 274) | NTNSLQT (SEQ ID NO: 310) | QQYNSWTT (SEQ ID NO: 337) |
| G2.631 rat | EVKLLESGGGLVQSGRSLKLSCAASGFIFSRFYMAWVRQAPRKGLEWVAYISNGAGSTYYRESVKGRFIISRDNAKSTLYLQMDSLRSEDTATYYCTTVAAPWNYVMDGWGQGASVTVSS (SEQ ID NO: 35) | RFYMA (SEQ ID NO: 92) | YISNGAGSTYYRESVKG (SEQ ID NO: 126) | VAAPWNYVMDG (SEQ ID NO: 169) | NIQITQSPSLLSASVGDRVTLSCKGSQNINNYLAWYQQKLGEAPKLLIYKTNSLHTGIPSRFSGSGSGTDYTLTISSLHSEDLATYYCYQYNNGYTFGAGTKLELK (SEQ ID NO: 216) | KGSQNINNYLA (SEQ ID NO: 282) | KTNSLHT (SEQ ID NO: 315) | YQYNNGYT (SEQ ID NO: 343) |

TABLE 2-continued

From left to right, 1st column: Anti-ABCG2 antibody name, 2nd column: VH region, 3rd column: HCDR1, 4th column: HCDR2, 5th column: HCDR3, 6th column: VL region, 7th column: LCDR1, 8th column: LCDR2, 9th column: LCDR3.

| Antibody | Heavy Chain Variable Region | CDRH1 | CDRH2 | CDRH3 | Light Chain Variable Region | CDRL1 | CDRL2 | CDRL3 |
|---|---|---|---|---|---|---|---|---|
| G2.636 rat | EVKLVESGGGLVQPGRSLKLSCAASGFTFSRFYMAWVRQAPTKGLEWVAHISHGGDTTYYRDSVKGRFTISRDNAKSTLFLQMDSLRSEDTATYYCTTSAAPWNYVMDGWGLGASVTVSS (SEQ ID NO: 36) | RFYMA (SEQ ID NO: 92) | HISHGGDTTYYRDSVKG (SEQ ID NO: 127) | SAAPWNYVMDG (SEQ ID NO: 170) | DIVMTQSPSLLSASVGDRVTLTCKGSQNINNFLAWYQQKLGEAPKLLIYKTNSLHTGIPSRFSGSGSGTDYTLTISSLHSEDLATYYCYQYNNGYTFGAGTKLELK (SEQ ID NO: 217) | KGSQNINNFLA (SEQ ID NO: 281) | KTNSLHT (SEQ ID NO: 315) | YQYNNGYT (SEQ ID NO: 343) |
| G2.641 rat | EVKLEESGGGLVQPGRSLKLSCAASGFTFSRFYMAWVRQAPTKGLEWVAHISHGGDTTYYRDSVKGRFTISRDNAKSTLFLQMDSLRSEDTATYYCTTSAAPWNYVMDGWGLGASVTVSS (SEQ ID NO: 37) | RFYMA (SEQ ID NO: 92) | HISHGGDTTYYRDSVKG (SEQ ID NO: 127) | SAAPWNYVMDG (SEQ ID NO: 170) | DIQMTQSPSLLSASVGDRVTLTCKGSQNINNFLAWYQQKLGEAPKLLIYKTNSLHTGIPSRFSGSGSGTDYTLTISSLHSEDLATYYCYQYNNGYTFGAGTKLELK (SEQ ID NO: 218) | KGSQNINNFLA (SEQ ID NO: 281) | KTNSLHT (SEQ ID NO: 315) | YQYNNGYT (SEQ ID NO: 343) |
| G2.642 rat | QIQLVQSGAELVKPGASVKLSCKTSGFTFSSNYISWLRQKPRQSLEWIAWIYSGTGGTYYNQKFTGKAQLTIDTSSNTAYMQLSSLTSEDSAIYYCARHVGLRYWYFDVWGAGTSVTVSS (SEQ ID NO: 38) | SNYIS (SEQ ID NO: 93) | WIYSGTGGTYYNQKFTG (SEQ ID NO: 128) | HVGLRYWYFDV (SEQ ID NO: 171) | DIVLTQSPASLTVSLGQRATISCRASESVDSNGNSFMHWYQQKPGQSPKVLIYRASNLESGVPARFSGSGSRTDFTLTINPVEADDVATYYCQQSNEDPWTFGGGTKLEIK (SEQ ID NO: 219) | RASESVDSNGNSFMH (SEQ ID NO: 283) | RASNLES (SEQ ID NO: 316) | QQSNEDPWT (SEQ ID NO: 344) |
| G2.368 rat | EVKLEESGGGFVQPGRSLKLSCAASGFTFRYFYMAWVRQAPTKGLEWVAYISTGGHSTYYRESVKGRFTISRDDAKSTLYLQMDSLRSEDTATYYCTTVSGDYSSYIYVMDAWGQGTLVTVSS (SEQ ID NO: 39) | YFYMA (SEQ ID NO: 94) | YISTGGHSTYYRESVKG (SEQ ID NO: 129) | VSGDYSSYIYVMDA (SEQ ID NO: 172) | VMTQSPVLAVSLGQRATLSCRASQSVTISGINLMHWYQQKPGQQPRLLVYRASNLASGIPARFSGSGSGTDFTLTIDPVQAAD1AAYYCQQTRVSPWTFGGGTKLEIK (SEQ ID NO: 220) | RASQSVTISGINLMH (SEQ ID NO: 284) | RASNLAS (SEQ ID NO: 317) | QQTRVSPWT (SEQ ID NO: 345) |
| G2.377 rat | EVQLKESGPGLVKPSQSLSLTCSVTGYTITSGYDWTWIRKFPGNKMEWMGYISYSGFTNYNPSLRSRISITRDTSKNQFFLQLNSVTTEDTATYYCTRTRGYNPFAYWGQGTLVTVSS (SEQ ID NO: 40) | SGYDWT (SEQ ID NO: 88) | YISYSGFTNYNPSLRS (SEQ ID NO: 120) | TRGYNPFAY (SEQ ID NO: 161) | VTQSPSLLSASVGDRVTLSCKAGRNINNYLAWYQQKLGKAPKLLIYNTNSLQTGIPSRFSGSGSGTDFTLTISSLQPEDVATYFCQQYNSWTTFGSGTKLELK (SEQ ID NO: 221) | KAGRNINNYLA (SEQ ID NO: 274) | NTNSLQT (SEQ ID NO: 310) | QQYNSWTT (SEQ ID NO: 337) |
| G2.379 rat | EVKLEESGGAFVQSGGSLKVSCAASGFIFSNYGMAWVRQAPTKGLEWVASITDSGGNTYYRDSVKGRFTISRDNAKSTLYLQMDSLRSADTATYYCTTLGVPMGMINWFVYWGQGTLVTVSS (SEQ ID NO: 41) | NYGMA (SEQ ID NO: 95) | SITDSGGNTYYRDSVKG (SEQ ID NO: 130) | LGVPMGMINWFVY (SEQ ID NO: 173) | TQSPPSLSASLGDKVTITCQASQYIYKYLAWYHQKPGKAPRLLIRYTSTLESGTPSRFSGSGSGRDYSFSISNVESGDFATYYCLQYVNLPFTFGAGTKLELK (SEQ ID NO: 222) | QASQYIYKYLA (SEQ ID NO: 285) | YTSTLES (SEQ ID NO: 318) | LQYVNLPFT (SEQ ID NO: 346) |

TABLE 2-continued

From left to right, 1st column: Anti-ABCG2 antibody name, 2nd column: VH region, 3rd column: HCDR1, 4th column: HCDR2, 5th column: HCDR3, 6th column: VL region, 7th column: LCDR1, 8th column: LCDR2, 9th column: LCDR3.

| Antibody | Heavy Chain Variable Region | CDRH1 | CDRH2 | CDRH3 | Light Chain Variable Region | CDRL1 | CDRL2 | CDRL3 |
|---|---|---|---|---|---|---|---|---|
| G2.396 rat | ESGPGLVQPSQTLSLTCTVSGFSLTSNGVTWIRHPPGKGLEWMGVIWSNGGTDYNSAIKSRLGISRDTSKSQVFLKMNSLQTEDTAIYFCARAIAASYVMDAWGPGASVTVSS (SEQ ID NO: 42) | SNGVT (SEQ ID NO: 96) | VIWSNGGTDYNSAIKS (SEQ ID NO: 131) | AIAASYVMDA (SEQ ID NO: 174) | MIQSPPSLSASLGDKVTITCQASHNIYKYVAWFQLKPGRAPRLLIRYTSTLQSGTPSRFSGSGSGRDYSFSISNVESEDFASYFCLQYVNLWTFGGGTKLELK (SEQ ID NO: 223) | QASHNIYKYVA (SEQ ID NO: 286) | YTSTLQS (SEQ ID NO: 319) | LQYVNLWT (SEQ ID NO: 347) |
| G2.410 rat | VQLKESGPGLVQPSQTLSLTCTVSGFSLTDTGVSWVRQPPGKGLEWIGAIWSGGVTDYNSALKSRLSISRDTSKSQVLLKMNSLQTEDTAMYFCARTLARHYIMDAWGQGVMVTVSS (SEQ ID NO: 43) | DTGVS (SEQ ID NO: 97) | AIWSGGVTDYNSALKS (SEQ ID NO: 132) | TLARHYIMDA (SEQ ID NO: 175) | DILMTKSPPSLSASLGDKVTITCQASQHINNYIAWYQQKPRKAPRLLIRYASTLQSGTPSRFSGSGSGRTYSFSISNVRSEDIASYYCLQYVNLPYTFGAGTKLELK (SEQ ID NO: 224) | QASQHINNYIA (SEQ ID NO: 287) | YASTLQS (SEQ ID NO: 320) | LQYVNLPYT (SEQ ID NO: 348) |
| G2.641 rat | EVKLEESGGGLVQPGRSLKLSCAASGFTFSRFYMAWVRQAPTKGLEWVAHISHGGDTTYYRDSVKGRFTISRDNAKSTLFLQMDSLRSEDTATYYCTTSAAPWNYVMDGWGLGASVTVSS (SEQ ID NO: 37) | RFYMA (SEQ ID NO: 92) | HISHGGDTTYYRDSVKG (SEQ ID NO: 127) | SAAPWNYVMDG (SEQ ID NO: 170) | DIQMTQSPSLLSASVGDRVTLTCKGSQNINNFLAWYQQKLGEAPKLLIYKTNSLHTGIPSRFSGSGSGTDYTLTISSLHSEDLATYYCYQYNNGYTFGAGTKLELK (SEQ ID NO: 218) | KGSQNINNFLA (SEQ ID NO: 281) | KTNSLHT (SEQ ID NO: 315) | YQYNNGYT (SEQ ID NO: 343) |
| G2.642 mouse | QIQLVQSGAELVKPGASVKLSCKTSGFTFSSNYISWLRQKPRQSLEWIAWIYSGTGGTYYNQKFTGKAQLTIDTSSNTAYMQLSSLTSEDSAIYYCARHVGLRYWYFDVWGAGTSVTVSS (SEQ ID NO: 38) | SNYIS (SEQ ID NO: 93) | WIYSGTGGTYYNQKFTG (SEQ ID NO: 128) | HVGLRYWYFDV (SEQ ID NO: 171) | IVLTQSPASLTVSLGQRATISCRASESVDSNGNSFMHWYQQKPGQSPKVLIYRASNLESGVPARFSGSGSRTDFTLTINPVEADDVATYYCQQSNEDPWTFGGGTKLEIK (SEQ ID NO: 225) | RASESVDSNGNSFMH (SEQ ID NO: 283) | RASNLES (SEQ ID NO: 316) | QQSNEDPWT (SEQ ID NO: 344) |
| G2.656 rat | EVQLVESGPGLVQPSQTLSLTCTVSGLSLTSNGVSWIRQPPGKGLEWLGVIWSDGGTDYNSAIRSRLTLSRDTSKSQVFLKMNSLQTEDTAMYFCARALAPSYVMGPWGQGASVTVSS (SEQ ID NO: 44) | SNGVS (SEQ ID NO: 89) | VIWSDGGTDYNSAIRS (SEQ ID NO: 133) | ALAPSYVMGP (SEQ ID NO: 176) | DIEMTQSPPSLSASLGDKVTITCQASQNIHKYIAWYQQKPGKAPRLLLRYTSTLESGTPSRFSGSGSGRDYSFSISNVESEDFASYYCLQYVNLWTFGGGTKLEIK (SEQ ID NO: 226) | QASQNIHKYIA (SEQ ID NO: 288) | YTSTLES (SEQ ID NO: 318) | LQYVNLWT (SEQ ID NO: 347) |
| G2.689 rat | EVKLVESGGGLVQPGNSLTLSCVAPGFTFSNYGMHWIRQAPKKGLEWIAMIYYDSSKVYYVDTVKGRFTISRDNSKNTLYLEMNSLRSEDTAMYYCAAPLITIAAGFAYWGQGTLVTVSS (SEQ ID NO: 45) | NYGMH (SEQ ID NO: 98) | MIYYDSSKVYYVDTVKG (SEQ ID NO: 134) | PLITIAAGFAY (SEQ ID NO: 177) | DIVMTQSPSSLAVSAGETVTINCKSSQSLFWSGSQMNYLAWYQQKPGQSPKLLIYYASTAQSGVPDRFIGSGSGTDFTLTISGVQAEDLAVYYCQHHYDSLPPYTFGAGTKLEIK (SEQ ID NO: 227) | KSSQSLFWSGSQMNYLA (SEQ ID NO: 289) | YASTAQS (SEQ ID NO: 321) | QHHYDSLPPYT (SEQ ID NO: 349) |

TABLE 2-continued

From left to right, 1st column: Anti-ABCG2 antibody name, 2nd column: VH region, 3rd column: HCDR1, 4th column: HCDR2, 5th column: HCDR3, 6th column: VL region, 7th column: LCDR1, 8th column: LCDR2, 9th column: LCDR3.

| Antibody | Heavy Chain Variable Region | CDRH1 | CDRH2 | CDRH3 | Light Chain Variable Region | CDRL1 | CDRL2 | CDRL3 |
|---|---|---|---|---|---|---|---|---|
| G2.709 rat | EVKLEESGPGLVQPSQTLSLTCSVSGFSLTSDGVSWVRQPPGKGLEWIATISSGGNTYYNSALKSRLSISRDTSKSQVFLKMNSLQTEDTAIYFCSRGGYYGYNPIWFVYWGQGTLVTVSS (SEQ ID NO: 46) | SDGVS (SEQ ID NO: 99) | TISSGGNTYYNSALKS (SEQ ID NO: 135) | GGYYGYNPIWFVY (SEQ ID NO: 178) | DVVMTQTPPTLSATIGQSVSISCRSSQSLLHSSGNTYLHWLLQRPGQPPQLLVYLVSRLESGVPNRFSGSGSGTDFTLRISGIEAEDLGVYYCVQSTHAPFTFGSGTKLEIK (SEQ ID NO: 228) | RSSQSLLHSSGNTYLH (SEQ ID NO: 290) | LVSRLES (SEQ ID NO: 312) | VQSTHAPFT (SEQ ID NO: 339) |
| G2.711 rat | EVQLKESGPGLVxPSKTLSLTCTVSGLSLTSNSVSWIRQPPGKGLRWMGVIWSNGGTDxNSAIKSRLIISKDTSNSQVFLKMNSLQTEDTALYFCARAIASSSVVNVWGQGSSVAVSS (SEQ ID NO: 47) | SNSVS (SEQ ID NO: 100) | VIWSNGGTDxNSAIKS (SEQ ID NO: 136) | AIASSSVVNV (SEQ ID NO: 179) | DIQMTQSPPSLSASLGDKVTITCQASQNIHKYIGWYQQKPGKAPRLLIRYTSTLESGTPSRFSGSGSGRYYSFSISNVESEDIASYYCLQYVNLWTFGGGTKLELK (SEQ ID NO: 229) | QASQNIHKYIG (SEQ ID NO: 291) | YTSTLES (SEQ ID NO: 318) | LQYVNLWT (SEQ ID NO: 347) |
| G2.726 rat | EVKLLESGGGLVQPGNSLTLSCVASGFTFSNYGMHWIRQAPKKGLEWIAMIYYDSSKMYFADTLKGRFTISRDNSKNTLYLEMNSLRSEDTAMYYCAAPLITLAAGFTYWGQGTLVTVSS (SEQ ID NO: 48) | NYGMH (SEQ ID NO: 98) | MIYYDSSKMYFADTLKG (SEQ ID NO: 137) | PLITLAAGFTY (SEQ ID NO: 180) | TQSPSSLAVSTGETVTINCKSSQSLFWSGSQMNYLAWYQQKPGQSPKLLIYYTSTRQSGVPDRFIGSGSGTDFTLTISGVQAEDLAVYYCQHHYDSLPPYTFGAGTKLELK (SEQ ID NO: 230) | KSSQSLFWSGSQMNYLA (SEQ ID NO: 289) | YTSTRQS (SEQ ID NO: 322) | QHHYDSLPPYT (SEQ ID NO: 349) |
| G2.738 rat | QLQQSGAEVAKPGSSVKISCKASGYTFTSNTMHWIKQTTGQALEWTGYISPGSGGTMYNEKFKGKATLTVDKSSSTAYMQLSSLTPVDTAVYYCVREGYYYSRYSFAYWGQGTLVTVSS (SEQ ID NO: 49) | SNTMH (SEQ ID NO: 101) | YISPGSGGTMYNEKFKG (SEQ ID NO: 138) | EGYYYSRYSFAY (SEQ ID NO: 181) | DVVLTQSPASLSASLEEIVTITCQASQDIGIWLAWYQQKPGKSPQLLIFGATSLADGVPSRFSGSRSGTQYSLKISRLQLEDIGIYYCQQASSAPWTFGGGTKLELK (SEQ ID NO: 231) | QASQDIGIWLA (SEQ ID NO: 292) | GATSLAD (SEQ ID NO: 323) | QQASSAPWT (SEQ ID NO: 350) |
| G2.746 rat | VKLEESGPGLVLPSQTLSLSCTVSGLSLISNSISWIRQPPGKGLEWMGVMWNNGGTDYNSAIKSRLSISRDTSKSQVFLKMNSLQTEDTAMYFCARGYSSYIFDYWGQGASVTVSS (SEQ ID NO: 50) | SNSIS (SEQ ID NO: 102) | VMWNNGGTDYNSAIKS (SEQ ID NO: 139) | GYSSYIFDY (SEQ ID NO: 182) | DILMTQSPPSLSASLGDKVTITCQASQNIHGYIAWYQQKPGRLPRLLIRLTSTLESGTPSRFSGSGSGRDYSFSISNVESEDLASYYCLQYVNLWTFGGGTKLELK (SEQ ID NO: 232) | QASQNIHGYIA (SEQ ID NO: 293) | LTSTLES (SEQ ID NO: 324) | LQYVNLWT (SEQ ID NO: 347) |
| G2.336 rat | EVQLTESGPGLVOPSQTLSLTCTVPGLSLTNTGVSWIRQPPGKGLEWMGVIWSDGGTDYNSAIKSRLSISRDTSKSQVFVKMNSLQTEDTAVYFCARALAPSYVMEAWGQGASVTVSS (SEQ ID NO: 51 | NTGVS (SEQ ID NO: 103) | VIWSDGGTDYNSAIKS (SEQ ID NO: 140) | ALAPSYVMEA (SEQ ID NO: 183) | DIQMTQSPPSLSASLGDKVTITCQASQNIHKYIAWYQQKPGKAPRLLIRYTSTLQSGTPSRFSGSGSGRDYSFSISNVESEDIASYYCLQYVNLWTFGGGTKLELK (SEQ ID NO: 233) | QASQNIHKYIA (SEQ ID NO: 288) | YTSTLQS (SEQ ID NO: 319) | LQYVNLWT (SEQ ID NO: 347) |

TABLE 2-continued

From left to right, 1st column: Anti-ABCG2 antibody name, 2nd column: VH region, 3rd column: HCDR1, 4th column: HCDR2, 5th column: HCDR3, 6th column: VL region, 7th column: LCDR1, 8th column: LCDR2, 9th column: LCDR3.

| Antibody | Heavy Chain Variable Region | CDRH1 | CDRH2 | CDRH3 | Light Chain Variable Region | CDRL1 | CDRL2 | CDRL3 |
|---|---|---|---|---|---|---|---|---|
| G2.354 rat | EVQLKESGPGLVQPSQTLSLTCTVSGLSLTSDSVSWIRQPPGKGLEWMGVIWSNGGTDYNSAIKSRLSISRDTSKSQVFLKMNSLQTEDTAMYFCARTIPYYVMDAWGQGASVTVSS (SEQ ID NO: 52) | SDSVS (SEQ ID NO: 104) | VIWSNGGTDYNSAIKS (SEQ ID NO: 131) | TIPYYVM (SEQ ID NO: 184) | DIQMTQSPPSLSASLGDKVTITCQASHNINKYIAWYQQKPRKAPRLLIRYTSTLQSGTPSRFSGSGSGRDYSFSISNVESEDIASYYCLQYVNLWTFGGGTKLELK (SEQ ID NO: 234) | QASHNINKYIA (SEQ ID NO: 294) | YTSTLQS (SEQ ID NO: 319) | LQYVNLWT (SEQ ID NO: 347) |
| G2.360 rat | QVQLRESGPGLVQPSQTLSLTCTVSGLSLTSNSISWIRQPPGKGLEWMGVIWSTGGTDYNSAIKSRLSISRDTSKSQVFLKMNSLQTEDTAMYFCARAIAASAVMDAWGQGASVTVSS (SEQ ID NO: 53) | SNSIS (SEQ ID NO: 102) | VIWSTGGTDYNSAIKS (SEQ ID NO: 141) | AIAASAVMDA (SEQ ID NO: 185) | DIQMTQSPPSLSASLGDKVTITCQASQNIHKYIGWYQQKPGKAPRLLIRYTSTLESGTPSRFSGSGSGRYYSFSISNVESEDIASYYCLQYVNLWTFGGGTKLELK (SEQ ID NO: 229) | QASQNIHKYIG (SEQ ID NO: 291) | YTSTLES (SEQ ID NO: 318) | LQYVNLWT (SEQ ID NO: 347) |
| G2.392 rat | VQLVESGPDLVQPSQTLSLTCTVSGLSLTSTGVSWIRQPPGRGLEWMGVIWSNGGTDYNSAIRSRLSISRDTSKSQVFLKMNSLQTEDTAMYFCARAIAASYIMDAWGQGASVTVSS (SEQ ID NO: 54) | STGVS (SEQ ID NO: 105) | VIWSNGGTDYNSAIRS (SEQ ID NO: 142) | AIAASYIMDA (SEQ ID NO: 186) | DIQMTQSPPSLSASLGDKVTITCQASQNIHKYIAWYRHKPGKPPRLLIRYTSTLQSGTPSRFSGSGSGRDYSFSISNVESEDIASYYCLQYVNLWTFGGGTKLELK (SEQ ID NO: 235) | QASQNIHKYIA (SEQ ID NO: 288) | YTSTLQS (SEQ ID NO: 319) | LQYVNLWT (SEQ ID NO: 347) |
| G2.418 rat | QVTLKESGPGILQPSHTLSLTCSFSGFSLSTYGMGVSWVRQPSGRGLEWLATIWWNGNTYNNPSLKSRLTVSKGTSNNQAFLKVTSVDTADTATYFCAHTLYYSTSSLFDYWGQGVVVTVSS (SEQ ID NO: 55) | TYGMGVS (SEQ ID NO: 106) | TIWWNGNTYNNPSLKS (SEQ ID NO: 143) | TLYYSTSSLFDY (SEQ ID NO: 187) | MIQSPPSLSASLGDKVTITCQASQNIHTYLAWYQQKPGKAPRLLIRYTSTLESGTPSRFSGGGSGRHYSFSISNVESEDVASYYCLQYVNLPTFGGGTKLELK (SEQ ID NO: 236) | QASQNIHTYLA (SEQ ID NO: 295) | YTSTLES (SEQ ID NO: 318) | LQYVNLPT (SEQ ID NO: 351) |
| G2.631 rat | EVKLLESGGGLVQSGRSLKLSCAASGFIFSRFYMAWVRQAPRKGLEWVAYISNGAGSTYYRESVKGRFIISRDNAKSTLYLQMDSLRSEDTATYYCTTVAAPWNYVMDGWGQGASVTVSS (SEQ ID NO: 35) | RFYMA (SEQ ID NO: 92) | YISNGAGSTYYRESVKG (SEQ ID NO: 126) | VAAPWNYVMDG (SEQ ID NO: 169) | NIQLTQSPSLLSASVGDRVTLSCKGSQNINNYLAWYQQKLGEAPKLLIYKTNSLHTGIPSRFSGSGSGTDYTLTISSLHSEDLATYYCYQYNNGYTFGAGTNLELK (SEQ ID NO: 237) | KGSQNINNYLA (SEQ ID NO: 282) | KTNSLHT (SEQ ID NO: 315) | YQYNNGYT (SEQ ID NO: 343) |
| G2.639 rat | VQLKESGPGLVQPSQTLSLTCTVSGFSLTSDGVSWVRQPPGKGLEWIAAISSGGSTYYNSALKSRLSISRDTSKSQVFLKMNSLQTEDTAIYFCTRDTYYGYNQIPFVYWGQGTLVTVSS (SEQ ID NO: 56) | SDGVS (SEQ ID NO: 99) | AISSGGSTYYNSALKS (SEQ ID NO: 144) | DTYYGYNQIPFVY (SEQ ID NO: 163) | DVVLTQTPPTLSATIGQSVSISCRSSQSLLHSSGNTYLNWLLQRPGQPPQFLIYLVSRLESRVPNRFSGSGSGTDFTLKISGVEAEDLGVYYCVQSTPAPRTFGGGTKLELK (SEQ ID NO: 238) | RSSQSLLHSSGNTYLN (SEQ ID NO: 276) | LVSRLES (SEQ ID NO: 312) | VQSTPAPRT (SEQ ID NO: 352) |

TABLE 2-continued

From left to right, 1st column: Anti-ABCG2 antibody name, 2nd column: VH region, 3rd column: HCDR1, 4th column: HCDR2, 5th column: HCDR3, 6th column: VL region, 7th column: LCDR1, 8th column: LCDR2, 9th column: LCDR3.

| Antibody | Heavy Chain Variable Region | CDRH1 | CDRH2 | CDRH3 | Light Chain Variable Region | CDRL1 | CDRL2 | CDRL3 |
|---|---|---|---|---|---|---|---|---|
| G2.643 mouse | VNLVESGPELVKPGTSVKISCKASGYRFTSYYVHWVKQRPGQGLEWIGWIFPGSDNTKYNEKFKGKATLTADTSSSTAYMQLSSLTSEDSAVYFCASIYYGYDGTLYFDYWGQGTSVTVSS (SEQ ID NO: 57) | SYYVH (SEQ ID NO: 107) | WIFPGSDNTKYNEKFKG (SEQ ID NO: 145) | IYYGYDGTLYFDY (SEQ ID NO: 188) | DIVMTQSHTFMSTSVGDRVSVTCKASQNVGNNVAWYQQKPGQSPNALIYSASYRYSGVPDRFTGSGSGTDFTLTISNVQSEDLAEYFCQQYDRYPLTFGGGTKLEIK (SEQ ID NO: 239) | KASQNVGNNVA (SEQ ID NO: 296) | SASYRYS (SEQ ID NO: 325) | QQYDRYPLT (SEQ ID NO: 353) |
| G2.732 rat | VQLKESGPGLVQPSQTLSLTCTVSGLSLTSTGVSWIRQPPGKGLEWMGVIWSNGGTDYNSAIKSRLSISRDTSKSQVFLKMNSLQTEDTAMYFCARAIAPSYIMDAWGQGASVTVSS (SEQ ID NO: 58) | STGVS (SEQ ID NO: 105) | VIWSNGGTDYNSAIKS (SEQ ID NO: 131) | AIAPSYIMDA (SEQ ID NO: 189) | DIQMTQSPPSLSASLGDKVTITCQASQNIHKYIAWYRQKPGKPPRLLIRYTSTLQSGTPSRFSGSGSGRDYSFSISNVESEDIASYYCLQYVNLWTFGGGTKLELK (SEQ ID NO: 240) | QASQNIHKYIA (SEQ ID NO: 288) | YTSTLQS (SEQ ID NO: 319) | LQYVNLWT (SEQ ID NO: 347) |
| G2.745 rat | QVQLQQSGAEVAKPGSSVKISCKASGYTFTSNTMHWIKQTTGQALEWTGYISPGSGGTMYNEKFKGKATLTVDKSSSTAYMQLSSLTPVDTAVYYCVREGYYYSRYSFAYWGQGTLVTVSS (SEQ ID NO: 59) | SNTMH (SEQ ID NO: 101) | YISPGSGGTMYNEKFKG (SEQ ID NO: 138) | EGYYYSRYSFAY (SEQ ID NO: 181) | DVVLTQSPASLSASLEEIVTITCQASQDIGIWLAWYQQKPGKSPQLLIFGATSLADGVPSRFSGSRSGTQYSLKISRLQLEDIGIYYCQQASSAPWTFGGGTKLELK (SEQ ID NO: 231) | QASQDIGIWLA (SEQ ID NO: 292) | GATSLAD (SEQ ID NO: 323) | QQASSAPWT (SEQ ID NO: 350) |
| G2.748 rat | QVSLKESGPGMLQPSKTLSLTCSFSGFSLSTSGMVVNWIRQPSGKSLEWLAAIDWDGDKYYNPSLKHRLTVSKDTSNTQVVLKITSVDTADTATYYCARSIAPYRGWFGYWGQGTLVTVSS (SEQ ID NO: 60) | TSGMVVN (SEQ ID NO: 108) | AIDWDGDKYYNPSLKH (SEQ ID NO: 146) | SIAPYRGWFGY (SEQ ID NO: 190) | EIVLIQSPSSLPASLGERVTIICRASQDIGNNLNWYQQKPDGTIKPLIYFTSNFQSGVPSSFSGSRSGTDFSLTISSLEAEDFAMYYCQQDASLPWTFGGGTKLEIK (SEQ ID NO: 241) | RASQDIGNNLN (SEQ ID NO: 297) | FTSNFQS (SEQ ID NO: 326) | QQDASLPWT (SEQ ID NO: 354) |
| G2.757 rat | QVTLKESGPGILRPSHTLSLTCSFSGFSLTTYGICVSWIRQPSGKGLEWLANICWEDSKAYNPSLKNRLTISKDTSNNQVFLRIPSVDTADSAIYYCARVFNNYPFPYWGQGTLVTVSS (SEQ ID NO: 61) | TYGICVS (SEQ ID NO: 109) | NICWEDSKAYNPSLKN (SEQ ID NO: 147) | VFNNYPFPY (SEQ ID NO: 191) | TQSPPSLSASLGDKVTITCQASQNINKYVAWYQQKPGKAPRLLIRYTSTLESGTPSRFSGSGSWRDYSFSISNVESEDIADYYCLQYVNLWTFGGGTKLELK (SEQ ID NO: 242) | QASQNINKYVA (SEQ ID NO: 298) | YTSTLES (SEQ ID NO: 318) | LQYVNLWT (SEQ ID NO: 347) |
| G2.758 rat | QGTLKESGPGIVQSSHTLSLTCSFSGFSLSTYGMGVSWIRQPSGKGLEWLASVWWNGDTSNNPSLKSRLTVSKDTS (SEQ ID NO: 62) | TYGMGVS (SEQ ID NO: 106) | SVWWNGDTSNNPSLKS (SEQ ID NO: 148) | TLYNNYPFDY (SEQ ID NO: 192) | DIQMTQSPPSLSASLGDKVTITCQASQNIYKYIAWYQQKPGKAPRLLIRYTSTLHFGTPSRFSGSGSGRDYSFSISNVESEDIARYYCQQYVKFPNTFGAGTILELK (SEQ ID NO: 243) | QASQNIYKYIA (SEQ ID NO: 299) | YTSTLHF (SEQ ID NO: 327) | QQYVKFPNT (SEQ ID NO: 355) |

TABLE 2-continued

From left to right, 1st column: Anti-ABCG2 antibody name, 2nd column: VH region, 3rd column: HCDR1, 4th column: HCDR2, 5th column: HCDR3, 6th column: VL region, 7th column: LCDR1, 8th column: LCDR2, 9th column: LCDR3.

| Antibody | Heavy Chain Variable Region | CDRH1 | CDRH2 | CDRH3 | Light Chain Variable Region | CDRL1 | CDRL2 | CDRL3 |
|---|---|---|---|---|---|---|---|---|
| G2.760 rat | EVQLVESGGGLVQPGRSMKLSCAASGFTFSKSDMAWVRQAPTKGLKWVASIRYDGGNTYYRDSVRGRFTISRDNAKSTLYLQMDSLRSEDTATYYCSTAKAAISTPSYYVLDAWGQGASVTVSS (SEQ ID NO: 63) | KSDMA (SEQ ID NO: 110) | SIRYDGGNTYYRDSVRG (SEQ ID NO: 149) | AKAAISTPSYYVLDA (SEQ ID NO: 193) | DIGMTQSPTSMSKSVGDRVTMNCKASQNVGSNVDWFQQKTGQSPKLLIYKSSNRYTGVPARFTGSGSGTDFTFTISNMQAEDLAVYYCMQSNSYPPTFGGGTKLELK (SEQ ID NO: 244) | KASQNVGSNVD(SEQ ID NO: 300) | KSSNRYT (SEQ ID NO: 328) | MQSNSYPPT (SEQ ID NO: 356) |
| G2.767 rat | QVQLKESGPGLVQPSQTLSLTCTVSGLSLSSNSVSWIRQPPGKGLEWMGVIWNNGGTDYNSAIKSRLSISRDTSKSQVFLKLSSLQTEDTAMYFCARGYSSYIFDYWGQGVMVTVSS (SEQ ID NO: 64) | SNSVS (SEQ ID NO: 100) | VIWNNGGTDYNSAIKS (SEQ ID NO: 150) | GYSSYIFDY (SEQ ID NO: 182) | DIQMTQSPPSLSASLGDKVTITCQSSQNINNYIAWYQQKPGEAPRVLIRYTSTLQSGAPSRFSGSGSWRDYSFTISNVESEDIADYYCLQYVNLWTFGGGTKLEIK (SEQ ID NO: 245) | QSSQNINNYIA (SEQ ID NO: 301) | YTSTLQS (SEQ ID NO: 319) | LQYVNLWT (SEQ ID NO: 347) |
| G2.629.hz12 humanized | EVQLVESGGGLVQPGGSLRLSCAASGFIFSRFYMAWVRQAPGKGLEWVAYINTGGGTTYYRDSVKGRFTISRDNSKNTLYLQMNSLRAEDTAVYYCTTLAAPWNYVMDAWGQGTLVTVSS (SEQ ID NO: 65) | RFYMA (SEQ ID NO: 92) | YINTGGGTTYYRDSVKG (SEQ ID NO: 125) | LAAPWNYVMDA (SEQ ID NO: 168) | DIQMTQSPSSLSASVGDRVTITCKGSQNINNFLAWYQQKPGKAPKSLIYKTNSLHTGIPSRFSGSGSGTDYTLTISSLQPEDFATYYCYQYNSGYTFGQGTKLEIK (SEQ ID NO: 246) | KGSQNINNFLA (SEQ ID NO: 281) | KTNSLHT (SEQ ID NO: 315) | YQYNSGYT (SEQ ID NO: 357) |
| G2.629.hz14 humanized | EVQLVESGGGLVQPGGSLRLSCAASGFIFSRFYMAWVRQAPGKGLEWVAYINTGGGTTYYRDSVKGRFTISRDNSKNTLYLQMNSLRAEDTAVYYCTTLAAPWNYVMDAWGQGTLVTVSS (SEQ ID NO: 65) | RFYMA (SEQ ID NO: 92) | YINTGGGTTYYRDSVKG (SEQ ID NO: 125) | LAAPWNYVMDA (SEQ ID NO: 168) | DIQMTQSPSSLSASVGDRVTITCKGSQNINNFLAWYQQKPGKAPKSLIYKTNSLHTGIPSRFSGSGSGTDYTLTISSLQPEDFATYYCYQYNDGYTFGQGTKLEIK (SEQ ID NO: 247) | KGSQNINNFLA (SEQ ID NO: 281) | KTNSLHT (SEQ ID NO: 315) | YQYNDGYT (SEQ ID NO: 358) |
| G2.631.hz13 humanized | EVQLLESGGGLVQPGGSLRLSCAASGFIFSRFYMAWVRQAPGKGLEWVAYISNGAGSTYYRESVKGRFTISRDNSKNTLYLQMNSLRAEDTAVYYCTTVAAPWNYVMDGWGQGTLVTVSS (SEQ ID NO: 66) | RFYMA (SEQ ID NO: 92) | YISNGAGSTYYRESVKG (SEQ ID NO: 126) | VAAPWNYVMDG (SEQ ID NO: 169) | DIQMTQSPSSLSASVGDRVTITCKGSQNINNFLAWYQQKPGKAPKSLIYKTNSLHTGIPSRFSGSGSGTDYTLTISSLQPEDFATYYCYQYNQGYTFGQGTKLEIK (SEQ ID NO: 248) | KGSQNINNFLA (SEQ ID NO: 281) | KTNSLHT (SEQ ID NO: 315) | YQYNQGYT (SEQ ID NO: 359) |
| G2.631.hz14 humanized | EVQLLESGGGLVQPGGSLRLSCAASGFIFSRFYMAWVRQAPGKGLEWVAYISNGAGSTYYRESVKGRFTISRDNSKNTLYLQMNSLRAEDTAVYYCTTVAAPWNYVMDGWGQGTLVTVSS (SEQ ID NO: 66) | RFYMA (SEQ ID NO: 92) | YISNGAGSTYYRESVKG (SEQ ID NO: 126) | VAAPWNYVMDG (SEQ ID NO: 169) | DIQMTQSPSSLSASVGDRVTITCKGSQNINNFLAWYQQKPGKAPKSLIYKTNSLHTGIPSRFSGSGSGTDYTLTISSLQPEDFATYYCYQYNDGYTFGQGTKLEIK (SEQ ID NO: 247) | KGSQNINNFLA (SEQ ID NO: 281) | KTNSLHT (SEQ ID NO: 315) | YQYNDGYT (SEQ ID NO: 358) |

TABLE 2-continued

From left to right, 1st column: Anti-ABCG2 antibody name, 2nd column: VH region, 3rd column: HCDR1, 4th column: HCDR2, 5th column: HCDR3, 6th column: VL region, 7th column: LCDR1, 8th column: LCDR2, 9th column: LCDR3.

| Antibody | Heavy Chain Variable Region | CDRH1 | CDRH2 | CDRH3 | Light Chain Variable Region | CDRL1 | CDRL2 | CDRL3 |
|---|---|---|---|---|---|---|---|---|
| G2.631.hz21 humanized | EVQLLESGGGLVQPGGSLRLSCAASGFIFSRFYMAWVRQAPGKGLEWVAYISSGAGSTYYRESVKGRFTISRDNSKNTLYLQMNSLRAEDTAVYYCTTVAAPWNYVMDGWGQGTLVTVSS (SEQ ID NO: 67) | RFYMA (SEQ ID NO: 92) | YISSGAGSTYYRESVKG (SEQ ID NO: 151) | VAAPWNYVMDG (SEQ ID NO: 169) | DIQMTQSPSSLSASVGDRVTITCKGSQNINNFLAWYQQKPGKAPKSLIYKTNSLHTGIPSRFSGSGSGTDYTLTISSLQPEDFATYYCYQYNNGYTFGQGTKLEIK (SEQ ID NO: 249) | KGSQNINNFLA (SEQ ID NO: 281) | KTNSLHT (SEQ ID NO: 315) | YQYNNGYT (SEQ ID NO: 343) |
| G2.631.h222 humanized | EVQLLESGGGLVQPGGSLRLSCAASGFIFSRFYMAWVRQAPGKGLEWVAYISSGAGSTYYRESVKGRFTISRDNSKNTLYLQMNSLRAEDTAVYYCTTVAAPWNYVMDGWGQGTLVTVSS (SEQ ID NO: 67) | RFYMA (SEQ ID NO: 92) | YISSGAGSTYYRESVKG (SEQ ID NO: 151) | VAAPWNYVMDG (SEQ ID NO: 169) | DIQMTQSPSSLSASVGDRVTITCKGSQNINNFLAWYQQKPGKAPKSLIYKTNSLHTGIPSRFSGSGSGTDYTLTISSLQPEDFATYYCYQYNSGYTFGQGTKLEIK (SEQ ID NO: 246) | KGSQNINNFLA (SEQ ID NO: 281) | KTNSLHT (SEQ ID NO: 315) | YQYNSGYT (SEQ ID NO: 357) |
| G2.631.h223 humanized | EVQLLESGGGLVQPGGSLRLSCAASGFIFSRFYMAWVRQAPGKGLEWVAYISSGAGSTYYRESVKGRFTISRDNSKNTLYLQMNSLRAEDTAVYYCTTVAAPWNYVMDGWGQGTLVTVSS (SEQ ID NO: 67) | RFYMA (SEQ ID NO: 92) | YISSGAGSTYYRESVKG (SEQ ID NO: 151) | VAAPWNYVMDG (SEQ ID NO: 169) | DIQMTQSPSSLSASVGDRVTITCKGSQNINNFLAWYQQKPGKAPKSLIYKTNSLHTGIPSRFSGSGSGTDYTLTISSLQPEDFATYYCYQYNQGYTFGQGTKLEIK (SEQ ID NO: 248) | KGSQNINNFLA (SEQ ID NO: 281) | KTNSLHT (SEQ ID NO: 315) | YQYNQGYT (SEQ ID NO: 359) |
| G2.631.h224 humanized | EVQLLESGGGLVQPGGSLRLSCAASGFIFSRFYMAWVRQAPGKGLEWVAYISSGAGSTYYRESVKGRFTISRDNSKNTLYLQMNSLRAEDTAVYYCTTVAAPWNYVMDGWGQGTLVTVSS (SEQ ID NO: 67) | RFYMA (SEQ ID NO: 92) | YISSGAGSTYYRESVKG (SEQ ID NO: 151) | VAAPWNYVMDG (SEQ ID NO: 169) | DIQMTQSPSSLSASVGDRVTITCKGSQNINNFLAWYQQKPGKAPKSLIYKTNSLHTGIPSRFSGSGSGTDYTLTISSLQPEDFATYYCYQYNDGYTFGQGTKLEIK (SEQ ID NO: 247) | KGSQNINNFLA (SEQ ID NO: 281) | KTNSLHT (SEQ ID NO: 315) | YQYNDGYT (SEQ ID NO: 358) |
| G2.631.h231 humanized | EVQLLESGGGLVQPGGSLRLSCAASGFIFSRFYMAWVRQAPGKGLEWVAYISQGAGSTYYRESVKGRFTISRDNSKNTLYLQMNSLRAEDTAVYYCTTVAAPWNYVMDGWGQGTLVTVSS (SEQ ID NO: 68) | RFYMA (SEQ ID NO: 92) | YISQGAGSTYYRESVKG (SEQ ID NO: 152) | VAAPWNYVMDG (SEQ ID NO: 169) | DIQMTQSPSSLSASVGDRVTITCKGSQNINNFLAWYQQKPGKAPKSLIYKTNSLHTGIPSRFSGSGSGTDYTLTISSLQPEDFATYYCYQYNNGYTFGQGTKLEIK (SEQ ID NO: 249) | KGSQNINNFLA (SEQ ID NO: 281) | KTNSLHT (SEQ ID NO: 315) | YQYNNGYT (SEQ ID NO: 343) |
| G2.631.h232 humanized | EVQLLESGGGLVQPGGSLRLSCAASGFIFSRFYMAWVRQAPGKGLEWVAYISQGAGSTYYRESVKGRFTISRDNSKNTLYLQMNSLRAEDTAVYYCTTVAAPWNYVMDGWGQGTLVTVSS (SEQ ID NO: 68) | RFYMA (SEQ ID NO: 92) | YISQGAGSTYYRESVKG (SEQ ID NO: 152) | VAAPWNYVMDG (SEQ ID NO: 169) | DIQMTQSPSSLSASVGDRVTITCKGSQNINNFLAWYQQKPGKAPKSLIYKTNSLHTGIPSRFSGSGSGTDYTLTISSLQPEDFATYYCYQYNSGYTFGQGTKLEIK (SEQ ID NO: 246) | KGSQNINNFLA (SEQ ID NO: 281) | KTNSLHT (SEQ ID NO: 315) | YQYNSGYT (SEQ ID NO: 357) |

TABLE 2-continued

From left to right, 1st column: Anti-ABCG2 antibody name, 2nd column: VH region, 3rd column: HCDR1, 4th column: HCDR2, 5th column: HCDR3, 6th column: VL region, 7th column: LCDR1, 8th column: LCDR2, 9th column: LCDR3.

| Antibody | Heavy Chain Variable Region | CDRH1 | CDRH2 | CDRH3 | Light Chain Variable Region | CDRL1 | CDRL2 | CDRL3 |
|---|---|---|---|---|---|---|---|---|
| G2.631.hz34 humanized | EVQLLESGGGLVQPGGSLRLSCAASGFIFSRFYMAWVRQAPGKGLEWVAYISQGAGSTYYRESVKGRFTISRDNSKNTLYLQMNSLRAEDTAVYYCTTVAAPWNYVMDGWGQGTLVTVSS (SEQ ID NO: 68) | RFYMA (SEQ ID NO: 92) | YISQGAGSTYYRESVKG (SEQ ID NO: 152) | VAAPWNYVMDG (SEQ ID NO: 169) | DIQMTQSPSSLSASVGDRVTITCKGSQNINNFLAWYQQKPGKAPKSLIYKTNSLHTGIPSRFSGSGSGTDYTLTISSLQPEDFATYYCYQYNDGYTFGQGTKLEIK (SEQ ID NO: 247) | KGSQNINNFLA (SEQ ID NO: 281) | KTNSLHT (SEQ ID NO: 315) | YQYNDGYT (SEQ ID NO: 358) |
| G2.318-hl1 humanized | EVQLQESGPGLVKPSETLSLTCAVSGYTITSGYDWTWIRKPPGKGMEWMGYISYSGWTNYNPSLRSRITISRDTSKNQFSLKLSSVTAADTAVYYCARVRGYNPFAYWGQGTLVTVSS (SEQ ID NO: 69) | SGYDWT (SEQ ID NO: 88) | YISYSGWTNYNPSLRS (SEQ ID NO: 119) | VRGYNPFAY (SEQ ID NO: 160) | DIQMTQSPSSLSASVGDRVTITCKAGRNVNNYLAWYQQKPGKPPKLLIYNSNSLQTGIPSRFSGSGSGTDFTLTISSLQPEDVATYFYCQQYNSWTTFGQGTKLEIK (SEQ ID NO: 250) | KAGRNVNNYLA (SEQ ID NO: 275) | NSNSLQT (SEQ ID NO: 311) | CQQYNSWTT (SEQ ID NO: 360) |
| G2.343-hl1 humanized | EVQLQESGPGLVKPSETLSLTCTVSGFSLTSNGVSWVRQPPGKGLEWIAAISSGGSTYYNSVLKSRLTISRDTSKNQVSLKLSSVTAADTAVYFCTRDTYYGYNQIPFVYWGQGTLVTVSS (SEQ ID NO: 70) | SNGVS (SEQ ID NO: 89) | AISSGGSTYYNSVLKS (SEQ ID NO: 121) | DTYYGYNQIPFVY (SEQ ID NO: 163) | DVVLTQTPLSLSVTPGQPASISCRSSQSLLHSSGNTYLNWLLQKPGQPPQLLIYLVSRLESGVPDRFSGSGSGTDFTLKISRVEAEDVGVYYCVQSTHAPRTFGGGTKLEIK (SEQ ID NO: 251) | RSSQSLLHSSGNTYLN (SEQ ID NO: 276) | LVSRLES (SEQ ID NO: 312) | VQSTHAPRT (SEQ ID NO: 338) |
| G2.629.hu25 humanized | EVQLVESGGGLVQPGGSLRLSCAASGFIFSRFYMAWVRQAPGKGLEWVAYINTGGGTTYYRDSVKGRFTISRDNSKNTLYLQMNSLRAEDTAVYYCTTLAAPWNYVMDAWGQGTLVTVSS (SEQ ID NO: 65) | RFYMA (SEQ ID NO: 92) | YINTGGGTTYYRDSVKG (SEQ ID NO: 125) | LAAPWNYVMDA (SEQ ID NO: 168) | AIQLTQSPSSLSASVGDRVTITCKGSQNINNFLAWYQQKPGKAPKLLIYKTNSLHTGIPSRFSGSGSGTDYTLTISSLQPEDFATYYCYQYNNGYTFGQGTKLEIK (SEQ ID NO: 252) | KGSQNINNFLA (SEQ ID NO: 281) | KTNSLHT (SEQ ID NO: 315) | YQYNNGYT (SEQ ID NO: 343) |
| G2.631.hu55 humanized | EVQLLESGGGLVQPGGSLRLSCAASGFIFSRFYMAWVRQAPGKGLEWVAYISNGAGSTYYRESVKGRFTISRDNSKNTLYLQMNSLRAEDTAVYYCTTVAAPWNYVMDGWGQGTLVTVSS (SEQ ID NO: 66) | RFYMA (SEQ ID NO: 92) | YISNGAGSTYYRESVKG (SEQ ID NO: 126) | VAAPWNYVMDG (SEQ ID NO: 169) | DIQITQSPSSLSASVGDRVTITCKGSQNINNYLAWYQQKPGKAPKLLIYKTNSLHTGIPSRFSGSGSGTDYTLTISSLQPEDFATYYCYQYNNGYTFGQGTKLEIK (SEQ ID NO: 253) | KGSQNINNYLA (SEQ ID NO: 282) | KTNSLHT (SEQ ID NO: 315) | YQYNNGYT (SEQ ID NO: 343) |
| G2.333.hu23 humanized | EIQLQESGPGLVKPSETLSLTCAVSGYTITSGYDWTWLRKPPGKGMEWMGYISYSGFTNYNPSLRSRITISRDTSKNQFSLKLSSVTAADTAVYYCARTRGYNPFPYWGQGTLVTVSS (SEQ ID NO: 71) | SGYDWT (SEQ ID NO: 88) | YISYSGFTNYNPSLRS (SEQ ID NO: 120) | TRGYNPFPY (SEQ ID NO: 162) | DIQMTQSPSSLSASVGDRVTITCKAGRNVNNYLAWYQQKPGKPPKLLIYNSNSLQTGIPSRFSGSGSGTDFTLTISSLQPEDVATYYCQQYNSWTTFGQGTKLEIK (SEQ ID NO: 254) | KAGRNVNNYLA (SEQ ID NO: 275) | NSNSLQT (SEQ ID NO: 311) | QQYNSWTT (SEQ ID NO: 337) |

TABLE 2-continued

From left to right, 1st column: Anti-ABCG2 antibody name, 2nd column: VH region, 3rd column: HCDR1, 4th column: HCDR2, 5th column: HCDR3, 6th column: VL region, 7th column: LCDR1, 8th column: LCDR2, 9th column: LCDR3.

| Antibody | Heavy Chain Variable Region | CDRH1 | CDRH2 | CDRH3 | Light Chain Variable Region | CDRL1 | CDRL2 | CDRL3 |
|---|---|---|---|---|---|---|---|---|
| G2.318.hu33 humanized | EVQLQESGPGLVKPSETLSLTCA VSGYTITSGYDWSWIRKPPGKG MEWMGYISYSGWTNYNPSLRS RITISRDTSKNQFSLKLSSVTAAD TAVYYCARVRGYNPFAYWGQG TLVTVSS (SEQ ID NO: 72) | SGYDWS (SEQ ID NO: 87) | YISYSGWTNY NPSLRS (SEQ ID NO: 119) | VRGYNPFAY (SEQ ID NO: 160) | DIQMTQSPSSLSASVGDRVTITCKA GQNINNYLAWYQQKPGKAPKLLIY NANSLQTGIPSRFSGSGSGTDFTLTI SSLQPEDFATYYCQQYNSWTTFGQ GTKLEIK (SEQ ID NO: 255) | KAGQNINN YLA (SEQ ID NO: 273) | NANSLQT (SEQ ID NO: 309) | QQYNSWTT (SEQ ID NO: 337) |
| G2.636.hu25 humanized | EVQLVESGGGLVQPGGSLRLSCA ASGFTFSRFYMAWVRQAPGKG LEWVAHISHGGDTTYYRDSVKG RFTISRDNSKNTLYLQMNSLRAE DTAVYYCTTSAAPWNYVMDG WGQGTLVTVSS (SEQ ID NO: 73) | RFYMA (SEQ ID NO: 92) | HISHGGDTTY YRDSVKG (SEQ ID NO: 127) | SAAPWNYV MDG (SEQ ID NO: 170) | AIQLTQSPSSLSASVGDRVTITCKGS QNINNFLAWYQQKPGKAPKLLIYK TNSLHTGIPSRFSGSGSGTDYTLTIS SLQPEDFATYYCYQYNNGYTFGQG TKLEIK (SEQ ID NO: 252) | KGSQNINN FLA (SEQ ID NO: 281) | KTNSLHT (SEQ ID NO: 315) | YQYNNGYT (SEQ ID NO: 343) |
| G2.636.hu27 humanized | EVQLVESGGGLVQPGGSLRLSCA ASGFTFSRFYMAWVRQAPGKG LEWVAHISHGGDTTYYRDSVKG RFTISRDNSKNTLYLQMNSLRAE DTAVYYCTTSAAPWNYVMDG WGQGTLVTVSS (SEQ ID NO: 73) | RFYMA (SEQ ID NO: 92) | HISHGGDTTY YRDSVKG (SEQ ID NO: 127) | SAAPWNYV MDG (SEQ ID NO: 170) | DIQLTQSPSSLSASVGDRVTLTCKG SQNINNFLAWYQQKPGKAPKLLIY KTNSLHTGIPSRFSGSGSGTDYTLTI SSLQPEDFATYYCYQYNNGYTFGQ GTKLEIK (SEQ ID NO: 256) | KGSQNINN FLA (SEQ ID NO: 281) | KTNSLHT (SEQ ID NO: 315) | YQYNNGYT (SEQ ID NO: 343) |
| G2.636.hu45 humanized | EVQLVESGGGLVQPGGSLRLSCA ASGFTFSRFYMAWVRQAPGKG LEWVAHISHGGDTTYYRDSVKG RFTISRDNSKNTLYLQMNSLRAE DTAVYYCTTSAAPWNYVMDG WGQGATVTVSS (SEQ ID NO: 74) | RFYMA (SEQ ID NO: 92) | HISHGGDTTY YRDSVKG (SEQ ID NO: 127) | SAAPWNYV MDG (SEQ ID NO: 170) | AIQLTQSPSSLSASVGDRVTITCKGS QNINNFLAWYQQKPGKAPKLLIYK TNSLHTGIPSRFSGSGSGTDYTLTIS SLQPEDFATYYCYQYNNGYTFGQG TKLEIK (SEQ ID NO: 252) | KGSQNINN FLA (SEQ ID NO: 281) | KTNSLHT (SEQ ID NO: 315) | YQYNNGYT (SEQ ID NO: 343) |
| G2.636.hu47 humanized | EVQLVESGGGLVQPGGSLRLSCA ASGFTFSRFYMAWVRQAPGKG LEWVAHISHGGDTTYYRDSVKG RFTISRDNSKNTLYLQMNSLRAE DTAVYYCTTSAAPWNYVMDG WGQGATVTVSS (SEQ ID NO: 74) | RFYMA (SEQ ID NO: 92) | HISHGGDTTY YRDSVKG (SEQ ID NO: 127) | SAAPWNYV MDG (SEQ ID NO: 170) | DIQLTQSPSSLSASVGDRVTLTCKG SQNINNFLAWYQQKPGKAPKLLIY KTNSLHTGIPSRFSGSGSGTDYTLTI SSLQPEDFATYYCYQYNNGYTFGQ GTKLEIK (SEQ ID NO: 256) | KGSQNINN FLA (SEQ ID NO: 281) | KTNSLHT (SEQ ID NO: 315) | YQYNNGYT (SEQ ID NO: 343) |
| G2.643.hu11 humanized | EVQLVQSGAEVKKPGASVKVSC KASGYRFTSYYVHWVRQAPGQR LEWIGWIFPGSDNTKYNEKFKG RATLTADTSASTAYMELSSLRSE DTAVYFCASIYYGYDGTLYFDYW GQGTLVTVss(SEQ ID NO: 75) | SYYVH (SEQ ID NO: 107) | WIFPGSDNTK YNEKFKG (SEQ ID NO: 145) | IYYGYDGTLY FDY (SEQ ID NO: 188) | DIQMTQSPSSLSASVGDRVTITCKA SQNVGNNVAWYQQKPGKSPKALI YSASYRYSGVPSRFSGSGSGTDFTL TISSLQPEDFATYFCQQYDRYPLTF GGGTKLEIK (SEQ ID NO: 257) | KASQNVGN NVA (SEQ ID NO: 296) | SASYRYS (SEQ ID NO: 325) | QQYDRYPLT (SEQ ID NO: 353) |

TABLE 2-continued

From left to right, 1st column: Anti-ABCG2 antibody name, 2nd column: VH region, 3rd column: HCDR1, 4th column: HCDR2, 5th column: HCDR3, 6th column: VL region, 7th column: LCDR1, 8th column: LCDR2, 9th column: LCDR3.

| Antibody | Heavy Chain Variable Region | CDRH1 | CDRH2 | CDRH3 | Light Chain Variable Region | CDRL1 | CDRL2 | CDRL3 |
|---|---|---|---|---|---|---|---|---|
| G2.643.hu22 humanized | EVQLVQSGAEVKKPGASVKVSC KASGYRFTSYYVHWVRQAPGQR LEWIGWIFPGSDNTKYNEKFKG RATLTADTSASTAYMELSSLRSE DTAVYYCASIYYGYDGTLYFDYW GQGTLVTV (SEQ ID NO: 76) | SYYVH (SEQ ID NO: 107) | WIFPGSDNTK YNEKFKG (SEQ ID NO: 145) | IYYGYDGTLY FDY (SEQ ID NO: 188) | DIQMTQSPSSLSASVGDRVTITCKA SQNVGNNVAWYQQKPGKSPKALI YSASYRYSGVPSRFSGSGSGTDFTL TISSLQPEDFATYYCQQYDRYPLTF GGGTKLEIK (SEQ ID NO: 258) | KASQNVGN NVA (SEQ ID NO: 296) | SASYRYS (SEQ ID NO: 325) | QQYDRYPLT (SEQ ID NO: 353) |
| G2.643.hu23 humanized | EVQLVQSGAEVKKPGASVKVSC KASGYRFTSYYVHWVRQAPGQR LEWIGWIFPGSDNTKYNEKFKG RATLTADTSASTAYMELSSLRSE DTAVYYCASIYYGYDGTLYFDYW GQGTLVTV (SEQ ID NO: 76) | SYYVH (SEQ ID NO: 107) | WIFPGSDNTK YNEKFKG (SEQ ID NO: 145) | IYYGYDGTLY FDY (SEQ ID NO: 188) | EIVMTQSPATLSVSPGERATLSCKA SQNVGNNVAWYQQKPGQSPRALI YSASYRYSGVPARFSGSGSGTEFTL TISSLQSEDFAVYYCQQYDRYPLTF GGGTKLEIK (SEQ ID NO: 259) | KASQNVGN NVA (SEQ ID NO: 296) | SASYRYS (SEQ ID NO: 325) | QQYDRYPLT (SEQ ID NO: 353) |
| G2.643.hu24 humanized | EVQLVQSGAEVKKPGASVKVSC KASGYRFTSYYVHWVRQAPGQR LEWIGWIFPGSDNTKYNEKFKG RATLTADTSASTAYMELSSLRSE DTAVYYCASIYYGYDGTLYFDYW GQGTLVTV (SEQ ID NO: 76) | SYYVH (SEQ ID NO: 107) | WIFPGSDNTK YNEKFKG (SEQ ID NO: 145) | IYYGYDGTLY FDY (SEQ ID NO: 188) | DIQMTQSPSSLSASVGDRVTITCKA SQNVGNNVAWYQQKPGKAPKLLI YSASYRYSGVPSRFSGSGSGTDFTL TISSLQPEDFATYYCQQYDRYPLTF GQGTKLEIK (SEQ ID NO: 260) | KASQNVGN NVA (SEQ ID NO: 296) | SASYRYS (SEQ ID NO: 325) | QQYDRYPLT (SEQ ID NO: 353) |
| G2.643.hu25 humanized | EVQLVQSGAEVKKPGASVKVSC KASGYRFTSYYVHWVRQAPGQR LEWIGWIFPGSDNTKYNEKFKG RATLTADTSASTAYMELSSLRSE DTAVYYCASIYYGYDGTLYFDYW GQGTLVTV (SEQ ID NO: 76) | SYYVH (SEQ ID NO: 107) | WIFPGSDNTK YNEKFKG (SEQ ID NO: 145) | IYYGYDGTLY FDY (SEQ ID NO: 188) | DIQMTQSPSSLSASVGDRVTITCKA SQNVGNNVAWYQQKPGKAPKALI YSASYRYSGVPSRFSGSGSGTDFTL TISSLQPEDFATYYCQQYDRYPLTF GQGTKLEIK (SEQ ID NO: 261) | KASQNVGN NVA (SEQ ID NO: 296) | SASYRYS (SEQ ID NO: 325) | QQYDRYPLT (SEQ ID NO: 353) |
| G2.643.hu26 humanized | EVQLVQSGAEVKKPGASVKVSC KASGYRFTSYYVHWVRQAPGQR LEWIGWIFPGSDNTKYNEKFKG RATLTADTSASTAYMELSSLRSE DTAVYYCASIYYGYDGTLYFDYW GQGTLVTV (SEQ ID NO: 76) | SYYVH (SEQ ID NO: 107) | WIFPGSDNTK YNEKFKG (SEQ ID NO: 145) | IYYGYDGTLY FDY (SEQ ID NO: 188) | DIQMTQSPSSLSASVGDRVTVTCK ASQNVGNNVAWYQQKPGKAPKA LIYSASYRYSGVPSRFSGSGSGTDFT LTISSVQPEDFATYYCQQYDRYPLT FGQGTKLEIK (SEQ ID NO: 262) | KASQNVGN NVA (SEQ ID NO: 296) | SASYRYS (SEQ ID NO: 325) | QQYDRYPLT (SEQ ID NO: 353) |
| G2.643.hu42 humanized | QVQLVQSGAEVKKPGASVKVSC KASGYRFTSYYVHWVRQAPGQ GLEWMGWIFPGSDNTKYNEKF KGRVTMTADTSTSTAYMELSSLR SEDTAVYYCASIYYGYDGTLYFDY WGQGTTVTVSS (SEQ ID NO: 77) | SYYVH (SEQ ID NO: 107) | WIFPGSDNTK YNEKFKG (SEQ ID NO: 145) | IYYGYDGTLY FDY (SEQ ID NO: 188) | DIQMTQSPSSLSASVGDRVTITCKA SQNVGNNVAWYQQKPGKSPKALI YSASYRYSGVPSRFSGSGSGTDFTL TISSLQPEDFATYYCQQYDRYPLTF GGGTKLEIK (SEQ ID NO: 258) | KASQNVGN NVA (SEQ ID NO: 296) | SASYRYS (SEQ ID NO: 325) | QQYDRYPLT (SEQ ID NO: 353) |

TABLE 2-continued

From left to right, 1st column: Anti-ABCG2 antibody name, 2nd column: VH region, 3rd column: HCDR1, 4th column: HCDR2, 5th column: HCDR3, 6th column: VL region, 7th column: LCDR1, 8th column: LCDR2, 9th column: LCDR3.

| Antibody | Heavy Chain Variable Region | CDRH1 | CDRH2 | CDRH3 | Light Chain Variable Region | CDRL1 | CDRL2 | CDRL3 |
|---|---|---|---|---|---|---|---|---|
| G2.643.hu43 humanized | QVQLVQSGAEVKKPGASVKVSCKASGYRFTSYYVHWVRQAPGQGLEWMGWIFPGSDNTKYNEKFKGRVTMTADTSTSTAYMELSSLRSEDTAVYYCASIYYGYDGTLYFDYWGQGTTVTVSS (SEQ ID NO: 77) | SYYVH (SEQ ID NO: 107) | WIFPGSDNTKYNEKFKG (SEQ ID NO: 145) | IYYGYDGTLYFDY (SEQ ID NO: 188) | EIVMTQSPATLSVSPGERATLSCKASQNVGNNVAWYQQKPGQSPRALIYSASYRYSGVPARFSGSGSGTEFTLTISSLQSEDFAVYYCQQYDRYPLTFGGGTKLEIK (SEQ ID NO: 259) | KASQNVGNNVA (SEQ ID NO: 296) | SASYRYS (SEQ ID NO: 325) | QQYDRYPLT (SEQ ID NO: 353) |
| G2.643.hu44 humanized | QVQLVQSGAEVKKPGASVKVSCKASGYRFTSYYVHWVRQAPGQGLEWMGWIFPGSDNTKYNEKFKGRVTMTADTSTSTAYMELSSLRSEDTAVYYCASIYYGYDGTLYFDYWGQGTTVTVSS (SEQ ID NO: 77) | SYYVH (SEQ ID NO: 107) | WIFPGSDNTKYNEKFKG (SEQ ID NO: 145) | IYYGYDGTLYFDY (SEQ ID NO: 188) | DIQMTQSPSSLSASVGDRVTITCKASQNVGNNVAWYQQKPGKAPKLLIYSASYRYSGVPSRFSGSGSGTDFTLTISSLQPEDFATYYCQQYDRYPLTFGQGTKLEIK (SEQ ID NO: 260) | KASQNVGNNVA (SEQ ID NO: 296) | SASYRYS (SEQ ID NO: 325) | QQYDRYPLT (SEQ ID NO: 353) |
| G2.643.hu45 humanized | QVQLVQSGAEVKKPGASVKVSCKASGYRFTSYYVHWVRQAPGQGLEWMGWIFPGSDNTKYNEKFKGRVTMTADTSTSTAYMELSSLRSEDTAVYYCASIYYGYDGTLYFDYWGQGTTVTVSS (SEQ ID NO: 77) | SYYVH (SEQ ID NO: 107) | WIFPGSDNTKYNEKFKG (SEQ ID NO: 145) | IYYGYDGTLYFDY (SEQ ID NO: 188) | DIQMTQSPSSLSASVGDRVTITCKASQNVGNNVAWYQQKPGKAPKALIYSASYRYSGVPSRFSGSGSGTDFTLTISSLQPEDFATYYCQQYDRYPLTFGQGTKLEIK (SEQ ID NO: 261) | KASQNVGNNVA (SEQ ID NO: 296) | SASYRYS (SEQ ID NO: 325) | QQYDRYPLT (SEQ ID NO: 353) |
| G2.643.hu46 humanized | QVQLVQSGAEVKKPGASVKVSCKASGYRFTSYYVHWVRQAPGQGLEWMGWIFPGSDNTKYNEKFKGRVTMTADTSTSTAYMELSSLRSEDTAVYYCASIYYGYDGTLYFDYWGQGTTVTVSS (SEQ ID NO: 77) | SYYVH (SEQ ID NO: 107) | WIFPGSDNTKYNEKFKG (SEQ ID NO: 145) | IYYGYDGTLYFDY (SEQ ID NO: 188) | DIQMTQSPSSLSASVGDRVTVTCKASQNVGNNVAWYQQKPGKAPKALIYSASYRYSGVPSRFSGSGSGTDFTLTISSVQPEDFATYYCQQYDRYPLTFGQGTKLEIK (SEQ ID NO: 262) | KASQNVGNNVA (SEQ ID NO: 296) | SASYRYS (SEQ ID NO: 325) | QQYDRYPLT (SEQ ID NO: 353) |
| G2.643.hu52 humanized | QVQLVQSGAEVKKPGASVKISCKASGYRFTSYYVHWVRQAPGQGLEWIGWIFPGSDNTKYNEKFKGRATLTADTSTSTAYMELSSLRSEDTAVYYCASIYYGYDGTLYFDYWGQGTTVTVSS (SEQ ID NO: 78) | SYYVH (SEQ ID NO: 107) | WIFPGSDNTKYNEKFKG (SEQ ID NO: 145) | IYYGYDGTLYFDY (SEQ ID NO: 188) | DIQMTQSPSSLSASVGDRVTITCKASQNVGNNVAWYQQKPGKSPKALIYSASYRYSGVPSRFSGSGSGTDFTLTISSLQPEDFATYYCQQYDRYPLTFGGGTKLEIK (SEQ ID NO: 258) | KASQNVGNNVA (SEQ ID NO: 296) | SASYRYS (SEQ ID NO: 325) | QQYDRYPLT (SEQ ID NO: 353) |
| G2.643.hu53 humanized | QVQLVQSGAEVKKPGASVKISCKASGYRFTSYYVHWVRQAPGQGLEWIGWIFPGSDNTKYNEKFKGRATLTADTSTSTAYMELSSLRSEDTAVYYCASIYYGYDGTLYFDYWGQGTTVTVSS (SEQ ID NO: 78) | SYYVH (SEQ ID NO: 107) | WIFPGSDNTKYNEKFKG (SEQ ID NO: 145) | IYYGYDGTLYFDY (SEQ ID NO: 188) | EIVMTQSPATLSVSPGERATLSCKASQNVGNNVAWYQQKPGQSPRALIYSASYRYSGVPARFSGSGSGTEFTLTISSLQSEDFAVYYCQQYDRYPLTFGGGTKLEIK (SEQ ID NO: 259) | KASQNVGNNVA (SEQ ID NO: 296) | SASYRYS (SEQ ID NO: 325) | QQYDRYPLT (SEQ ID NO: 353) |

TABLE 2-continued

From left to right, 1st column: Anti-ABCG2 antibody name, 2nd column: VH region, 3rd column: HCDR1, 4th column: HCDR2, 5th column: HCDR3, 6th column: VL region, 7th column: LCDR1, 8th column: LCDR2, 9th column: LCDR3.

| Antibody | Heavy Chain Variable Region | CDRH1 | CDRH2 | CDRH3 | Light Chain Variable Region | CDRL1 | CDRL2 | CDRL3 |
|---|---|---|---|---|---|---|---|---|
| G2.643.hu54 humanized | QVQLVQSGAEVKKPGASVKISCK ASGYRFTSYYVHWVRQAPGQGL EWIGWIFPGSDNTKYNEKFKGR ATLTADTSTSTAYMELSSLRSEDT AVYYCASIYYGYDGTLYFDYWG QGTTVTVSS (SEQ ID NO: 78) | SYYVH (SEQ ID NO: 107) | WIFPGSDNTK YNEKFKG (SEQ ID NO: 145) | IYYGYDGTLY FDY (SEQ ID NO: 188) | DIQMTQSPSSLSASVGDRVTITCKA SQNVGNNVAWYQQKPGKAPKLLI YSASYRYSGVPSRFSGSGSGTDFTL TISSLQPEDFATYYCQQYDRYPLTF GQGTKLEIK (SEQ ID NO: 260) | KASQNVGN NVA (SEQ ID NO: 296) | SASYRYS (SEQ ID NO: 325) | QQYDRYPLT (SEQ ID NO: 353) |
| G2.643.hu55 humanized | QVQLVQSGAEVKKPGASVKISCK ASGYRFTSYYVHWVRQAPGQGL EWIGWIFPGSDNTKYNEKFKGR ATLTADTSTSTAYMELSSLRSEDT AVYYCASIYYGYDGTLYFDYWG QGTTVTVSS (SEQ ID NO: 78) | SYYVH (SEQ ID NO: 107) | WIFPGSDNTK YNEKFKG (SEQ ID NO: 145) | IYYGYDGTLY FDY (SEQ ID NO: 188) | DIQMTQSPSSLSASVGDRVTITCKA SQNVGNNVAWYQQKPGKAPKALI YSASYRYSGVPSRFSGSGSGTDFTL TISSLQPEDFATYYCQQYDRYPLTF GQGTKLEIK (SEQ ID NO: 261) | KASQNVGN NVA (SEQ ID NO: 296) | SASYRYS (SEQ ID NO: 325) | QQYDRYPLT (SEQ ID NO: 353) |
| G2.643.hu56 humanized | QVQLVQSGAEVKKPGASVKISCK ASGYRFTSYYVHWVRQAPGQGL EWIGWIFPGSDNTKYNEKFKGR ATLTADTSTSTAYMELSSLRSEDT AVYYCASIYYGYDGTLYFDYWG QGTTVTVSS (SEQ ID NO: 78) | SYYVH (SEQ ID NO: 107) | WIFPGSDNTK YNEKFKG (SEQ ID NO: 145) | IYYGYDGTLY FDY (SEQ ID NO: 188) | DIQMTQSPSSLSASVGDRVTVTCK ASQNVGNNVAWYQQKPGKAPKA LIYSASYRYSGVPSRFSGSGSGTDFT LTISSVQPEDFATYYCQQYDRYPLT FGQGTKLEIK (SEQ ID NO: 262) | KASQNVGN NVA (SEQ ID NO: 296) | SASYRYS (SEQ ID NO: 325) | QQYDRYPLT (SEQ ID NO: 353) |
| G2.636.hu48 humanized | EVQLVESGGGLVQPGGSLRLSCA ASGFTFSRFYMAWVRQAPGKG LEWVAHISHGGDTTYYRDSVKG RFTISRDNSKNTLYLQMNSLRAE DTAVYYCTTSAAPWNYVMDG WGQGATVTVSS (SEQ ID NO: 74) | RFYMA (SEQ ID NO: 92) | HISHGGDTTY YRDSVKG (SEQ ID NO: 127) | SAAPWNYV MDG (SEQ ID NO: 170) | DIQLTQSPSSLSASVGDRVTLTCKG SQNINNFLAWYQQKPGKAPKLLIY KTNSLHTGIPSRFSGSGSGTDYTLTI SSLQPEDFATYYCYQYNQGYTFGQ GTKLEIK (SEQ ID NO: 263) | KGSQNINN FLA (SEQ ID NO: 281) | KTNSLHT (SEQ ID NO: 315) | YQYNQGYT (SEQ ID NO: 359) |
| G2.636.hu49 humanized | EVQLVESGGGLVQPGGSLRLSCA ASGFTFSRFYMAWVRQAPGKG LEWVAHISHGGDTTYYRDSVKG RFTISRDNSKNTLYLQMNSLRAE DTAVYYCTTSAAPWNYVMDG WGQGATVTVSS (SEQ ID NO: 74) | RFYMA (SEQ ID NO: 92) | HISHGGDTTY YRDSVKG (SEQ ID NO: 127) | SAAPWNYV MDG (SEQ ID NO: 170) | DIQLTQSPSSLSASVGDRVTLTCKG SQNINNFLAWYQQKPGKAPKLLIY KTNSLHTGIPSRFSGSGSGTDYTLTI SSLQPEDFATYYCYQYNSGYTFGQ GTKLEIK (SEQ ID NO: 264) | KGSQNINN FLA (SEQ ID NO: 281) | KTNSLHT (SEQ ID NO: 315) | YQYNSGYT (SEQ ID NO: 357) |
| G2.636.hu67 humanized | EVQLVESGGGLVQPGGSLRLSCA ASGFTFSRFYMAWVRQAPGKG LEWVAHISHGGDTTYYRDSVKG RFTISRDNSKNTLYLQMNSLRAE DTAVYYCTTSAAPWNYVMQG WGQGATVTVSS (SEQ ID NO: 79) | RFYMA (SEQ ID NO: 92) | HISHGGDTTY YRDSVKG (SEQ ID NO: 127) | SAAPWNYV MQG (SEQ ID NO: 194) | DIQLTQSPSSLSASVGDRVTLTCKG SQNINNFLAWYQQKPGKAPKLLIY KTNSLHTGIPSRFSGSGSGTDYTLTI SSLQPEDFATYYCYQYNNGYTFGQ GTKLEIK (SEQ ID NO: 256) | KGSQNINN FLA (SEQ ID NO: 281) | KTNSLHT (SEQ ID NO: 315) | YQYNNGYT (SEQ ID NO: 343) |

TABLE 2-continued

From left to right, 1st column: Anti-ABCG2 antibody name, 2nd column: VH region, 3rd column: HCDR1, 4th column: HCDR2, 5th column: HCDR3, 6th column: VL region, 7th column: LCDR1, 8th column: LCDR2, 9th column: LCDR3.

| Antibody | Heavy Chain Variable Region | CDRH1 | CDRH2 | CDRH3 | Light Chain Variable Region | CDRL1 | CDRL2 | CDRL3 |
|---|---|---|---|---|---|---|---|---|
| G2.636.hu68 humanized | EVQLVESGGGLVQPGGSLRLSCAASGFTFSRFYMAWVRQAPGKGLEWVAHISHGGDTTYYRDSVKGRFTISRDNSKNTLYLQMNSLRAEDTAVYYCTTSAAPWNYVMQGWGQGATVTVSS (SEQ ID NO: 79) | RFYMA (SEQ ID NO: 92) | HISHGGDTTYYRDSVKG (SEQ ID NO: 127) | SAAPWNYVMQG (SEQ ID NO: 194) | DIQLTQSPSSLSASVGDRVTLTCKGSQNINNFLAWYQQKPGKAPKLLIYKTNSLHTGIPSRFSGSGSGTDYTLTISSLQPEDFATYYCYQYNQGYTFGQGTKLEIK (SEQ ID NO: 263) | KGSQNINNFLA (SEQ ID NO: 281) | KTNSLHT (SEQ ID NO: 315) | YQYNQGYT (SEQ ID NO: 359) |
| G2.636.hu69 humanized | EVQLVESGGGLVQPGGSLRLSCAASGFTFSRFYMAWVRQAPGKGLEWVAHISHGGDTTYYRDSVKGRFTISRDNSKNTLYLQMNSLRAEDTAVYYCTTSAAPWNYVMQGWGQGATVTVSS (SEQ ID NO: 79) | RFYMA (SEQ ID NO: 92) | HISHGGDTTYYRDSVKG (SEQ ID NO: 127) | SAAPWNYVMQG (SEQ ID NO: 194) | DIQLTQSPSSLSASVGDRVTLTCKGSQNINNFLAWYQQKPGKAPKLLIYKTNSLHTGIPSRFSGSGSGTDYTLTISSLQPEDFATYYCYQYNSGYTFGQGTKLEIK (SEQ ID NO: 264) | KGSQNINNFLA (SEQ ID NO: 281) | KTNSLHT (SEQ ID NO: 315) | YQYNSGYT (SEQ ID NO: 357) |
| G2.766 rat | QGTLKESGPGIVQSSHTLSLTCSFSGFSLSTYGMGVSWIRQPSGKGLEWLASVWWNGDTSNNPSLKSRLTVSKDTSNNQAFLKVTSVDTADTATYYCAHTLYNNYPFDYWGQGVMVTVSS (SEQ ID NO: 80) | TYGMGVS (SEQ ID NO: 106) | SVWWNGDTSNNPSLKS (SEQ ID NO: 148) | TLYNNYPFDY (SEQ ID NO: 192) | DIQMTQSPPSLSASLGDKVTITCQASQNIYKYIAWYQQKPGKAPRLLIRYTSTLDSGTPSRFSGSGSGRDYSFSISNVESEDIASYYCQQYVNFPNTFGAGTNLELK (SEQ ID NO: 265) | QASQNIYKYIA (SEQ ID NO: 299) | YTSTLDS (SEQ ID NO: 329) | QQYVNFPNT (SEQ ID NO: 361) |

The anti-ABCG2 antibodies listed in Table 2 are also referred to as anti-KPG2 antibodies and can be referred to by the antibody number listed in Table 2.

The term "antibody molecule" encompasses antibodies as defined herein and includes antigen-binding fragments thereof. In certain aspects, the antibody molecule includes two variable light (VL) and two variable heavy (VH) chains. In certain aspects, the antibody molecule includes heavy chain and light chain constant regions as well. The heavy and light chain constant regions may be from a human antibody, e.g., human IgG1 antibody. The human IgG1 heavy chain (HC) constant region may be modified to include mutations that reduce antibody dependent cellular cytotoxicity (ADCC). In addition, or alternatively, the two VH chains may each be conjugated to a different human IgG1 HC constant region where the individual human IgG1 HC constant region has substitutions that favour formation of dimers between the different human IgG1 HC constant regions. Such HC regions are described in further detail herein. In certain aspects, where the antibody molecule is a bispecific antibody molecule, one of the human IgG1 HC constant regions may include substitutions to introduce one or more amino acids having a positively-charged side chain and the other human IgG1 HC constant region may include substitutions to introduce one or more amino acids having a negatively-charged side chain to favour formation of dimers between the two different HCs.

In certain aspects, the antibody molecule comprises HCDRs 1-3 and/or LCDRs 1-3 of a pair of VH region and VL region of an antibody listed in Table 2. In one aspect, the antibody molecule comprises the HCDRs 1-3 and/or LCDRs 1-3 of the G2.248 antibody listed in Table 2. In one aspect, the antibody molecule comprises the HCDRs 1-3 and/or LCDRs 1-3 of the G2.255 antibody listed in Table 2. In one aspect, the antibody molecule comprises the HCDRs 1-3 and/or LCDRs 1-3 of the G2.256 antibody listed in Table 2. In one aspect, the antibody molecule comprises the HCDRs 1-3 and/or LCDRs 1-3 of the G2.65 antibody listed in Table 2. In one aspect, the antibody molecule comprises the HCDRs 1-3 and/or LCDRs 1-3 of the G2.30 antibody listed in Table 2. In one aspect, the antibody molecule comprises the HCDRs 1-3 and/or LCDRs 1-3 of the G2.173 antibody listed in Table 2. In one aspect, the antibody molecule comprises the HCDRs 1-3 and/or LCDRs 1-3 of the G2.333 antibody, the G2.343 antibody, the G2.636 antibody, the G2.629 antibody, the G2.643 antibody, the G2.420 antibody, or the G2.631 antibody listed in Table 2. In one aspect, the antibody molecule comprises the HCDRs 1-3 and/or LCDRs 1-3 of the G2.636 antibody listed in Table 2. In one aspect, the antibody molecule comprises the HCDRs 1-3 and/or LCDRs 1-3 of the G2.318 antibody listed in Table 2.

In certain aspects, the antibody comprises HCDRs 1-3 and/or LCDRs 1-3 of a pair of VH region and VL region of an antibody listed in Table 2 and lowers IC50 of a chemotherapeutic agent by a factor of 5 or more, factor of 6 or more, factor of 7 or more, factor of 8 or more, factor of 9 or more, ore factor of 10 or more, e.g., by a factor of 5 to 10.

EC50 may be the antibody concentration that produces 50% maximal response (e.g., the response is the binding of the antibody to its antigen). In one aspect, the antibody has an EC50 of 100 nM or lower and/or EC50 that is at least half of the EC50 of an anti-ABCG2 antibody such as 5D3 and comprises the HCDRs 1-3 and/or LCDRs 1-3 of the G2.248 antibody listed in Table 2. In one aspect, the antibody has an EC50 of 100 nM or lower and/or EC50 that is at least half of the EC50 of an anti-ABCG2 antibody such as 5D3 and comprises the HCDRs 1-3 and/or LCDRs 1-3 of the G2.255 antibody listed in Table 2. In one aspect, the antibody has an EC50 of 100 nM or lower and/or EC50 that is at least half of the EC50 of an anti-ABCG2 antibody such as 5D3 and comprises the HCDRs 1-3 and/or LCDRs 1-3 of the G2.256 antibody listed in Table 2. In one aspect, the antibody has an EC50 of 100 nM or lower and/or EC50 that is at least half of the EC50 of an anti-ABCG2 antibody such as 5D3 and comprises the HCDRs 1-3 and/or LCDRs 1-3 of the G2.65 antibody listed in Table 2. In one aspect, the antibody has an EC50 of 100 nM or lower and/or EC50 that is at least half of the EC50 of an anti-ABCG2 antibody such as 5D3 and comprises the HCDRs 1-3 and/or LCDRs 1-3 of the G2.30 antibody listed in Table 2. In one aspect, the antibody has an EC50 of 100 nM or lower and/or EC50 that is at least half of the EC50 of an anti-ABCG2 antibody such as 5D3 and comprises the HCDRs 1-3 and/or LCDRs 1-3 of the G2.173 antibody listed in Table 2.

In some embodiments, the antibody comprises a VL region and a VH region that are present in separate polypeptides; in other embodiments, the VL region and a VH region are contained within a single polypeptide.

The antibody of the present disclosure may include a humanized light chain, a humanized heavy chain, or both. In certain aspects, the antibody may be a humanized antibody comprising a VH region as set forth for the G2.173 humanized 1, G2.173 humanized 1, or G2.173 humanized 1 antibody in Table 2. In certain aspects, the antibody may be a humanized antibody comprising a VL region as set forth for the G2.173 humanized 1, G2.173 humanized 1, or G2.173 humanized 1 antibody in Table 2. In certain aspects, the antibody may be a humanized antibody comprising a VH and a VL region as set forth for the G2.173 humanized 1, G2.173 humanized 1, or G2.173 humanized 1 antibody in Table 2.

The antibody of the present disclosure may be selected from the group consisting of an Ig monomer, a Fab fragment, a $F(ab')_2$ fragment, a Fd fragment, a scFv, a scAb, a dAb, and a Fv.

Multi-Specific Antibodies

In certain aspects, the antibody of the present disclosure is a multi-specific capable of binding epitopes present on two different target proteins. The number of different target proteins, and thus different epitopes, bound by a multi-specific antibody may vary and may be two (i.e., bispecific), three (tri-specific), four, or greater.

In certain aspects, the antibody of the present disclosure is a multi-specific (e.g., a bispecific) antibody capable of binding at least two different epitopes, where one of the epitopes is on ABCG2 (e.g., human ABCG2) and the other epitope is on a tumor-associated antigen (TAA) expressed on the cell surface of a cancer cell. In another aspect, a multi-specific antibody of the present disclosure binds to human ABCG2 and to the efflux pump MDR-1. In certain aspects, the VH and VL chains of the bispecific antibodies of the present disclosure are selected such that the antibody binds to a cell, e.g., a cancer cell, expressing both antigens but shows substantially reduced binding to a cell that expresses only one of the antigens.

In certain aspects, the VH and VL chains of the bispecific antibodies of the present disclosure are selected such that the antibody binds to a cell that overexpresses both of the antigens and shows substantially less binding to cells that express both antigens at normal levels or express or overexpress only one of the antigens. Such antibodies bind specifically to cancer cells that overexpress both antigens and thus have minimal off-target effects due to decreased binding to normal cells. As used herein, the term overexpressed is meant to encompass an expression level that is higher than that detected in a normal cell. For example, a cancer cell overexpressing a TAA expresses a level of the TAA that is higher than the level of the TAA in a normal cell of the same type as the cancer cell, e.g., an epithelial cell. A normal cell may not express a TAA or may express a certain level of the TAA. A cancer cell may overexpress the TAA as compared to the expression level in a normal cell of the same type.

A tumor-associated antigen (also referred to herein as a cancer-associated antigen) means an antigen that is overexpressed in a cancer cell as compared to the expression level in a non-cancerous cell of the same type. For example, the TAA may be an antigen that is not expressed at detectable levels in a normal cell and is expressed in cancer cells, where the normal and cancer cells are the same cell type, e.g., epithelial cells. In other aspects, a TAA is an antigen that is expressed in normal cells but is expressed at higher levels in cancer cells. The TAA may be expressed on the cell surface of a mammalian cancer cell. In certain aspects, the TAA may be CD47, PDL1, erbB-1, erbB-2, or EGFR. A tumor-associated antigen may be a neoantigen. Neoantigens are a class of tumor antigens that arise from a tumor-specific mutation(s) which alters the amino acid sequence of encoded proteins as compared to the amino acid sequence of the unmutated protein.

In certain aspects, the bispecific antibody specifically binds to a cancer cell that overexpresses both ABCG2 and, efflux pump MDR-1 or a cancer-associated antigen. In certain aspects, the bispecific antibody binds to a cancer cell that overexpresses both ABCG2 and MDR-1 and shows substantially less binding to a cell that does not overexpresses both ABCG2 and MDR-1.

In certain aspects, the bispecific antibody specifically binds to a cancer cell that overexpresses both ABCG2 and a TAA. In certain aspects, the bispecific antibody binds to a cancer cell that overexpresses both ABCG2 and a TAA and shows substantially less binding to a cell that does not overexpresses both ABCG2 and the TAA.

In certain aspects, a bispecific antibody of the present disclosure can be selected based on binding to a cell that expresses both ABCG2 and a TAA or MDR-1 at a level that is 2× or more (e.g., at least 3×, 4×, 5×, 10×, or more) than that expressed by normal cells and shows substantially less binding to the normal cell or to a cell overexpressing only one of ABCG2 and a TAA or MDR-1.

In certain aspects, the bispecific antibody increases sensitivity of cancer cells to treatment with a chemotherapeutic agent thereby lowering the IC50 of the chemotherapeutic agent by at least a factor of 2 when co-administered with the multi-specific antibody as compared to the IC50 of the chemotherapeutic agent when co-administered with an anti-ABCG2 monospecific bivalent antibody. The IC50 may be measured by a method as provided herein. The chemotherapeutic agent may be topotecan. The cancer cell may be a drug-resistant cancer cell. In certain aspects, the multi-specific antibodies of the present disclosure may lower the IC50 of the chemotherapeutic agent by factor of 5 or more, e.g., factor of 6 or more, factor of 7 or more, factor of 8 or more, factor of 9 or more, ore factor of 10 or more, e.g., by a factor of 5 to 10.

In certain aspects, the bispecific antibody may have in vivo cell killing activity, e.g., reduction of tumor volume even in absence of administration of a chemotherapeutic agent, such as, topotecan.

In some embodiments, multi-specific antibodies, e.g., bispecific antibodies, of the present disclosure may include a common light chain. As used herein, the term "common light chain" will generally refer to the use, and incorporation, of two copies of the same light chain into the multi-specific antibody. Put another way, a light chain, in the assembled multi-specific antibody, will associate with the ABCG2-specific heavy chain and a second copy of the same light chain will associate with the TAA-specific heavy chain or the MDR-1 antigen specific heavy chain. The common light chain may be from an anti-ABCG2 antibody, such as, an antibody having a VL chain comprising the LCDRs1-3 of the antibodies listed in Table 2, e.g., G2.248, G2.255, G2.256, G2.65, G2.302, G2.173, G2.173.humanized 1, G2.173.humanized 2, or G2.173.humanized 3 antibody. In other aspects, the common light chain may be from an anti-MDR-1 antibody, such as, MRK16 or 15D3. In other aspects, the common light chain may be from an unrelated antibody, an antibody library or a source of synthetically designed or in vitro generated antibodies. In another example, a bispecific antibody may not include a common light chain and instead include a first heavy chain and a first light chain that bind to G2 and a second heavy chain and a second light chain that bind to another antigen.

Bispecific Antibody Against ABCG2 and MDR1

In certain aspects, a bispecific antibody molecule that binds ABCG2 and MDR1 may include two identical variable light (VL) chains, a first variable heavy (VH) chain, and a second VH chain, wherein the VL chains each comprise an antigen-binding site for MDR1, the first VH chain comprises an antigen-binding site for MDR1, and the second VH chain comprises an antigen-binding site for ABCG2, and wherein the second VH chain binds ABCG2 when paired with one of the light chains. In certain aspects, the second VH chain comprises HCDRs1-3 of the VH chain of an anti-G2 antibody listed in Table 2 and second VH chain comprises HCDRs1-3 of the VH chain of the anti-MDR1 antibody, such as 15D3, and the common light chain comprises LCDRs 1-3 of the VL region of the anti-MDR1 antibody 15D3 or another anti-MDR1 antibody, such as MRK16.

In certain aspects, the first VH chain of the bispecific antibody comprises HCDRs 1-3 of a VH chain from an anti-MDR1 antibody, such as 15D3, wherein HCDR1 comprises the sequence: GFTFSRYTMS (SEQ ID NO:419), HCDR2 comprises the sequence: VATISSGGGNTYYPDSVKG (SEQ ID NO:362), VATISSGGGQTYYPDSVKG (SEQ ID NO:363), or VATISSGGGSTYYPDSVKG (SEQ ID NO:364), and HCDR3 comprises the sequence: ARYGAGDAWFAY (SEQ ID NO:365). In certain aspects, the second VH chain of the bispecific antibody comprises HCDRs 1-3 of a VH chain of an anti-ABCG2 antibody having a sequence set forth in Table 2. In certain aspects, the common VL chain of the bispecific antibody comprises LCDRs1-3 of the VL chain of the anti-MDR1 antibody 15D3.

In certain aspects, the second VH chain of the bispecific antibody comprises HCDRs 1-3 of a VH chain of the anti-ABCG2 antibody, G2.255 listed in Table 2. In certain aspects, the second VH chain comprises an amino acid sequence at least 90%, at least 95%, at least 99%, or 100% identical to the amino acid sequence:

(SEQ ID NO: 366)
EVMLVESGGALVKPGGSLKLSCAASGFTFSNNAMSWVRQTPETRLEWVAT

ITGGGSYTYYPDSVKGRFTISRDNARNTLYLQMSSLRSEDTATYYCASPD

GNYEGVLAYWGQGTLVTVS.

In certain aspects, the two identical VL chains comprise LCDRs 1-3 of the VL chain of the anti-MDR1 antibody 15D3 having the amino acid sequence:

(SEQ ID NO: 367)
DVLMTQTPLSLPVSLGDQASISCRSSQSIVHSTGNTYLEWYLQKPGQSPK

LLIYKVSNRFSGVPDRFSGSGSGTDFTLKISRLEAEDLGVYYCFQGSHFP

RTFGGGTRLEIK.

In certain aspects, the two identical VL chains comprise LCDRs 1-3 of an anti-MDR1 antibody, wherein:

(i) the LCDR1 comprises the sequence: RSSQSIVHSTGNTYLE (SEQ ID NO:368);

(ii) the LCDR2 comprises the sequence: KVSNRFS (SEQ ID NO:305); and (iii) the LCDR3 comprises the sequence: QGSHFPRT (SEQ ID NO:369).

In certain aspects, the two identical VL chains comprise LCDRs 1-3 of the VL chain of anti-MDR1 antibody having the amino acid sequence:

(SEQ ID NO: 370)
DVLMTQTPVSLSVSLGDQASISCRSSQSIVHSTGX$^2$TYLEWYLQKPGQSP

KLLIYKISNRFSGVPDRFSGSGSGTDFTLKISRVEAEDLGVYYCFQASHF

PRTFGGGTKLEIK, wherein X$^2$ is N, Q or S.

In certain aspects, the two identical VL chains comprise LCDRs 1-3 of an anti-MDR1 antibody, wherein:

(i) the LCDR1 comprises the sequence: RSSQSIVHSTGX$^2$TYLE (SEQ ID NO:371);

(ii) the LCDR2 comprises the sequence: KISNRFS (SEQ ID NO:372); and (iii) the LCDR3 comprises the sequence: FQASHFPRT (SEQ ID NO:373);

wherein X$^2$ is N, Q or S.

In certain aspects, a subject antibody may include a VH chain comprising HCDRs of a VH chain listed in Table 2 (e.g., the G2.255 antibody) and a VL chain comprising LCDRs of the MRK16 antibody or 15D3 antibody or a humanized version thereof. The HCDRs and the LCDRs may be as defined per Kabat nomenclature.

The amino acid sequence of the VL chain of the MRK16 antibody is as follows:

(SEQ ID NO: 374)
DVLMTQTPVSLSVSLGDQASISCRSSQSIVHSTGNTYLEWYLQKPGQSPK

LLIYKISNRFSGVPDRFSGSGSGTDFTLKISRVEAEDLGVYYCFQASHFP

RTFGGGTKLEIK.

The amino acid sequence of a humanized version of the VL chain of the MRK16 antibody is as follows:

(SEQ ID NO: 375)
DIVMTQTPLSSPVTLGQPASISCRSSQSIVHSTGX$^2$TYLEWYQQRPGQPP

RLLIYKISNRFSGVPDRFSGSGAGTDFTLKISRVEAEDVGVYYCFQASHF

PRTFGGGTKLEIKR, where X$^2$ is N, Q or S.

The VL chain LCORs1-3 may have the following sequences: CDR1 (RSSQSIVHSTG X$^2$TYLEW; SEQ ID NO:376), where X$^2$ is N, Q or S, CDR2 (KISNRFSG; SEQ ID NO:377), and CDR3 (FQASHFPRTF; SEQ ID NO:378).

In certain aspects, the VL chain may have a sequence that is at least 85%, 86%, 87%, 88%, 89%, 90%, 91%, 92%, 93%, 94%, 95%, 96%, 97%, 98%, 99%, or more, including 100%, identical to the MRK16 VL chain sequence: DVLMTQTPVSLSVSLGDQASISCRSSQSIVHSTGN-TYLEWYLQKPGQSPKLLIYKISNRFSG VPDRFS GSGSGTDFTLKISRVEAEDLGVYYCFQASHFPRTF GGGTKLEIK (SEQ ID NO:374) or a humanized version of this sequence, having the sequence: DIVMTQTP LSSPVTLGQPASISCRSSQSIVHSTGX$^2$TYLEWYQQ-RPGQPPRLLIYKISNRFSG VPDRFSGSGAGTDFTLKI SRVEAEDVGVYYCFQASHFPRTFGGGTKLEIKR (SEQ ID NO:375), where X$^2$ is N, Q or S.

In certain aspects, the LCDRs are from 15D3 VL chain:

(SEQ ID NO: 367)
DVLMTQTPLSLPVSLGDQASISCRSSQSIVHSTGNTYLEWYLQKPGQSPK

LLIYKVSNRFSGVPDRFSGSGSGTDFTLKISRLEAEDLGVYYCFQGSHFP

RTFGGGTRLEIK.

15D3 LCDRs 1-3 sequences defined per Kabat nomenclature are as follows:

(SEQ ID NO: 368)
15D3 LCDR1: RSSQSIVHSTGNTYLE (SEQ ID NO: 305)
15D3 LCDR2: KVSNRFS (SEQ ID NO: 369)
15D3 LCDR3: QGSHFPRT

In certain aspects, the VL chain may have a sequence that is at least 85%, 86%, 87%, 88%, 89%, 90%, 91%, 92%, 93%, 94%, 95%, 96%, 97%, 98%, 99%, or more, including 100%, identical to the 15D3 VL chain sequence:

(SEQ ID NO: 367)
DVLMTQTPLSLPVSLGDQASISCRSSQSIVHSTGNTYLEWYLQKPGQSPK

LLIYKVSNRFSGVPDRFSGSGSGTDFTLKISRLEAEDLGVYYCFQGSHFP

RTFGGGTRLEIK.

In certain aspects, a subject antibody may include a VL chain comprising LCDRs of a VL chain listed in Table 2 and a VH chain comprising HCDRs of the MRK16 antibody or 15D3 antibody or a humanized version thereof. The HCDRs and the LCDRs may be as defined per Kabat nomenclature.

The amino acid sequence of the VH chain of the MRK16 antibody is as follows:

(SEQ ID NO: 379)
EVILVESGGGLVKPGGSLKLSCAASGFTFSSYTMSWVRQTPEKRLEWVAT

ISSGGGNTYYPDSVKGRFTISRDNAKNNLYLQMSSLRSEDTALYYCARYY

RYEAWFASWGQGTLVTVSA.

The amino acid sequence of the VH chain of the 15D3 antibody is as follows:

```
                                           (SEQ ID NO: 380)
EVKVVESGGVLVRPGGSLKLSCAASGFTFSRYTMSWVRQTPEKRLEWVAT

ISSGGGNTYYPDSVKGRFTVSRDNAMSSLYLQMSSLRSEDTALYYCARYG

AGDAWFAYWGQGTLVTVSS.
```

The amino acid sequence of a humanized version of the VH chain of the 15D3 antibody is as follows: EVQLVESGGVVVQPGGSLRLSCAASGFTFSRYTMSWVRQ AP GK GLEWVATISSG GG$X^2$TYYPDSVKGRFTVSRDNSK NSLYLQMNSLRTEDTALYYCARYGAGDAWFAY WGQG TLVTVSSA (SEQ ID NO:381), wherein $X^2$ is N, Q, or S.

15D3 HCDRs 1-3 sequences defined per Kabat nomenclature are as follows:

15D3 HCDR1: RYTMS (SEQ ID NO:382);

15D3 HCDR2: TISSGGG $X^2$TYYPDSVKG (SEQ ID NO:383), wherein $X^2$ is N, Q or S

15D3 HCDR3: YGAGDAWFAY (SEQ ID NO:384) In certain aspects, the VH chain may have a sequence that is at least 85%, 86%, 87%, 88%, 89%, 90%, 91%, 92%, 93%, 94%, 95%, 96%, 97%, 98%, 99%, or more, including 100%, identical to the 15D3 VH chain sequence:

EVKVVESGGVLVRPGGSLKLSCAASGFTFSRYTMSWVRQTPEKRLEWVATISSGG GNTYYPDSVKGRFTVSRDNAMSSLYLQM SSLRSEDTALYYCARYGAGDAWFAYWGQGTL VTVSS (SEQ ID NO:380), or a humanized version thereof having the sequence:

EVQLVESGGVVVQPGGSLRLSCAASGFTFSRYT MSWVRQAPGKGLEWVATISSG GG$X^2$TY YPD SVK GRFTVSRDNSKNSLYLQMNSLRTEDTALY YCARYGAGDAWFAYWGQG TLVTVSSA (SEQ ID NO:381), wherein $X^2$ is N, Q, or S.

In certain aspects, the second VH chain comprises a humanized version of the VH chain of an antibody listed in Table 2 and the second VH chain comprises a humanized version of the VH chain of the anti-MDR1 antibody 15D3, where the humanized 15D3 VH chain has the sequence:

EVQLVESGGVVVQPGGSLRLSCAASGFTFSRYTMSWVRQAPGKGLEWVATISSG GGNTYYPDSVKGRFTVSRDNSKNSLYLQMNSLRTEDTALYYCARYGAGDAWFAYWGQG TLVTVSS (SEQ ID NO:385);

EVQLVESGGVVVQPGGSLRLSCAASGFTFSRYTMSWVRQAPGKGLEWVATISSG GGQTYYPDSVKGRFTVSRDNSKNSLYLQMNSLRTEDTALYYCARYGAGDAWFAYWGQG TLVTVSS (SEQ ID NO:386); or

EVQLVESGGVVVQPGGSLRLSCAASGFTFSRYTMSWVRQAPGKGLEWVATISSG GGSTYYPDSVKGRFTVSRDNSKNSLYLQMNSLRTEDTALYYCARYGAGDAWFAYWGQGT LVTVSS (SEQ ID NO:387); and a common light chain comprising LCDRs1-3 of the VL region of the anti-MDR1 antibody 15D3.

In certain aspects, the bispecific antibody binds to MDR1 and ABCG2 and lowers the IC50 of a chemotherapeutic agent by factor of 2 or more (e.g., 3, 4, 5, 6, 7, 8, 9, 10, or more) and comprises a common light chain, a VH chain comprising HCDRs from a VH chain listed in Table 2 and a VH chain comprising HCDRs from an anti-MDR1 antibody, such as, 15D3. The common light chain may include LCDRs from a VL chain listed in Table 2 (e.g., the VL of an antibody in Table 2 from which the VH HCDRs are derived) or from an anti-MDR1 antibody, such as, MRK16 or 15D3. In certain aspects, the chemotherapeutic agent is topotecan.

Bispecific Antibody Against ABCG2 and TAA

Also provided herein are bispecific antibodies having at least one or more properties as described above. In certain aspects, a bispecific antibody molecule of the present disclosure binds ATP Binding Cassette Subfamily G Member 2 (ABCG2) and a tumor associated antigen (TAA), the antibody molecule comprising two identical variable light (VL) chains, a first variable heavy (VH) chain, and a second VH chain, wherein the VL chains each comprise an antigen-binding site for ABCG2, the first VH chain comprises an antigen-binding site for ABCG2, and the second VH chain comprises an antigen-binding site for the TAA, and wherein the second VH chain binds TAA when paired with one of the light chains, or wherein the VL chains each comprise an antigen-binding site for the TAA, the first VH chain comprises an antigen-binding site for ABCG2, and the second VH chain comprises an antigen-binding site for the TAA, and wherein the first VH chain binds ABCG2 when paired with one of the light chains. The TAA may be CD47, PDL1, EGFR, erbB-1, or erbB-2.

In certain aspects, the VL chains each comprise an antigen-binding site for ABCG2, the first VH chain comprises an antigen-binding site for ABCG2, and the second VH chain comprises an antigen-binding site for the TAA, and wherein the second VH chain binds TAA when paired with one of the light chains.

In certain aspects, the first VH chain comprises heavy chain complementarity determining regions 1-3 (HCDRs1-3) of an anti-ABCG2 antibody listed in Table 2.

In certain aspects, the first VH chain comprises heavy chain complementarity determining regions 1-3 (HCDRs1-3), wherein the HCDR1 comprises the sequence: DDYVH (SEQ ID NO:85); the HCDR2 comprises the sequence: RIDPANGNTRYAPKFRG (SEQ ID NO:115); and the HCDR3 comprises the sequence: PLWVGGFAY (SEQ ID NO:157) or wherein the first VH chain comprises an amino acid sequence at least 90%, at least 95%, or a 100% identical to the amino acid sequence:

```
                                           (SEQ ID NO: 16)
QVQLQQSGADLVRPGASVKLSCTASGFNIKDDYVHWVKQRPEQGLEWIGR
IDPANGNTRYAPKFRGKATMTADTSSNTAYLQLSSLTSADTAVYYCSPPL
WGGFAYWGQGTLVTVSS,
or

                                           (SEQ ID NO: 17)
EVQLVQSGAEVKKPGASVKVSCKASGFNIKDDYVHWVRQAPGQGLEWIGR
IDPANGNTRYAPKFRGRATMTADTSISTAYMELSRLRSDDTAVYYCSPPL
WVGGFAYWGQGTLVTVSS,
or

                                           (SEQ ID NO: 18)
EVQLVQSGAEVKKPGASVKVSCKASGFNIKDDYVHWVRQAPGQGLEWIGR
IDPAQGNTRYAPKFRGRATMTADTSISTAYMELSRLRSDDTAVYYCSPPL
WVGGFAYWGQGTLVTVSS,
or

                                           (SEQ ID NO: 19)
EVQLVQSGAEVKKPGASVKVSCKASGFNIKDDYVHWVRQAPGQGLEWIGR
IDPASGNTRYAPKFRGRATMTADTSISTAYMELSRLRSDDTAVYYCSPPL
WVGGFAYWGQGTLVTVSS.
```

In some aspects, the antigen-binding site of the two VL chains comprises light chain CDRs 1-3 (LCDRs 1-3) of an antibody listed in Table 2.

In some aspects, the antigen-binding site of the two VL chains comprises, LCDR1 comprising the sequence: RSSQSLVHSDVNTYLH (SEQ ID NO:270), LCDR2 comprising the sequence: KVSNRFS (SEQ ID NO:305), and LCDR3 comprising the sequence: SQTTHVPYT (SEQ ID NO:334), or wherein the VL chain comprises an amino acid sequences at least 90%, at least 95%, or a 100% identical to the amino acid sequence:

(SEQ ID NO: 199)
DVVMTQTPLSLPVSLGDQASISCRSSQSLVHSDVNTYLHWYLQRPGQSPK
LLIYKVSNRFSGVPDRFSGSGSGTDFTLKISRVESEDLGIYFCSQTTHVP
YTFGGGTKLEIK,
or (SEQ ID NO: 200)
DVVMTQSPLSLPVTLGQPASISCRSSQSLVHSDVNTYLHWYQQRPGQSPR
LLIYKVSNRFSGVPDRFSGSGSGTDFTLKISRVEAEDVGVYFCSQTTHVP
YTFGGGTKLEIK.

In certain aspects, the first VH chain comprises heavy chain complementarity determining regions 1-3 (HCDRs1-3), wherein the HCDR1 comprises the sequence: SGYIS; the HCDR2 comprises the sequence: WIYAGTGISNFNQKFTG; and the HCDR3 comprises the sequence: GARKTLDF or wherein the first VH chain comprises an amino acid sequence at least 90%, at least 95%, or a 100% identical to the amino acid sequence:

(SEQ ID NO: 15)
QGQMHQSGAELVKPGASVKLSCKTSGFTFNSGYISWLKQKPRQSLEWIAW

IYAGTGISNFNQKFTGKAQLTVDTSSSTAYMQLSSLTSADSAIYFCASGA

RKTLDFWGQGTSVTVSS.

In certain aspects, the antigen-binding site of the two VL chains comprises light chain CDRs 1-3 (LCDRs 1-3) of an antibody listed in Table 2.

In certain aspects, the antigen-binding site of the two VL chains comprises LCDR1 comprising the sequence:G2.65 KASDQINYWLA (SEQ ID NO:269), LCDR2 comprising the sequence: GATSLET (SEQ ID NO:10), and LCDR3 comprising the sequence: QQYWTTPYT (SEQ ID NO:333), or wherein the VL chain comprises an amino acid sequences at least 90%, at least 95%, or a 100% identical to the amino acid sequence:

(SEQ ID NO: 198)
DIQMTQSSSYLSVSVGGRVTITCKASDQINYWLAWYQQKPGNAPRLLISG

ATSLETGVPSRFSGSGSGKDYTLSITSFQTEDVATYYCQQYWTTPYTFGG

GTKVEIK

In some aspects, the TAA is EGFR and wherein the second VH chain comprises heavy chain complementarity determining regions 1-3 (HCDRs1-3) of the VH chain of the 6B3S antibody comprising the amino acid sequence:

(SEQ ID NO: 388)
QVQLQESGPGLVKPSQTLSLTCTVSGGSISSGDYYWSWIRQPPGKGLEWI

GYIYYSGSTDYNPSLKSRVTMSVDTSKNQFSLKVNSVTAADTAVYYCARV

SIFGVGTFDYWGQGTLVTVSS

In certain aspects, the bispecific antibody comprises the combination of the first VH chain comprising HCDRs 1-3, the second VH chain comprising HCDRs 1-3, and the common VL chain comprising LCDRs 1-3 as set out in the table below:

| 1st VH HCDRs 1-3 | 2nd VH HCDRs 1-3 | Common VL LCDRs1-3 | TAA |
|---|---|---|---|
| G2.248 HCDRs 1-3 | Trastuzumab HCDRs 1-3 | G2.248 LCDRs 1-3 | erbB-2 |
| G2.302 HCDRs 1-3 | Trastuzumab HCDRs 1-3 | G2.302 LCDRs 1-3 | erbB-2 |
| G2.65 HCDRs 1-3 | Necitumumab HCDRs 1-3 | G2.65 LCDRs 1-3 | erbB-1 |
| G2.248 HCDRs 1-3 | Necitumumab HCDRs 1-3 | G2.248 LCDRs 1-3 | erbB-1 |
| G2.248 HCDRs 1-3 | Atezolizumab HCDRs 1-3 | G2.248 LCDRs 1-3 | PD-L1 |
| G2.318 HCDRs 1-3 | Atezolizumab HCDRs 1-3 | G2.318 LCDRs 1-3 | PD-L1 |
| G2.248 HCDRs 1-3 | 5F9 HCDRs 1-3 | G2.248 LCDRs 1-3 | CD47 |
| G2.65 HCDRs 1-3 | 5F9 HCDRs 1-3 | G2.65 LCDRs 1-3 | CD47 |
| G2.255 HCDRs 1-3 | 5F9 HCDRs 1-3 | G2.255 LCDRs 1-3 | CD47 |
| G2.318 HCDRs 1-3 | 5F9 HCDRs 1-3 | G2.318 LCDRs 1-3 | CD47 |
| G2.318 HCDRs 1-3 | Cetuximab HCDRs 1-3 | G2.318 LCDRs 1-3 | EGFR |

In addition to binding to ABCG2, the bispecific antibody binds to the TAA listed in the Table. The HCDRs for the anti-G2 antibodies may be as set forth in Table 2. The sequences for the 2nd VH region of the bispecific antibody are set forth below:

Trastuzumab heavy chain:
(SEO ID NO: 389)
EVQLVESGGGLVQPGGSLRLSCAASGFNIKDTYIHWVRQAPGKGLEWVAR

IYPTNGYTRYADSVKGRFTISADTSKNTAYLQMNSLRAEDTAVYYCSRWG

GDGFYAMDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQT

YICNVNHKPSNTKVDKKVEPKSCDKTHTCPPCPAPELLGGPSVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPGK

VH region is underlined. CDRs are as per Kabat nomenclature and are indicated in bold.

Necitumumab heavy chain:
(SEQ ID NO: 390)
QVQLQESGPGLVKPSQTLSLTCTVSGGSISSGDYYWSWIRQPPGKGLEWI

GYIYYSGSTDYNPSLKSRVTMSVDTSKNQFSLKVNSVTAADTAVYYCARV

SIFGVGTFDYWGQGTLVTVSSASTKGPSVLPLAPSSKSTSGGTAALGCLV

KDYFPEPVTVSWNSGALTSGVHTFPAVLQSSGLYSLSSVVTVPSSSLGTQ

TYICNVNHKPSNTKVDKRVEPKSCDKTHTCPPCPAPELLGGPSVFLFPPK

PKDTLMISRTPEVTCVVVDVSHEDPEVKFNWYVDGVEVHNAKTKPREEQY

NSTYRVVSVLTVLHQDWLNGKEYKCKVSNKALPAPIEKTISKAKGQPREP

QVYTLPPSREEMTKNQVSLTCLVKGFYPSDIAVEWESNGQPENNYKTTPP

VLDSDGSFFLYSKLTVDKSRWQQGNVFSCSVMHEALHNHYTQKSLSLSPG

K

VH region is underlined. HCDRs1-3 as per Kabat nomenclature are indicated in bold. The HCDRs 1-3 have the following sequence:

HCDR 1: GGSISSGDY (SEQ ID NO:421);
HCDR 2: YYSGS (SEQ ID NO:422); and
HCDR 3: VSIFGVGTFDY (SEQ ID NO:423).

```
Atezolizumab heavy chain:
                                        (SEQ ID NO: 391)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYAST

YRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPGK
```

VH region is underlined and has the following sequence: EVQLVESGGGLVQPGGSLRLSCAASGFTFSD-SWIHWVRQAPGKGLEWVAWISPYGGSTY YADSVKGRFTISADTSKNTAYLQMNSLRAEDTAVYY-CARRHWPGGFDYWGQGTLVTVSS (SEQ ID NO:427). HCDRs1-3 as per Kabat nomenclature are indicated in bold. The HCDRs 1-3 have the following sequence:

HCDR 1: GFTFSDS (SEQ ID NO:424);
HCDR 2: SPYGGS (SEQ ID NO:425); and
HCDR 3: RHWPGGFDY (SEQ ID NO:426).

```
5F9 VH chain:
                                        (SEQ ID NO: 392)
QVQLVQSGAEVKKPGASVKVSCKASGYTFTNYNMHWVRQAPGQRLEWMG

TIYPGNDDTSYNQKFKDRVTITADTSASTAYMELSSLRSEDTAVYYCAR

GGYRAMDYWGQGTLVTVSS
```

HCDRs1-3 as per Kabat are indicated in bold and are underlined.

In some aspects, a bispecific antibody that binds to both G2 and a TAA may comprise a first VH chain comprising HCDRs1-3 from an anti-G2 antibody listed in Table 2 (e.g., G2.255), a second VH chain comprising HCDRs1-3 from an anti-TAA antibody (e.g., anti-CD47 antibody 5F9) and a common VL chain, where the VL chain comprises LCDRS1-3 from an anti-MDR1 antibody (e.g., MRK16).

In some aspects, a bispecific antibody that binds to both G2 and a TAA may comprise: a first VH chain comprising HCDRs1-3 from an anti-G2 antibody listed in Table 2, a first VL chain comprising LCDRs1-3 from an anti-G2 antibody listed in Table 2, where the HCDRs1-3 and LCDRs1-3 may be from the VH and VL chain, respectively, of the same antibody or two different antibodies listed in Table 2; and a second VH chain comprising HCDRs1-3 from an anti-TAA antibody such as an anti-TAA antibody described herein and a second VL chain comprising LCDRs1-3 from an anti-TAA antibody such as an anti-TAA antibody described herein, where the HCDRs1-3 and LCDRs1-3 may be from the VH and VL chain, respectively, of the same anti-TAA antibody or two different anti-TAA antibodies, wherein the first VH and first VL chains bind to G2 and the second VH and VL chains bind to the TAA.

In some aspects, a subject antibody is a recombinant or modified antibody, e.g., a chimeric, humanized, deimmunized or an in vitro generated antibody. The term "recombinant" or "modified" antibody as used herein is intended to include all antibodies that are prepared, expressed, created, or isolated by recombinant means, such as (i) antibodies expressed using a recombinant expression vector transfected into a host cell; (ii) antibodies isolated from a recombinant, combinatorial antibody library; (iii) antibodies isolated from an animal (e.g. a mouse) that is transgenic for human immunoglobulin genes; or (iv) antibodies prepared, expressed, created, or isolated by any other means that involves splicing of human immunoglobulin gene sequences to other DNA sequences. Such recombinant antibodies include humanized, CDR grafted, chimeric, deimmunized, and in vitro generated antibodies; and can optionally include constant regions derived from human germline immunoglobulin sequences.

Modified antibodies may include modified domains, including where any antibody domain may be modified from a naturally occurring form. In some embodiments, a modified antibody may include a modified heavy chain, including a modified Fc domain, including a modified CH2 and/or modified CH3 domain. In some instances, modified Fc domains may employ electrostatic steering effects, including but not limited to e.g., through the use of the procedures described in Gunasekeran et al, (2010) Journal of Biological Chemistry 285, 19637-19646; the disclosure of which is incorporated herein by reference in its entirety. In some instances, a bispecific antibody is assembled through charge pair substitutions at the CH3 domain, including but not limited to e.g., where one heavy chain is modified to contain K392D and K409D substitutions (referred to as "DD") and the other heavy chain is modified to contained E356K and D399K substitutions (referred to as "KK"). Charge pair substituted chains may preferentially form a heterodimer with one another. The numbering of the amino acid substitutions is per EU numbering system for Ig HCs.

In some instances, an antibody of the present disclosure includes charge pair substitutions. In some instances, an antibody of the present disclosure does not include charge pair substitutions. In some instances, an alternative means of promoting preferential heterodimer formation of desired chains may be employed.

In some instances, a modified heavy chain may include a knob-into-hole modification. "Knobs-into-holes" amino acid modification is a rational design strategy in antibody engineering, used for heterodimerization of the heavy chains, in the production of multi-specific antibodies, including bispecific IgG antibodies. For example, in incorporating the knobs-into-holes strategy into a bispecific antibody made from two monoclonal antibodies of different specificities, amino acid changes are engineered in order to create a "knob" on the CH3 of the heavy chain of monoclonal antibody 1 (mAb1) and a "hole" on the CH3 of the heavy chain of monoclonal antibody 2 (mAb2). The knob may be represented by a large amino acid, such as e.g., a tyrosine (Y), whereas the hole may be represented by small amino acid, such as a threonine (T). For example, a knobs-into-holes pair modification may be created a T22Y substitution in a first CH3 domain and Y86T substitution in the partner CH3 domain. Examples of knobs-into-holes modifications are described in Carter, J. Immunol. Methods, 248(1-2):7-15 (2001); Ridgway, J. B. et al. Protein Eng. 9(7):617-2 (1996); and Merchant, A. M. et al. Nat. Biotechnol. 16(7):677-81 (1998); the disclosures of which are incorporated herein in their entirety. In antibodies generated from paired knob-into-hole modified domains the bispecific heterodimer will generally represent the major fraction. The numbering of the amino acid substitutions is per EU numbering system for Ig HCs.

As noted above, the subject anti-ABCG2 antibody specifically binds one or more epitopes of ABCG2. Thus, the epitope is an ABCG2 epitope. The size of a ABCG2 epitope bound by anti-ABCG2 antibody may vary, including where the ABCG2 epitope is formed by a polypeptide having a contiguous stretch of an ABCG2 sequence that may range from 3 aa or less to 12 aa or more, including but not limited to e.g., 4 aa, 5 aa, 6 aa, 7 aa, 8 aa, 9 aa, 10 aa, 11 aa, 12 aa, 4 aa to 10 aa, 5 aa to 10 aa, 6 aa to 10 aa, 4 aa to 8 aa, 5 aa to 8 aa, 6 aa to 8 aa, etc.

In some embodiments, the ABCG2 epitope can be formed by a polypeptide having at least about 75%, at least about 80%, at least about 85%, at least about 90%, at least about 95%, at least about 98%, at least about 99%, or 100%, amino acid sequence identity to a contiguous stretch of a ABCG2 sequence, including but not limited to e.g., the human ABCG2 sequence:

```
MSSSNVEVFIPVSQGNTNGFPATASNDLKAFTEGAVLSFHNICYRVKLK
SGFLPCRKPVEKEILSNINGIMKPGLNAILGPTGGGKSSLLDVLAARKD
PSGLSGDVLINGAPRPANFKCNSGYVVQDDVVMGTLTVRENLQFSAALR
LATTMTNHEKNERINRVIQELGLDKVADSKVGTQFIRGVSGGERKRTSI
GMELITDPSILFLDEPTTGLDSSTANAVLLLLKRMSKQGRTIIFSIHQP
RYSIFKLFDSLTLLASGRLMFHGPAQEALGYFESAGYHCEAYNNPADFF
LDIINGDSTAVALNREEDFKATEIIEPSKQDKPLIEKLAEIYVNSSFYK
ETKAELHQLSGGEKKKKITVFKEISYTTSFCHQLRWWSKRSFKNLLGNP
QASIAQIIVTVVLGLVIGAIYFGLKNDSTGIQNRAGVLFFLTTNQCFSS
VSAVELFVVEKKLFIHEYISGYYRVSSYFLGKLLSDLLPMRMLPSIIFT
CIVYFMLGLKPKADAFFVMMFTLMMVAYSASSMALAIAAGQSVVSVATL
LMTICFVFMMIFSGLLVNLTTIASWLSWLQYFSIPRYGFTALQHNEFLG
QNFCPGLNATGNNPCNYATCTGEEYLVKQGIDLSPWGLWKNHVALACMI
VIFLTIAYLKLLFLKKYS (SEQ ID NO: 393), or the ECD1
(417-428) thereof: KNDSTGIQNRAG (SEQ ID NO: 1);
the ECD2 (499-506) thereof: LKPKADAF (SEQ ID NO:
2); the ECD3 (557-630) thereof:
NLTTIASWLSWLQYFSIPRYGFTALQHNEFLGQNFCPGLNATGNNPCNY
ATCTGEEYLVKQGIDLSPWGLWKNH (SEQ ID NO: 3); or a
```

*Mus musculus* ABCG2 sequence:

```
MSSSNDHVLVPMSQRNNNGLPRTNSRAVRTLAEGDVLSFHHITYRVKVK
SGFLVRKTVEKEILSDINGIMKPGLNAILGPTGGGKSSLLDVLAARKDP
KGLSGDVLINGAPQPAHFKCCSGYVVQDDVVMGTLTVRENLQFSAALRL
PTTMKNHEKNERINTIIKELGLEKVADSKVGTQFIRGISGGERKRTSIG
MELITDPSILFLDEPTTGLDSSTANAVLLLLKRMSKQGRTIIFSIHQPR
YSIFKLFDSLTLLASGKLVFHGPAQKALEYFASAGYHCEPYNNPADFFL
DVINGDSSAVMLNREEQDNEANKTEEPSKGEKPVIENLSEFYINSAIYG
```

-continued

```
ETKAELDQLPGAQEKKGTSAFKEPVYVTSFCHQLRWIARRSFKNLLGNP
QASVAQLIVTVILGLIIGAIYFDLKYDAAGMQNRAGVLFFLTTNQCFSS
VSAVELFVVEKKLFIHEYISGYYRVSSYFFGKVMSDLLPMRFLPSVIFT
CVLYFMLGLKKTVDAFFIMMFTLIMVAYTASSMALAIATGQSVVSVATL
LMTIAFVFMMLFSGLLVNLRTIGPWLSWLQYFSIPRYGFTALQYNEFLG
QEFCPGFNVTDNSTCVNSYAICTGNEYLINQGIELSPWGLWKNHVALAC
MIIIFLTIAYLKLLFLKKYS (SEQ ID NO: 394), or the
ECD1 (415-428) thereof: DLKYDAAGMQNRAG (SEQ ID
NO: 395); the ECD2 (499-506) thereof: LKKTVDAF
(SEQ ID NO: 396); the ECD3 (557-632) thereof:
NLRTIGPWLSWLQYFSIPRYGFTALQYNEFLGQEFCPGFNVTDNSTCVN
SYAICTGNEYLINQGIELSPWGLWKNH (SEQ ID NO: 397); a
non-human primate sequence, such as e.g., the
```

*Macaca fascicularis* (Crab-eating macaque) sequence:

```
MSSSNVEVFIPMSQENTNGFPTTTSNDRKAFTEGAVLSFHNICYRVKVK
SGFLPGRKPVEKEILSNINGIMKPGLNAILGPTGGGKSSLLDVLAARKD
PSGLSGDVLINGALRPTNFKCNSGYWQDDWMGTLTVRENLQFSAALRLP
TTMTNHEKNERINRVIQELGLDKVADSKVGTQFIRGVSGGERKRTSIGM
ELITDPSILFLDEPTTGLDSSTANAVLLLLKRMSKQGRTIIFSIHQPRY
SIFKLFDSLTLLASGRLMFHGPAQEALGYFESAGYHCEAYNNPADFFLD
IINGDSTAVALNREEDFKATEIIEPSKRDKPLVEKLAEIYVDSSFYKET
KAELHQLSGGEKKKKITVFKEISYTTSFCHQLRWVSKRSFKNLLGNPQA
SIAQIIVTVILGLVIGAIYFGLNNDSTGIQNRAGVLFFLTTNQCFSSVS
AVELFVVEKKLFIHEYISGYYRVSSYFFGKLLSDLLPMRMLPSIIFTCI
VYFMLGLKPTADAFFIMMFTLMMVAYSASSMALAIAAGQSVVSVATLLM
TICFVFMMIFSGLLVNLTTIASWLSWLQYFSIPRYGFTALQHNEFLGQN
FCPGLNATVNNTCNYATCTGEEYLTKQGIDLSPWGLWKNHVALACMIVI
FLTIAYLKLLFLKKYS (SEQ ID NO: 398), or the ECD1
(417-428) thereof: NNDSTGIQNRAG (SEQ ID NO:
399); the ECD2 (499-506) thereof: LKPTADAF
(SEQ ID NQ: 400); the ECD3 (557-630) thereof:
NLTTIASWLSWLQYFSIPRYGFTALQHNEFLGQNFCPGLNATVNNTCNY
ATCTGEEYLTKQGIDLSPWGLWKNH (SEQ ID NO: 401), or
```

*Pan troglodytes* ABCG2 sequence:

```
MSSSNVEVFIPMSQGNTNGFPATTSNDLKAFTEGAVLSFHNICYRVKLK
SGFLPCRKPVEKEILSNINGIMKPGLNAILGPTGGGKSSLLDVLAARKD
PSGLSGDVLINGAPRPANFKCNSGYVVQDDVVMGTLTVRENLQFSAALR
LPTTMTNHEKNERINRVIQELGLDKVADSKVGTQFIRGVSGGERKRTSI
GMELITDPSILFLDEPTTGLDSSTANAVLLLLKRMSKQGRTIIFSIHQP
RYSIFKLFDSLTLLASGRLMFHGPAQEALGYFESAGYHCEAYNNPADFF
LDIINGDSTAVALNREEDFKATEIIEPSKQDKPLIEKLAEIYVNSSFYK
```

-continued

ETKAELHQLSGGEKKKKITVFKEISYTTSFCHQLRWVSKRSFKNLLGNP
QASIAQIIVTVILGLVIGAIYFGLKNDSTGIQNRAGVLFFLTTNQCFSS
VSAVELFWEKKLFIHEYISGYYRVSSYFLGKLLSDLLPMRMLPSIIFTC
IVYFMLGLKPKADAFFVMMFTLMMVAYSASSMALAIAAGQSVVSVATLL
MTICFVFMMIFSGLLVNLTTIASWLSWLQYFSIPRYGFTALQHNEFLGQ
NFCPGLNATGNNPCNYATCTGEEYLVKQGIDLSPWGLWKNHVALACMIV
IFLTIAYLKLLFLKKYS (SEQ ID NO: 402), or the like.

In some embodiments, the ABCG2 epitope can be formed by a mutated ABCG2 polypeptide. The mutated ABCG2 polypeptide may be derived from a human ABCG2 polypeptide. The human ABCG2 polypeptide may include a mutation that results in the ABCG2 polypeptide having an open configuration. A mutant human ABCG2 polypeptide having an open configuration may include the substitution: E211Q, numbered with reference to the sequence of human ABCG2 polypeptide as provided herein. In certain aspects, a mutant human ABCG2 polypeptide having an open configuration may comprise an amino acid sequence that is at least 80% (e.g. at least 85%, at least about 90%, at least about 95%, at least about 98%, at least about 99%, or 100%) identical to the amino acid sequence:

(SEQ ID NO: 403)
MSSSNVEVFIPVSQGNTNGFPATASNDLKAFTEGAVLSFHNICYRVKLK
SGFLPCRKPVEKEILSNINGIMKPGLNAILGPTGGGKSSLLDVLAARKD
PSGLSGDVLINGAPRPANFKCNSGYVVQDDVVMGTLTVRENLQFSAALR
LATTMTNHEKNERINRVIQELGLDKVADSKVGTQFIRGVSGGERKRTSI
GMELITDPSILFLDQPTTGLDSSTANAVLLLLKRMSKQGRTIIFSIHQP
RYSIFKLFDSLTLLASGRLMFHGPAQEALGYFESAGYHCEAYNNPADFF
LDIINGDSTAVALNREEDFKATEIIEPSKQDKPLIEKLAEIYVNSSFYK
ETKAELHQLSGGEKKKKITVFKEISYTTSFCHQLRWWSKRSFKNLLGNP
QASIAQIIVTVVLGLVIGAIYFGLKNDSTGIQNRAGVLFFLTTNQCFSS
VSAVELFVVEKKLFIHEYISGYYRVSSYFLGKLLSDLLPMRMLPSIIFT
CIVYFMLGLKPKADAFFVMMFTLMMVAYSASSMALAIAAGQSVVSVATL
LMTICFVFMMIFSGLLVNLTTIASWLSWLQYFSIPRYGFTALQHNEFLG
QNFCPGLNATGNNPCNYATCTGEEYLVKQGIDLSPWGLWKNHVALACMI
VIFLTIAYLKLLFLKKYS.

In some embodiments, the mutated ABCG2 polypeptide may be derived from a human ABCG2 polypeptide that includes a mutation that results in the ABCG2 polypeptide having a closed configuration. A mutant human ABCG2 polypeptide having a closed configuration may include the substitution: K86M.S87A, K86M.S87A.Q126A, or K86M.S87A.Q126A.R246E, numbered with reference to the sequence of human ABCG2 polypeptide as provided herein. In certain aspects, a mutant human ABCG2 polypeptide having a closed configuration may comprise an amino acid sequence that is at least 80% (e.g. at least 85%, at least about 90%, at least about 95%, at least about 98%, at least about 99%, or 100%) identical to the amino acid sequence:

(SEQ ID NO: 404)
MSSSNVEVFIPVSQGNTNGFPATASNDLKAFTEGAVLSFHNICYRVKLKS
GFLPCRKPVEKEILSNINGIMKPGLNAILGPTGGGMASLLDVLAARKDPS
GLSGDVLINGAPRPANFKCNSGYVVQDDVVMGTLTVRENLQFSAALRLAT
TMTNHEKNERINRVIQELGLDKVADSKVGTQFIRGVSGGERKRTSIGMEL
ITDPSILFLDEPTTGLDSSTANAVLLLLKRMSKQGRTIIFSIHQPRYSIF
KLFDSLTLLASGRLMFHGPAQEALGYFESAGYHCEAYNNPADFFLDIING
DSTAVALNREEDFKATEIIEPSKQDKPLIEKLAEIYVNSSFYKETKAELH
QLSGGEKKKKITVFKEISYTTSFCHQLRWSKRSFKNLLGNPQASIAQIIV
TVVLGLVIGAIYFGLKNDSTGIQNRAGVLFFLTTNQCFSSVSAVELFVVE
KKLFIHEYISGYYRVSSYFLGKLLSDLLPMRMLPSIIFTCIVYFMLGLKP
KADAFFVMMFTLMMVAYSASSMALAIAAGQSVVSVATLLMTICFVFMMIF
SGLLVNLTTIASWLSWLQYFSIPRYGFTALQHNEFLGQNFCPGLNATGNN
PCNYATCTGEEYLVKQGIDLSPWGLWKNHVALACMIVIFLTIAYLKLLFL
KKYS;

(SEQ ID NO: 405)
MSSSNVEVFIPVSQGNTNGFPATASNDLKAFTEGAVLSFHNICYRVKLKS
GFLPCRKPVEKEILSNINGIMKPGLNAILGPTGGGMASLLDVLAARKDPS
GLSGDVLINGAPRPANFKCNSGYVVADDVVMGTLTVRENLQFSAALRLAT
TMTNHEKNERINRVIQELGLDKVADSKVGTQFIRGVSGGERKRTSIGMEL
ITDPSILFLDEPTTGLDSSTANAVLLLLKRMSKQGRTIIFSIHQPRYSIF
KLFDSLTLLASGRLMFHGPAQEALGYFESAGYHCEAYNNPADFFLDIING
DSTAVALNREEDFKATEIIEPSKQDKPLIEKLAEIYVNSSFYKETKAELH
QLSGGEKKKKITVFKEISYTTSFCHQLRWVSKRSFKNLLGNPQASIAQII
VTVVLGLVIGAIYFGLKNDSTGIQNRAGVLFFLTTNQCFSSVSAVELFWE
KKLFIHEYISGYYRVSSYFLGKLLSDLLPMRMLPSIIFTCIVYFMLGLKP
KADAFFVMMFTLMMVAYSASSMALAIAAGQSVVSVATLLMTICFVFMMIF
SGLLVNLTTIASWLSWLQYFSIPRYGFTALQHNEFLGQNFCPGLNATGNN
PCNYATCTGEEYLVKQGIDLSPWGLWKNHVALACMMFLTIAYLKLLFLKK
YS;

or (SEQ ID NO: 406)
MSSSNVEVFIPVSQGNTNGFPATASNDLKAFTEGAVLSFHNICYRVKLKS
GFLPCRKPVEKEILSNINGIMKPGLNAILGPTGGGMASLLDVLAARKDPS
GLSGDVLINGAPRPANFKCNSGYVVADDVVMGTLTVRENLQFSAALRLAT
TMTNHEKNERINRVIQELGLDKVADSKVGTQFIRGVSGGERKRTSIGMEL
ITDPSILFLDEPTTGLDSSTANAVLLLLKRMSKQGRTIIFSIHQPEYSIF
KLFDSLTLLASGRLMFHGPAQEALGYFESAGYHCEAYNNPADFFLDIING
FSTAVALNREEDFKATEIIEPSKQDKPLIEKLAEIYVNSSFYKETKAELH
QLSGGEKKKKITVFKEISYTTSFCHQLRWSKRSFKNLLGNPQASIAQIIV
TVVLGLVIGAIYFGLKNDSTGIQNRAGVLFFLTTNQCFSSVSAVELFVVE
KKLFIHEYISGYYRVSSYFLGKLLSDLLPMRMLPSIIFTCIVYFMLGLKP
KADAFFVMMFTLMMVAYSASSMALAIAAGQSVVSVATLLMTICFVFMMIF

-continued

```
SGLLVNLTTIASWLSWLQYFSIPRYGFTALQHNEFLGQNFCPGLNATGNN

PCNYATCTGEEYLVKQGIDLSPWGLWKNHVALACMIVIFLTIAYLKLLFL

KKYS.
```

A subject anti-ABCG2 antibody exhibits high affinity binding to ABCG2. For example, a subject anti-ABCG2 antibody binds to a human ABCG2 with an affinity of at least about $10^{-7}$ M, at least about $10^{-8}$ M, at least about $10^{-9}$ M, at least about $10^{-10}$ M, at least about $10^{-11}$ M, or at least about $10^{-12}$ M, or greater than $10^{-12}$ M. A subject anti-ABCG2 antibody binds to an epitope present on ABCG2 with an affinity of from about $10^{-7}$ M to about $10^{-8}$ M, from about $10^{-8}$ M to about $10^{-9}$ M, from about $10^{-9}$ M to about $10^{-10}$ M, from about $10^{-10}$ M to about $10^{-11}$ M, or from about $10^{-11}$ M to about $10^{-12}$ M, or greater than $10^{-12}$ M.

A subject anti-ABCG2 antibody exhibits substantially no binding to any epitopes formed by amino acids within other related, but sequence dissimilar, proteins such as related but sequence dissimilar EPs. Any binding of a subject anti-ABCG2 antibody to an epitope formed by amino acids within a related, but sequence dissimilar, protein is generally non-specific binding of a substantially lower affinity than the specific binding of the anti-ABCG2 antibody to the epitope on ABCG2. A substantially lower affinity is generally at least a 2 fold, 3 fold, 5 fold, 10 fold, 50 fold, 100 fold, 500 fold, or 1000 fold lower affinity.

A subject anti-ABCG2 antibody can reduce transport of molecules through an ABCG2 transporter, e.g., a human ABCG2. For example, a subject anti-ABCG2 antibody can reduce transport by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the degree of transport in the absence of the anti-ABCG2 antibody.

In some embodiments, a subject antibody comprises FR regions that are mammalian sequences, including e.g., rodent, non-human primate, and human sequences (e.g., encoded by the respective heavy chain FR-encoding sequences).

A subject antibody can comprise a heavy chain variable (VH) region comprising an amino acid sequence that is 85%, 86%, 87%, 88%, 89%, 90%, 91%, 92%, 93%, 94%, 95%, 96%, 97%, 98%, 99%, or more, including 100%, identical to a sequence for a VH region of a VH-VL pair of an antibody set forth in Table 2. The subject antibody can comprise a light chain variable (VL) region comprising an amino acid sequence that is 85%, 86%, 87%, 88%, 89%, 90%, 91%, 92%, 93%, 94%, 95%, 96%, 97%, 98%, 99%, or more, including 100%, identical to a sequence for a VL of the VH-VL region pair of the antibody set forth in Table 2.

Regions and/or chains of the subject antibodies may or may not be joined by one or more linker regions. Where present, the linker region can be from about 5 amino acids to about 50 amino acids in length, e.g., from about 5 aa to about 10 aa, from about 10 aa to about 15 aa, from about 15 aa to about 20 aa, from about 20 aa to about 25 aa, from about 25 aa to about 30 aa, from about 30 aa to about 35 aa, from about 35 aa to about 40 aa, from about 40 aa to about 45 aa, or from about 45 aa to about 50 aa in length.

Linkers suitable for use a subject antibody include “flexible linkers”. If present, the linker molecules are generally of sufficient length to permit some flexible movement between linked regions. The linker molecules are generally about 6-50 atoms long. The linker molecules may also be, for example, aryl acetylene, ethylene glycol oligomers containing 2-10 monomer units, diamines, diacids, amino acids, or combinations thereof. Other linker molecules which can bind to polypeptides may be used in light of this disclosure.

Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers $(G)_n$, glycine-serine polymers (including, for example, $(GS)_n$, $GSGGS_n$ (SEQ ID NO:407) and $GGGS_n$ (SEQ ID NO:408), where n is an integer of at least one), glycine-alanine polymers, alanine-serine polymers, and other flexible linkers known in the art. Glycine and glycine-serine polymers are of interest since both of these amino acids are relatively unstructured, and therefore may serve as a neutral tether between components. Glycine polymers are of particular interest since glycine accesses significantly more phi-psi space than even alanine, and is much less restricted than residues with longer side chains (see Scheraga, Rev. Computational Chem. 11173-142 (1992)). Exemplary flexible linkers include, but are not limited to GGSG (SEQ ID NO:409), GGSGG (SEQ ID NO:410), GSGSG (SEQ ID NO:411), GSGGG (SEQ ID NO:412), GGGSG (SEQ ID NO:413), GSSSG (SEQ ID NO:414), and the like. The ordinarily skilled artisan will recognize that design of a peptide conjugated to any elements described above can include linkers that are all or partially flexible, such that the linker can include a flexible linker as well as one or more portions that confer less flexible structure.

In other instances, the flexibility of the hinge region of an antibody of the present disclosure may be reduced by either mutating amino acid C220 to serine or any other natural amino acid, by removing C220, by removing the complete hinge, or by replacing the IgG1 hinge with an IgG3 hinge, an antibody is formed in which the light chains are connected via their C-terminal cysteines, analogous to the situation found in the human isotype IgA2m. This results in a reduced flexibility of the Fabs relative to the Fc and consequently reduced cross-linking capacity. Another strategy to reduce the flexibility of an IgG1 molecule is to replace the IgG1 hinge with the IgG2 hinge or IgG2-like hinge. Alternatively, a variant of the IgG1 hinge that resembles the IgG2 hinge can be introduced. This mutant (TH7A6-9) contains mutation T223C and two deletions (K222 and T225) in order to create a shorter hinge with an additional cysteine.

The substitution of mouse CDRs into a human variable domain framework can result in retention of their correct spatial orientation where, e.g., the human variable domain framework adopts the same or similar conformation to the mouse variable framework from which the CDRs originated. This can be achieved by obtaining the human variable domains from human antibodies whose framework sequences exhibit a high degree of sequence identity with the murine variable framework domains from which the CDRs were derived. The heavy and light chain variable framework regions can be derived from the same or different human antibody sequences. The human antibody sequences can be the sequences of naturally occurring human antibodies or can be consensus sequences of several human antibodies. See Kettleborough et al., Protein Engineering 4:773 (1991); Kolbinger et al., Protein Engineering 6:971 (1993).

Having identified the complementarity determining regions of the murine donor immunoglobulin and appropriate human acceptor immunoglobulins, the next step is to determine which, if any, residues from these components should be substituted to optimize the properties of the resulting humanized antibody. In general, substitution of human amino acid residues with murine should be minimized, because introduction of murine residues increases the risk of the antibody eliciting a human-anti-mouse-antibody (HAMA) response in humans. Art-recognized methods of determining immune response can be performed to monitor a HAMA response in a particular patient or during clinical trials. Patients administered humanized antibodies can be given an immunogenicity assessment at the beginning and throughout the administration of said therapy. The HAMA response is measured, for example, by detecting antibodies to the humanized therapeutic reagent, in serum samples from the patient using a method known to one in the art, including surface plasmon resonance technology (BIACORE) and/or solid-phase ELISA analysis. In many embodiments, a subject humanized antibody does not substantially elicit a HAMA response in a human subject.

Certain amino acids from the human variable region framework residues are selected for substitution based on their possible influence on CDR conformation and/or binding to antigen. The unnatural juxtaposition of murine CDR regions with human variable framework region can result in conformational restraints, which, unless corrected by substitution of certain amino acid residues, lead to loss of binding affinity.

The selection of amino acid residues for substitution can be determined, in part, by computer modeling. Computer hardware and software for producing three-dimensional images of immunoglobulin molecules are known in the art. In general, molecular models are produced starting from solved structures for immunoglobulin chains or domains thereof. The chains to be modeled are compared for amino acid sequence similarity with chains or domains of solved three-dimensional structures, and the chains or domains showing the greatest sequence similarity is/are selected as starting points for construction of the molecular model. Chains or domains sharing at least 50% sequence identity are selected for modeling, and preferably those sharing at least 60%, 70%, 80%, 90% sequence identity or more are selected for modeling. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

In some embodiments, a subject antibody comprises scFv multimers. For example, in some embodiments, a subject antibody is an scFv dimer (e.g., comprises two tandem scFv ($scFv_2$)), an scFv trimer (e.g., comprises three tandem scFv (scFvs)), an scFv tetramer (e.g., comprises four tandem scFv ($scFv_4$)), or is a multimer of more than four scFv (e.g., in tandem). The scFv monomers can be linked in tandem via linkers of from about 2 amino acids to about 15 amino acids in length, e.g., 2 aa, 3 aa, 4 aa, 5 aa, 6 aa, 7 aa, 8 aa, 9 aa, 10 aa, 11 aa, 12 aa, 13 aa, 14 aa, or 15 aa in length. Suitable linkers include, e.g., $(Gly)_x$, (SEQ ID NO:420), where x is an integer from 2 to 15. Other suitable linkers are those discussed above. In some embodiments, each of the scFv monomers in a subject scFV multimer is humanized, as described above. In certain aspects, a bispecific antibody may be in any molecular format known in the literature. For example, a bispecific antibody of the present disclosure may have a molecular format described in Spiess C. et al., Mol Immunol. 2015 October; 67(2 Pt A):95-106.

In some embodiments, a subject antibody comprises a constant region of an immunoglobulin (e.g., an Fc region). The Fc region, if present, can be a human Fc region. If constant regions are present, the antibody can contain both light chain and heavy chain constant regions. Suitable heavy chain constant region include CH1, hinge, CH2, CH3, and CH4 regions. The antibodies described herein include antibodies having all types of constant regions, including IgM, IgG, IgD, IgA and IgE, and any isotype, including IgG1, IgG2, IgG3 and IgG4. An example of a suitable heavy chain Fc region is a human isotype IgG1 Fc. Light chain constant regions can be lambda or kappa. A subject antibody (e.g., a subject humanized antibody) can comprise sequences from more than one class or isotype. Antibodies can be expressed as tetramers containing two light and two heavy chains, as separate heavy chains, light chains, as Fab, Fab' F(ab')2, and Fv, or as single chain antibodies in which heavy and light chain variable domains are linked through a spacer.

In some embodiments, a subject antibody comprises a free thiol (—SH) group at the carboxyl terminus, where the free thiol group can be used to attach the antibody to a second polypeptide (e.g., another antibody, including a subject antibody), a scaffold, a carrier, etc.

A subject antibody can be covalently linked to a second moiety (e.g., a lipid, a polypeptide other than a subject antibody, a synthetic polymer, a carbohydrate, a toxin and the like) using for example, glutaraldehyde, a homobifunctional cross-linker, or a heterobifunctional cross-linker. Glutaraldehyde cross-links polypeptides via their amino moieties. Homobifunctional cross-linkers (e.g., a homobifunctional imidoester, a homobifunctional N-hydroxysuccinimidyl (NHS) ester, or a homobifunctional sulfhydryl reactive cross-linker) contain two or more identical reactive moieties and can be used in a one-step reaction procedure in which the cross-linker is added to a solution containing a mixture of the polypeptides to be linked. Homobifunctional NHS ester and imido esters cross-link amine containing polypeptides. In a mild alkaline pH, imido esters react only with primary amines to form imidoamides, and overall charge of the cross-linked polypeptides is not affected. Homobifunctional sulfhydryl reactive cross-linkers includes bismaleimidohexane (BMH), 1,5-difluoro-2,4-dinitrobenzene (DFDNB), and 1,4-Bis[3-(2-pyridyldithio)propionamido]butane (DPDPB).

Compositions and Formulations

The present disclosure provides a composition comprising a subject antibody. A subject antibody composition can comprise, in addition to a subject antibody, one or more of: a salt, e.g., NaCl, $MgCl_2$, KCl, $MgSO_4$, etc.; a buffering agent, e.g., a Tris buffer, a histidine buffer, N-(2-Hydroxyethyl)piperazine-N'-(2-ethanesulfonic acid) (HEPES), 2-(N-Morpholino)ethanesulfonic acid (MES), 2-(N-Morpholino) ethanesulfonic acid sodium salt (MES), 3-(N-Morpholino) propanesulfonic acid (MOPS), N-tris[Hydroxymethyl] methyl-3-aminopropanesulfonic acid (TAPS), etc.; a solubilizing agent; a detergent, e.g., a non-ionic detergent such as Tween-20, etc.; a protease inhibitor; glycerol; and the like.

Compositions of the present disclosure also include pharmaceutical compositions that include an antibody described herein. In general, a formulation comprises an effective amount of the subject antibody. An "effective amount" means a dosage sufficient to produce a desired result, e.g., reduction in a cancer of a subject, reduction in the growth rate of a cancer in a subject, amelioration of a symptom of cancer, and the like. Generally, the desired result is at least a reduction in a symptom of a cancer, reduction in the growth of a cancer, reduction in the size of a cancer, etc., as compared to a control. A subject antibody can be delivered, or be formulated, in such a manner as to avoid the blood-brain barrier.

In some instances, an antibody may include a delivery enhancer, including where such enhancers may facilitate crossing of the blood-brain barrier, increased permeability, e.g., allowing for efficient transdermal delivery, and the like.

In some instances, the antibodies of the present disclosure may not be administered in a formulation with a delivery enhancer. In some instances, the antibodies of the present disclosure may themselves enhance permeability across the blood-brain barrier. In some instances, the antibodies of the present disclosure may be used as a delivery enhancer to facilitate crossing of the blood-brain barrier by an anti-neoplastic agent, e.g., an immunotherapeutic agent or a chemotherapeutic agent. In some instances, the antibodies of the present disclosure may be used as a delivery enhancer to facilitate crossing of the blood-brain barrier, blood-cerebrospinal fluid (CSF) barrier, blood-testis barrier, or blood-placenta barrier by an active agent, such as, another antibody or a chemotherapeutic agent.

In the subject methods, a subject antibody can be administered to the host using any convenient means capable of resulting in the desired therapeutic effect or diagnostic effect. Thus, the agent can be incorporated into a variety of formulations for therapeutic administration. More particularly, a subject antibody can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, a subject antibody can be administered in conjunction with a pharmaceutically acceptable excipient, or they may also be used alone or in appropriate association, as well as in combination, with other pharmaceutically active compounds. The following methods and excipients are merely exemplary and are in no way limiting.

A subject antibody can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

Pharmaceutical compositions comprising a subject antibody are prepared by mixing the antibody having the desired degree of purity with optional physiologically acceptable carriers, excipients, stabilizers, surfactants, buffers and/or tonicity agents. Acceptable carriers, excipients and/or stabilizers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as Tween, Brij Pluronics, Triton-X, or polyethylene glycol (PEG).

The pharmaceutical composition may be in a liquid form, a lyophilized form or a liquid form reconstituted from a lyophilized form, wherein the lyophilized preparation is to be reconstituted with a sterile solution prior to administration.

Exemplary antibody concentrations in a subject pharmaceutical composition may range from about 1 mg/mL to about 200 mg/ml or from about 50 mg/mL to about 200 mg/mL, or from about 150 mg/mL to about 200 mg/mL.

An aqueous formulation of the antibody may be prepared in a pH-buffered solution, e.g., at pH ranging from about 4.0 to about 7.5 or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

In some embodiments, the aqueous formulation is isotonic, although hypertonic or hypotonic solutions may be suitable. The term "isotonic" denotes a solution having the same tonicity as some other solution with which it is compared, such as physiological salt solution or serum. Tonicity agents may be used in an amount of about 5 mM to about 350 mM, e.g., in an amount of 100 mM to 350 nM.

A surfactant may also be added to the antibody formulation to reduce aggregation of the formulated antibody and/or minimize the formation of particulates in the formulation and/or reduce adsorption. Exemplary surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulfate (SDS). Exemplary concentrations of surfactant may range from about 0.001% to about 1% w/v.

A lyoprotectant may also be added in order to protect the labile active ingredient (e.g. a protein) against destabilizing conditions during the lyophilization process. For example, known lyoprotectants include sugars (including glucose and sucrose); polyols (including mannitol, sorbitol and glycerol); and amino acids (including alanine, glycine and glutamic acid). Lyoprotectants can be included in an amount of about 10 mM to 500 nM.

In some embodiments, a subject formulation includes a subject antibody, and one or more of the above-identified agents (e.g., a surfactant, a buffer, a stabilizer, a tonicity agent) and is essentially free of one or more preservatives, such as ethanol, benzyl alcohol, phenol, m-cresol, p-chlor-m-cresol, methyl or propyl parabens, benzalkonium chloride, and combinations thereof. In other embodiments, a preservative is included in the formulation, e.g., at concentrations ranging from about 0.001 to about 2% (w/v).

For example, a subject formulation can be a liquid or lyophilized formulation suitable for parenteral administration, and can comprise: about 1 mg/mL to about 200 mg/mL of a subject antibody; about 0.001% to about 1% of at least one surfactant; about 1 mM to about 100 mM of a buffer; optionally about 10 mM to about 500 mM of a stabilizer; and about 5 mM to about 305 mM of a tonicity agent; and has a pH of about 4.0 to about 7.0.

A subject antibody can be utilized in aerosol formulation to be administered via inhalation. A subject antibody can be formulated into pressurized acceptable propellants such as dichlorodifluoromethane, propane, nitrogen and the like.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for a subject antibody may depend on the particular antibody employed and the effect to be achieved, and the pharmacodynamics associated with each antibody in the host.

A subject antibody can be administered as an injectable formulation. Typically, injectable compositions are prepared as liquid solutions or suspensions; solid forms suitable for solution in, or suspension in, liquid vehicles prior to injection may also be prepared. The preparation may also be emulsified or the antibody encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, a subject antibody is formulated in a controlled release formulation. Sustained-release preparations may be prepared using methods well known in the art.

Dosages

A suitable dosage can be determined by an attending physician or by other qualified medical personnel, based on various clinical factors. As is well known in the medical arts, dosages for any one patient depend upon many factors, including the patient's size, body surface area, age, the particular compound to be administered, sex of the patient, time, and route of administration, general health, and other drugs being administered concurrently. A subject antibody may be administered in amounts between 1 ng/kg body weight and 20 mg/kg body weight per dose, e.g. between 0.1 mg/kg body weight to 10 mg/kg body weight, e.g. between 0.5 mg/kg body weight to 5 mg/kg body weight; however, doses below or above this exemplary range are envisioned, especially considering the aforementioned factors. If the regimen is a continuous infusion, it can also be in the range of 1 μg to 10 mg per kilogram of body weight per minute.

Those of skill will readily appreciate that dose levels can vary as a function of the specific antibody, the severity of the symptoms and the susceptibility of the subject to side effects. Preferred dosages for a given compound are readily determinable by those of skill in the art by a variety of means.

Routes of Administration

A subject antibody is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, subcutaneous, intradermal, topical application, intravenous, intraarterial, rectal, nasal, oral, and other enteral and parenteral routes of administration. Routes of administration may be combined, if desired, or adjusted depending upon the antibody and/or the desired effect. A subject antibody composition can be administered in a single dose or in multiple doses. In some embodiments, a subject antibody composition is administered orally. In some embodiments, a subject antibody composition is administered via an inhalational route. In some embodiments, a subject antibody composition is administered intranasally. In some embodiments, a subject antibody composition is administered locally. In some embodiments, a subject antibody composition is administered intracranially. In some embodiments, a subject antibody composition is administered intravenously.

The agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of a subject antibody. Where systemic delivery is desired, administration typically involves invasive or systemically absorbed topical or mucosal administration of pharmaceutical preparations.

A subject antibody can also be delivered to the subject by enteral administration. Enteral routes of administration include, but are not necessarily limited to, oral and rectal (e.g., using a suppository) delivery.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as cancer and/or the growth of a cancer and pain associated therewith. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of subjects (wherein the term "subject" is used interchangeably herein with the terms "individual" and "patient") are treatable according to the presently disclosed methods. Generally, such subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the hosts will be humans.

Kits with unit doses of a subject antibody, e.g. in oral or injectable doses, are provided. In some embodiments, in addition to the containers containing the unit doses will be an informational package insert describing the use and attendant benefits of the antibody in treating pathological condition of interest.

Nucleic Acids

The present disclosure provides nucleic acids comprising nucleotide sequences encoding a subject antibody. A nucleotide sequence encoding a subject antibody can be operably linked to one or more regulatory elements, such as a promoter and enhancer, that allow expression of the nucleotide sequence in the intended target cells (e.g., a cell that is genetically modified to synthesize and/or secrete the encoded antibody).

Suitable promoter and enhancer elements are known in the art. For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

A nucleotide sequence encoding a subject antibody can be present in an expression vector and/or a cloning vector. Where a subject antibody comprises two or more separate polypeptides, nucleotide sequences encoding the two polypeptides can be cloned in the same or separate vectors. Separate polypeptides may be expressed from a single nucleic acid or single vector using various strategies, such as separate promoters, one or more internal ribosomal entry sites (IRES), one or more self-cleaving sequences (e.g., 2A cleavage sequences, e.g., P2A, T2A, E2A, and F2A), combinations thereof, and the like. An expression vector can include a selectable marker, an origin of replication, and other features that provide for replication and/or maintenance of the vector.

Large numbers of suitable vectors and promoters are known to those of skill in the art; many are commercially available for generating a subject recombinant construct. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus; adeno-associated virus; SV40; herpes simplex virus; human immunodeficiency virus; a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

Nucleic acids, e.g., as described herein, may, in some instances, be introduced into a cell, e.g., by contacting the cell with the nucleic acid. Cells with introduced nucleic acids will generally be referred to herein as genetically modified cells. Various methods of nucleic acid delivery may be employed including but not limited to e.g., naked nucleic acid delivery, viral delivery, chemical transfection, biolistics, and the like.

Cells

The present disclosure provides isolated genetically modified cells (e.g., in vitro cells, ex vivo cells, cultured cells, etc.) that are genetically modified with a subject nucleic acid. In some embodiments, a subject isolated genetically modified cell can produce a subject antibody. In some instances, a genetically modified cell can deliver an antibody, e.g., to a subject in need thereof. In some instances, a genetically modified cell may be used in the production, screening, and/or discovery of multi-specific antibodies.

Suitable cells include eukaryotic cells, such as a mammalian cell, an insect cell, a yeast cell; and prokaryotic cells, such as a bacterial cell. Introduction of a subject nucleic acid into the host cell can be affected, for example by calcium phosphate precipitation, DEAE dextran mediated transfection, liposome-mediated transfection, electroporation, or other known method.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells, CHO cells, 293 cells, 3T3 cells, Vero cells, Huh-7 cells, BHK cells, PC12 cells, COS cells, COS-7 cells, RAT1 cells, mouse L cells, human embryonic kidney (HEK) cells, HLHepG2 cells, and the like.

In some instances, useful mammalian cells may include cells derived from a mammalian tissue or organ. In some instances, cells employed are kidney cells, including e.g., kidney cells of an established kidney cell line, such as HEK 293T cells.

In some instances, cells of the present disclosure may be immune cells. As used herein, the term "immune cells" generally includes white blood cells (leukocytes) which are derived from hematopoietic stem cells (HSC) produced in the bone marrow. "Immune cells" includes, e.g., lymphocytes (T cells, B cells, natural killer (NK) cells) and myeloid-derived cells (neutrophil, eosinophil, basophil, monocyte, macrophage, dendritic cells). "T cell" includes all types of immune cells expressing CD3 including T-helper cells (CD4+ cells), cytotoxic T-cells (CD8+ cells), T-regulatory cells (Treg) and gamma-delta T cells. A "cytotoxic cell" includes CD8+ T cells, natural-killer (NK) cells, and neutrophils, which cells are capable of mediating cytotoxicity responses.

In some instances, useful cells expressing an antibody such as a multi-specific antibody of the present disclosure may include producer T cells. Producer T cells engineered to include nucleic acid sequence encoding an antibody of the present disclosure may, in some instances, be employed to deliver the antibody to a subject in need thereof.

In some instances, immune cells of the present disclosure include immune effector cell comprising a chimeric antigen receptor (CAR) comprising an ABCG2 binding domain, a transmembrane domain, and an intracellular signaling domain, and wherein the ABCG2 binding domain comprises heavy chain complementarity determining regions (HCDRs) and light chain CDRs (LCDRs) of a pair of variable heavy chain (VH) region and variable light chain (VL) region of an antibody listed in Table 2. In one aspect, the intracellular signaling domain may include one or more functional signaling domains derived from at least one costimulatory molecule, e.g., 4-1BB (i.e., CD137), CD27 and/or CD28.

The intracellular signaling domain may include a functional signaling domain derived from a costimulatory molecule and a functional signaling domain derived from a stimulatory molecule.

The immune effector cell may be a T-cell. The immune effector cell may be an autologous cell.

Methods

As summarized above, methods of the present disclosure include methods of contacting a cell with an antibody of the present disclosure, methods of treating a subject according to a method that involves administering to the subject an antibody of the present disclosure, methods of making elements described in the instant application, including e.g., antibodies, multi-specific antibodies, compositions and formulations, nucleic acids, expression vectors, cells, and the like.

As summarized above, methods of the present disclosure include contacting a cancer cell with an antibody of the present disclosure, e.g., to detect presence of expression of ABCG2 on the cancer cell, measure level of expression of ABCG2 on the cancer cell, or to facilitate and/or enhance killing of the cancer cell. In some instances, killing of the cancer cell is mediated by an immune response or immune cell acting upon the cancer cell bound by the antibody. In some instances, killing of the cancer cell is mediated by inhibition of cellular efflux of the cancer cell, e.g., as a result of ABCG2 inhibition by the antibody. In some instances, killing of the cancer cell is mediated by a combination of inhibition of cellular efflux of the cancer cell plus an immune mediated response (e.g., via Fc region of the antibody). In some instances, the cell contacted with the multi-specific antibody may be a multidrug resistant cancer cell. Methods that involve contacting a cancer cell with an antibody of the present disclosure may or may not include contacting the cancer cell with an additional therapy or active agent, including e.g., a chemotherapeutic, an immunotherapy, radiation therapy, or the like.

Contacting a cancer cell with a multi-specific antibody of the present disclosure will generally enhance the killing of the cancer cell, e.g., as compared to the level of killing of the cancer cell in the absence of the multi-specific antibody. In some instances, where an additional active agent is employed, enhanced killing of the cancer cell may be seen as compared to the level of killing observed using the additional active agent alone. The amount of enhancement of cancer cell killing attributable to the multi-specific antibody will vary and may range from at least a 5% increase in cancer cell killing to at least 90% or more, including but not limited to e.g., at least 10%, at least 20%, at least 30%, at least 40%, at least 50%, at least 60%, at least 70%, at least 80%, etc. Such increases may be compared to contacting with one or more additional active agents alone.

Enhanced killing of a cancer cell may be assessed by a variety of means including but not limited to e.g., observational studies, in vitro cell-based cytotoxicity assays, flow cytometry, cell viability labeling (e.g., using one or more cell viability stains), and the like.

Treatment Methods

The present disclosure provides methods of treating a cancer, the methods generally involving administering to an individual in need thereof (e.g., an individual having a cancer) an effective amount of an antibody as provided herein, alone (e.g., in monotherapy) or in combination (e.g., in combination therapy) with one or more additional therapeutic agents. Administration of an antibody of the present disclosure may be performed by any convenient and appropriate route of delivery.

Accordingly, administration includes but is not limited to e.g., delivery of the antibody by injection, delivery of the antibody by infusion, delivery of a nucleic acid or expression vector encoding the antibody, delivery of the antibody by administering to the subject a cell that expresses and secretes the antibody, delivery of an immune effector cell (e.g., a CAR-T cell) that expresses on the cell surface a chimeric antigen receptor (CAR) comprising a ABCG2 binding domain, a transmembrane domain, and an intracellular signaling domain, and wherein the ABCG2 binding domain comprises HCDRs and LCDRs of a pair of VH region and VL region of an antibody listed in Table 2, and the like. Administration of an agent, a nucleic acid encoding an agent, a cell expressing an agent, etc. may include contacting with the agent, contacting with the nucleic acid, contacting with the cell, and the like.

In some embodiments, an effective amount of a subject antibody is an amount that, when administered alone (e.g., in monotherapy) or in combination (e.g., in combination therapy) with one or more additional therapeutic agents, in one or more doses, is effective to reduce an adverse symptom of cancer by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the severity of the adverse symptom in the absence of treatment with the antibody.

In some embodiments, an effective amount of a subject antibody is an amount that, when administered alone (e.g., in monotherapy) or in combination (e.g., in combination therapy) with one or more additional therapeutic agents, in one or more doses, is effective to improve the cancer (i.e., slow the growth of the cancer, stop the growth of the cancer, reverse the growth of the cancer, kill cancer cells (including tumor cells, or the like) in the individual being treated. For example, an effective amount of a subject antibody can reduce a cancer growth rate or reduce a cancer size in an individual by at least about 5%, at least about 10%, at least about 15%, at least about 20%, at least about 25%, at least about 30%, at least about 40%, at least about 50%, or more, compared to in the absence of treatment with an antibody.

In some instances, a subject may be treated systemically, including with the subject antibody, with or without one or more additional reagents. By "systemic treatment", as used herein, is meant a treatment that is not directed solely to target a specific tumor (such as e.g., a primary tumor or a defined secondary tumor) or a specific cancer containing tissue (such as e.g., the liver in the case of liver cancer, the blood in the case of a blood cancer, etc.). Systemic treatments will generally be directed to the subject's body as a whole and may include but are not limited to e.g., systemic radiation therapy, systemic chemotherapy, systemic immunotherapy, combinations thereof and the like.

In some instances, a subject may be treated locally, including with the subject antibody, with or without one or more additional reagents. By "local treatment", as used herein, is meant a treatment that is specifically directed to the location of a tumor (such as e.g., a primary tumor or a defined secondary tumor) or specifically directed to a cancer containing tissue (such as e.g., the liver in the case of liver cancer, the blood in the case of a blood cancer, etc.). In some instances, local treatment may also be administered in such a way as to affect the environment surrounding a tumor, such as tissue surrounding the tumor, such as tissue immediately adjacent to the tumor. Local treatment will generally not affect or not be targeted to tissues distant from the site of cancer including the site of a tumor, such as a primary tumor. Useful local treatments that may be administered in addition to or in combination with a subject antibody, e.g., include but are not limited to surgery, local radiation therapy, local cryotherapy, local laser therapy, local topical therapy, combinations thereof, and the like.

In some embodiments, a subject treatment method involves administering a subject antibody and one or more additional therapeutic agents. Suitable additional therapeutic agents include, but are not limited to, chemotherapeutic agents, radiation therapy reagents, immunotherapy reagents, other antibody or multi-specific antibody agents, and the like. Additional therapies that may be administered to a subject before, during or after a subject administering a multi-specific antibody of the present disclosure will vary depending on numerous factors including e.g., the type of cancer, the subject's medical history, general state of health and/or any co-morbidities, and the like. Useful cancer therapies include but are not limited to e.g., radiation therapy, chemotherapy, immunotherapy, and the like.

Radiation therapy includes, but is not limited to, x-rays or gamma rays that are delivered from either an externally applied source such as a beam, or by implantation of small radioactive sources.

Suitable antibodies for use in cancer treatment include, but are not limited to, naked antibodies, e.g., trastuzumab (Herceptin), bevacizumab (Avastin™), cetuximab (Erbitux™) panitumumab (Vectibix™), Ipilimumab (Yervoy™), rituximab (Rituxan), alemtuzumab (Lemtrada™), Ofatumumab (Arzerra™), Oregovomab (OvaRex™), Lambrolizumab (MK-3475), pertuzumab (Perjeta™), ranibizumab (Lucentis™) etc., and conjugated antibodies, e.g., gemtuzumab ozogamicin (Mylortarg™), Brentuximab vedotin (Adcetris™), 90Y-labelled ibritumomab tiuxetan (Zevalin™), 1311-labelled tositumoma (Bexxar™), etc.

Suitable antibodies for use in cancer treatment also include, but are not limited to, antibodies raised against tumor-associated antigens. Such antigens include, but are not limited to, CD20, CD30, CD33, CD52, EpCAM, CEA, gpA33, Mucins, TAG-72, CAIX, PSMA, Folate-binding protein, Gangliosides (e.g., GD2, GD3, GM2, etc.), Ley, VEGF, VEGFR, Integrin alpha-V-beta-3, Integrin alpha-5-beta-1, EGFR, ERBB2, ERBB3, MET, IGF1R, EPHA3, TRAILR1, TRAILR2, RANKL, FAP, Tenascin, Programmed Death-Ligand 1 (PD-L1), androgen receptor (AR), Bruton's Tyrosine Kinase (BTK), BCR-Abl, c-kit, PIK3CA, EML4-ALK, KRAS, ALK, ROS1, AKT1, BRAF, MEKJ, MEK2, NRAS, RAC1, ESR1, CTLA-4, LAG-3 and TIM-3, etc. These antibodies may be administered as a combination therapy with an anti-ABCG2 antibody provided herein or as a multi-specific antibody comprising at least the antigen binding portion of one of these antibodies and the antigen-binding portion of an anti-ABCG2 antibody provided herein.

Conventional cancer therapies also include targeted therapies for cancer including but not limited to e.g., Ado-trastuzumab emtansine (Kadcyla) targeting HER2 (ERBB2/neu) (approved for use in Breast cancer); Afatinib (Gilotrif) targeting EGFR (HER1/ERBB1), HER2 (ERBB2/neu) (approved for use in Non-small cell lung cancer); Aldesleukin (Proleukin) targeting (approved for use in Renal cell carcinoma, Melanoma); Alectinib (Alecensa) targeting ALK (approved for use in Non-small cell lung cancer); Alemtuzumab (Campath) targeting CD52 (approved for use in B-cell chronic lymphocytic leukemia); Atezolizumab (Tecentriq) targeting PD-L1 (approved for use in Urothelial carcinoma, Non-small cell lung cancer); Avelumab (Bavencio) targeting PD-L1 (approved for use in Merkel cell carcinoma); Axitinib (Inlyta) targeting KIT, PDGFRβ, VEGFR1/2/3 (approved for use in Renal cell carcinoma); Belimumab (Benlysta) targeting BAFF (approved for use in Lupus erythematosus); Belinostat (Beleodaq) targeting HDAC (approved for use in Peripheral T-cell lymphoma); Bevacizumab (Avastin) targeting VEGF ligand (approved for use in Cervical cancer, Colorectal cancer, Fallopian tube cancer, Glioblastoma, Non-small cell lung cancer, Ovarian cancer, Peritoneal cancer, Renal cell carcinoma); Blinatumomab (Blincyto) targeting CD19/CD3 (approved for use in Acute lymphoblastic leukemia (precursor B-cell)); Bortezomib (Velcade) targeting Proteasome (approved for use in Multiple myeloma, Mantle cell lymphoma); Bosutinib (Bosulif) targeting ABL (approved for use in Chronic myelogenous leukemia); Brentuximab vedotin (Adcetris) targeting CD30 (approved for use in Hodgkin lymphoma, Anaplastic large cell lymphoma); Brigatinib (Alunbrig) targeting ALK (approved for use in Non-small cell lung cancer (ALK+)); Cabozantinib (Cabometyx, Cometriq) targeting FLT3, KIT, MET, RET, VEGFR2 (approved for use in Medullary thyroid cancer, Renal cell carcinoma); Carfilzomib (Kyprolis) targeting Proteasome (approved for use in Multiple myeloma); Ceritinib (Zykadia) targeting ALK (approved for use in Non-small cell lung cancer); Cetuximab (Erbitux) targeting EGFR (HER1/ERBB1) (approved for use in Colorectal cancer, Squamous cell cancer of the head and neck); Cobimetinib (Cotellic) targeting MEK (approved for use in Melanoma); Crizotinib (Xalkori) targeting ALK, MET, ROS1 (approved for use in Non-small cell lung cancer); Dabrafenib (Tafinlar) targeting BRAF (approved for use in Melanoma, Non-small cell lung cancer); Daratumumab (Darzalex) targeting CD38 (approved for use in Multiple myeloma); Dasatinib (Sprycel) targeting ABL (approved for use in Chronic myelogenous leukemia, Acute lymphoblastic leukemia); Denosumab (Xgeva) targeting RANKL (approved for use in Giant cell tumor of the bone); Dinutuximab (Unituxin) targeting B4GALNT1 (GD2) (approved for use in Pediatric neuroblastoma); Durvalumab (Imfinzi) targeting PD-L1 (approved for use in Urothelial carcinoma); Elotuzumab (Empliciti) targeting SLAMF7 (CS1/CD319/CRACC) (approved for use in Multiple myeloma); Enasidenib (Idhifa) targeting IDH2 (approved for use in Acute myeloid leukemia); Erlotinib (Tarceva) targeting EGFR (HER1/ERBB1) (approved for use in Non-small cell lung cancer, Pancreatic cancer); Everolimus (Afinitor) targeting mTOR (approved for use in Pancreatic, gastrointestinal, or lung origin neuroendocrine tumor, Renal cell carcinoma, Nonresectable subependymal giant cell astrocytoma, Breast cancer); Gefitinib (Iressa) targeting EGFR (HER1/ERBB1) (approved for use in Non-small cell lung cancer); Ibritumomab tiuxetan (Zevalin) targeting CD20 (approved for use in Non-Hodgkin's lymphoma); Ibrutinib (Imbruvica) targeting BTK (approved for use in Mantle cell lymphoma, Chronic lymphocytic leukemia, Waldenstrom's macroglobulinemia); Idelalisib (Zydelig) targeting PI3K5 (approved for use in Chronic lymphocytic leukemia, Follicular B-cell non-Hodgkin lymphoma, Small lymphocytic lymphoma); Imatinib (Gleevec) targeting KIT, PDGFR, ABL (approved for use in GI stromal tumor (KIT+), Dermatofibrosarcoma protuberans, Multiple hematologic malignancies); Ipilimumab (Yervoy) targeting CTLA-4 (approved for use in Melanoma); Ixazomib (Ninlaro) targeting Proteasome (approved for use in Multiple Myeloma); Lapatinib (Tykerb) targeting HER2 (ERBB2/neu), EGFR (HER1/ERBB1) (approved for use in Breast cancer (HER2+)); Lenvatinib (Lenvima) targeting VEGFR2

(approved for use in Renal cell carcinoma, Thyroid cancer); Midostaurin (Rydapt) targeting FLT3 (approved for use in acute myeloid leukemia (FLT3+)); Necitumumab (Portrazza) targeting EGFR (HER1/ERBB1) (approved for use in Squamous non-small cell lung cancer); Neratinib (Nerlynx) targeting HER2 (ERBB2/neu) (approved for use in Breast cancer); Nilotinib (Tasigna) targeting ABL (approved for use in Chronic myelogenous leukemia); Niraparib (Zejula) targeting PARP (approved for use in Ovarian cancer, Fallopian tube cancer, Peritoneal cancer); Nivolumab (Opdivo) targeting PD-1 (approved for use in Colorectal cancer, Head and neck squamous cell carcinoma, Hodgkin lymphoma, Melanoma, Non-small cell lung cancer, Renal cell carcinoma, Urothelial carcinoma); Obinutuzumab (Gazyva) targeting CD20 (approved for use in Chronic lymphocytic leukemia, Follicular lymphoma); Ofatumumab (Arzerra, HuMax-CD20) targeting CD20 (approved for use in Chronic lymphocytic leukemia); Olaparib (Lynparza) targeting PARP (approved for use in Ovarian cancer); Olaratumab (Lartruvo) targeting PDGFRα (approved for use in Soft tissue sarcoma); Osimertinib (Tagrisso) targeting EGFR (approved for use in Non-small cell lung cancer); Palbociclib (Ibrance) targeting CDK4, CDK6 (approved for use in Breast cancer); Panitumumab (Vectibix) targeting EGFR (HER1/ERBB1) (approved for use in Colorectal cancer); Panobinostat (Farydak) targeting HDAC (approved for use in Multiple myeloma); Pazopanib (Votrient) targeting VEGFR, PDGFR, KIT (approved for use in Renal cell carcinoma); Pembrolizumab (Keytruda) targeting PD-1 (approved for use in Classical Hodgkin lymphoma, Melanoma, Non-small cell lung cancer (PD-L1+), Head and neck squamous cell carcinoma, Solid tumors (MSI-H)); Pertuzumab (Perjeta) targeting HER2 (ERBB2/neu) (approved for use in Breast cancer (HER2+)); Ponatinib (Iclusig) targeting ABL, FGFR1-3, FLT3, VEGFR2 (approved for use in Chronic myelogenous leukemia, Acute lymphoblastic leukemia); Ramucirumab (Cyramza) targeting VEGFR2 (approved for use in Colorectal cancer, Gastric cancer or Gastroesophageal junction (GEJ) adenocarcinoma, Non-small cell lung cancer); Regorafenib (Stivarga) targeting KIT, PDGFRβ, RAF, RET, VEGFR1/2/3 (approved for use in Colorectal cancer, Gastrointestinal stromal tumors, Hepatocellular carcinoma); Ribociclib (Kisqali) targeting CDK4, CDK6 (approved for use in Breast cancer (HR+, HER2−)); Rituximab (Rituxan, Mabthera) targeting CD20 (approved for use in Non-Hodgkin's lymphoma, Chronic lymphocytic leukemia, Rheumatoid arthritis, Granulomatosis with polyangiitis); Rituximab/hyaluronidase human (Rituxan Hycela) targeting CD20 (approved for use in Chronic lymphocytic leukemia, Diffuse large B-cell lymphoma, Follicular lymphoma); Romidepsin (Istodax) targeting HDAC (approved for use in Cutaneous T-cell lymphoma, Peripheral T-cell lymphoma); Rucaparib (Rubraca) targeting PARP (approved for use in Ovarian cancer); Ruxolitinib (Jakafi) targeting JAK1/2 (approved for use in Myelofibrosis); Siltuximab (Sylvant) targeting IL-6 (approved for use in Multicentric Castleman's disease); Sipuleucel-T (Provenge) targeting (approved for use in Prostate cancer); Sonidegib (Odomzo) targeting Smoothened (approved for use in Basal cell carcinoma); Sorafenib (Nexavar) targeting VEGFR, PDGFR, KIT, RAF (approved for use in Hepatocellular carcinoma, Renal cell carcinoma, Thyroid carcinoma); Temsirolimus (Torisel) targeting mTOR (approved for use in Renal cell carcinoma); Tositumomab (Bexxar) targeting CD20 (approved for use in Non-Hodgkin's lymphoma); Trametinib (Mekinist) targeting MEK (approved for use in Melanoma, Non-small cell lung cancer); Trastuzumab (Herceptin) targeting HER2 (ERBB2/neu) (approved for use in Breast cancer (HER2+), Gastric cancer (HER2+)); Vandetanib (Caprelsa) targeting EGFR (HER1/ERBB1), RET, VEGFR2 (approved for use in Medullary thyroid cancer); Vemurafenib (Zelboraf) targeting BRAF (approved for use in Melanoma); Venetoclax (Venclexta) targeting BCL2 (approved for use in Chronic lymphocytic leukemia); Vismodegib (Erivedge) targeting PTCH, Smoothened (approved for use in Basal cell carcinoma); Vorinostat (Zolinza) targeting HDAC (approved for use in Cutaneous T-cell lymphoma); Ziv-aflibercept (Zaltrap) targeting PIGF, VEGFA/B (approved for use in Colorectal cancer); and the like. These antibodies may be administered as a combination therapy with an anti-ABCG2 antibody provided herein.

Biological response modifiers suitable for use in connection with the methods of the present disclosure include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) interferon-α; (7) interferon-γ; (8) colony-stimulating factors; (9) inhibitors of angiogenesis; and (10) antagonists of tumor necrosis factor.

Chemotherapeutic agents or antineoplastic agents are non-peptidic (i.e., non-proteinaceous) compounds that reduce proliferation of cancer cells, and encompass cytotoxic agents and cytostatic agents. Non-limiting examples of chemotherapeutic agents include alkylating agents (e.g., nitrosoureas), antimetabolites (e.g., methotrexate), antitumor antibiotics (e.g., anthracyclins), plant alkaloids (e.g., *vinca* alkaloids, taxanes, etc.), toposiomerase inhibitors, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB3717), 5,8-dideazatetrahydrofolic acid (DDATHF), leucovorin, fludarabine phosphate, pentostatine, and gemcitabine.

Suitable natural products and their derivatives, (e.g., *vinca* alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar; alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolstatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysterin, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and pregestins, e.g. hydroxyprogesterone caproate, medroxyprogesterone acetate, megestrol acetate, estradiol, clomiphene, tamoxifen; etc.; and adrenocortical suppressants, e.g. aminoglutethimide; 17α-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex. Estrogens stimulate proliferation and differentiation, therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, paclitaxel-xylose, or protein bound paclitaxel such as Abraxane®).

Also included within the term "taxane" are a variety of known derivatives, including both hydrophilic derivatives, and hydrophobic derivatives. Taxane derivatives include, but are not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Useful immunotherapies include anti-PD-1/PD-L1 immunotherapies, and/or other immunotherapy targets, such as e.g., immune check point markers, such as CTLA-4, LAG-3 and TIM-3, that may be targeted in treatment methods. Anti-PD-1/PD-L1 immunotherapies which include but are not limited to e.g., those therapies that include administering to a subject an effective amount of one or more anti-PD-1/PD-L1 therapeutic antagonists where such antagonists include but are not limited to e.g., OPDIVO® (nivolumab), KEYTRUDA® (pembrolizumab), Tecentriq™ (atezolizumab), durvalumab (MED14736), avelumab (MSB0010718C), BMS-936559 (MDX-1105), CA-170, BMS-202, BMS-8, BMS-37, BMS-242 and the like. These antibodies may be administered as a combination therapy with an anti-ABCG2 antibody provided herein.

CTLA-4, also known as CD152, binds to CD80 and CD86. Antibodies against CTLA-4 have been approved for treating some cancer types. The co-inhibitory effect of CTLA-4 with other immunotherapies make CTLA-4 a good candidate for use in combination with other immunotherapies to treat certain cancers. TIM-3 may also be targeted for immunotherapy for several cancer types.

LAG-3 is in clinical trials for treating cancers. Anti-LAG-3 immunotherapies include those that employ antagonist LAG-3 antibodies that can both activate T effector cells (by downregulating the LAG-3 inhibiting signal into pre-activated LAG-3+ cells) and inhibit induced (i.e. antigen-specific) Treg suppressive activity. Useful LAG-3 antagonistic antibodies include relatlimab (BMS-986016; developed by Bristol-Myers Squibb), IMP701 (developed by Immutep), TSR-033 (anti-LAG-3 mAb; developed by TESARO, Inc.), and the like.

Immunotherapies also include T cell-based immunotherapies such as e.g., adoptive cell therapy (ACT) and chimeric antigen receptor (CAR) T cell therapies. For example, a subject may be administered a population of CAR T cells engineered to target an antigen expressed by the subject's cancer. A T cell-based therapy may involve, in some instances, obtaining a cellular sample from a subject, such as a blood sample or a tumor biopsy, and culturing immune cells from the sample ex vivo, with or without genetic modification of the cultured immune cells. As an example, immune cells may be obtained from a subject, cultured ex vivo and modified with a CAR specific for an antigen expressed by the cancer to produce a population of CAR T cells. Then, the CAR T cells may be reintroduced into the subject to target the cancer. T cell-based immunotherapies may be configured in various ways, e.g., by targeting various antigens, by collecting/culturing various cell types, etc., depending on a particular cancer to be treated. In addition, T cell-based immunotherapies may be administered systemically, e.g., by intravenous injection, or locally, e.g., by infusion (e.g., intraperitoneal infusion, pleural catheter infusion, etc.), direct injection, and the like.

In some instances, a method of treatment described herein may include administering to a subject one or more inhibitors of a multidrug resistance transporter, including but not limited to e.g., a multidrug resistance transporter other than ABCG2. Useful inhibitors of multidrug resistance transporters include e.g., tyrosine kinase inhibitors, natural products, microRNAs, and small molecule inhibitors. Inhibitors of multidrug resistance transporters include ABC transporter inhibitors.

Individuals suitable for treatment using a method of the present disclosure include an individual having a cancer; an individual diagnosed as having a cancer; an individual being treated for a cancer with chemotherapy, radiation therapy, antibody therapy, surgery, etc.); an individual who has been treated for a cancer (e.g., with one or more of chemotherapy, radiation therapy, antibody therapy, surgery, etc.), and who has failed to respond to the treatment; an individual who has been treated for a cancer (e.g., with one or more of chemotherapy, radiation therapy, antibody therapy, surgery, etc.), and who initially responded to the treatment but who subsequently relapsed, i.e., the cancer recurred.

The methods of the present disclosure may be employed to target and treat a variety of cancers, including e.g., primary cancer, secondary cancers, re-growing cancers, recurrent cancers, refractory cancers and the like. For example, in some instances, the methods of the present disclosure may be employed as an initial treatment of a primary cancer identified in a subject. In some instances, the methods of the present disclosure may be employed as a non-primary (e.g., secondary or later) treatment, e.g., in a subject with a cancer that is refractory to a prior treatment, in a subject with a cancer that is re-growing following a prior treatment, in a subject with a mixed response to a prior treatment (e.g., a positive response to at least one tumor in the subject and a negative or neutral response to at least a second tumor in the subject), and the like.

In some instances, the methods of the present disclosure may be employed to treat a subject with a drug resistant cancer, such as a multi-drug resistant cancer. Multidrug resistance (MDR) is the mechanism by which many cancers develop resistance to chemotherapy drugs, resulting in minimal cell death and the expansion of drug-resistant tumors. MDR cancers may involve one or more resistance mechanisms including but not limited to e.g., increased expression of efflux pumps, decreased absorption of drug, inhibition of cell death or apoptosis, modulating drug metabolism, and the like. In some instances, the methods of the present disclosure may prevent, reverse or circumvent MDR.

In some instances, methods of the present disclosure may include treating a subject having a cancer that is resistant to a first agent with an effective amount of a subject antibody described herein in combination with a second agent that is different from the first agent. For example, in some instances, cancer of a subject may be resistant to a first chemotherapeutic and the subject may be treated by administering an effective amount of a subject antibody as described herein in combination with a second chemotherapeutic that is different from the first. Various combinations of first and second chemotherapeutics may be employed depending on e.g., the type of cancer to be treated, the likelihood of developing resistance, etc.

Numerous cancers are known to develop drug resistance. For this and other reasons the methods of the present disclosure may find use in treating various cancers including but not limited to, e.g., Acute Lymphoblastic Leukemia (ALL), Acute Myeloid Leukemia (AML), Adrenocortical Carcinoma, AIDS-Related Cancers (e.g., Kaposi Sarcoma, Lymphoma, etc.), Anal Cancer, Appendix Cancer, Astrocytomas, Atypical Teratoid/Rhabdoid Tumor, Basal Cell Carcinoma, Bile Duct Cancer (Extrahepatic), Bladder Cancer, Bone Cancer (e.g., Ewing Sarcoma, Osteosarcoma and Malignant Fibrous Histiocytoma, etc.), Brain Stem Glioma, Brain Tumors (e.g., Astrocytomas, Central Nervous System Embryonal Tumors, Central Nervous System Germ Cell Tumors, Craniopharyngioma, Ependymoma, etc.), Breast Cancer (e.g., female breast cancer, male breast cancer, childhood breast cancer, etc.), Bronchial Tumors, Burkitt Lymphoma, Carcinoid Tumor (e.g., Childhood, Gastrointestinal, etc.), Carcinoma of Unknown Primary, Cardiac (Heart) Tumors, Central Nervous System (e.g., Atypical Teratoid/Rhabdoid Tumor, Embryonal Tumors, Germ Cell Tumor, Lymphoma, etc.), Cervical Cancer, Childhood Cancers, Chordoma, Chronic Lymphocytic Leukemia (CLL), Chronic Myelogenous Leukemia (CML), Chronic Myeloproliferative Neoplasms, Colon Cancer, Colorectal Cancer, Craniopharyngioma, Cutaneous T-Cell Lymphoma, Duct (e.g., Bile Duct, Extrahepatic, etc.), Ductal Carcinoma In Situ (DCIS), Embryonal Tumors, Endometrial Cancer, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer (e.g., Intraocular Melanoma, Retinoblastoma, etc.), Fibrous Histiocytoma of Bone (e.g., Malignant, Osteosarcoma, ect.), Gallbladder Cancer, Gastric (Stomach) Cancer, Gastrointestinal Carcinoid Tumor, Gastrointestinal Stromal Tumors (GIST), Germ Cell Tumor (e.g., Extracranial, Extragonadal, Ovarian, Testicular, etc.), Gestational Trophoblastic Disease, Glioma, Hairy Cell Leukemia, Head and Neck Cancer, Heart Cancer, Hepatocellular (Liver) Cancer, Histiocytosis (e.g., Langerhans Cell, etc.), Hodgkin Lymphoma, Hypopharyngeal Cancer, Intraocular Melanoma, Islet Cell Tumors (e.g., Pancreatic Neuroendocrine Tumors, etc.), Kaposi Sarcoma, Kidney Cancer (e.g., Renal Cell, Wilms Tumor, Childhood Kidney Tumors, etc.), Langerhans Cell Histiocytosis, Laryngeal Cancer, Leukemia (e.g., Acute Lymphoblastic (ALL), Acute Myeloid (AML), Chronic Lymphocytic (CLL), Chronic Myelogenous (CML), Hairy Cell, etc.), Lip and Oral Cavity Cancer, Liver Cancer (Primary), Lobular Carcinoma In Situ (LCIS), Lung Cancer (e.g., Non-Small Cell, Small Cell, etc.), Lymphoma (e.g., AIDS-Related, Burkitt, Cutaneous T-Cell, Hodgkin, Non-Hodgkin, Primary Central Nervous System (CNS), etc.), Macroglobulinemia (e.g., Waldenström, etc.), Male Breast Cancer, Malignant Fibrous Histiocytoma of Bone and Osteosarcoma, Melanoma, Merkel Cell Carcinoma, Mesothelioma, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia (e.g., Chronic (CML), etc.), Myeloid Leukemia (e.g., Acute (AML), etc.), Myeloproliferative Neoplasms (e.g., Chronic, etc.), Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer (e.g., Lip, etc.), Oropharyngeal Cancer, Osteosarcoma and Malignant Fibrous Histiocytoma of Bone, Ovarian Cancer (e.g., Epithelial, Germ Cell Tumor, Low Malignant Potential Tumor, etc.), Pancreatic Cancer, Pancreatic Neuroendocrine Tumors (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Pleuropulmonary Blastoma, Primary Central Nervous System (CNS) Lymphoma, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Sarcoma (e.g., Ewing, Kaposi, Osteosarcoma, Rhabdomyosarcoma, Soft Tissue, Uterine, etc.), Sézary Syndrome, Skin Cancer (e.g., Childhood, Melanoma, Merkel Cell Carcinoma, Nonmelanoma, etc.), Small Cell Lung Cancer, Small Intestine Cancer, Soft Tissue Sarcoma, Squamous Cell Carcinoma, Squamous Neck Cancer (e.g., with Occult Primary, Metastatic, etc.), Stomach (Gastric) Cancer, T-Cell Lymphoma, Testicular Cancer, Throat Cancer, Thymoma and Thymic Carcinoma, Thyroid Cancer, Transitional Cell Cancer of the Renal Pelvis and Ureter, Ureter and Renal Pelvis Cancer, Urethral Cancer, Uterine Cancer (e.g., Endometrial, etc.), Uterine Sarcoma, Vaginal Cancer, Vulvar Cancer, Waldenström Macroglobulinemia, Wilms Tumor, and the like.

The methods of treating described herein may, in some instances, be performed in a subject that has previously undergone one or more conventional treatments. For example, in the case of oncology, the methods described herein may, in some instances, be performed following a conventional cancer therapy including but not limited to e.g., conventional chemotherapy, conventional radiation therapy, conventional immunotherapy, surgery, etc. In some instances, the methods described herein may be used when a subject has not responded to or is refractory to a conventional therapy. In some instances, the methods described herein may be used when a subject has responded to a conventional therapy.

In some instances, the method of the present disclosure may be employed to target, treat or clear a subject for minimal residual disease (MRD) remaining after a prior cancer therapy. Targeting, treating and/or clearance of MRD may be pursued using the instant methods whether the MRD is or has been determined to be refractory to the prior treatment or not. In some instances, a method of the present disclosure may be employed to target, treat and/or clear a subject of MRD following a determination that the MRD is refractory to a prior treatment or one or more available treatment options other than those employing the herein described multi-specific antibodies.

In some instances, the instant methods may be employed prophylactically for surveillance. For example, a subject in need thereof may be administered a treatment involving one or more of the herein described mono or multi-specific antibodies when the subject does not have detectable disease but is at risk of developing a recurrent cancer, including e.g., a drug resistant cancer. In some instances, a prophylactic approach may be employed when a subject is at particularly high risk of developing a primary cancer that would be predicted to be drug resistant or expected to become drug resistant. In some instances, a prophylactic approach may be employed when a subject has been previously treated for a cancer and is at risk of reoccurrence or development of drug resistance.

In some instances, methods of the present disclosure may involve analyzing a cancer for expression of one or more markers or therapeutic targets. For example, in some instances, methods may involve analyzing a sample of a cancer from a subject to determine whether the cancer expresses ABCG2 above a predetermined threshold, a cancer-associated antigen or MDR-1 above a predetermined threshold, or both ABCG2 and TAA or both ABCG2 and MDR1 above a predetermined threshold.

In some instances, whether a subject is treated with an antibody of the present disclosure may depend on the results of ABCG2 expression assessment, cancer-associated antigen expression or both. For example, in some instances, if a cancer expresses ABCG2 at or above a predetermined threshold then the subject may be treated with an anti-ABCG2 antibody of the present disclosure or a multi-specific antibody of the present disclosure, and if the cancer expresses ABCG2 below the predetermined threshold then the subject may not be treated with an anti-ABCG2 antibody but treated with a multi-specific antibody of the present disclosure.

Any convenient assay may be employed for analyzing ABCG2 and/or cancer-associated antigen levels, including but not limited to e.g., flow cytometry, nucleic acid-based assays (e.g., amplification, sequencing, etc.), cell cytometry, immunohistochemistry, and the like. Any convenient biological sample may be employed, including but not limited to e.g., cancer biopsy samples. Useful predetermined thresholds for assessing expression of one or more markers and/or targets may be determined by any convenient and appropriate method, including comparison of the measured level of expression to a corresponding control. For example, in some instances, a useful predetermined threshold for the level of ABCG2 and/or a cancer-associated antigen assayed in a sample may correspond to a level of ABCG2 and/or cancer-associated antigen as measured in a reference cell, such as a healthy/normal cell.

Methods of Making

As summarized above, methods of the present disclosure also include methods or making and/or identifying antibodies as described herein. A subject antibody can be produced by any known method, e.g., conventional synthetic methods for protein synthesis; recombinant DNA methods; etc.

Where a subject antibody is a single chain polypeptide, it can be synthesized using standard chemical peptide synthesis techniques. Where a polypeptide is chemically synthesized, the synthesis may proceed via liquid-phase or solid-phase. Solid phase polypeptide synthesis (SPPS), in which the C-terminal amino acid of the sequence is attached to an insoluble support followed by sequential addition of the remaining amino acids in the sequence, is an example of a suitable method for the chemical synthesis of a subject antibody. Various forms of SPPS, such as Fmoc and Boc, are available for synthesizing a subject antibody.

Standard recombinant methods can be used for production of a subject antibody. For example, nucleic acids encoding light and heavy chain variable regions, optionally linked to constant regions, are inserted into expression vectors. The light and heavy chains can be cloned in the same or different expression vectors. The DNA segments encoding immunoglobulin chains are operably linked to control sequences in the expression vector(s) that ensure the expression of immunoglobulin polypeptides. Expression control sequences include, but are not limited to, promoters (e.g., naturally-associated or heterologous promoters), signal sequences, enhancer elements, and transcription termination sequences. The expression control sequences can be eukaryotic promoter systems in vectors capable of transforming or transfecting eukaryotic host cells (e.g., COS or CHO cells). Once the vector has been incorporated into the appropriate host, the host is maintained under conditions suitable for high level expression of the nucleotide sequences, and the collection and purification of the antibodies.

Because of the degeneracy of the genetic code, a variety of nucleic acid sequences can encode each immunoglobulin amino acid sequence. The desired nucleic acid sequences can be produced by de novo solid-phase DNA synthesis or by polymerase chain reaction (PCR) mutagenesis of an earlier prepared variant of the desired polynucleotide. Oligonucleotide-mediated mutagenesis is an example of a suitable method for preparing substitution, deletion and insertion variants of target polypeptide DNA. See Adelman et al., DNA 2:183 (1983). Briefly, the target polypeptide DNA is altered by hybridizing an oligonucleotide encoding the desired mutation to a single-stranded DNA template. After hybridization, a DNA polymerase is used to synthesize an entire second complementary strand of the template that incorporates the oligonucleotide primer, and encodes the selected alteration in the target polypeptide DNA.

Suitable expression vectors are typically replicable in the host organisms either as episomes or as an integral part of the host chromosomal DNA. Commonly, expression vectors contain selection markers (e.g., ampicillin-resistance, hygromycin-resistance, tetracycline resistance, kanamycin resistance or neomycin resistance) to permit detection of those cells transformed with the desired DNA sequences.

*Escherichia coli* is an example of a prokaryotic host cell that can be used for cloning a subject antibody-encoding polynucleotide. Other microbial hosts suitable for use include bacilli, such as *Bacillus subtilis*, and other enterobacteriaceae, such as *Salmonella, Serratia*, and various *Pseudomonas* species.

Other microbes, such as yeast, are also useful for expression. *Saccharomyces* (e.g., *S. cerevisiae*) and *Pichia* are examples of suitable yeast host cells, with suitable vectors having expression control sequences (e.g., promoters), an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

In addition to microorganisms, mammalian cells (e.g., mammalian cells grown in in vitro cell culture) can also be used to express and produce the polypeptides of the present invention (e.g., polynucleotides encoding immunoglobulins or fragments thereof). See Winnacker, From Genes to Clones, VCH Publishers, N.Y., N.Y. (1987). Suitable mammalian host cells include CHO cell lines, various Cos cell lines, HeLa cells, HEK cells, myeloma cell lines, and transformed B-cells or hybridomas. Expression vectors for these cells can include expression control sequences, such as an origin of replication, a promoter, and an enhancer (Queen et al., Immunol. Rev. 89:49 (1986)), and necessary processing information sites, such as ribosome binding sites, RNA splice sites, polyadenylation sites, and transcriptional terminator sequences. Examples of suitable expression control sequences are promoters derived from immunoglobulin genes, SV40, adenovirus, bovine papilloma virus, cytomegalovirus and the like. See Co et al., J. Immunol. 148: 1149 (1992).

Once synthesized (either chemically or recombinantly), the whole antibodies, their dimers, individual light and heavy chains, or other forms of a subject antibody (e.g., scFv, etc.) can be purified according to standard procedures of the art, including ammonium sulfate precipitation, affinity columns, column chromatography, high performance liquid chromatography (HPLC) purification, gel electrophoresis, and the like (see generally Scopes, Protein Purification (Springer-Verlag, N.Y., (1982)). A subject antibody can be substantially pure, e.g., at least about 80% to 85% pure, at least about 85% to 90% pure, at least about 90% to 95% pure, or 98% to 99%, or more, pure, e.g., free from contaminants such as cell debris, macromolecules other than a subject antibody, etc.

In some embodiments, methods of generating a multi-specific antibody of the present disclosure may include producing candidate antibodies and screening for activity. Such methods may generate a multi-specific antibody that specifically binds a cell expressing both ABCG2 and a cancer-associated antigen or MDR1 through the use of a series of steps. Steps of such methods may include: producing a multi-specific antibody or a plurality of antibodies that each include or are expected to include a ABCG2-binding domain and a cancer-associated antigen-binding domain/MDR1-binding domain; contacting a first test cell expressing ABCG2 and cancer-associated antigen or MDR-1 with the multi-specific antibody or plurality of antibodies; contacting a second cell expressing either ABCG2 or the cancer-associated antigen/MDR1 with the multi-specific antibody or plurality of antibodies; comparing the binding of the multi-specific antibody to the first cell with the binding of the multi-specific antibody to the second cell to determine a binding-specificity ratio; and identifying the multi-specific antibody, or one or more of the antibodies of the plurality, as specific for the cell expressing both ABCG2 and the cancer-associated antigen/MDR1 when the ratio is above a predetermined threshold. Where such a threshold for comparative binding is employed, the threshold may vary and may range from 1.5:1 or more, including but not limited to e.g., 2:1, 3:1, 4:1, 5:1, 6:1, 7:1, 8:1, 9:1, 10:1, 20:1, 50:1, 100:1, etc.

Various cells may be used in such methods, including but not limited to e.g., the cells described herein. In some instances, the binding of the antibody to both ABCG2-only expressing cells and the cancer-associated antigen-only expressing cells may be performed. For example, in some instances, the method may include, relative to the steps described above, where the second cell expresses ABCG2 and not the cancer-associated antigen and the method further comprises contacting a third cell expressing the cancer-associated antigen but not ABCG2 with the multi-specific antibody.

In some instances, such methods may employ one or more controls, including but not limited to e.g., control cells, control reagents, and the like. Useful control cells include those that have a known expression or known lack of expression of one or more relevant genes or proteins. Useful control reagents may include but are not limited to e.g., control antibodies such as but not limited to e.g., monospecific antibodies to known targets. For example, in some instances, such methods of the present disclosure may further include contacting the first cell, the second cell, and/or the third cell with a control antibody selected from: a monospecific anti-ABCG2 antibody and a monospecific anti-cancer-associated antigen antibody. Depending on the particular method used, various other or additional controls, as appropriate, may be employed.

Kits

Aspects of the present disclosure also include kits. The kits may include, e.g., any combination of the antibodies, multi-specific antibodies, reagents, compositions, formulations, cells, nucleic acids, expression vectors, or the like, described herein. A subject kit can include one or more of: a subject antibody, a nucleic acid encoding the same, or a cell comprising a subject nucleic acid. Kits may be configured for various purposes, including e.g., treatment kits (e.g., where a kit may include an anti-ABCG2 antibody or a multi-specific antibody and e.g., one or more additional active agents, such as a chemotherapeutic), kits for producing antibodies, kits for screening antibodies, and the like.

Optional components of the kit will vary and may, e.g., include: a buffer; a protease inhibitor; etc. Where a subject kit comprises a subject nucleic acid, the nucleic acid may also have restrictions sites, multiple cloning sites, primer sites, etc. The various components of the kit may be present in separate containers or certain compatible components may be pre-combined into a single container, as desired.

In addition to above-mentioned components, a subject kit can include instructions for using the components of the kit to practice a subject method. The instructions for practicing a subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. compact disc-read only memory (CD-ROM), digital versatile disk (DVD), diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Exemplary Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure are provided below. As will be apparent to those of ordinary skill in the art upon reading this disclosure, each of the individually numbered aspects may be used or combined with any of the preceding or following individually numbered aspects. This is intended to provide support for all such combinations of aspects and is not limited to combinations of aspects explicitly provided below. It will be apparent to one of ordinary skill in the art that various changes and modifications can be made without departing from the spirit or scope of the invention.

The following example(s) is/are offered by way of illustration and not by way of limitation.

Examples

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, cells, and kits for methods referred to in, or related to, this disclosure are available from commercial vendors such as BioRad, Agilent Technologies, Thermo Fisher Scientific, Sigma-Aldrich, New England Biolabs (NEB), Takara Bio USA, Inc., and the like, as well as repositories such as e.g., Addgene, Inc., American Type Culture Collection (ATCC), and the like.

Example 1: Generation of Antibodies that Bind Specifically to Cells Expressing ABCG2

Materials and Methods

Antibody Generation

Wild type (WT) human and mutant ABCG2 were used for immunization. Various mutants of ABCG2 that constrain the pump in either an open or a closed conformation were generated. The mutations in the human and *Macaca fascicularis* ABCG2 to generate ABCG2 mutants that are constrained in an open configuration are as follows: E221Q. The mutations in the human ABCG2 to generate ABCG2 mutants that are constrained in a closed configuration are as follows: (i) K86M, S87A; (ii) K86M, S87A, Q126A; and/or (iii) K86M, S87A, Q126A, R246E.

3T3-ABCG2 and C6-ABCG2 expressing stable cells were generated by transfecting 3T3 and C6 cells with pMono-hygro-ABCG2 plasmids, followed by 0.2 mg/ml or 0.5 mg/ml hygromycin selection. Virus-like particles displaying AGCG2 proteins were produced by co-transfection of 293T cells with plasmids carrying AGCG2 genes and the retroviral Gag protein, as previously described (Popova et al. 2008, J Virol 82(3): 1389-1398).

Female mice or rats were immunized with ABCG2 (wild type or mutated) human and cynomolgus DNA and/or ABCG2 (wild type or mutated) expressing cells or virus-like particles using various prime-boost strategies for 8-12 weeks. In some instances, more than one antigen (one or more of WT or mutated ABCG2) were used for immunization to increase the diversity of the generated antibodies and boost the immune response. Spleen and lymph node cells from the vaccinated animals were fused with SP2/0 myeloma cells (hybridoma technology). Hybridoma supernatants were screened for the presence of anti-ABCG2 antibodies by flow cytometry, then for functional activity in cell killing (chemo-sensitization) assays and efflux inhibition assays. CDRs from selected murine IgGs were cloned into mammalian IgG1 backbone expression vectors for full-length IgG1 antibody expression and production in HEK 293 host cells via transfection using standard protocols and as described below.

Expression Vectors

For the generation of the antibody expression vectors, the variable regions of heavy and light chain DNA sequences were subcloned in frame with either the human IgG1 constant heavy chain or the human IgG1 kappa constant light chain pre-inserted into the respective generic recipient expression vectors optimized for expression in mammalian cell lines. The genes to be expressed were cloned into the pCI-neo Mammalian Expression Vector (Promega) that uses the full-length human cytomegalovirus (CMV) immediate-early promoter for high level gene expression. The two antibody chains were cloned into two different vectors.

The N-terminal signal sequences from mouse IgG heavy chain and kappa light chain were used for the secreted expression of the heavy and light chain, respectively. The signal peptide was cleaved during expression, leaving intact N-terminus. In the Fab constructs, the C-terminus of the CH1 IgG1 constant region was fused with a 6×His tag for purification.

Production of mAb

Antibody constructs were expressed using polymer-based co-transfection of Expi293 cells (A14527, ThermoFisher) cells growing in suspension with the mammalian expression vectors following the manufacturer's recommendations.

About six days after transfection the cells were harvested by centrifugation. In detail, 1 μg of total encoding DNA per 1 ml of transfected culture was diluted into of Opti-MEM® medium (Life Technologies), and incubated with Expifectamine reagent (Life Technologies) in the same medium for 20 min. The mixture was then added into the Expi293@cells growing in suspension in Expi293@Expression medium (Life Technologies) at 2.5 million cells/ml at 37° C. with and overlay of 8% of CO2 in air. After 6 days, the medium containing the antibody construct was harvested by centrifugation.

Purification of mAbs

To purify antibody formats containing the human and mouse Fc, 10 μl of MabSelect™ SuRe™ (GE Healthcare) per 1 ml of supernatant were added to the harvested medium and kept stirring at 4° C. overnight. The next day, the protein A resin was applied in a 24 well filter plate using a vacuum manifold unit (Pall Lifesciences, USA). The resin was washed with PBS and the antibody eluted in 50 mM phosphate pH 3 and neutralized with 10×PBS pH 13.

Analytical Test for mAbs (GXII Reduced and Non-Reduced)

Purity and monomer content of the final protein preparation was determined by high-throughput analysis on the Caliper's LabChip GXII using Protein Express LabChip Kit (Perkin-Elmer) as described by the manufacturer. The chip was automatically primed on the instrument with polymer solution containing 0.2% SDS and fluorescent staining dye. The destain channels were filled with polymer solution free of SDS and dye. Briefly, proteins in reducing and not reducing conditions were prepared by mixing a small volume (2-5 μL) of sample with the caliper sample buffer with or without DDT. The samples were denatured at 75° C. for 5 minutes, centrifuged at 2000 g for 3 minutes, and then run. Electropherograms were generated by LabChip GXII Touch software (Perkin Elmer).

Analytical Test for mAbs (HPLC)

Purity and monomer content of the final protein preparation was determined by high-throughput analysis on HPLC. Size exclusion chromatography (SEC) was performed using an Advancebio SEC 300A 4.6×300 mm, 2.7 um (p/n PL1580-5301) (Agilent Technologies) on an Infinity 1260 Agilent HPLC system. Injections were made under isocratic elution conditions using a mobile phase of PBS, 400 mM sodium chloride, pH 7.4, and detected with absorbance at 280 nm. Quantification is based on the relative area of detected peaks.

A subject antibody can be substantially pure, e.g., at least about 80% to 85% pure, at least about 85% to 90% pure, at least about 90% to 95% pure, or 98% to 99%, or more, pure, e.g., free from contaminants such as cell debris, macromolecules other than a subject antibody, etc.

Transient Transfection of 293T Cells 293T cells were transiently transfected with the Human P Glycoprotein Tagged ORF Clone in pLenti-C-Myc-DDK-P2A-Puro plasmid using the optimized PEIPro™ transfection protocol (Polyplus). DNA and JetPEI® were respectively diluted in culture media before being gently mixed for approximately 10 min. This mixing led to the formation of a transfection complex, which was directly added to the cell culture. Efflux blockade was measure using the Multidrug Resistance Direct Dye Efflux Assay (Chemicon) following the manufacturer's protocol.

Efflux Blockade Experimental Procedure

293T_ABCG2_OX cells were washed several times and aliquoted into 96-well plates as 50 μl aliquots/well at a cell density of 2×10e6 cells per ml in phenol red-free DMEM. Cells were mixed with 50 μl antibodies or the small molecule inhibitors of ABCG2:-fumitremorgin C (FTC), or its tetracyclic analogue K0143, with a final concentration of 1 μM. Cells were then incubated in the presence of 2.5 μM Mitoxantrone 1 h at 37° C. The cells were subsequently washed twice and finally resuspended in 200 ml PBS. Mitoxantrone fluorescence was measured using excitation at 635 nM and emission at 647 nM. Protocols was measuring efflux blockade are found in Szabó E, et al., PLoS One. 2018 Jan. 17; 13(1):e0190629; Deeken J F, et al., Mol Pharmacol. 2009 November; 76(5):946-56).

Monoclonal Antibody Titration Binding to KPG2

Binding titration of recombinant antibodies to KPG2 transfectants was performed by serial dilution of antibodies from about 666 nM. Diluted antibody in flow cytometry buffer was incubated with cells on ice for 30 min. After 2 washes with flow cytometry buffer, bound antibody was detected with PE-labeled $F(ab')_2$ fragment goat anti-human IgG (Jackson ImmunoResearch) diluted 1:200 in flow cytometry buffer and incubated with cells for 20 min on ice. After 2 washes with flow cytometry buffer fluorescence was measured on an Attune NxT flow cytometer. Data were analyzed with GraphPad Prism 8.0 software to determine EC50's.

The bispecific antibodies were characterized by binding titration and chemotoxicity assay.

Cell Binding Assays. Antibody binding to cells was evaluated by flow cytometry. 293T cells stably transfected to express human or cynomolgus ABCG2 (293T_ABCG2_OX) were washed once in flow cytometry buffer (PBS+2% FBS+0.02% sodium azide), resuspended at 2×10^6 cells/mL in flow cytometry buffer, and dispensed into 96-well microtiter plates at 0.1 mL/well. Recombinant antibodies were added to cells at 5 μg/mL for initial binding confirmation, or serially diluted from 100 μg/mL in flow cytometry buffer. After incubating cells on ice for 30 min, cells were washed twice with flow cytometry buffer. Bound antibody was detected with PE-labeled $F(ab')_2$ fragment goat anti-human IgG (Jackson ImmunoResearch) and evaluated on an Attune NxT flow cytometer. EC50 is calculated to be the concentration of antibody that gives half maximal response.

Cytotoxicity Assays. The effect of antibodies on topotecan cytotoxicity was evaluated on 293T_ABCG2_OX cells, 293T cells stably transfected to express ABCG2. Cells were plated in 0.05 mL of Assay Media (DMEM+10% FBS) at 5000 cells/well in white, flat bottom 96-well tissue culture plates. Topotecan was prepared at 2× final assay concentration by serial dilution from 200 uM in assay media containing test antibodies or control antibodies at 100 μg/mL (2× final concentration), or Fumitremorgin C, a small molecule ABCG2 inhibitor at 20 uM (2× final concentration). An equivalent volume (0.05 mL) of the topotecan/antibody mixture was added to the 293T_ABCG2_OX cells in 96-well plates. The plates were then incubated at 37° C., in 5% CO2. After 72-96 hr plates were equilibrated to room temperature and cell viability assessed using Promega® CellTiter-Glo® Luminescent Cell Viability Assay according to the manufacturer's recommended protocol. Luminescence was measured on a Molecular Devices® FlexStation® 3 Multi-Mode Microplate Reader and data analyzed using GraphPad Prism 8.0 software. Half maximal inhibitory concentration (IC50) is the concentration of drug (topotecan or other chemotherapy cytotoxic agent) where the response (cell growth) is reduced by 50%.

Xenograft studies

Materials:

Cells: HT1376 (ATCC CRL-1472) human urinary bladder carcinoma cell lines.

Mice: Sixty-five 5-6-weeks-old female SCID-Biege mice (Charles River).

Reagents: G2KT9 anti-ABCG2×anti-CD4 BsAb produced as described above, Human Isotype IgG1 (Bioxcell), topotecan.

Methods:

Cell culture: HT1376 cells were maintained in RPMI medium supplemented with 10% FBS and 1% penicillin and 1% streptomycin at 37° C., 5% $CO_2$. Cell lines used were authentic and confirmed to be *mycoplasma* negative.

Inoculation-2×$10^6$ cells diluted in PBS:Matrigel (1:1) were subcutaneously injected using a 27G insulin syringe into fifty anesthetized 5-6-week-old female SCID-Biege mice under sterile conditions.

Results

FIG. 1A depicts FACS analysis of binding of anti-ABCG2 antibodies, G2.65 and G.302, to HEK 293 naïve cells, HEK 293 cells overexpressing human ABCG2 ("hG2"), and HEK 293 cells overexpressing cynomolgus ABCG2 ("cG2").

Anti-ABCG2 antibody, G2.65 binds to 293 cells overexpressing human ABCG2 ("hG2") but does not significantly bind to 293 naïve cells or to 293 cells overexpressing cynomolgus ABCG2 ("cG2").

Anti-ABCG2 antibody, G2.302 binds to 293 cells overexpressing human ABCG2 ("hG2") and to 293 cells overexpressing cynomolgus ABCG2 ("cG2") but does not significantly bind to 293 naïve cells.

Figure 1B:
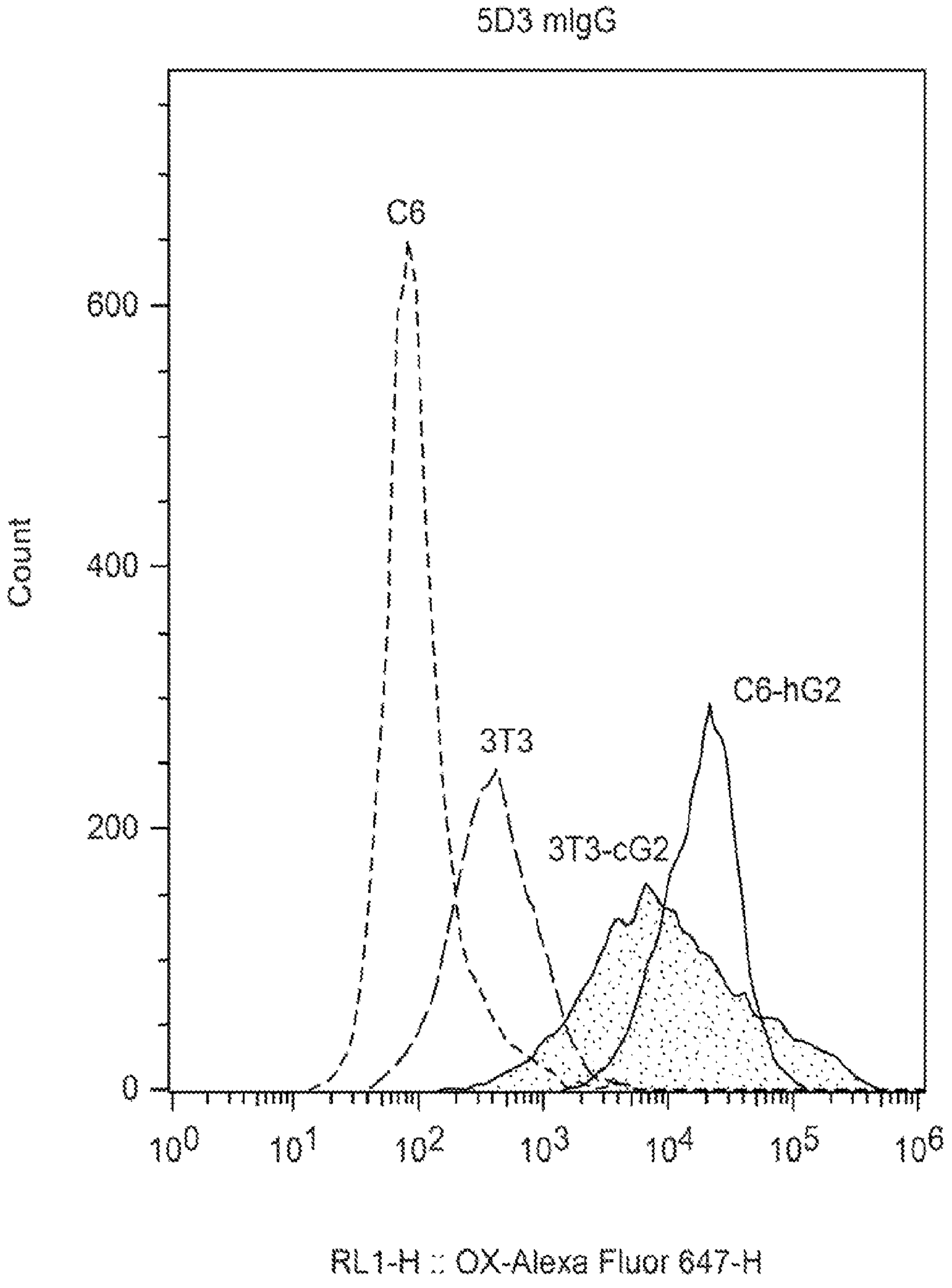

FIG. 1B shows that the anti-human ABCG2 antibody 5D3 binds human ABCG2 expressed on 3T3 and C6 cell lines and to cynomolgus ABCG2 (cG2) expressed by 3T3 cells stably transfected with cABCG2 and to human ABCG2 (hG2) expressed by C6 cells stably transfected with hABCG2.

Figure 2A:
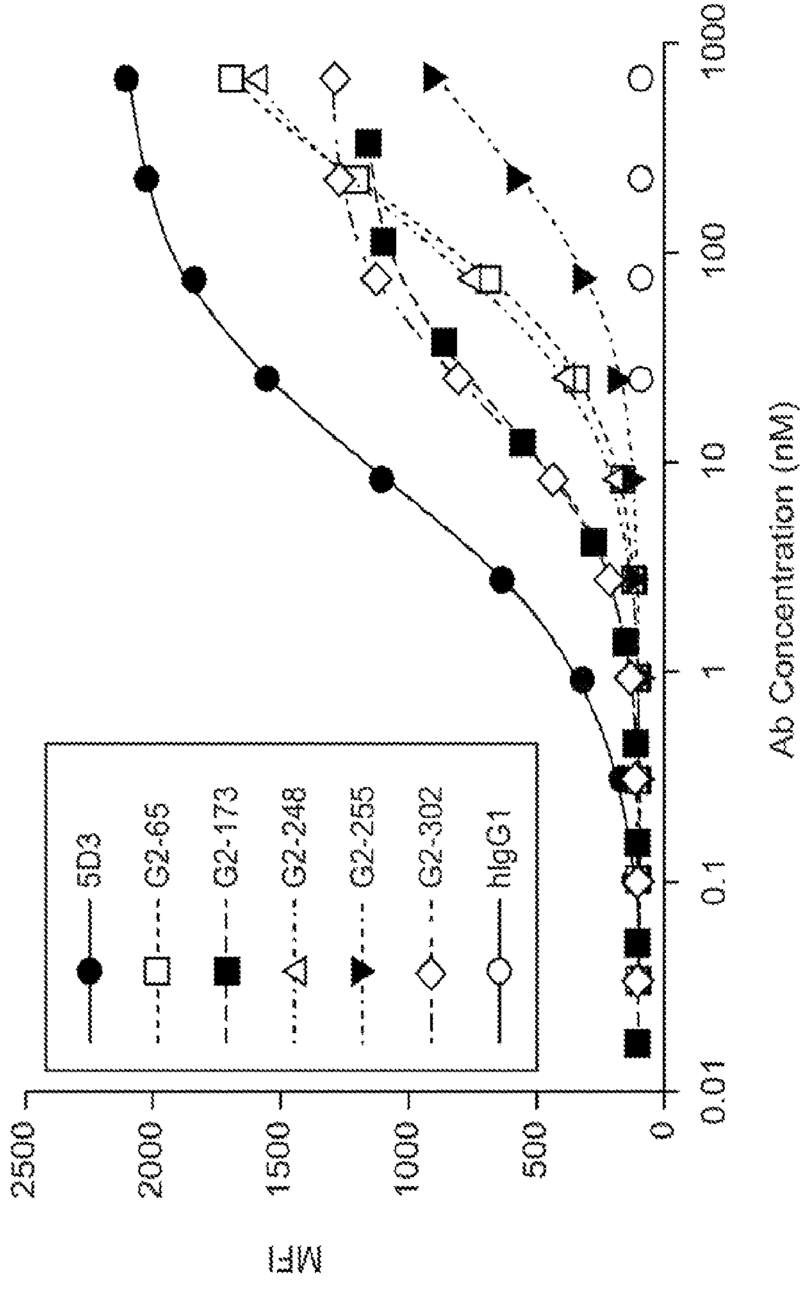
FIGS. 2A-2F depicts characteristics of anti-ABCG2 antibodies.
Figure 2B:
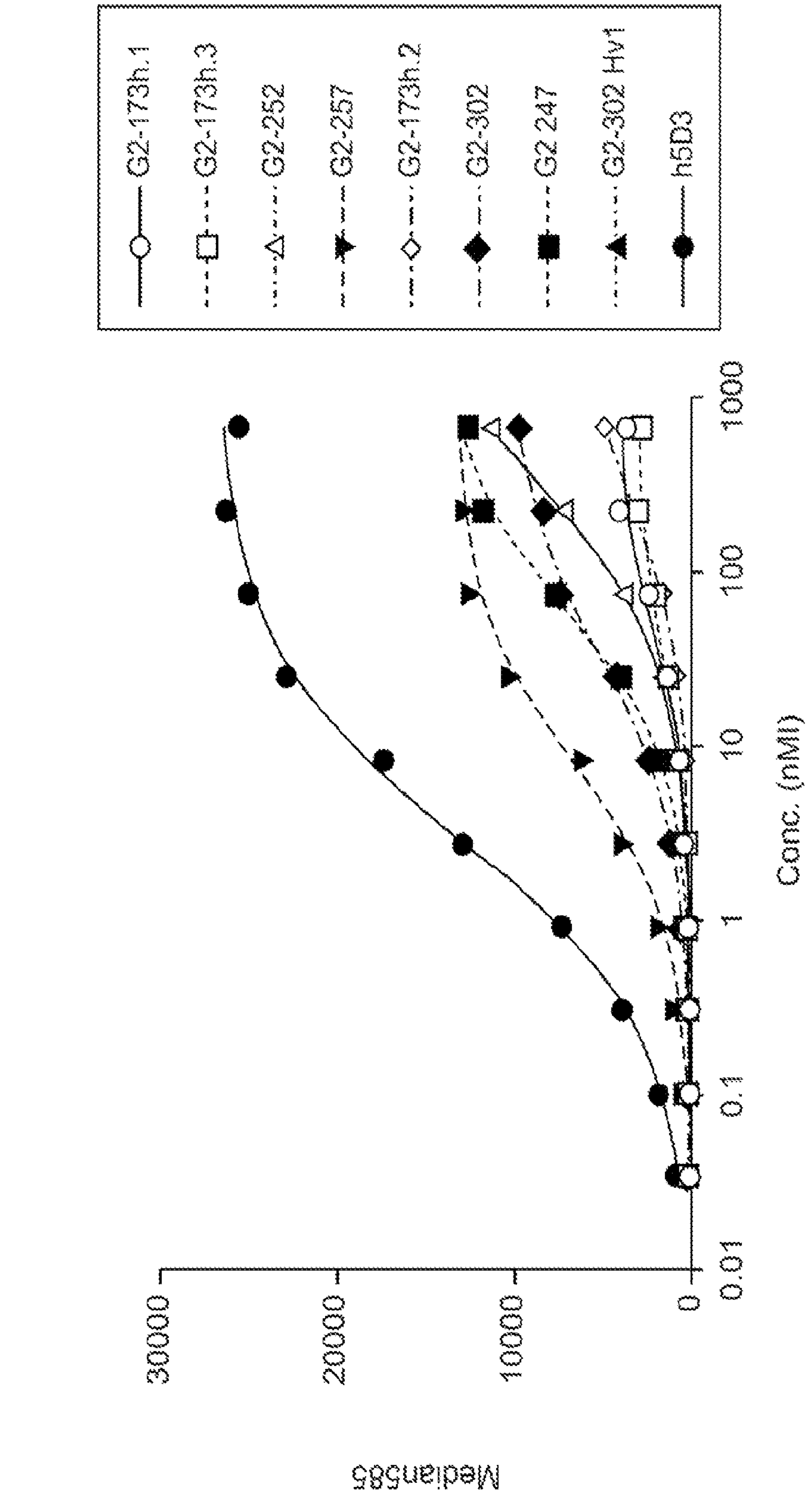

FIGS. 2A-2B. Binding of the anti-ABCG2 antibodies to 293 cells overexpressing human ABCG2. As compared to anti-ABCG2 antibody 5D3, the listed anti-ABCG2 antibodies have a lower affinity for ABCG2. The anti-ABCG2 antibodies having a lower affinity for ABCG2 as compared to 5D3 may be more suitable for (i) making antibodies, potentially conjugated to cytotoxic molecules, that bind preferentially to cancer cells as compared to non-cancer cells due to higher level of expression of G2 by the cancer cells; and/or (ii) making bispecific antibody molecules that preferentially bind to cells expressing both ABCG2 and the second antigen targeted by the bispecific antibody while binding significantly less to a cell expressing only G2.

Figure 2C:
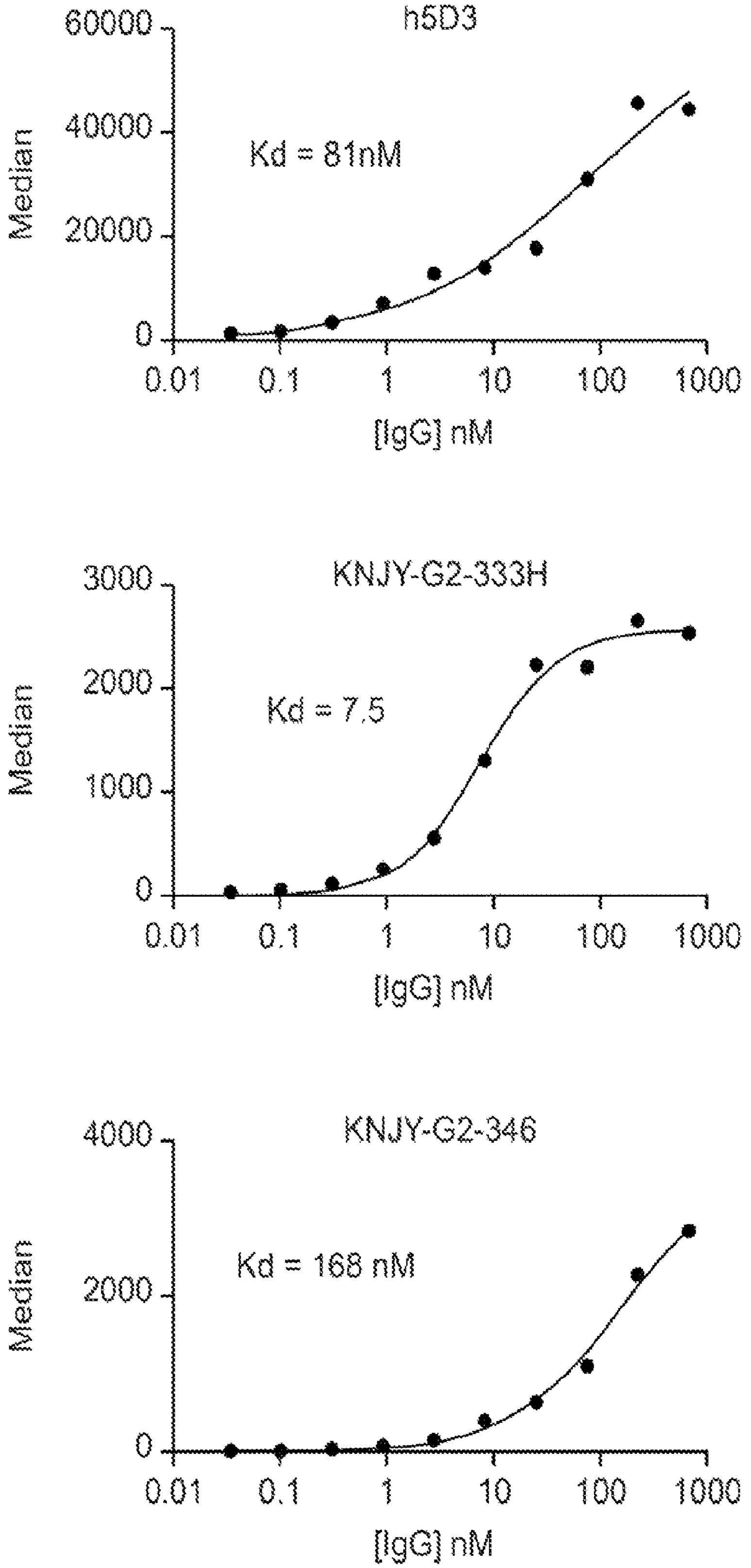
Figure 2C:
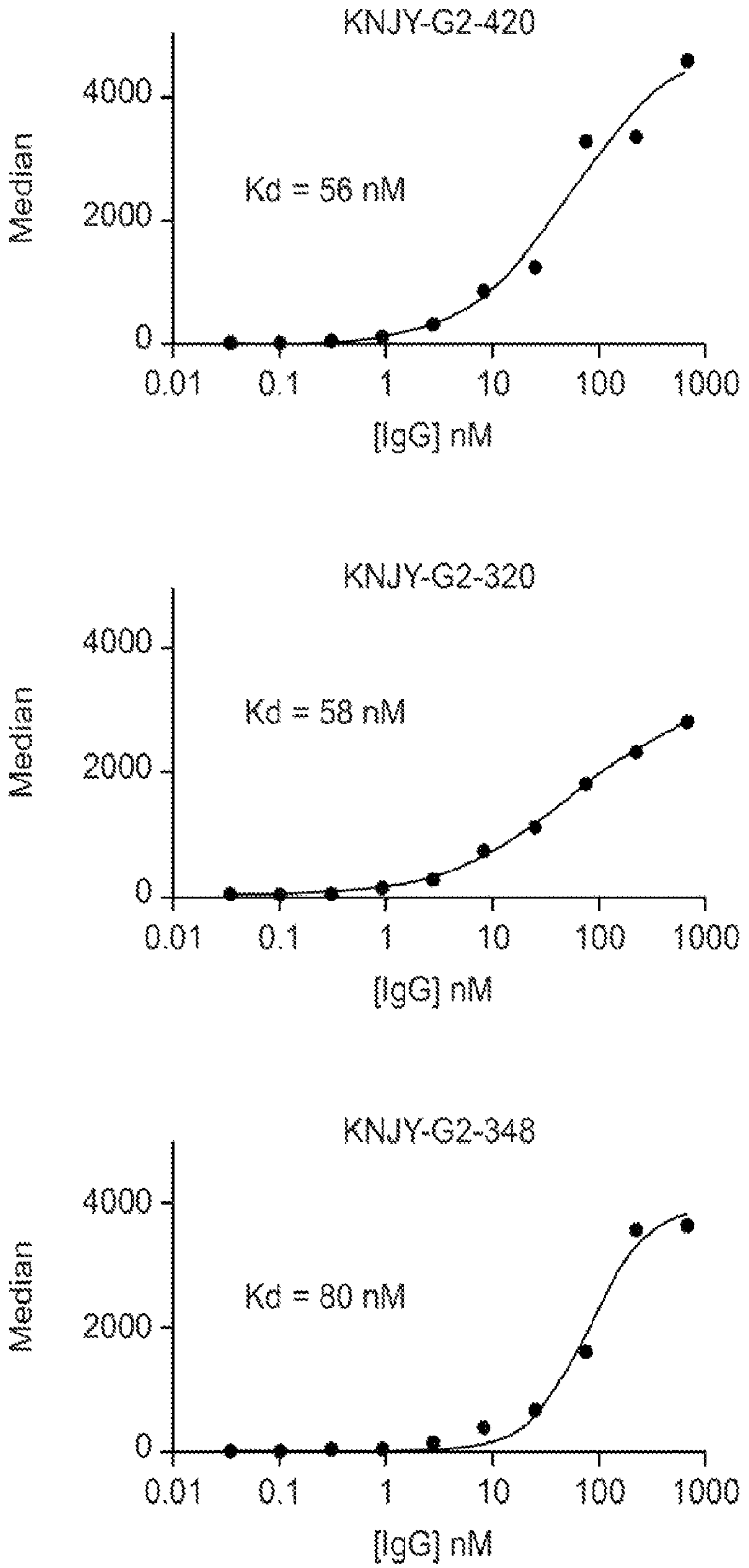
Figure 2C:
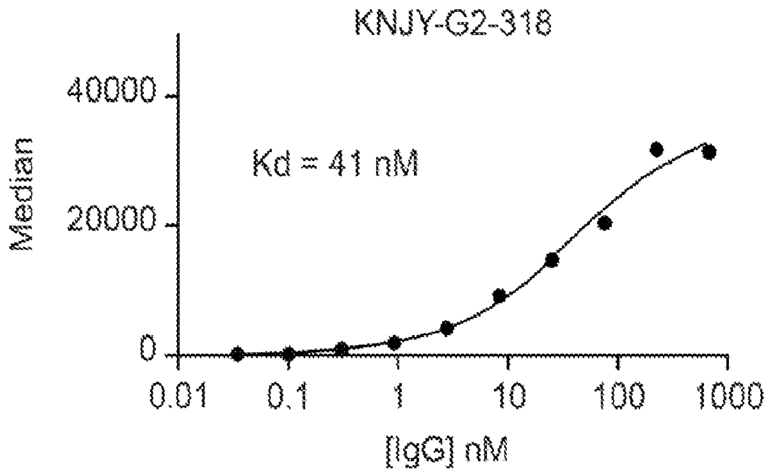
Figure 2C:
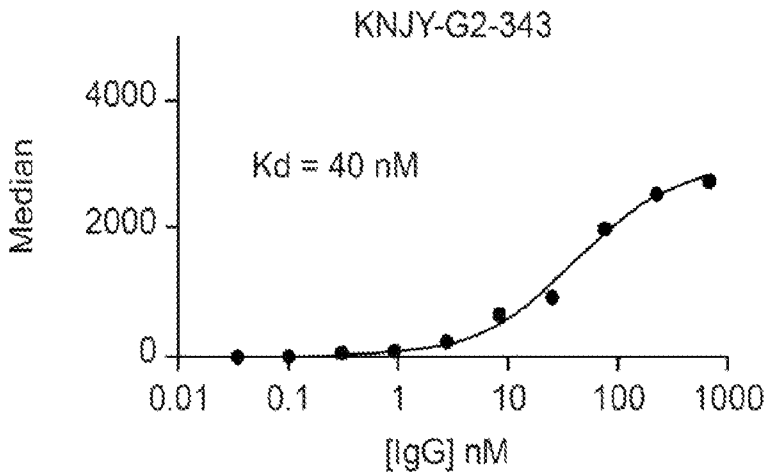
Figure 2C:
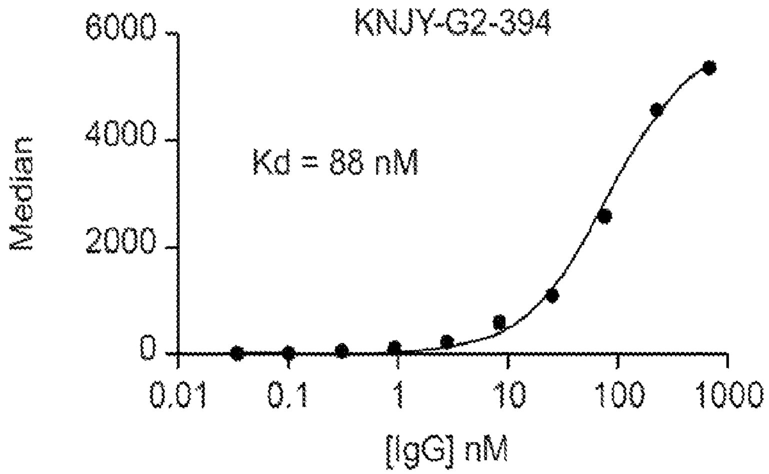

FIG. 2C shows dissociation constant for the indicated anti-G2 antibodies for binding to 293T_ABCG2_OX cells. These antibodies are select antibodies from those listed in Tables 2 and 3. For example, KNJY-G2-420 is an alternate name for the G.420 antibody.

Figure 2D:
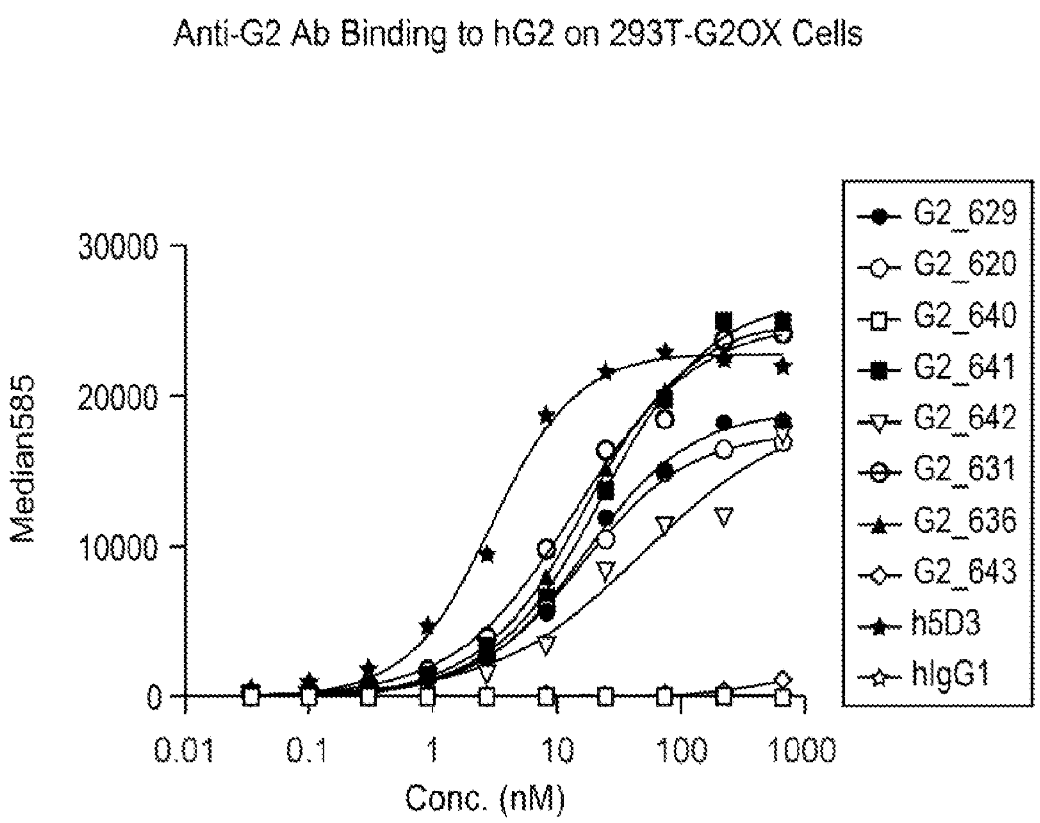

FIG. 2D shows the dissociation constant for the indicated anti-G2 antibodies for binding to 293T_ABCG2_OX cells. These antibodies are select antibodies from those listed in Tables 2 and 3.

Figure 2E:
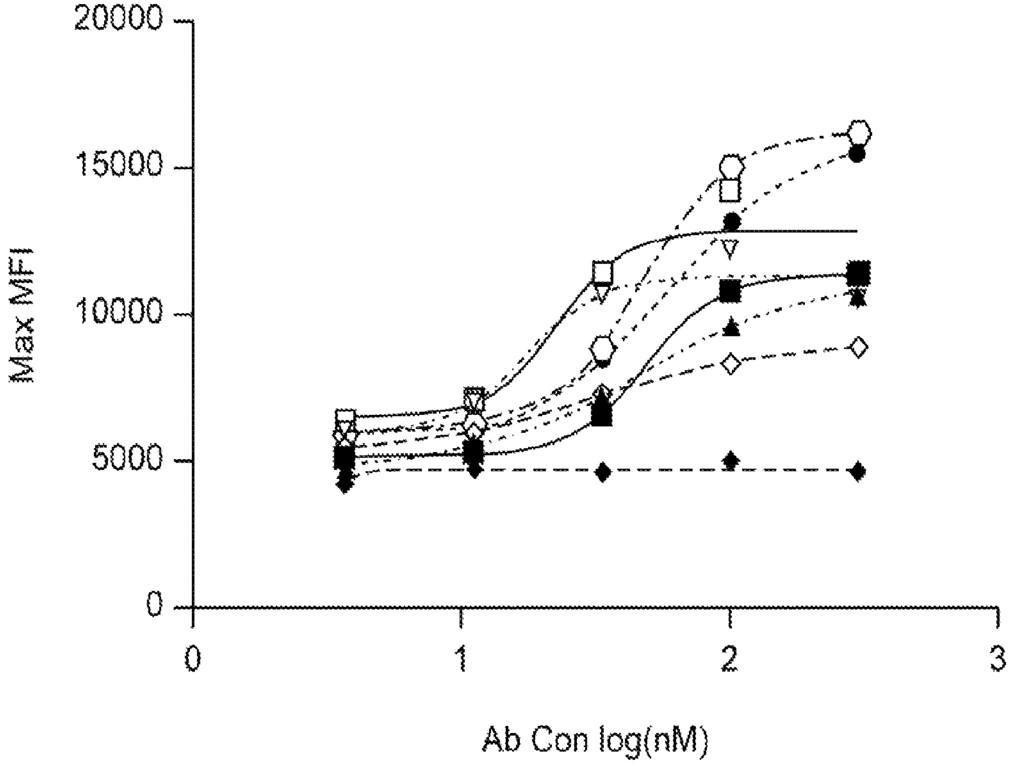
Figure 2E:
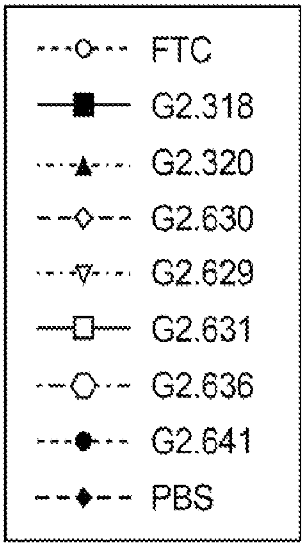

FIG. 2E depicts results for Efflux Blockade (EC50 Shift) on 293T.G2 cells by a variety of anti ABCG2 mAbs (listed with their respective $K_D$ values).

Table 3 lists the following characteristics of the anti-ABCG2 antibodies: binding to 293T cells stably transfected to express human ABCG2 (293T_ABCG2_OX) measured by FACS; binding affinity to 293T_ABCG2_OX cells (binding="+"; non-significant binding="−"); binding to cynomolgus ABCG2 (binding="+"; non-significant binding="−"); block efflux of topotecan by 293T_ABCG2_OX cells (efflux blocked="+"; no significant efflux blocking activity="−"); effect of the listed antibodies on cell killing by topotecan evaluated on 293T ABCG2 OX cells (killing="+"; no significant killing="−").

| Antibody | Binding by FACS | Affinity for human ABCG2 (nM) | Cynomolgus ABCG2 binding | Block Efflux | Killing |
|---|---|---|---|---|---|
| 5D3 | + | 5 | + | + | ++ |
| G2.248 mouse | + | 125 | − | − | − |
| G2.255 mouse | + | 363 | − | − | − |
| G2.256 mouse | + | ND | − | − | − |
| G2.65 mouse | + | 179 | − | − | − |
| G2.173 mouse | + | 17 | − | − | − |
| G2.173 Humanized 1 | + | 46 | − | − | − |
| G2.173 Humanized 2 | + | 273 | − | − | − |
| G2.173 Humanized 3 | + | 44 | − | − | − |
| G2.302 mouse | + | 25 | + | − | − |
| G2.302 Humanized | + | 59 | + | − | ND |
| G2.247 mouse | + | 59 | − | − | ND |
| G2.257 mouse | + | 7.9 | + | − | ND |
| G2.252 mouse | + | 347 | − | − | ND |
| G2.318 rat | + | 41 | + | + | + |
| G2.320 rat | + | 58 | + | + | + |
| G2.333 rat | + | 33 | + | + | + |
| G2.343 rat | + | 40 | + | + | ND |
| G2.346 rat | + | 168 | + | − | ND |
| G2.348 rat | + | 80 | + | − | ND |
| G2.394 rat | + | 88 | + | − | ND |
| G2.420 rat | + | 56 | + | + | ND |
| G2.629 rat | + | 16.8 | ++ | + | + |
| G2.630 rat | + | 15.8 | + | + | + |
| G2.631 rat | + | 14.2 | ++ | + | ++ |
| G2.636 rat | + | 17 | ++ | ++ | +++ |
| G2.641 rat | + | 23 | + | ++ | ++ |
| G2.642 rat | + | 48 | − | − | − |

Cell Killing:
ND, Not Determined;
+++, viability <10% of IgG control;
++, viability ≥10% and <30% of IgG control;
+, viability ≥30% and <50% of IgG control;
−, ≥75% of IgG control Anti-G2 antibody, G2.640 and G.643, raised in rats, did not show significant binding to human or cynomolgus G2 overexpressed in the 293T cell line. The G2.640 antibody has the following sequence:

VH:

(SEQ ID NO: 415)
EVKLEESGPGLVQPSQTLSLTCTVSGFSLTSDGVSWRQPPGKGLEWIAAI
SSGGSTYYNSALKSRLSISRDTSKSQVFLKMNSLQTEDTAIYFCTRDTYY
GYNQIPFVYWGQGTLVTVSS

VL:

(SEQ ID NO: 416)
DIVIIQSPPSLSASLGDKVTISCQASQNIHRYIAWYQQKPGKAPRLLIRY
TSTLESGTPSRFSGSGSGRDYSFSISNVESEDIASYYCLQYVNLWTFGGG
TKLELK

Underlining denotes the CDRs.

Table 4 shows the IC50 (nM) for topotecan cytotoxicity in 293T_ABCG2_OX cells in the presence of the listed anti-G2 antibodies:

| Treatment | IC50 |
|---|---|
| topotecan | 7.61 |
| FTC | 0.09 |
| hIgG1 | 6.87 |
| 5D3 | 0.30 |
| G2-629 | 2.21 |
| G2-630 | 3.01 |
| G2-631 | 1.42 |
| G2-636 | 0.45 |
| G2-640 | 6.90 |
| G2-641 | 1.04 |
| G2-642 | 9.08 |
| G2-318 | 2.72 |
| G2-333 | 2.54 |

Figure 2F:
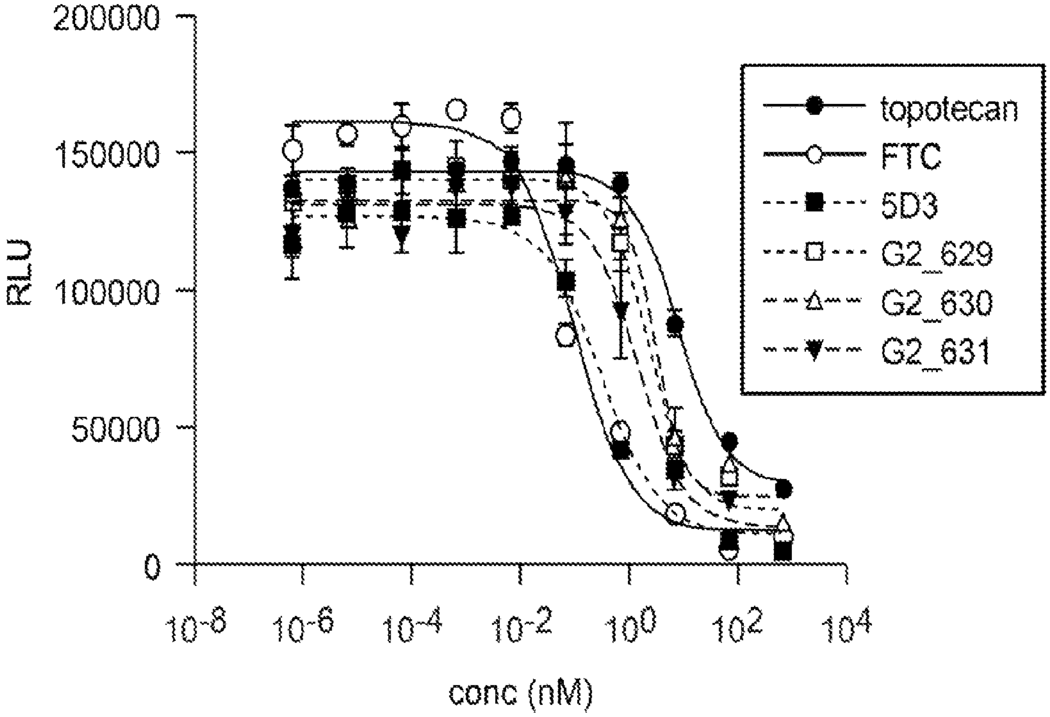
Figure 2F:
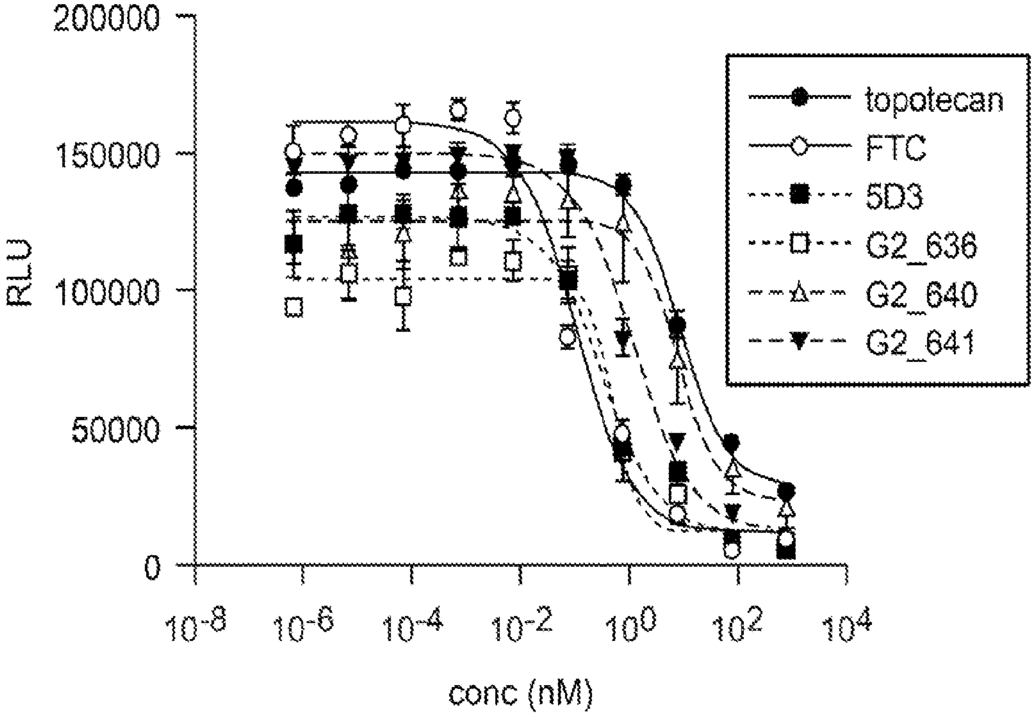
Figure 2F:
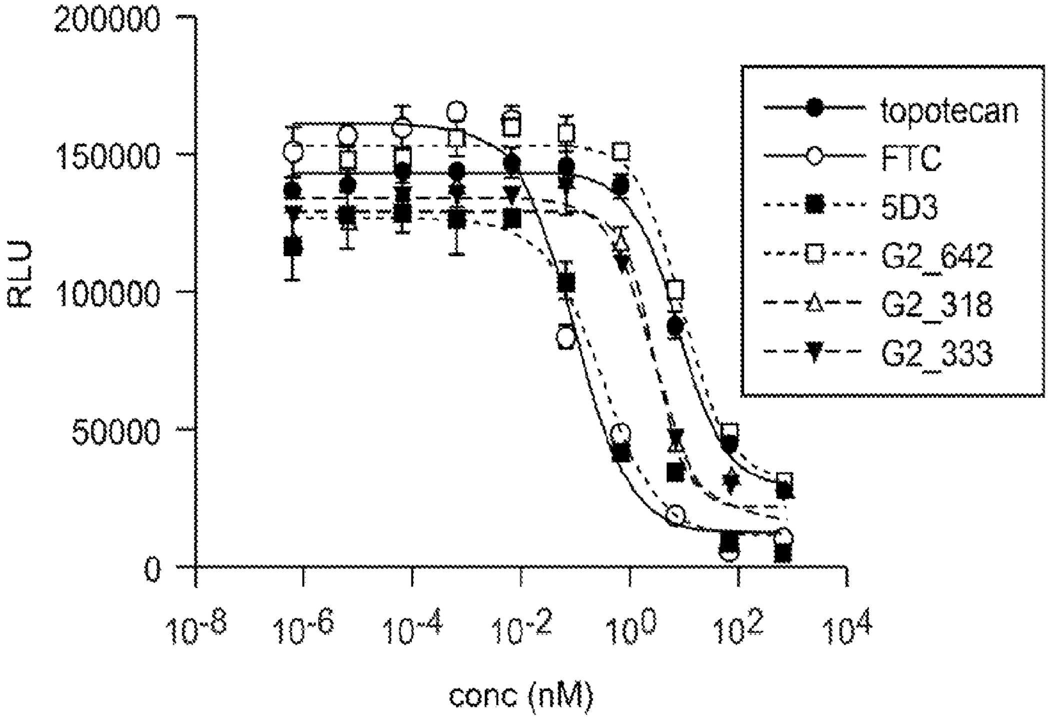

FIG. 2F shows the measurement of IC50 for topotecan cytotoxicity in 293T_ABCG2_OX cells when they are exposed to anti-G2 antibodies.

Example 2: Bi-Specific Antibodies that Bind to ABCG2 and MDR1

Figure 3:
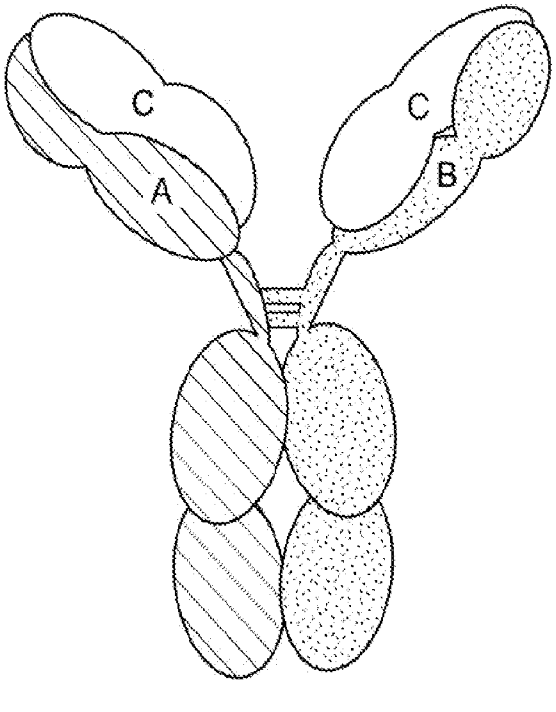
FIG. 3 provides a schematic of a bispecific antibody molecule that includes a first variable heavy chain A, a second variable heavy chain B, and a common light chain C.
Figure 4:
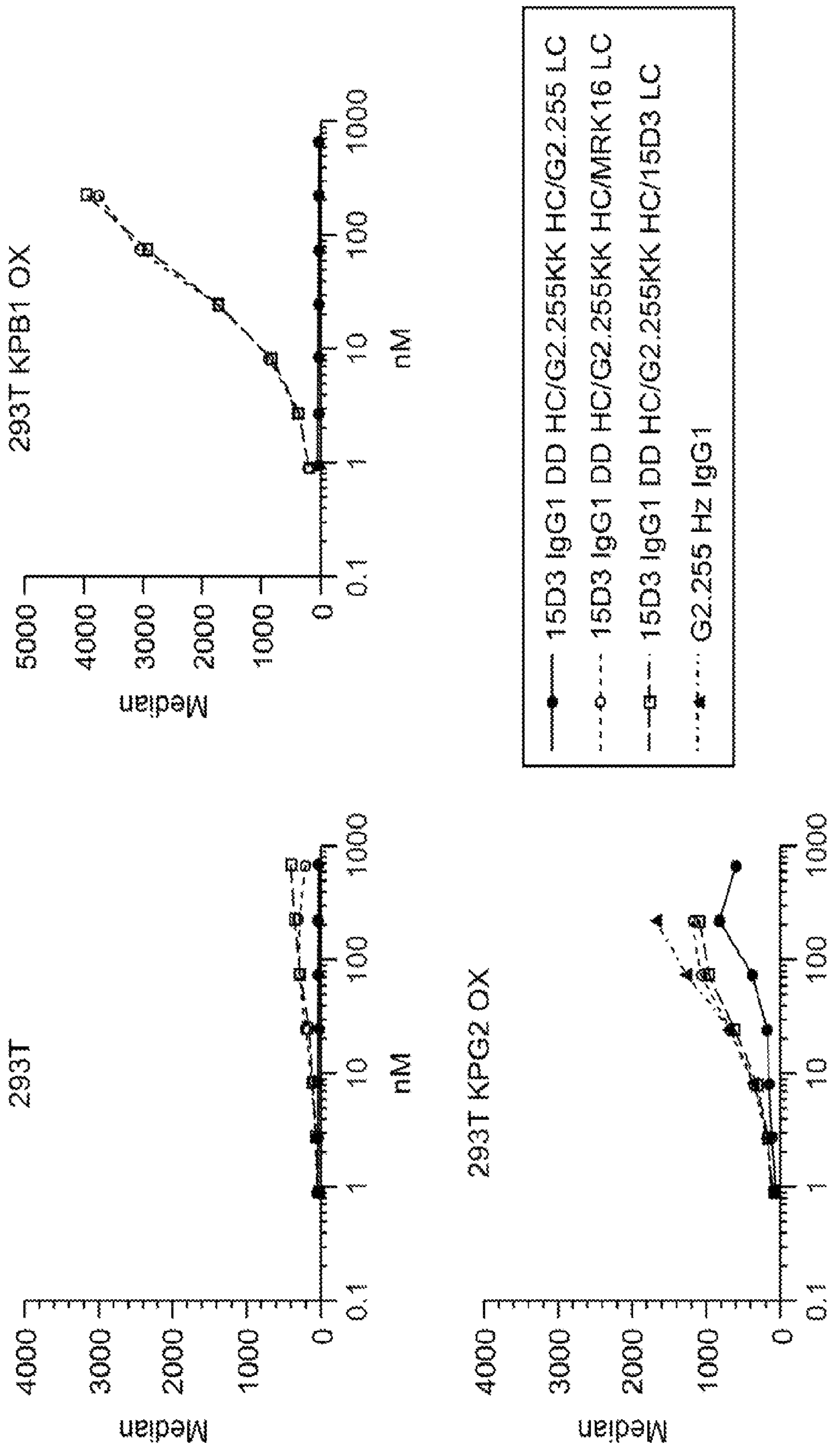
FIG. 4 depicts binding of the indicated bispecific antibodies to 293T cells, 293T cells overexpressing KPB1 (KBP1 OX), and 293T cells overexpressing KPG2 (KBG2 OX). KPB1 refers to MDR1. KPG2 refers to ABCG2. The bispecific antibodies tested are: 15D3 IgG1 DD HC/G2.255KK HC/G2.255 LC; 15D3 IgG1 DD HC/G2.255KK HC/MRK16 LC; and 15D3 IgG1 DD HC/G2.255KK HC/15D3 LC. A humanized version of the bivalent monospecific anti-ABCG2 antibody was also tested.

This example demonstrates the development of antibody molecules that can bind to extracellular domains of EPs. EP blockade results in the re-sensitization and killing of cells that are resistant to chemotherapeutic agents. In this example bispecific antibody molecules have been constructed that bind the extracellular domain (ECD) of two EPs, ABCG2 and MDR1. A schematic of a bispecific antibody molecule is depicted in FIG. 3. Arm A can be a variable heavy chain of an anti-ABCG2 antibody, arm B can be a variable heavy chain of an anti-MDR1 antibody (or an anti-TAA antibody), and arm C is a common light chain, which may be derived from the anti-ABCG2 antibody, the anti-MDR1 antibody, a different anti-ABCG2 antibody, a different anti-MDR1 antibody, or an unrelated antibody.

Materials and Methods

Cell Lines and Cell Viability Experiments

HEK 293T, MCF-7, N6ADR and SKNF7 cell lines expressing PgP were obtained from the American Type Culture Collection. All cell lines and lines derived from them were maintained in RPMI 1640 or DMEM supplemented with up to 10% fetal bovine serum (Sigma), nonessential amino acids, and 2 mmol/L L-glutamine at 37° C. and 5% CO2 in a humidified incubator (unless otherwise indicated). Cells were used as supplied or were modified to overexpress (Ox) PgP or were subject to having PgP expression knocked down (KD) with lentiviral-mediated short hairpin RNA or knock out (KO) of functional genes by CRISPR/Cas-mediated knock out technology essentially as described (Cong, L. et al. (2013) Science 339, 819-823). For vincristine and paclitaxel IC50 determination, cells were plated in normal growth medium and allowed to adhere overnight. Paclitaxel, vincristine or topotecan (Sigma) were added in a dilution series and any modulators were added within ranges of 1 to 500 μM/L. Cell viability was measured 72 h later using the Celltiter-Glo Luminescent Cell Viability Assay (Promega). The concentration of drug resulting in 50% inhibition of cell viability (IC50) was calculated from a multi-parameter curve analysis (GraphPad Prism software GraphPad Software, Inc.) and was determined from a minimum of 2 repeats. Cell lines that did not show 50% reduction in cell viability in response to drug and/or modulator treatment in the majority of experiments conducted were considered to not have reached an IC50 by definition and are listed as having an IC50 of >1000 nmol/L for paclitaxel or the drug/modulator combination under study.

Recombinant cell lines with stable expression of the described monoclonal antibodies (mAbs) were also produced.

Cell Culture Techniques and Antibody Production

Standard cell culture techniques are used as described in Current Protocols in Cell Biology (2000), Bonifacino, J. S., Dasso, M., Harford, J. B., Lippincott-Schwartz, J. and Yamada, K. M. (eds.), John Wiley & Sons, Inc.

293 & CHO cells were used for transient production of mAbs, Fab'2s, Fabs and bispecific mAbs. Different antibody constructs were expressed using polymer-based co-transfection of Expi293 cells (A14527, ThermoFisher). Cells were grown in suspension with the mammalian expression vectors following the manufacturer's recommendations.

For preparation of bispecific antibody molecules, cells were transfected with the corresponding expression vectors in a 1:1:4 ratio (heavy chain KK: heavy chain DD: light chain). For standard antibody expression a 1:2 ratio (heavy chain: light chain) was used.

Six days after transfection the cells were harvested by centrifugation. In detail, 1 μg of total encoding DNA per 1 ml of transfected culture was diluted into of Opti-MEM® medium (Life Technologies), and incubated with Expifectamine reagent (Life Technologies) in the same medium for 20 min. The mixture was then added into the Expi293@cells growing in suspension in Expi293@Expression medium (Life Technologies) at 2.5 million cells/ml at 37° C. with and overlay of 8% of $CO_2$ in air. After 6 days, the medium containing the antibody construct was harvested by centrifugation.

Reagent Cell Lines Used to Test: Binding, Efflux Blockade, Cell Sensitization to Chemotherapeutics Human embryonic kidney (HEK) cell line HEK 293FT (Life Technologies) was maintained in Dulbecco's modified Eagle's Medium (DMEM) supplemented with 10% fetal bovine serum (HyClone), 2 mM GlutaMAX (Life Technologies), 100 U/mL penicillin, and 100 g/mL streptomycin at 37° C. with 5% $CO_2$ incubation.

293T cells were transiently transfected with the Human P Glycoprotein Tagged ORF Clone in pLenti-C-Myc-DDK-P2A-Puro plasmid using the optimized PEIPro™ transfection protocol (Polyplus). DNA and JetPEI® were respectively diluted in culture media before being gently mixed for approximately 10 min. This mixing led to the formation of a transfection complex, which was directly added to the cell culture. Efflux blockade was measure using the Multidrug Resistance Direct Dye Efflux Assay (Chemicon) following the manufacturer's protocol.

Sources of Target Sequences, Antibody Sequences and Specific Anti-Target Antibody Sequences P Glycoprotein (PgP), also known as Multidrug resistance protein 1 (MDR1), (gene ABCB1) (NM_000927) Human Tagged ORF Clone in pLenti-C-Myc-DDK-P2A-Puro and ABCG2 ABCG2 (NM_004827) Human Tagged ORF Clone in pCMV6-XL5 were obtained from Origene, anti CD47 antibody (CC2C6, Seiffert M, et al. (1999) Blood 94:3633) from Biolegend, anti-ABCB1 JSB-1 (MAB4120) from Millipore, anti-Human ABCG2 Antibody (Clone 5D3) from R&D Systems. MDR1 is also referred to herein as KPB1. ABCG2 is also referred to herein as KPG2.

Generation of a Stable ABCB1 Overexpressing (Ox) Cell Lines

In order to characterize both binding and in vitro efficacy, a cell line that stably overexpressed ABCB1 was developed. Adherent 293T naïve cells obtained from American Type Culture Collection (ATCC) were utilized. As characterized by flow cytometry using a commercially available ABCB1 antibody (Biolegend, clone 4E3.16), this cell line expresses ABCB1 endogenously at a low to moderate degree on the cell surface. 293T naïve cells were transfected with ABCB1 using Polyplus PEIpro reagent. Three days after transfection, cells were put under selection using a Hygromycin B solution (Millipore Sigma). Fourteen days after continuous Hygromycin B selection 293T cells were evaluated for ABCB1 cell surface expression. To ensure non-transfected cells would not expand in future cultures, a bulk sort using fluorescent activated cell sorting (FACS) of ABCB1 positive 293T cells was performed using a FACSArial (BD Biosciences). The bulk sorted 293T ABCB1 over-expressing cells were expanded and ABCB1 over-expression was subsequently re-confirmed.

Generation of a Stable ABCG2 Overexpressing (Ox) Cell Lines

In order to characterize both binding and in vitro efficacy, a cell line that stably overexpressed ABCG2 was developed. Adherent 293T, 3T3 and C6 naïve cells obtained from American Type Culture Collection (ATCC) were utilized. As characterized by flow cytometry using a commercially available ABCG2 antibody (R&D System, clone 5D3), this cell line expresses ABCG2 endogenously at a low to moderate degree on the cell surface. 293T naïve cells were transfected with ABCG2 using lipofectamine 3000 reagent, while 3T3 and C6 were transfected using Neon electroporation. Three days after transfection, cells were put under selection using a Hygromycin B solution (Millipore Sigma). Fourteen days after continuous Hygromycin B selection transfected cells were evaluated for ABCG2 cell surface expression. Stable ABCG2 cells were single sorted using a FACSArial (BD Biosciences) and expanded, and ABCG2 over-expression was subsequently re-confirmed.

Generation of a Stable ABCB1 KD 293T Cell Line

In order to characterize both binding and in vitro efficacy a cell line that had a stable knockdown of ABCB1 expression was developed. Lentivirus was produced in 293T naïve cells by transfection with a R8.74 helper plasmid, a VSVG envelope plasmid, and a GE Dharmacon GIPZ lentiviral vector containing a shRNA for ABCB1. Harvested lentivirus was then used to transduce adherent 293T naïve cells. Three days post transduction, the 293T transduced cells were evaluated for ABCB1 cell surface expression by flow cytometry (Biolegend, clone 4E3.16). As compared to 293T naïve cells, which express ABCB1 endogenously at a low level, the transduced 293T cells had no ABCB1 expression. In addition to this, the GIPZ lentiviral vector contains GFP. All transduced 293T cells were GFP+, indicating, in conjunction with the decrement in expression, that the transduction was successful. A lack of ABCB1 expression was re-confirmed by flow cytometry in subsequent passages.

Generation of KO Cell Lines

To construct ABCG2 gene knockout HEK293 cell lines, HEK293 host cells were first cultured in DMEM (Dulbecco's Modified Eagle's Medium, Gibco, Grand Island, N.Y., USA) supplemented with 10% (v/v) FBS, and glutamine via adhesion culture. Cells were cultivated at 37° C. with 5% CO2 at saturated humidity.

The design of the gRNAs was performed using the online CHOPCHOP web tool for selecting target sites for CRISPR/Cas9, CRISPR/Cpf1 or TALEN-directed mutagenesis. (see Kornel Labun et al., (2016). Nucleic Acids Research; and Tessa G. Montague et at., (2014) *Nucleic Acids Res.* 42:W401-W407). All designed gRNAs were chemically synthesized (ThermoFisher).

Transfection of 293T cells was performed by lipid-based transfection using CRISPRMax reagent (ThermoFisher) according to the manufacturer's protocol. Briefly, one day prior to transfection, adherent cells were plated onto 96-well plates at $0.2\times10^5$ cells per well. On the day of transfection, a solution of GeneArt Platinum Cas9 protein, gRNA and transfecting reagent was added to cells. 72 h post-transfection, cell culture was continued for 2 weeks in a 96 well plate format after the selection of single cells by a limiting dilution method. Subsequently, the picked clones were passaged to 24-well plates and tested by genotype confirmation using Guide-it kit (Takara) according to the manufacturer's protocol. The genomic region surrounding a CRISPR target site for each gene was PCR amplified to determine whether gene editing resulted in indels on one allele (monoallelic) or both alleles (biallelic) in singly isolated clones. The expression of the protein of interest on the clones with mutations in both alleles where tested by FACS.

Construction of the Sequences of the Molecules as Tested (Human Fc, Mouse Fvs or Human Fc, or Humanized Fvs Expression Vectors: For the generation of the antibody expression vectors, the variable regions of heavy and light chain DNA sequences were subcloned in frame with either the human IgG1 constant heavy chain or the human IgG1 kappa constant light chain pre-inserted into the respective generic recipient expression vector optimized for expression in mammalian cell lines. The genes to be expressed were cloned into the pCI-neo Mammalian Expression Vector (Promega) that uses the full-length human cytomegalovirus (CMV) immediate-early promoter for high level gene expression. The two antibody chains were cloned into two different vectors.

The N-terminal signal sequences from mouse IgG heavy chain and kappa light chain were used for the secreted expression of the heavy and light chain, respectively. The signal peptide was cleaved during expression, leaving intact N-terminus. In the Fab constructs, the C-terminus of the CH1 IgG1 constant region was fused with a 6×His tag to facilitate purification.

For the generation of bispecific antibody vectors, the IgG1 derived bispecific molecules include at least of two antigen binding moieties capable of binding specifically to two distinct targets: the pair: PgP (ABCB1) and ABCG2. The antigen binding moieties are Fab fragments composed of a heavy and a light chain, each including a variable and a constant region. A common light chain was identified that was able to pair and effect acceptable binding both as Fab Fab anti-PgP (aPgP) and Fab anti-ABCG2 (aABCG2); its use enabled the avoidance of LC mispairing. Bispecific constructs were made based on electrostatic steering effects, (see e.g., Gunasekeran et al, (2010) Journal of Biological Chemistry 285, 19637-19646; the disclosure of which is incorporated herein by reference in its entirety). Briefly, the polypeptide chains or half antibodies against the targets are assembled as a bispecific antibody through charge pair substitutions at the CH3 domain: one heavy chain contained K392D and K409D substitutions ("DD") and the other contained E356K and D399K substitutions ("KK").

The bispecific mAb molecule included a variable heavy chain comprising HCDRs1-3 from the anti-MDR1 antibody 15D3; a variable heavy chain comprising HCDRs1-3 from the anti-G2 antibody G2-255 both on a human IgG1 Fc, and a common light chain kappa sequence derived from the anti-MDR1 antibody MRK16.

Monoclonal antibody 15D3 (see e.g., U.S. Pat. No. 5,959,084; the disclosure of which is incorporated herein by reference in its entirety) and MRK16 (Iwahashi et al., Cancer Research 53, 1993; the disclosure of which is incorporated herein by reference in its entirety) monoclonal antibodies raised previously against PgP were cloned as recombinant engineered antibodies into a Human IgG1/Kappa expression vector.

Variable heavy and light chain fragments from mouse hybridoma sequences are available and were cloned into the same background of leader sequence and constant region.

Anti ABCG2 monoclonal antibody sequences are disclosed in Table 2; antibody variable heavy and light fragments were cloned into the same background of leader sequence and constant region in two separate vectors.

Results

Detection of ABCB1 and ABCG2 Specific Binding

Binding specificity of the mAbs, Fab and Bispecific IgG1 was tested by FACS using 293T naïve cells overexpressing human ABCB1 target, 293T naïve cells overexpressing human ABCG2. Briefly, the different cell lines were incubated with various amounts of mAbs or bispecific mAbs, or a human IgG1 isotype control antibody on ice for 1 hr. The cells were washed three times with FACS buffer (PBS containing 0.5% BSA). Alexa647 labeled goat anti-human antibody was added as a secondary antibody, and the samples were incubated on ice for another 1 hour. Samples were washed and analyzed using a BD FACS Canto (BD Biosciences).

Binding specificity of the mAbs, Fab and Bispecific IgG1 was tested by FACS using 293T cell lines, 293T naïve cells overexpressing the human ABCB1 target, and 293T cells overexpressing human ABCG2. Briefly, the different cell lines were incubated with various amounts of mAbs or bispecific mAbs, or a human IgG1 isotype control antibody on ice for 1 hr. The cells were washed three times with FACS buffer (PBS containing 0.5% BSA). Alexa647 labeled goat anti-human antibody was added as a secondary antibody, and the samples were incubated on ice for another 1 hour. Samples were washed and analyzed using a BD FACS Canto (BD Biosciences).

This example demonstrates that construction of a bispecific hetero-bivalent antibody molecule, one arm of which binds to the efflux pump MDR1/PgP and the other arm of which binds to the efflux pump ABCG2. When both targets are simultaneously present on the surface of a cell, the bispecific antibody binds to the cell with relatively high affinity/avidity. In comparison, if either MDR1/PgP or ABCG2 are absent, or substantially reduced, the binding of the bispecific antibody is significantly reduced or undetectable.

The bispecific antibody contains one arm that binds to and antagonizes a transporter protein, (the efflux pump PgP), and renders the cells more sensitive to chemotherapeutic agents. At the same time the other arm binds to another efflux pump ABCG2.

Example 3: Bi-Specific Antibodies that Bind to ABCG2 and EGFR

This example demonstrates the development of antibody molecules that can to extracellular domains of ABCG2 and EGFR. EP blockade results in the re-sensitization and killing of cells that are resistant to chemotherapeutic agents.

Materials and Methods are similar to those described in the Example 2. 293T cells were transiently transfected with the ABCG2 (NM_004827) Human Tagged ORF Clone in pCMV6-XL5 plasmid using the optimized PEIPro™ transfection protocol (Polyplus). For the generation of bispecific antibody vectors, the IgG1 derived bispecific antibody molecules include at least of two antigen binding moieties capable of binding specifically to two distinct targets: ABCG2 and EGFR. The antigen binding moieties are Fab fragments composed of a heavy and a light chain, each including a variable and a constant region. A common light chain was identified that was able to pair and effect acceptable binding both as Fab anti-EGFR and Fab anti-ABCG2 (aABCG2).

Figure 5:
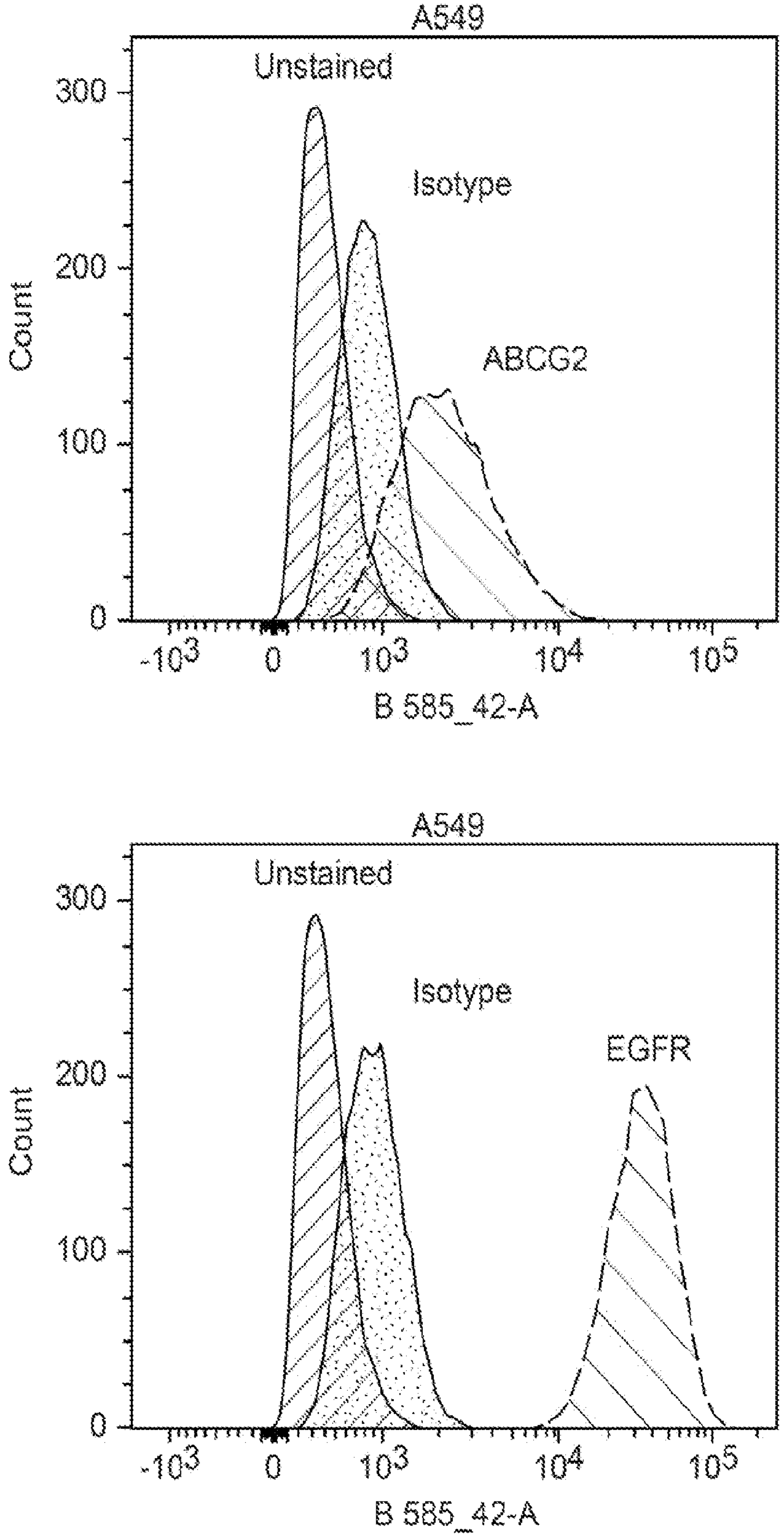
FIG. 5 FACS analysis showing both ABCG2 and EGFR are expressed on A549 cells.

FIG. 5 FACS analysis showing both ABCG2 and EGFR are expressed on A549 cells. Cells were stained with PE-conjugated anti-human ABCG2 antibody, clone 5D3, and PE-conjugated anti-human EGFR antibody, clone AY13.

Anti ABCG2 KNJY-G2-65 antibody variable heavy and light fragments were cloned into the same background of leader sequence and constant region in two separate vectors.

The anti EGFR antibody, 6B3S (Cetuximab), sequence and the corresponding structure, is available at https://www.ncbi.nlm.nih.gov/Structure/pdb/6B3S (Molecular Basis for Necitumumab Inhibition of EGFR Variants Associated with Acquired Cetuximab Resistance, Bagchi A, Haidar J N, Eastman S W, Vieth M, Topper M, lacolina M D, Walker J M, Forest A, Shen Y, Novosiadly R D, Ferguson K M, Mol. Cancer Ther. (2018) 17 p. 521-531), and the sequence is reproduced here for reference:

6B3S antibody variable heavy chain sequence is as follows:

(SEQ ID NO: 388)

QVQLQESGPGLVKPSQTLSLTCTVSGGSISSGDYYWSWIRQPPGKGLEWI

GYIYYSGSTDYNPSLKSRVTMSVDTSKNQFSLKVNSVTAADTAVYYCARV

SIFGVGTFDYWGQGTLVTVSS

6B3S antibody variable light chain sequence is as follows:

(SEQ ID NO: 417)

EIVMTQSPATLSLSPGERATLSCRASQSVSSYLAWYQQKPGQAPRLLIYD

ASNRATGPARFSGSGSGTDFTLTISSLEPEDFAVYYCHQYGSTPLTFGGG

TKAEIK

The CDRs for the antibody according to Kabat nomenclature are indicated in bold and are underlined.

Results

Detection of EGFR and ABCG2 Specific Binding

Binding specificity of the mAbs, Fab and Bispecific IgG1 targeting EGFR was tested by ELISA using rhEGFR-his tagged protein (Sino Biological). Briefly, microtiter plates were coated with 50 μl purified human HGFR-his protein at 2 μg/ml in PBS, and then blocked with 100 μl of 0.4% BSA in PBS. Dilutions of the different antibody formats were added in 1/3 sequential dilutions to each well and incubated for 1 hour at room temperature. The anti-EGFR antibody 6B3S was used as a positive control, and human IgG1 was used as an isotype control. Plates were subsequently washed three times with PBS/Tween and then incubated with HRP-conjugated donkey anti-human constant specific secondary reagent for 1 hour at room temperature. After washing, plates were developed with HRP substrate. The reaction was stopped with 2M $H_2SO_4$, and OD was measured at 520 nM.

Binding specificity of the mAbs, Fab and Bispecific IgG1 was tested by FACS using 293T naïve cells overexpressing human ABCG2 and A549 naïve cell naturally expressing EGFR and ABCG2. Briefly, the different cell lines were incubated with various amounts of mAbs or bispecific mAbs, or a human IgG1 isotype control antibody on ice for 1 hr. The cells were washed three times with FACS buffer (PBS containing 0.5% BSA). Alexa647 labeled goat anti-human antibody was added as a secondary antibody, and the samples were incubated on ice for another 1 hour. Samples were washed and analyzed using a BD FACS Canto (BD Biosciences).

Figure 6:
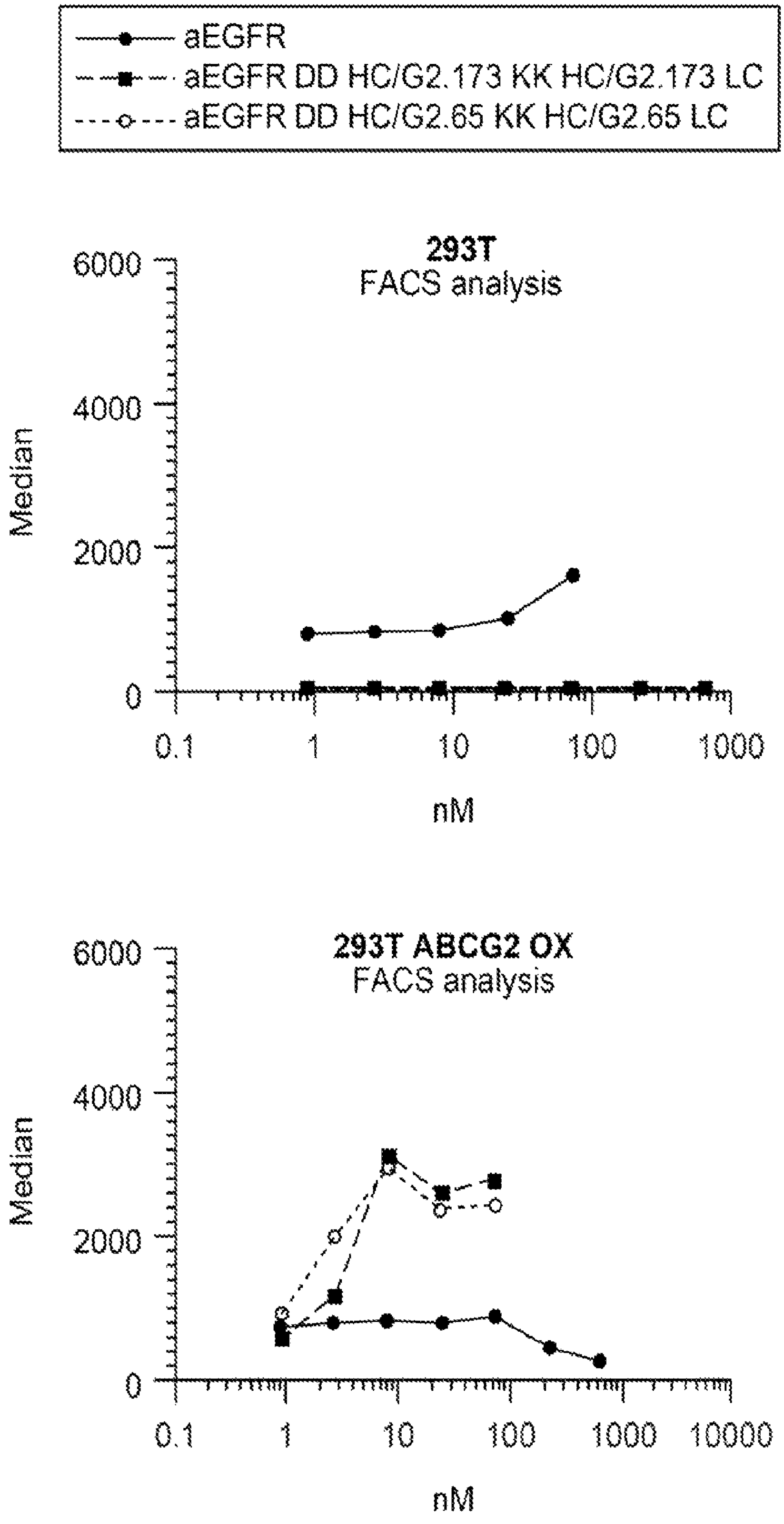
FIG. 6 Binding analysis by FACS and ELISA of two different bispecific antibodies that bind to AGCG2 and EGFR.
Figure 6:
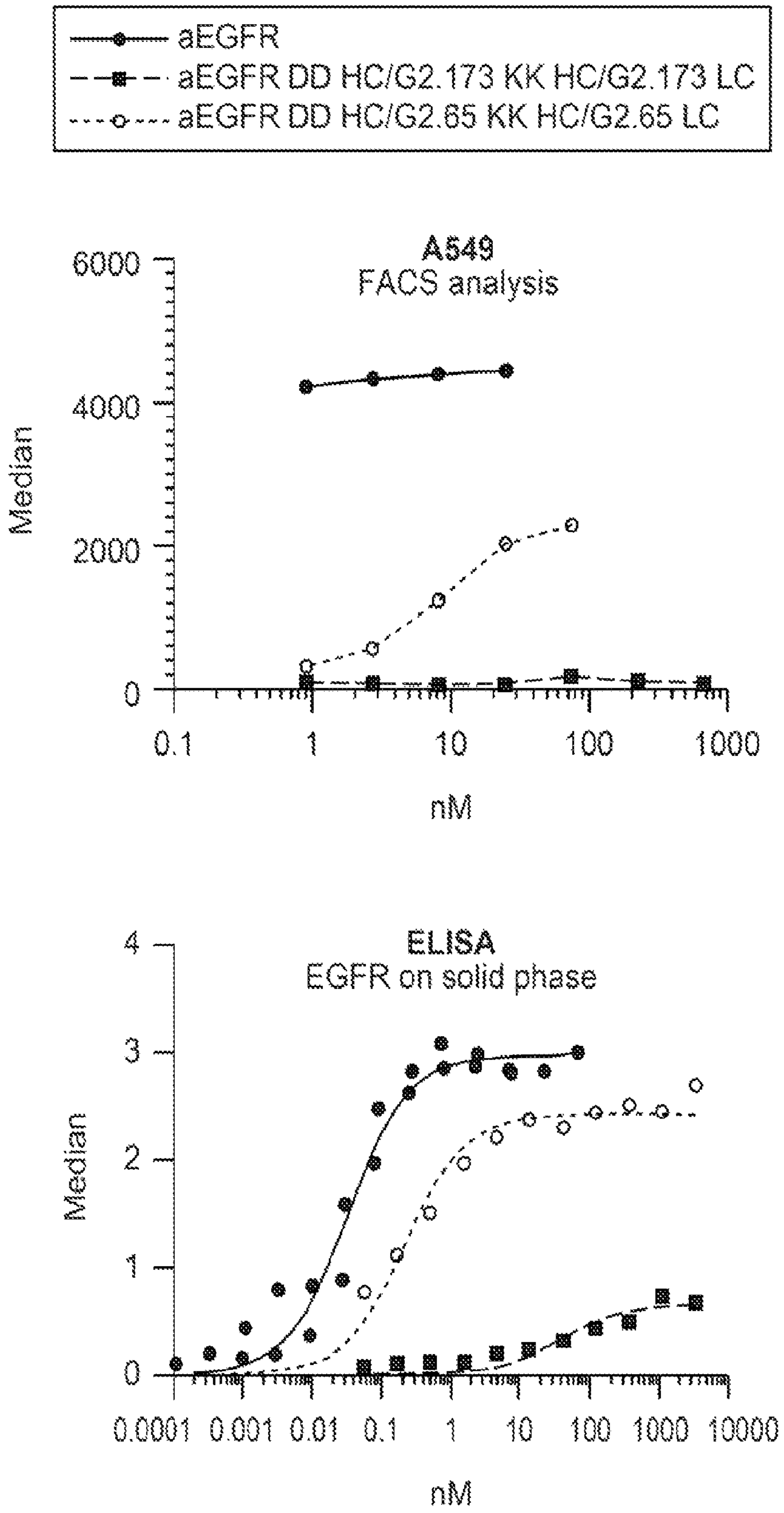

FIG. 6 provides binding data for two different bispecific mAbs that bind to EGFR and ABCG2. aEGFR indicates anti-EGFR antibody, 6B3S. Bispecific antibody: aEGFR DD HC/G2.173KK HC/G.173 LC includes a variable heavy chain from anti-EGFR antibody, 6B3S fused to human IgG1 with the DD substitutions; a variable heavy chain from anti-ABCG2 antibody G2.173 fused to human IgG1 with the KK substitutions; and two copies of the variable light chain of the anti-ABCG2 antibody G2.173 fused to a kappa sequence. Bispecific antibody: aEGFR DD HC/G2.65KK HC/G.65 LC include a variable heavy chain from 6B3S fused to human IgG1 with the DD substitutions; a variable heavy chain from anti-ABCG2 antibody G2.65 fused to human IgG1 with the KK substitutions; and two copies of the variable light chain of the anti-ABCG2 antibody G2.65 fused to kappa sequence.

This example demonstrates that construction of a bispecific hetero-bivalent antibody molecule, one arm of which binds to the efflux pump ABCG2 and the other arm of which binds to the EGFR Target. When both targets are simultaneously present on the surface of a cell, the bispecific antibody binds to the cell with relatively high affinity/avidity. As can be seen in FIG. 6, the G2.6.5-based bispecific antibody has some advantages in the binding studies shown; it demonstrates a stronger affinity for EGFR (by ELISA) and stronger binding for the A549 cells where both targets are displayed whereas both bispecific antibodies bind similarly when the ABCG2 efflux pump is overexpressed.

Figure 7:
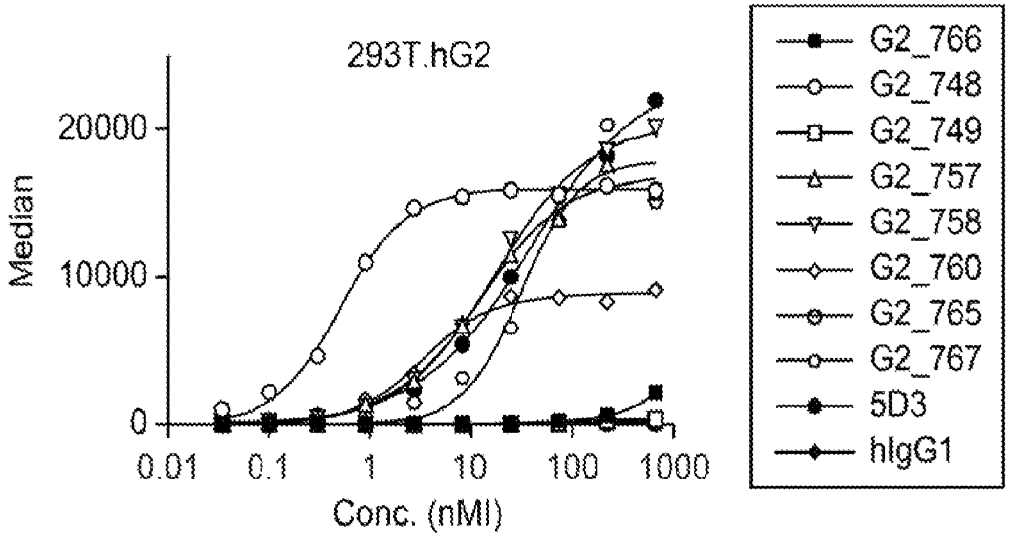
FIG. 7 depicts binding of the indicated anti-ABCG2 monoclonal antibodies to 293T cells overexpressing human ABCG2 ("hG2") and cynomolus ABCG2 (cG2), respectively, along with the corresponding dissociation constants (Kd).
Figure 7:
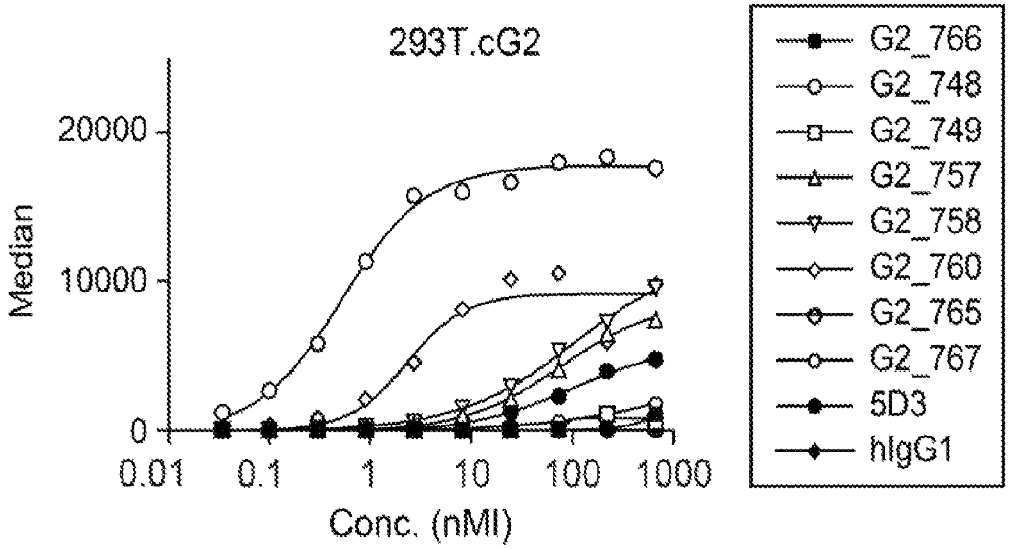

FIG. 7 depicts binding of the indicated anti-ABCG2 monoclonal antibodies to 293T cells overexpressing human ABCG2 ("hG2") and cynomolus ABCG2 (cG2), respectively. As the dissociation constants (Kd) show, antibodies G2.748, G2.757, G2.758, and G2.760 bind both human and cynomolgus ABCG2 with good binding affinity.

Figure 8:
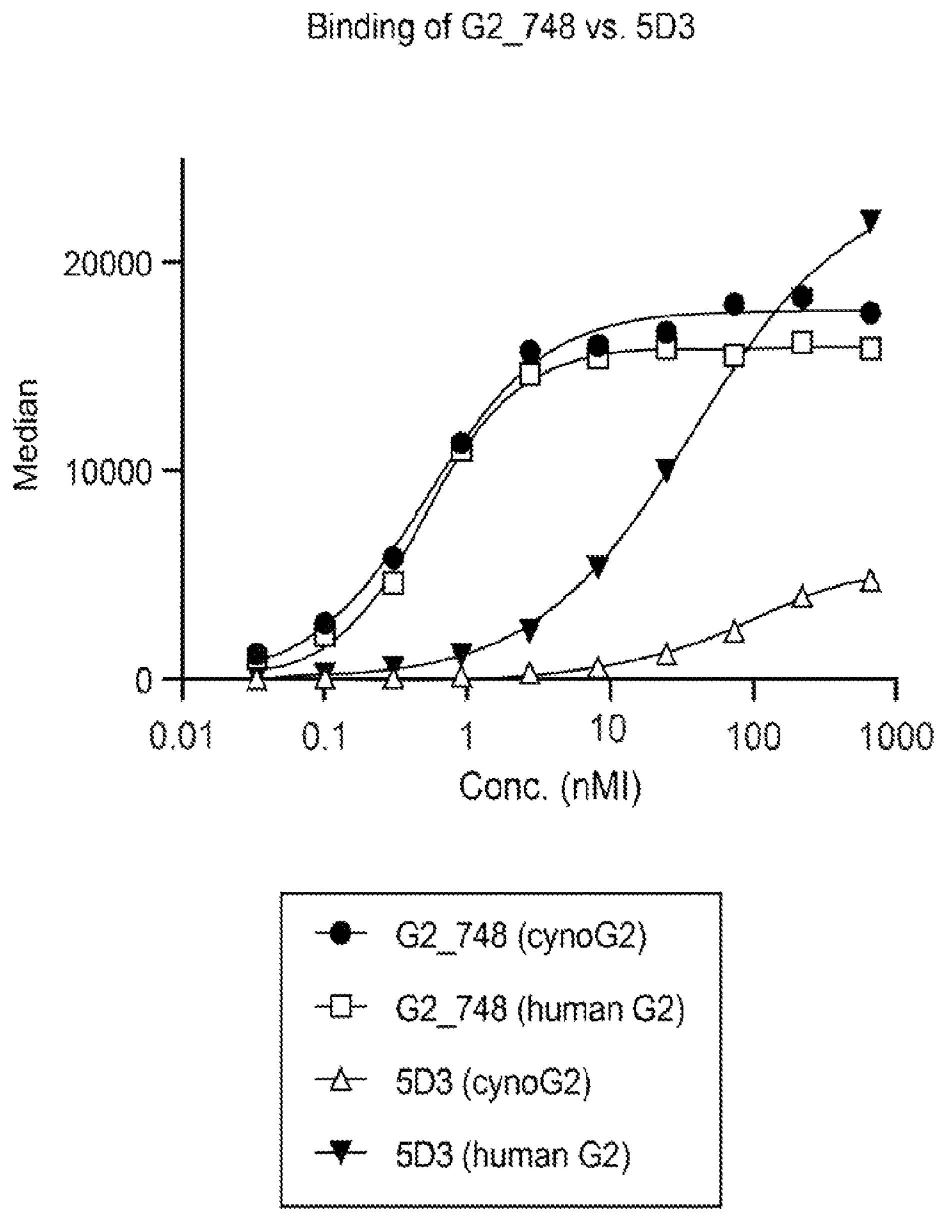
FIG. 8 shows the binding of the anti-ABCG2 antibody G2.748 to 293T cells overexpressing human or cynomolgus ABCG2, in comparison to anti-ABCG2 antibody 5D3, along with the corresponding dissociation constants (Kd).
Figure 9:
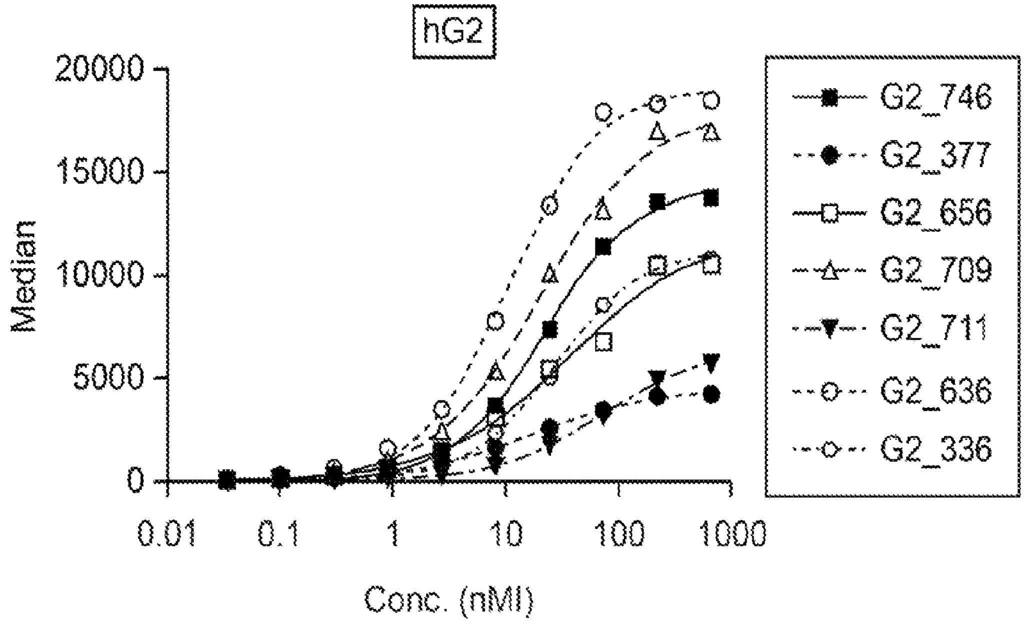
FIGS. 9-11 depict the binding of various recombinant anti-ABCG2 antibodies (panels #1-#3) to 293T cells overexpressing human and cynomolgus ABCG2, respectively, as well as the corresponding Kd values.
Figure 9:
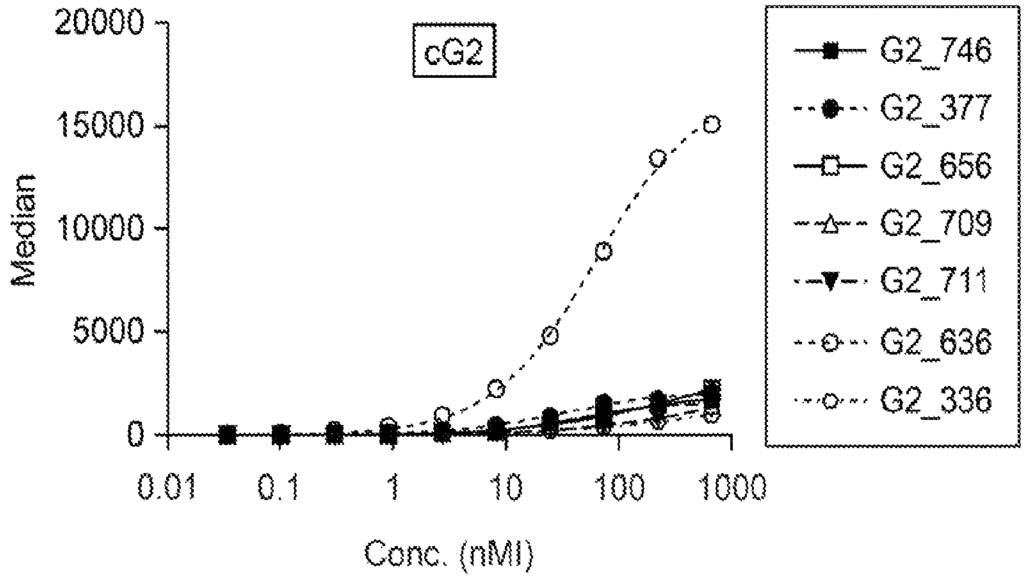
Figure 10:
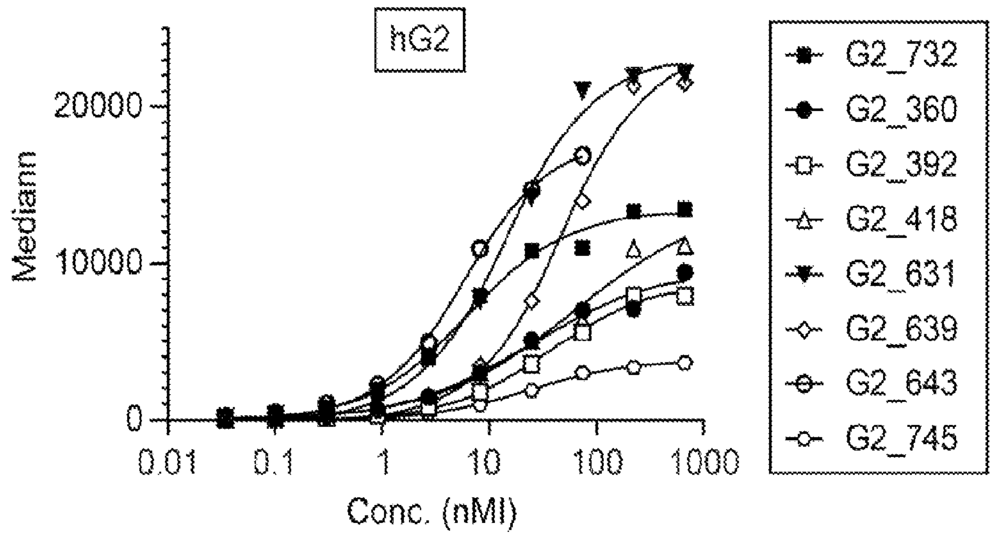
Figure 10:
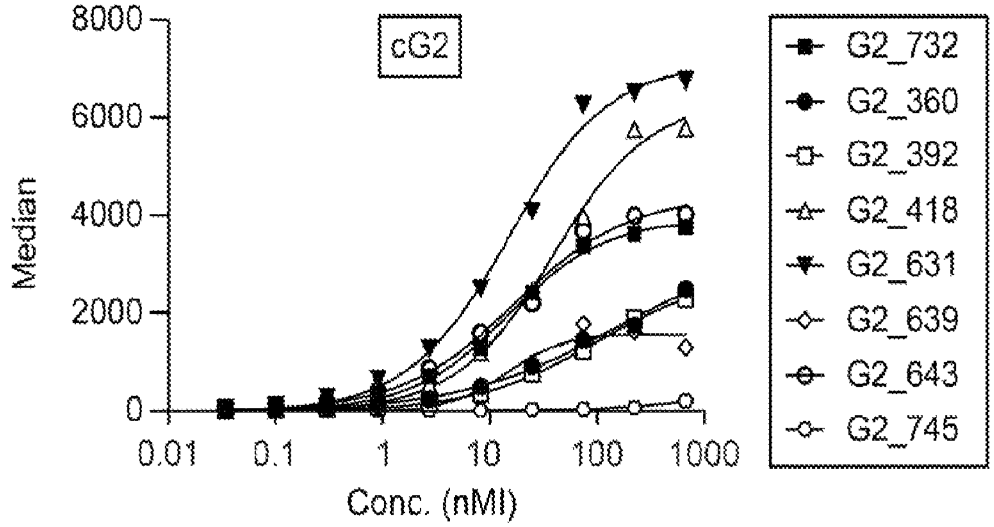
Figure 11:
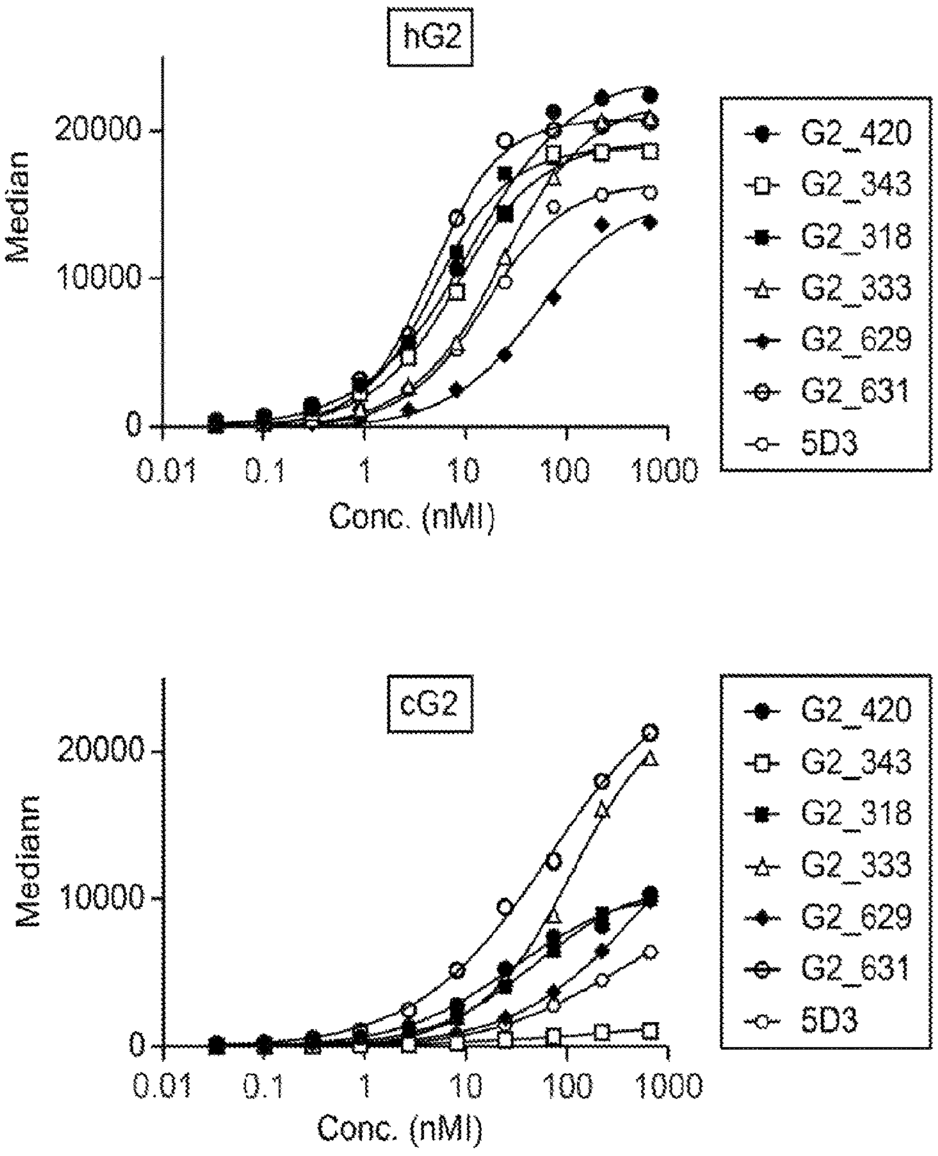

FIG. 8 shows the binding of the anti-ABCG2 antibody G2.748 to 293T cells overexpressing human or cynomolgus ABCG2, in comparison to anti-ABCG2 antibody 5D3, along with the corresponding dissociation constants (Kd). As the Kd values show, G2.748 binds both human and cynomolgus ABCG2 with good binding affinity, FIGS. 9-11 depict the binding of various recombinant anti-ABCG2 antibodies (panels #1-#3) to 293T cells overexpressing human and cynomolgus ABCG2, respectively, as well as the corresponding Kd values. Especially noteworthy is the strong binding of antibodies G2.636, G2.631 and G2.643 to both human and cynomolgus ABCG2.

Figure 12:
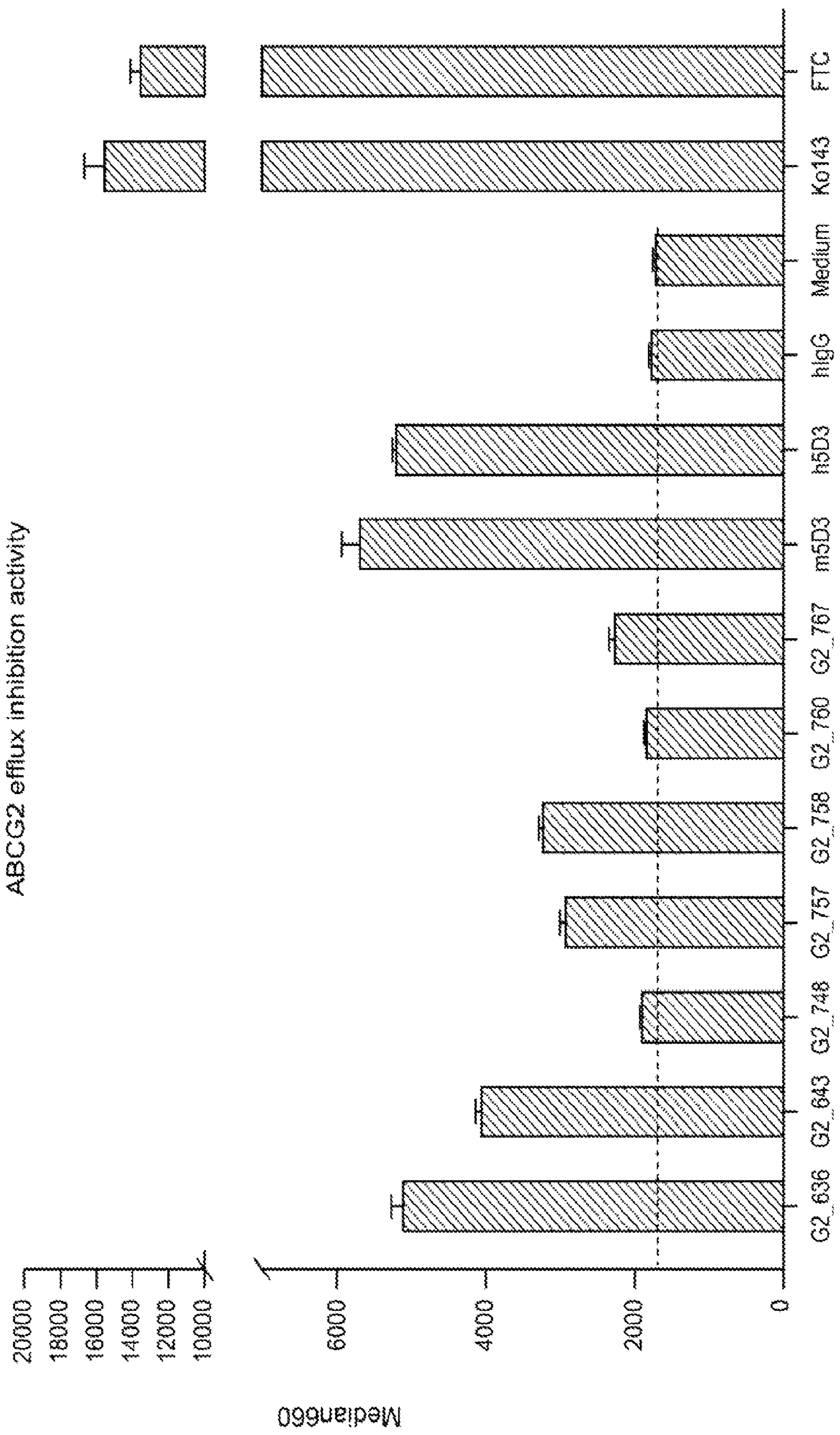
FIGS. 12 and 13 show the result of testing the listed recombinant anti-ABCG2 antibodies for efflux inhibition activity using small molecule ABCG2 inhibitors Fumitremorgin C (FTC) and Ko143 as positive controls, following the efflux blockade experimental procedure described herein.
Figure 13:
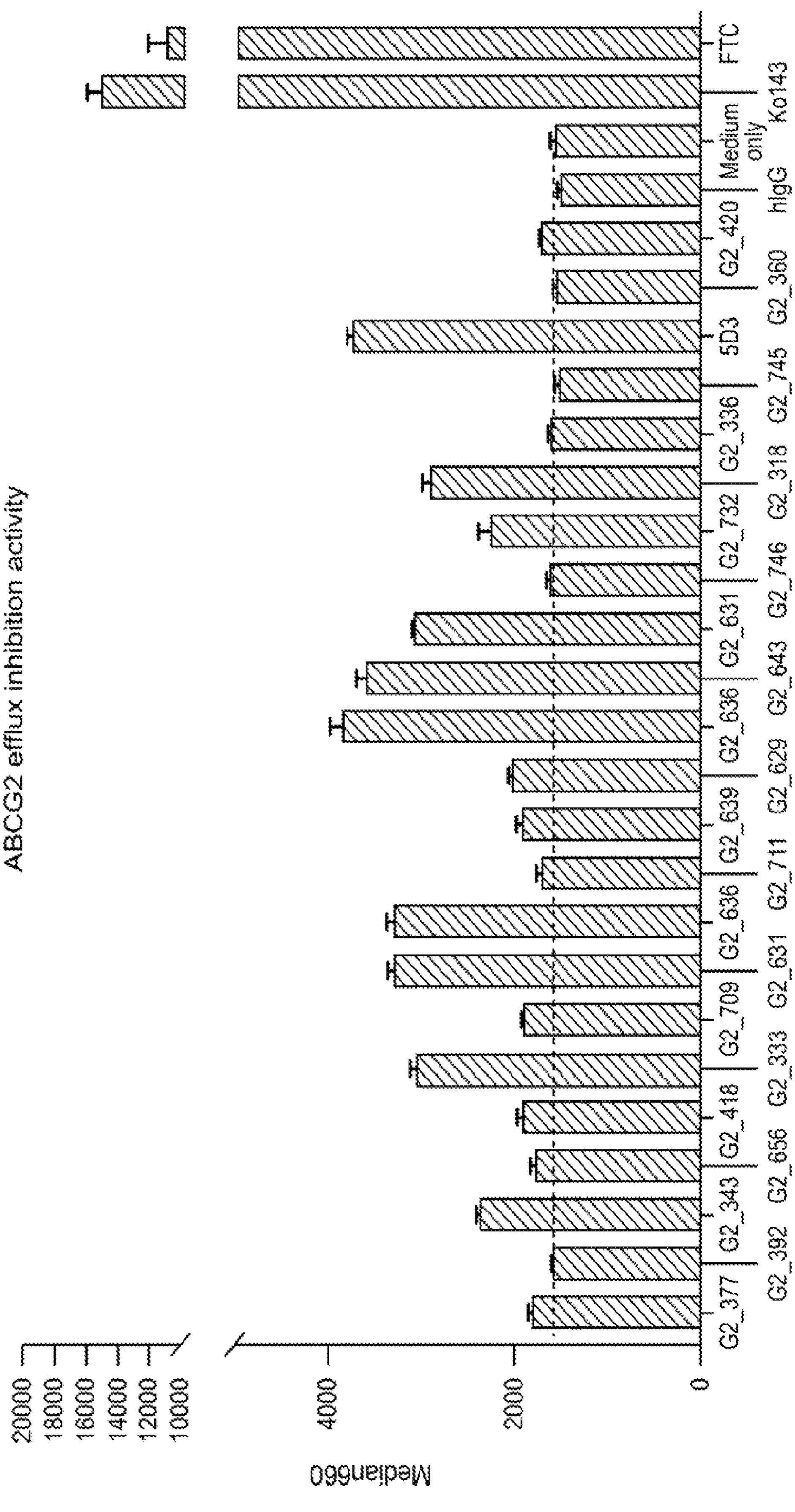

FIGS. 12 and 13 show the result of testing the listed recombinant anti-ABCG2 antibodies for efflux inhibition activity using small molecule ABCG2 inhibitors Fumitremorgin C (FTC) and Ko143 as positive controls, following the efflux blockade experimental procedure described earlier. Especially antibodies G2.636, G2.643, G2.333, G2.631, and G2.318 show strong efflux inhibition activity, G2.636 and G2.643 being particularly efficacious.

Figure 14:
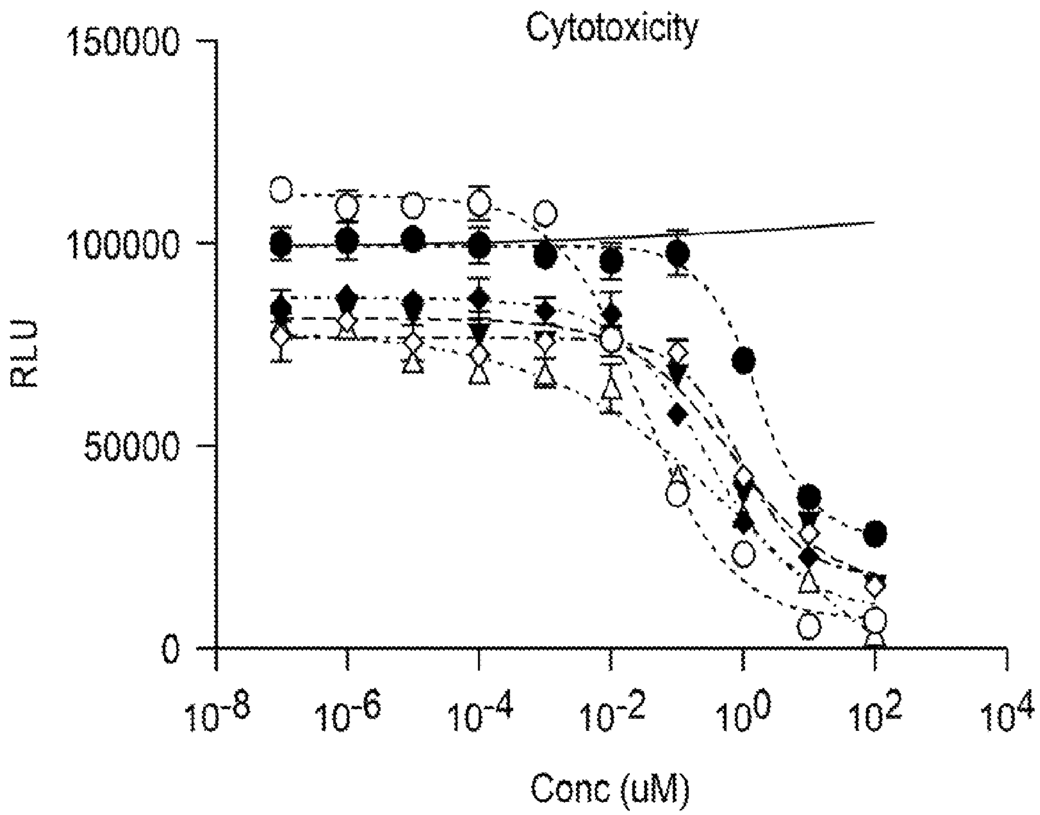
FIG. 14 shows the effect of anti-ABCG2 antibodies G2.643, G2.420 and G.631 on topotecan cytotoxicity on 293T_ABCG2_OX cells, 293T cells stably transfected to express ABCG2, using FTC and 5D3 as positive controls.
Figure 14:
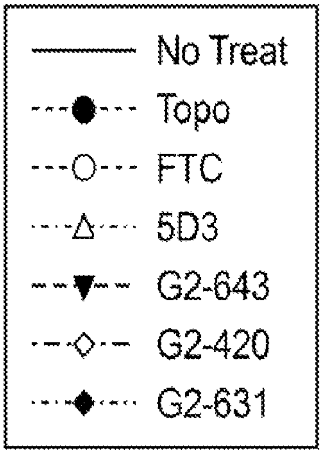

FIG. 14 shows the effect of anti-ABCG2 antibodies G2.643, G2.420 and G2.631 on topotecan cytotoxicity on 293T_ABCG2_OX cells, 293T cells stably transfected to express ABCG2, using FTC and 5D3 as positive controls. All three antibodies tested significantly increased the cytotoxic activity of topotecan.

Figure 15:
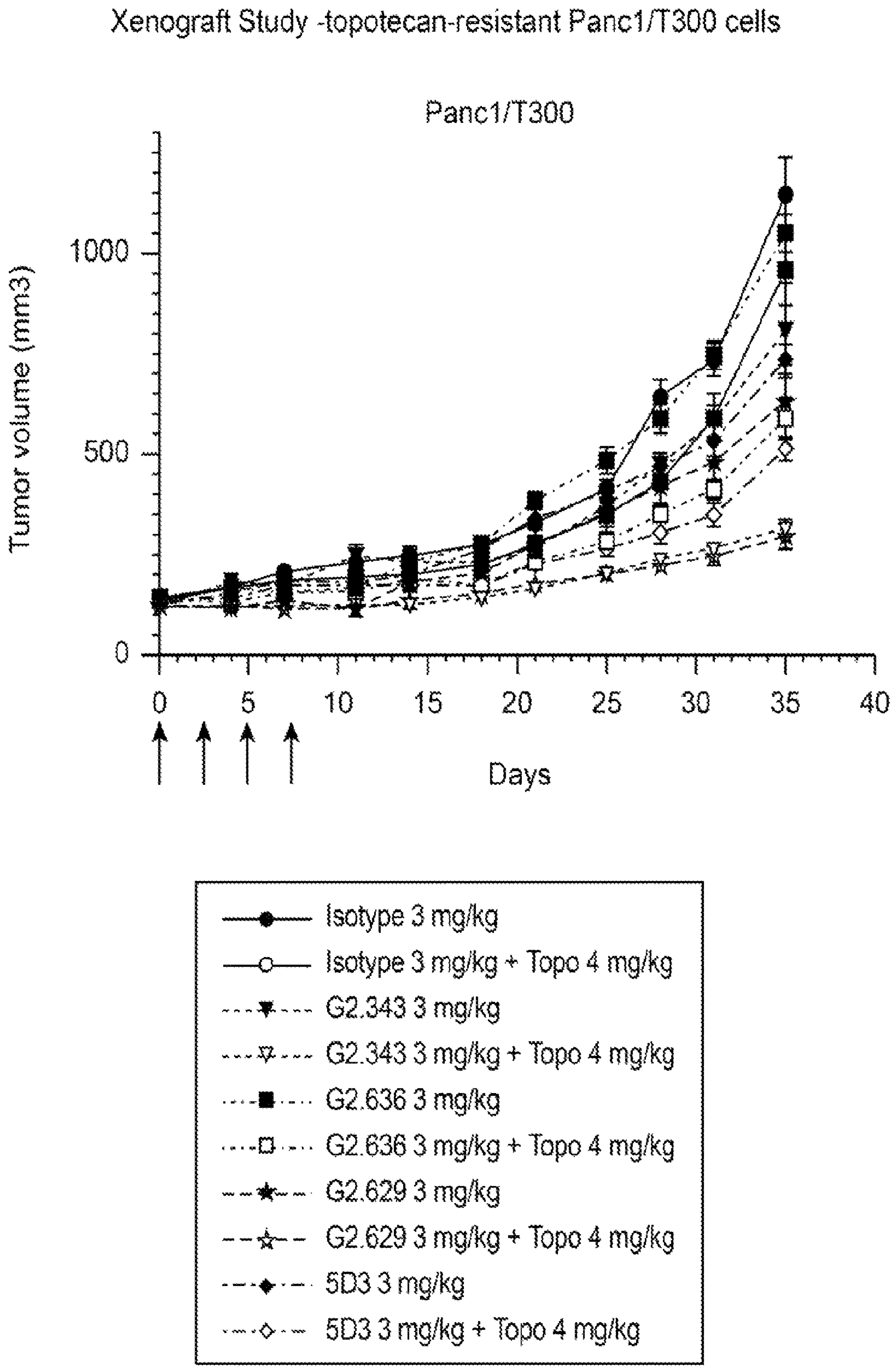
FIG. 15 shows the results of a xenograft study testing the efficacy of anti-ABCG2 antibodies G2.343, G2.636 and G2.629 alone and in combination with topotecan using topotecan-resistant Pancl/T300 cells. The arrows indicate the dosing schedule.

FIG. 15 shows that combinations of anti-ABCG2 antibodies G2.343, G2.636 and G2.629 with topotecan are efficacious in reducing tumor volume in xenograft studies using topotecan-resistant Panc1/T300 cells. PANC1 (ATCC, CRL-1469) is a pancreatic ductal epithelial carcinoma cell line. The topotectan-resistant Panc1/T300 cells were developed by continuously incubating PANC1 cells in the culture medium containing increasing concentration of topotecan of 25, 50, 100, 200 and 300 nM. The selected cells showed elevated expression of ABCG2 and were resistant to topotecan compared to parental PANC1 cells. The arrows indicate the dosing schedule.

Figure 16:
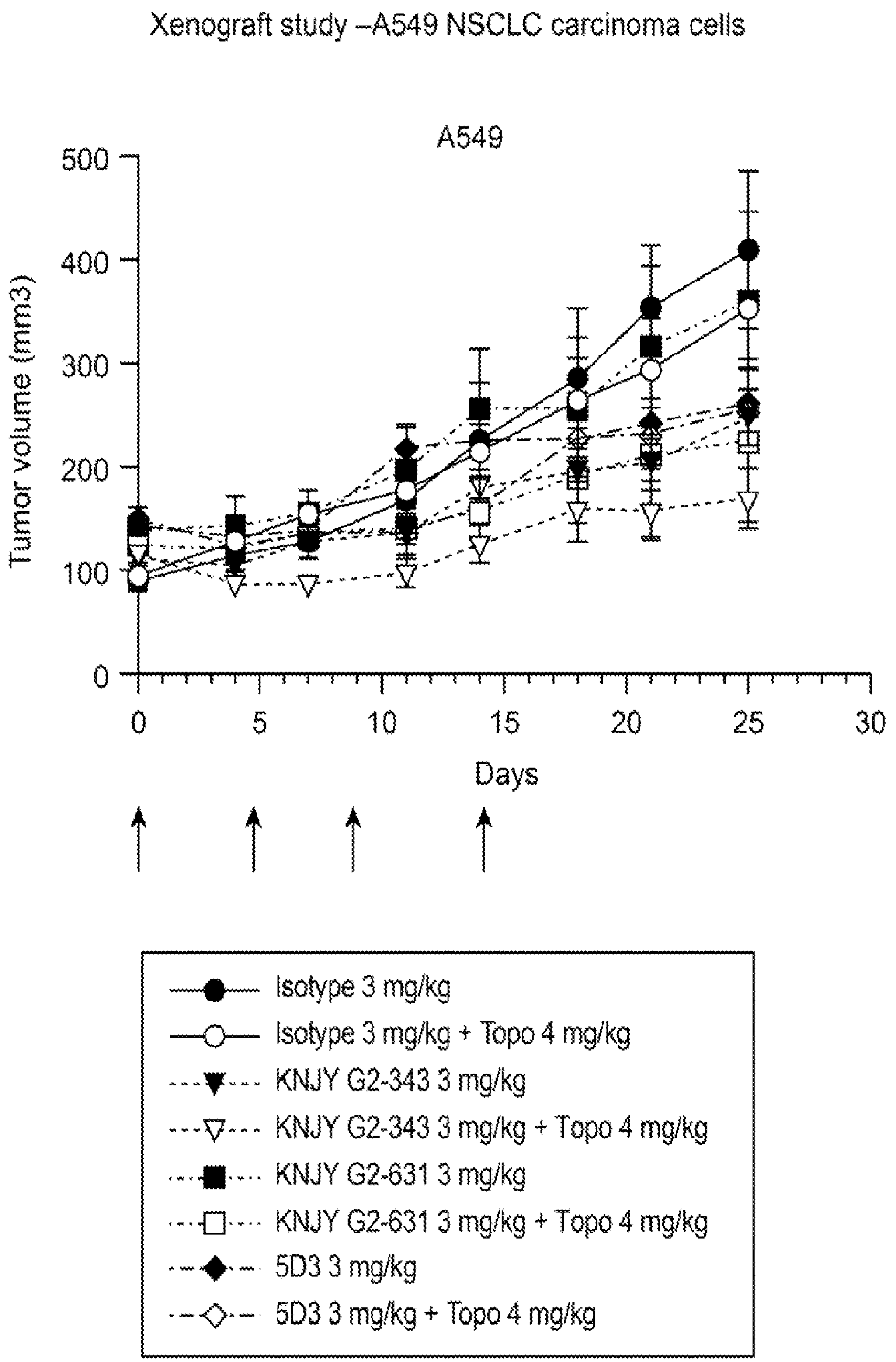
FIG. 16 shows the results of a xenograft study testing the efficacy of anti-ABCG2 antibodies G2.343 and G2.631 alone and in combination with topotecan, using the non-small-cell lung carcinoma (NSCLC) epithelial carcinoma cell line A549 (ATCC, CCL-185). The arrows indicate the dosing schedule.

FIG. 16 shows that combinations of anti-ABCG2 antibodies G2.343 and G2.631 with topotecan are efficacious in reducing tumor volume in xenograft studies using the non-small-cell lung carcinoma (NSCLC) epithelial carcinoma cell line A549 (ATCC, CCL-185). The arrows indicate the dosing schedule. While all combinations reduce tumor volume, the G2.343/topotecan combination is shown to be particularly efficacious.

Figure 17:
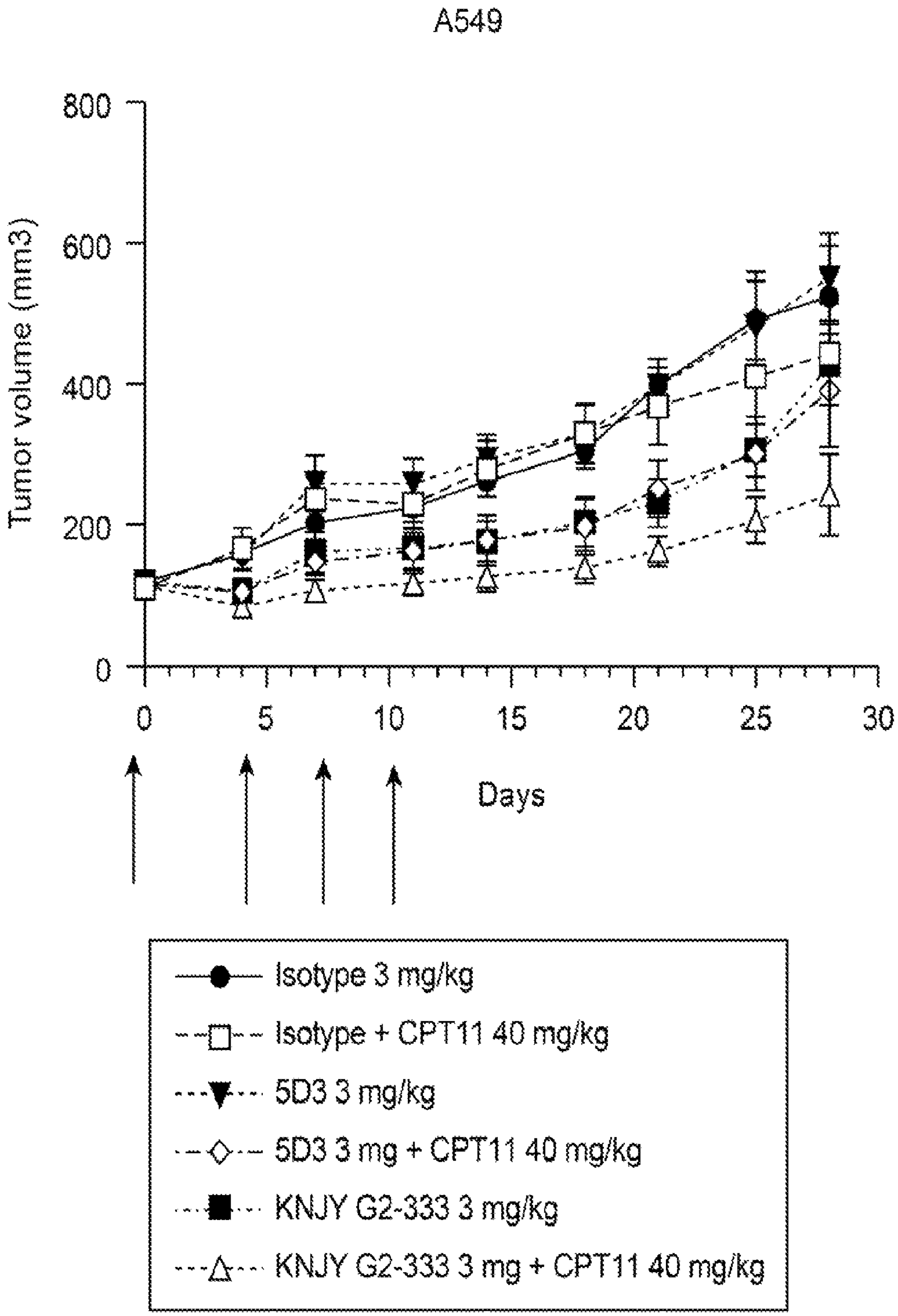
FIG. 17 shows the results of a xenograft study testing the efficacy of anti-ABCG2 antibody G2.333, administered alone or in combination with Camptothecin-11 (CPT11, Irinotecan), using the non-small-cell lung carcinoma (NSCLC) epithelial carcinoma cell line A549 (ATCC, CCL-185). The arrows indicate the dosing schedule.

FIG. 17 shows the efficacy of anti-ABCG2 antibody G2.333, administered alone or in combination with Camptothecin-11 (CPT11, Irinotecan), in xenograft studies using the non-small-cell lung carcinoma (NSCLC) epithelial carcinoma cell line A549 (ATCC, CCL-185). The arrows indicate the dosing schedule. The efficacy of the G2.33/CPT11 combination significantly exceeds the efficacy of the 5D3/CPT11 combination in this experiment.

Figure 18:
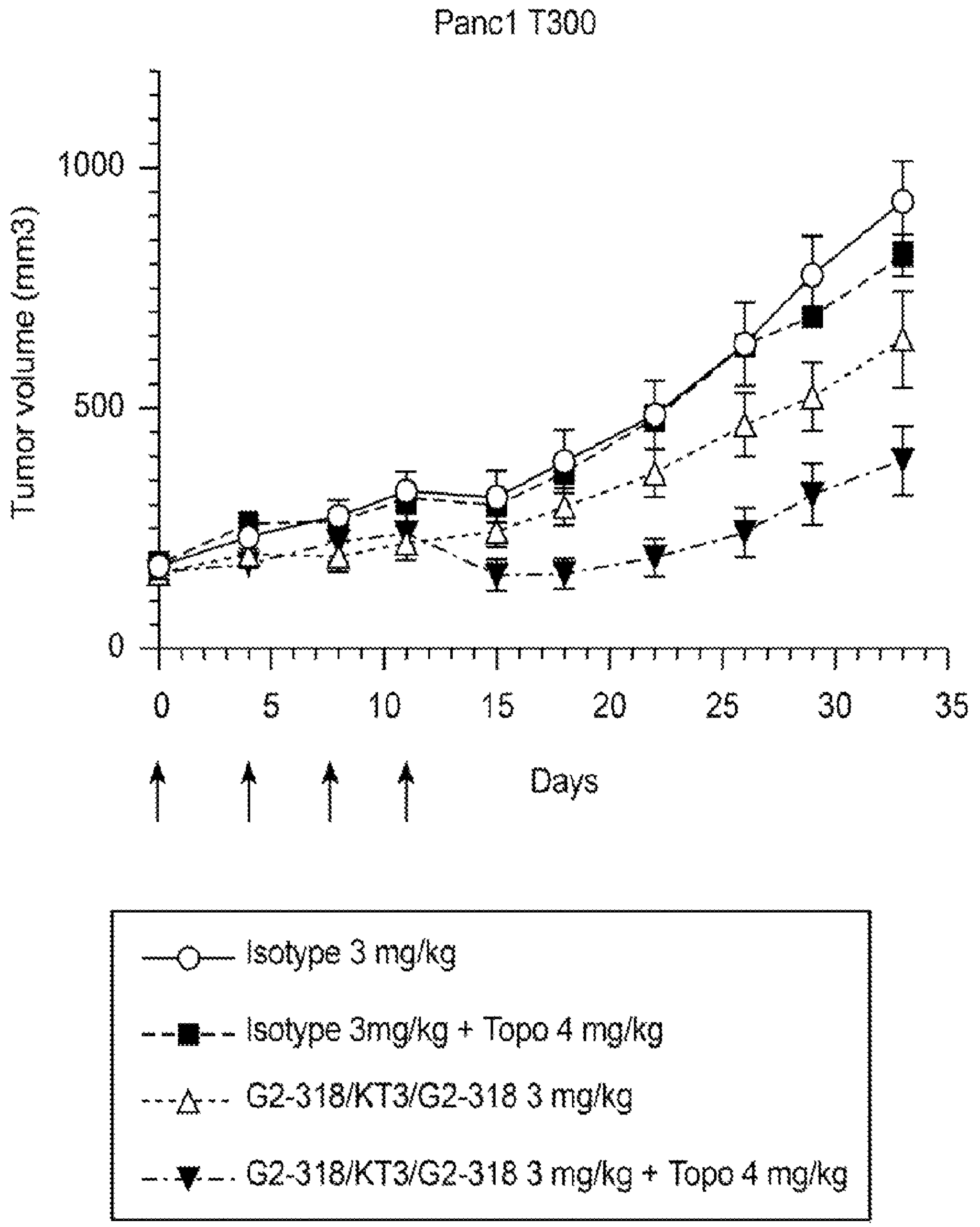
FIG. 18 shows the results of a xenograft study testing the efficacy of bispecific anti-ABCG2 antibody G2.318/KT3/G2.318, administered alone or in combination with topotecan, using topotecan-resistant Panc1/T300 cells. The arrows indicate the dosing schedule. KT3=cetuximab, an anti-EGFR antibody.

FIG. 18 shows the efficacy of bispecific anti-ABCG2 antibody G2.318/KT3/G2.318, administered alone or in combination with topotecan, in xenograft studies using topotecan-resistant Panc1/T300 cells. The arrows indicate the dosing schedule. KT3=cetuximab, an anti-EGFR antibody. The tested bispecific antibody significantly decreased tumor volume both as a single agent and in combination with topotecan.

Figure 19:
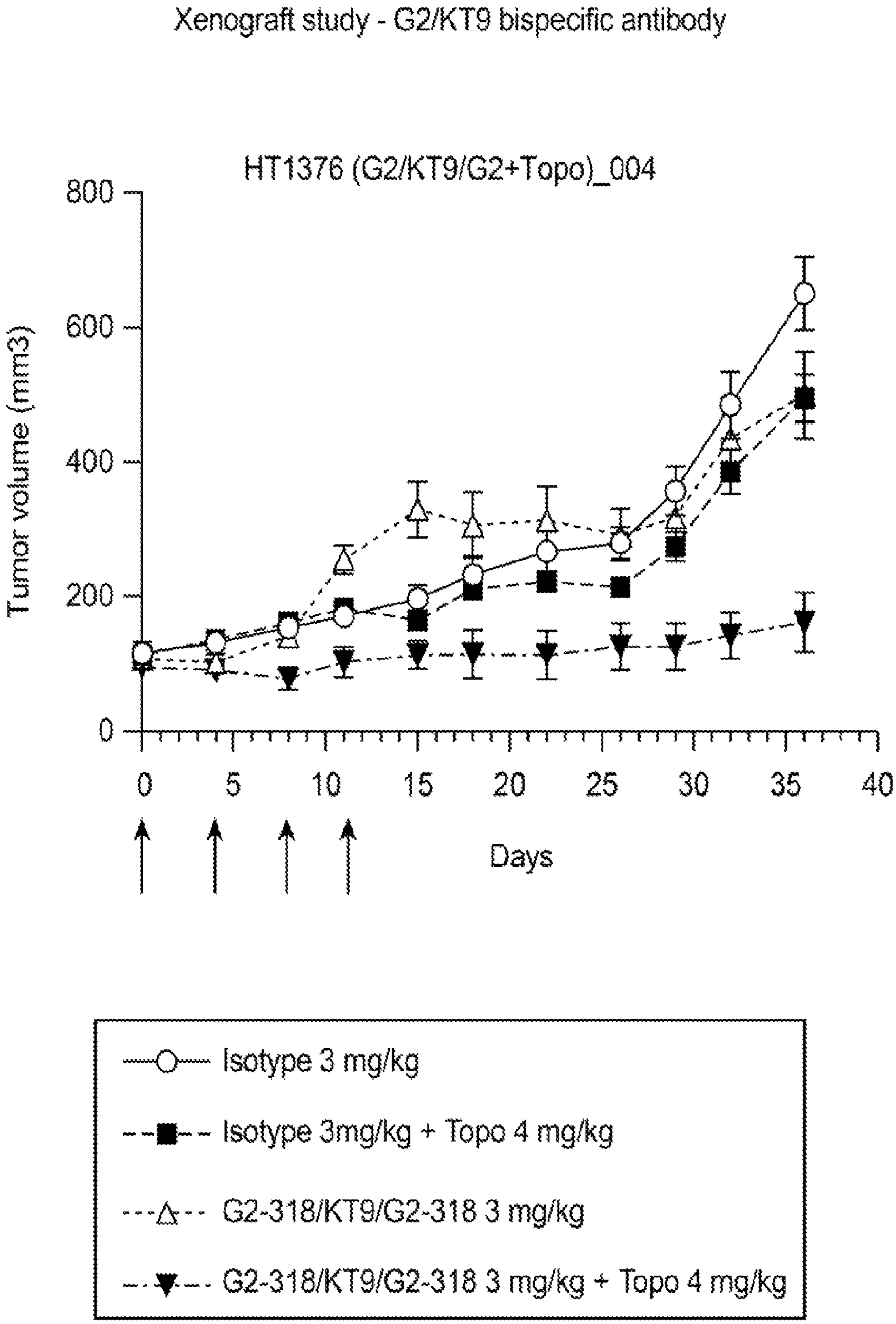
FIG. 19 shows the result of a xenograft study testing the efficacy of bispecific anti-ABCG2 antibody G2.318/KT9/G2.318, administered alone or in combination with topotecan, using the HT1376 (ATCC, CRL-1472) urinary bladder epithelial carcinoma cell line. The arrows indicate the dosing schedule. KT9=atezolizumab, an anti-PL-L1 antibody.

FIG. 19 shows the efficacy of bispecific anti-ABCG2 antibody G2.318/KT9/G2.318, administered alone or in combination with topotecan, in xenograft studies using the HT1376 (ATCC, CRL-1472) urinary bladder epithelial carcinoma cell line. The arrows indicate the dosing schedule. KT9=atezolizumab, an anti-PD-L1 antibody. The combination of the tested bispecific antibody and topotecan is shown to be efficacious in reducing tumor volume.

Figure 20:
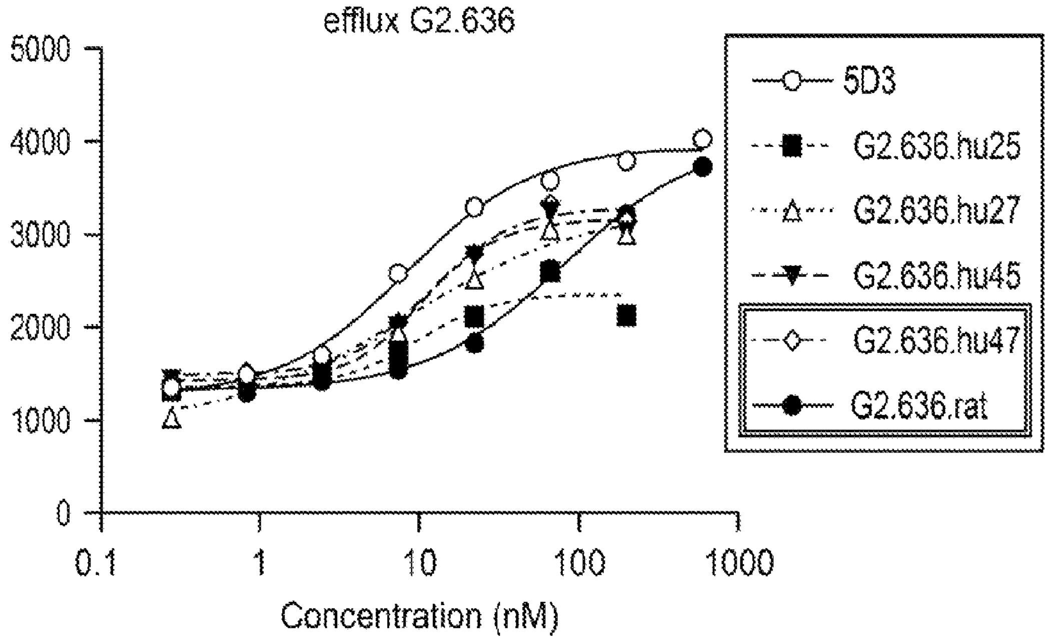
FIG. 20 shows the efflux inhibition activities and binding to human and cynomolgus ABCG2 of various humanized G2.636 anti-ABCG2 antibodies.
Figure 20:
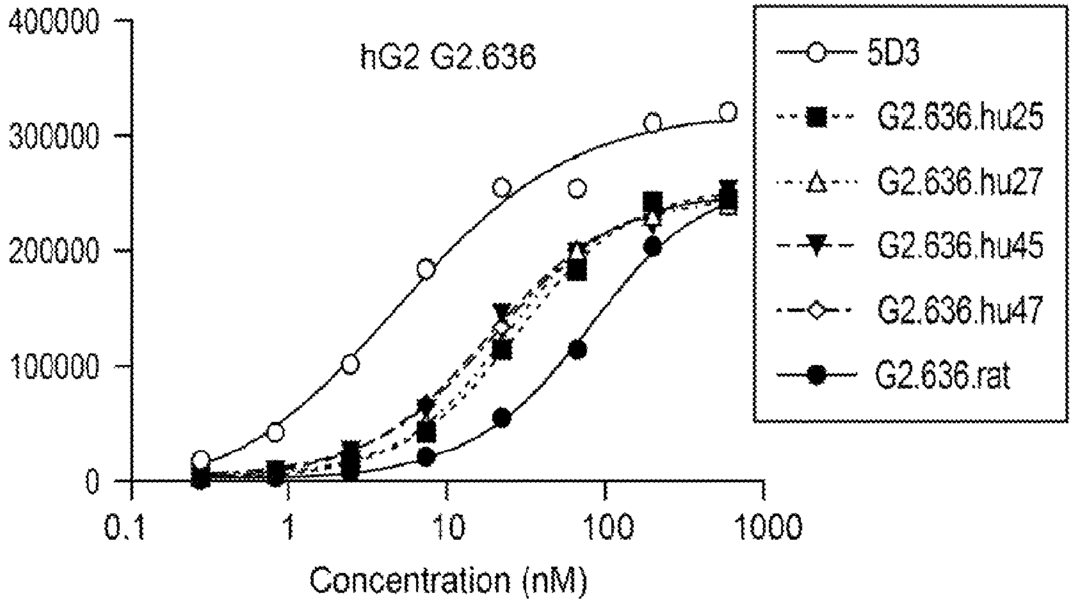
Figure 20:
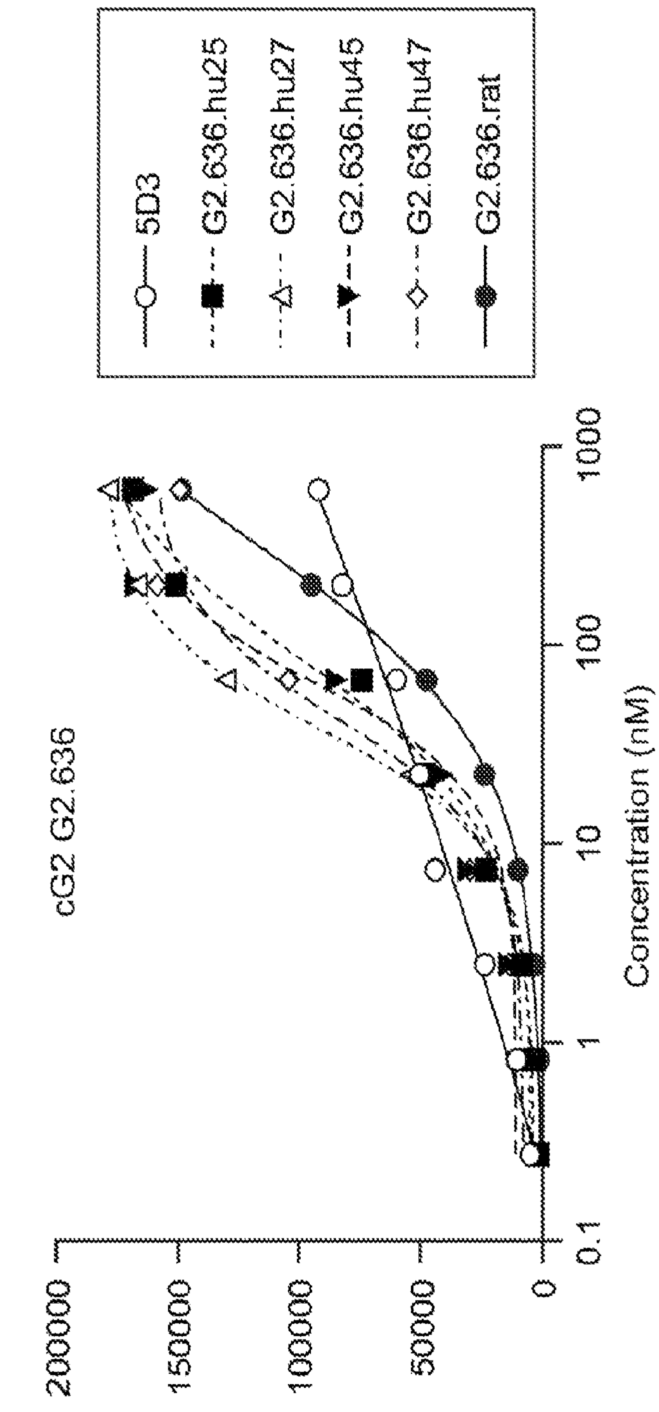

FIG. 20 shows the efflux inhibition activities and binding to human and cynomolgus ABCG2 of various humanized G2.636 anti-ABCG2 antibodies. All humanized variants of the anti-ABCG2 antibody G2.636 retain activity, the G2.636.hu47 variant showing particularly good expression and activity.

Figure 21:
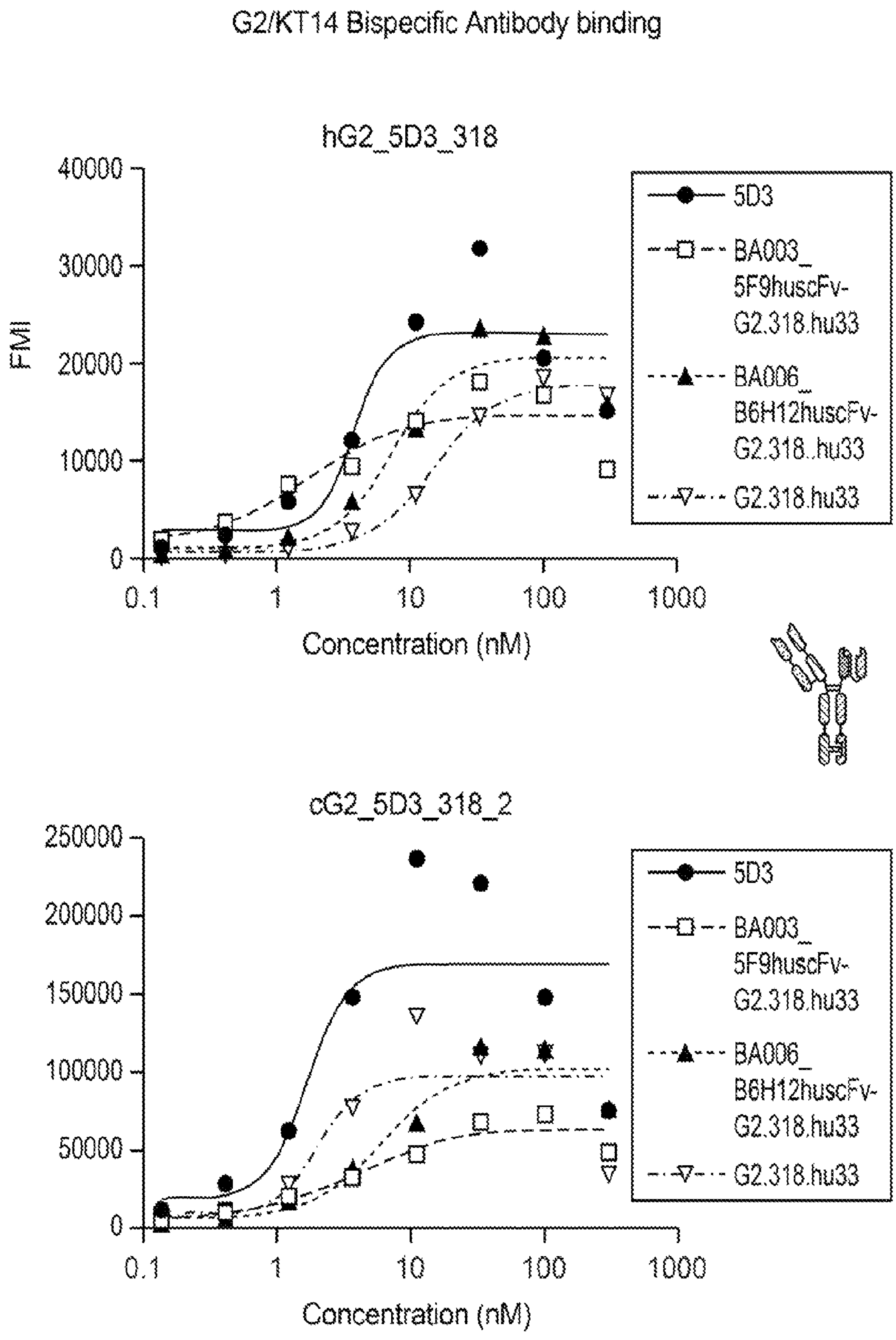
FIG. 21 shows the schematic structure and binding of two humanized ABCG2/CD47 bispecific antibodies (5F9huscFv-G2.318.hu33 and B6H12huscFv-G2.318.hu33) to human and cynomolgus ABCG2, in comparison with G2.318.hu33 and 5D3, respectively.

FIG. 21 shows the schematic structure and binding of two humanized ABCG2/CD47 bispecific antibodies (5F9huscFv-G2.318.hu33 and B6H12huscFv-G2.318.hu33) to human and cynomolus ABCG2, in comparison with G2.318.hu33 and 5D3, respectively. Both humanized antibodies show good binding.

Figure 22:
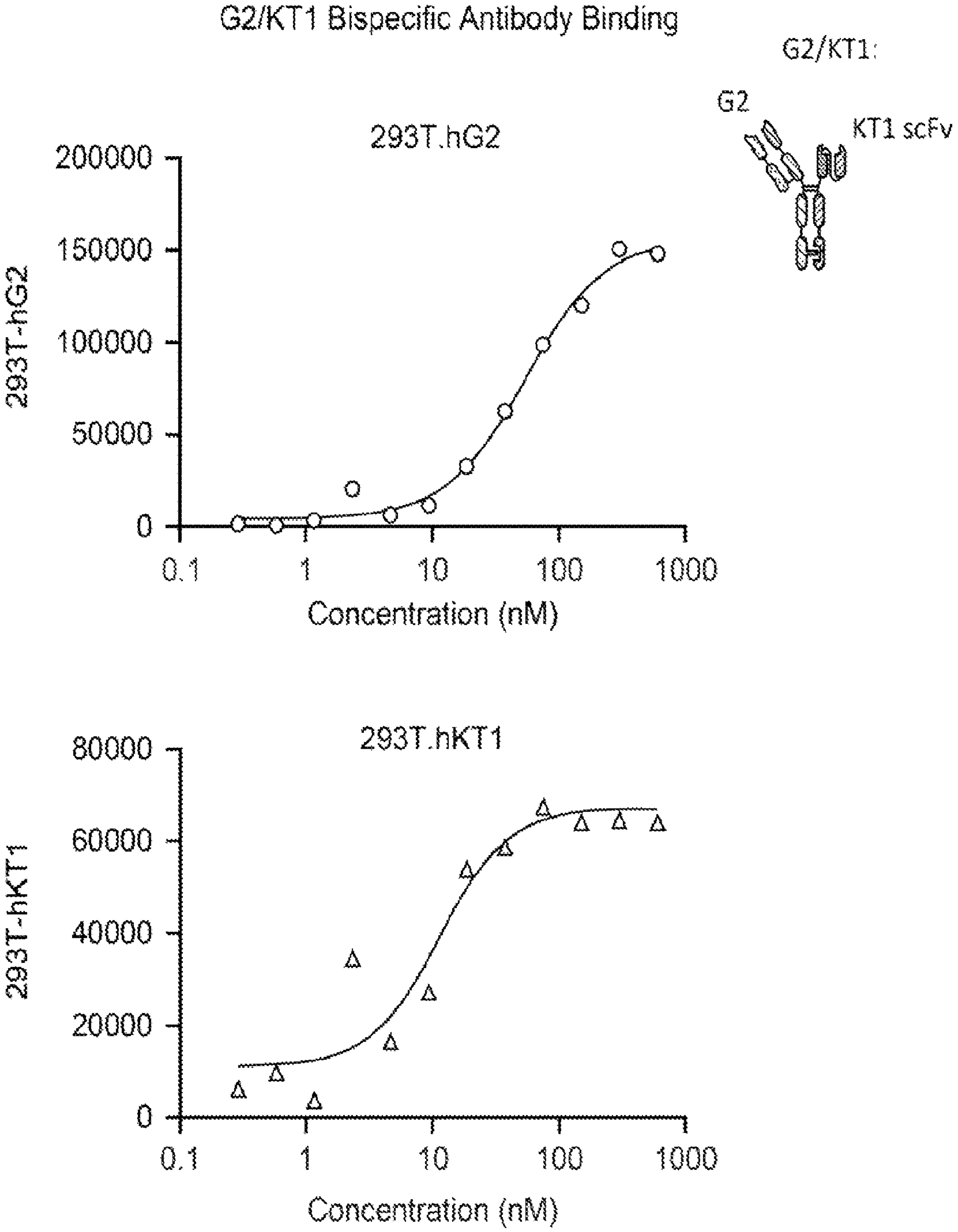
FIG. 22 shows the schematic structure and binding to human ABCG2 and human HER2 of humanized ABCG2/HER2 bispecific antibody KT1scFv-G2.318.hu33. KT1=HER2.

FIG. 22 shows the schematic structure and binding of humanized ABCG2/HER2 bispecific antibody KT1scFv-G2.318.hu33 to human ABCG2 and human HER2, respectively. KT1=HER2. The bispecific antibody shows strong binding to both ABCG2 and HER2.

Figure 23A:
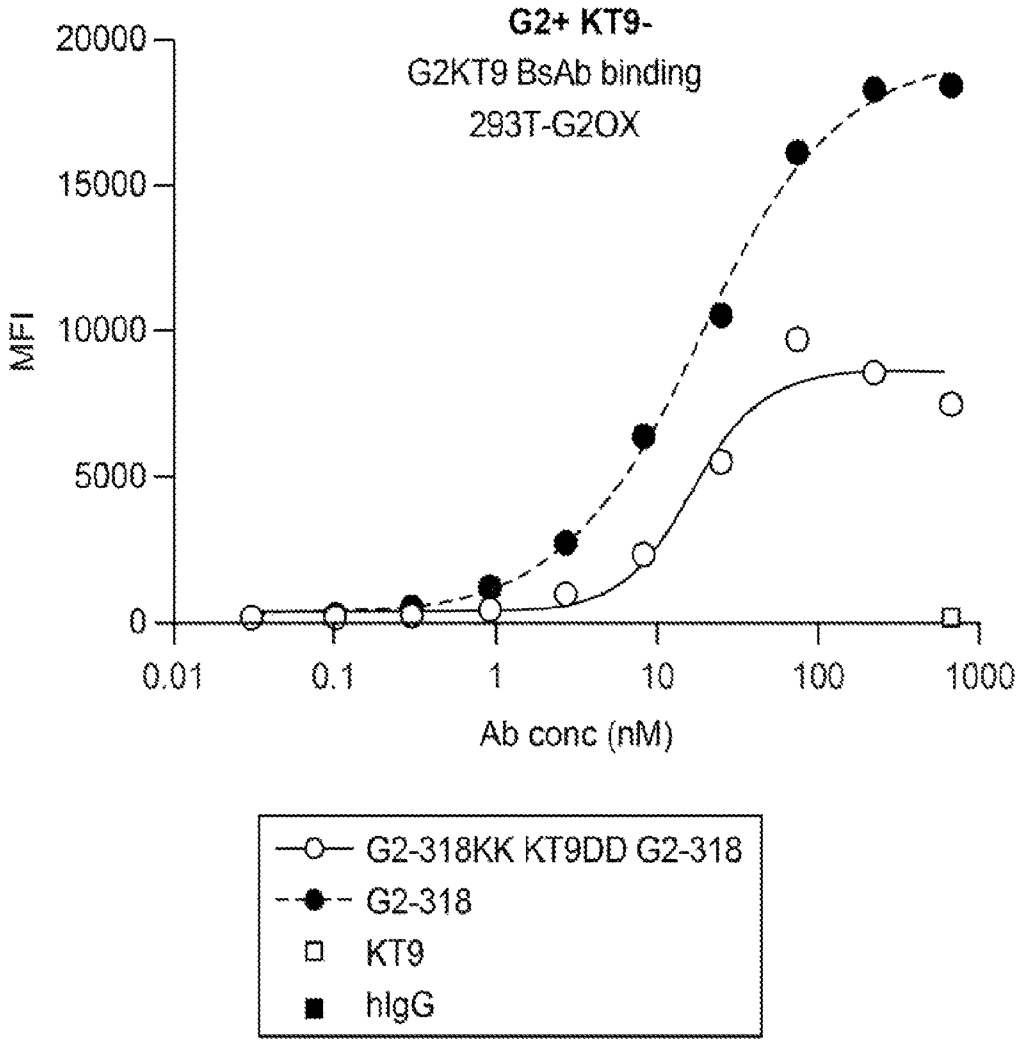
FIG. 23 shows the schematic structure and binding of the bispecific antibody G2.318KK KT9DD G2.318 to ABCG2+ KT9−, ABCG2− KT9+ and ABCG2+KT9+293T cells. KT9=atezolizumab, an anti-PDL-1 monoclonal antibody.
Figure 23B:
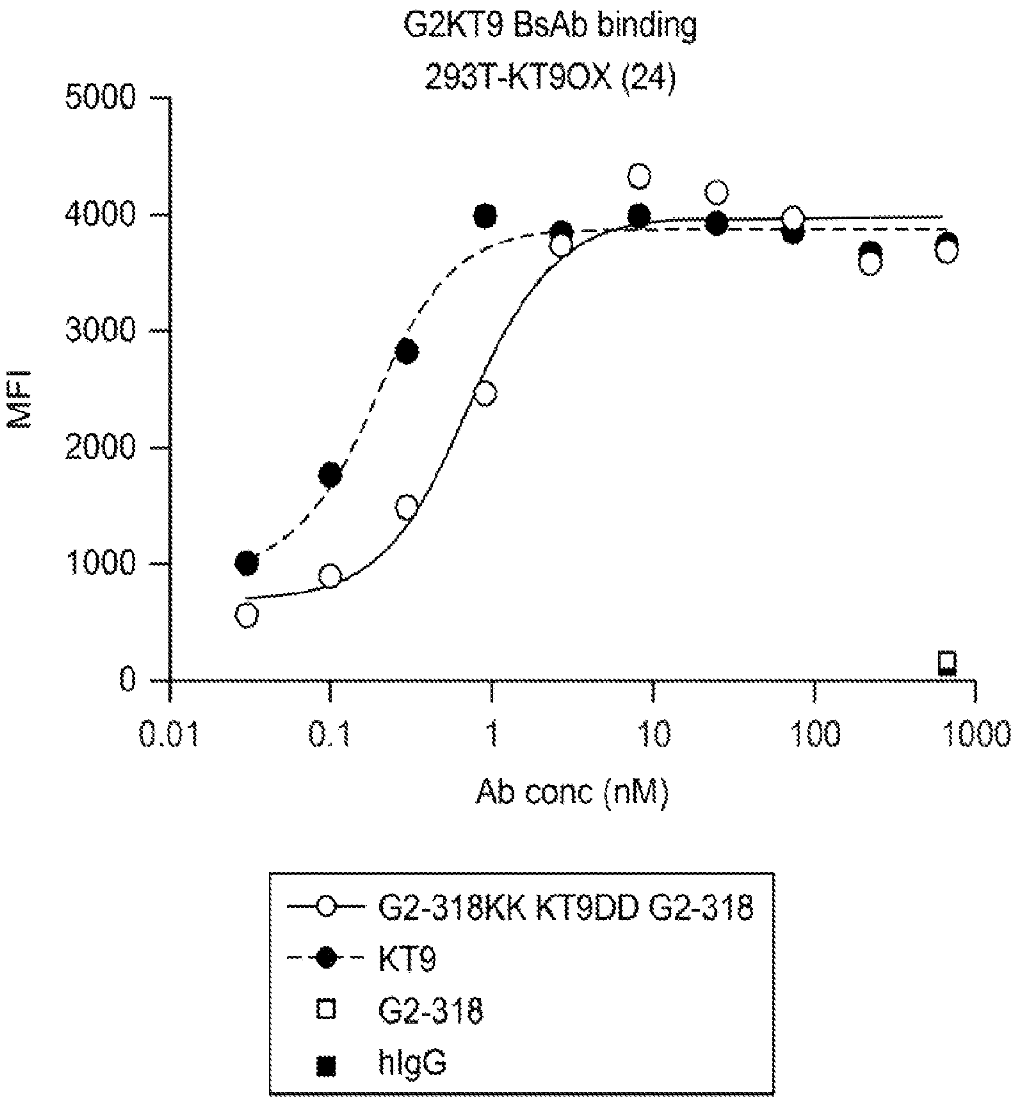
Figure 23C:
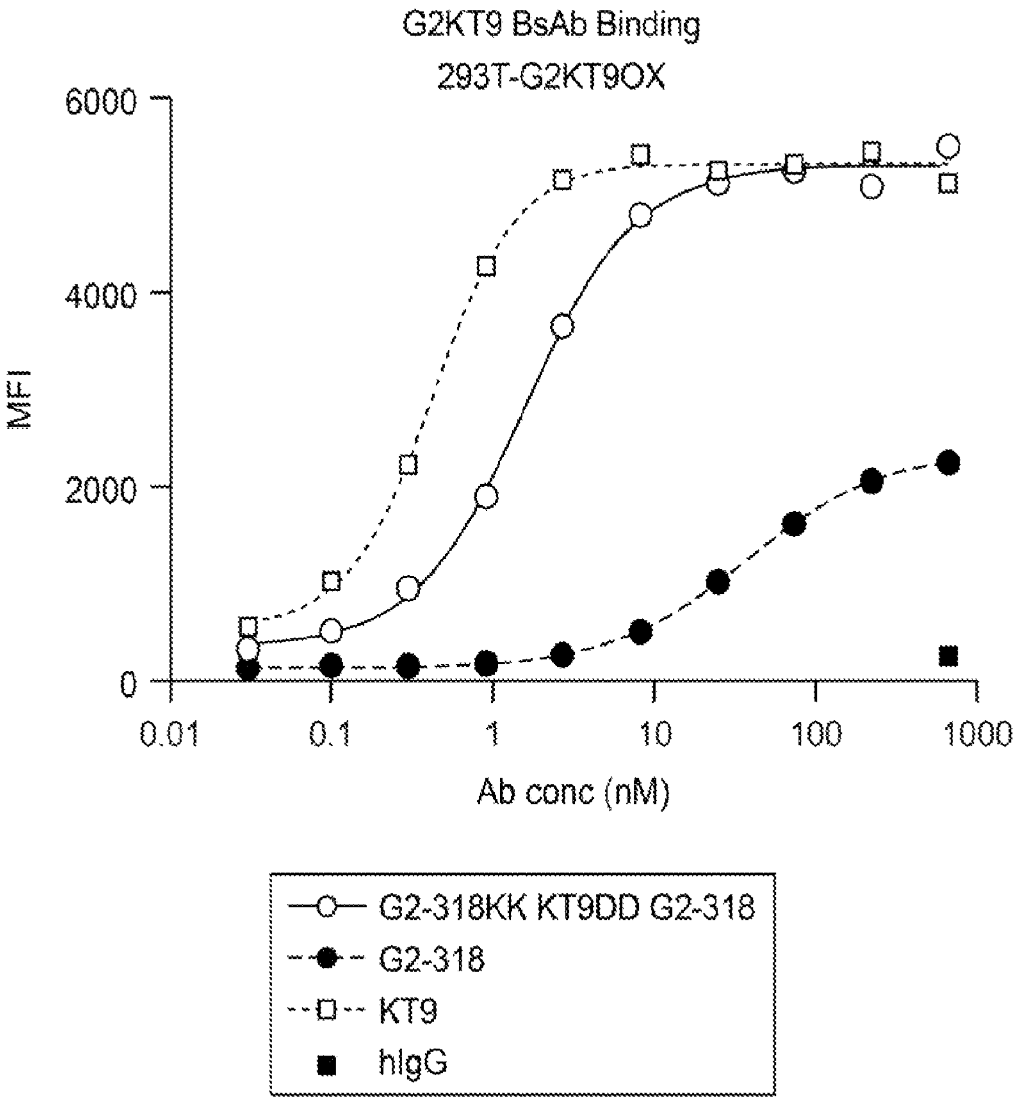
Figure 24A:
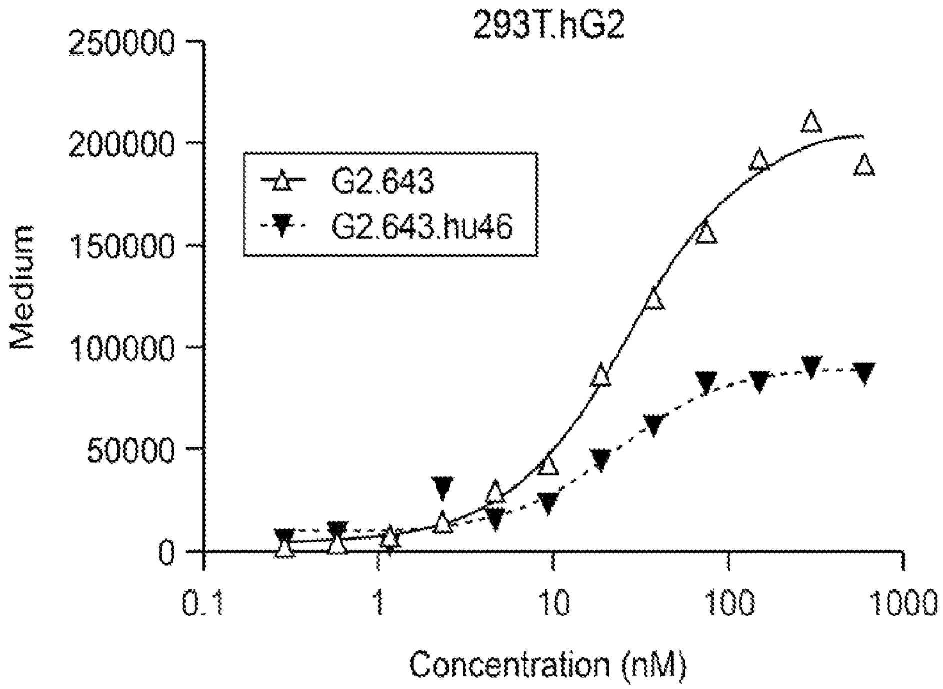
Figure 24A:
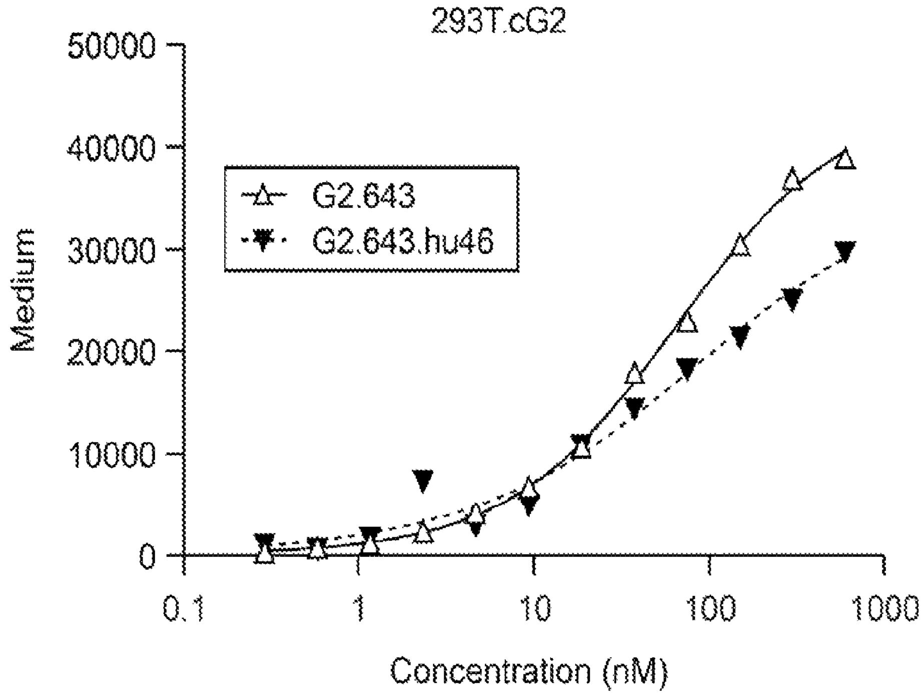
Figure 24B:
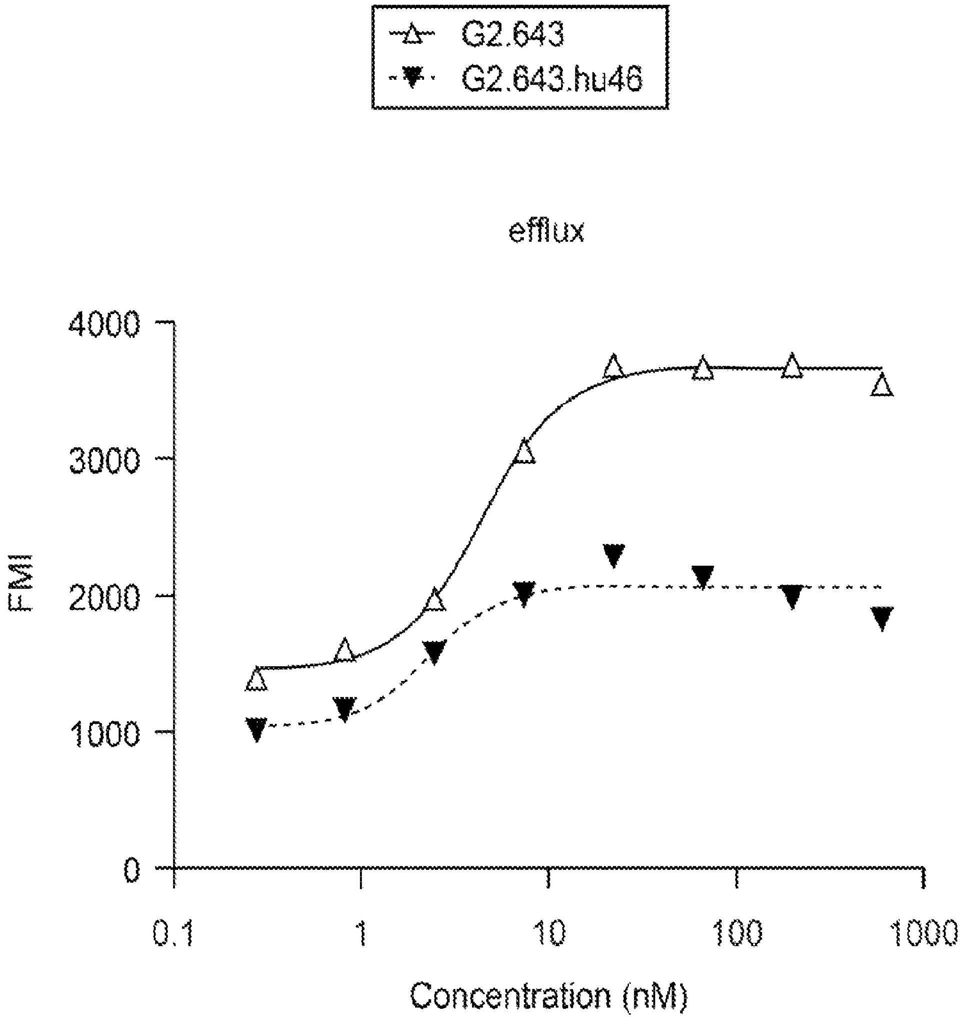

FIG. 23 shows the schematic structure and binding of the bispecific antibody G2.318KK KT9DD G2.318 to ABCG2+ KT9−, ABCG2− KT9+ and ABCG2+ KT9+ 293T cells. KT9=atezolizumab, an anti-PD-L-1 monoclonal antibody. The antibody shows good binding to both ABCG2 and PD-1.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A bispecific antibody molecule that binds ATP Binding Cassette Subfamily G Member 2 (ABCG2) and a tumor associated antigen (TAA), wherein the TAA is EGFR or PD-L1, the bispecific antibody molecule comprising two identical variable light (VL) chains, a first variable heavy (VH) chain, and a second VH chain, wherein the VL chains each comprise an antigen-binding site for ABCG2 comprising LCDRs 1-3: KAGQNINNYLA (SEQ ID NO:273); NANSLQT (SEQ ID NO:309); and QQYNSWTT (SEQ ID NO:337);

the first VH chain comprises an antigen-binding site for ABCG2 comprising HCDRs 1-3: SGYDWS (SEQ ID NO:87); YISYSGWTNYNPSLRS (SEQ ID NO:119); and VRGYNPFAY (SEQ ID NO:160); and the second VH chain comprises an antigen-binding site for the EGFR comprising HCDRs 1-3: GGSISSGDY (SEQ ID NO:421); YYSGS (SEQ ID NO:422); VSIFGVGTFDY (SEQ ID NO:423);

or the second VH chain comprises an antigen-binding site for the PD-L1 comprising HCDRs 1-3: GFTFSDS (SEQ ID NO:424); SPYGGS (SEQ ID NO:425); RHWPGGFDY (SEQ ID NO:426).

2. The bispecific antibody molecule of claim 1, wherein the VL chains each comprise an amino acid sequence having at least 90% sequence identity to the amino acid sequence:

(SEQ ID NO: 206)
DIVMTQSPSLLSASVGDRVTLSCKAGQNINNYLAWYQQKLGEAPKLLIY

NANSLQTGIPSRFSGSGSGTDFTLTISSLOPEDVATYFCQQYNSWTTFG

SGTKLEIK.

3. The bispecific antibody molecule of claim 1, wherein the first VH chain comprises an amino acid sequence having at least 90% sequence identity to the amino acid sequence:

(SEQ ID NO: 25)
EVKLLESGPGLVKPSQSLSLTCSVTGYTITSGYDWSWIRKFPGNKMEWM

GYISYSGWTNYNPSLRSRISISRDTSKNQFFLQLNSVTTEDTATYYCAR

VRGYNPFAYWGQGTLVTVSS.

4. The bispecific antibody molecule of claim 1, wherein the second VH chain comprises an amino acid sequence having at least 90% sequence identity to the amino acid sequence:

(SEQ ID NO: 388)
QVQLQESGPGLVKPSQTLSLTCTVSGGSISSGDYYWSWIRQPPGKGLEW

IGYIYYSGSTDYNPSLKSRVTMSVDTSKNQFSLKVNSVTAADTAVYYCA

RVSIFGVGTFDYWGQGTLVTVSS.

5. The bispecific antibody molecule of claim 1, wherein the second VH chain comprises an amino acid sequence having at least 90% sequence identity to the amino acid sequence:

(SEQ ID NO: 427)
EVOLVESGGGLVQPGGSLRLSCAASGFTFSDSWIHWVRQAPGKGLEWVA

WISPYGGSTYYADSVKGRFTISADTSKNTAYLQMNSLRAEDTAVYYCAR

RHWPGGFDYWGQGTLVTVSS.

6. The bispecific antibody molecule of claim 1, wherein the VL chains each comprise the amino acid sequence set forth in SEQ ID NO:206, the first VH chain comprises the amino acid sequence set forth in SEQ ID NO:25 and the second VH chain comprises the amino acid sequence set forth in SEQ ID NO:388.

7. The bispecific antibody molecule of claim 1, wherein the VL chains each comprise the amino acid sequence set forth in SEQ ID NO:206, the first VH chain comprises the amino acid sequence set forth in SEQ ID NO:25 and the second VH chain comprises the amino acid sequence set forth in SEQ ID NO:427.

8. A pharmaceutical composition comprising the bispecific antibody molecule of claim 1 and a pharmaceutically acceptable excipient.

9. The pharmaceutical composition of claim 8, further comprising an additional active agent, wherein the additional active agent is:

(i) a chemotherapeutic agent;

(ii) an inhibitor of a multidrug resistance transporter; or (iii) an immunotherapy agent.

10. One or more nucleic acids comprising one or more sequences encoding the bispecific antibody molecule of claim 1.

11. One or more recombinant expression vectors comprising the one or more nucleic acids of claim 10.

12. A method of treating cancer in a subject having the cancer, the method comprising administering to the subject a therapeutically effective amount of the bispecific antibody molecule of claim 1, thereby treating the cancer in the subject.

13. An antibody that binds to ATP Binding Cassette Subfamily G Member 2 (ABCG2), the antibody comprising:

a VL chain comprising LCDRs 1-3: KAGQNINNYLA (SEQ ID NO:273); NANSLQT (SEQ ID NO:309); and QQYNSWTT (SEQ ID NO:337); and a VH chain comprising HCDRs 1-3: SGYDWS (SEQ ID NO:87); YISYSGWTNYNPSLRS (SEQ ID NO:119); and VRGYNPFAY (SEQ ID NO:160).

14. The antibody of claim 13, wherein the VL chain comprises an amino acid sequence having at least 90% sequence identity to the amino acid sequence set forth in SEQ ID NO:206.

15. The antibody of claim 13, wherein the VH comprises an amino acid sequence having at least 90% sequence identity to the amino acid sequence set forth in SEQ ID NO:25.

16. One or more nucleic acids comprising one or more sequences encoding the antibody of claim 13.

17. One or more recombinant expression vectors comprising the one or more nucleic acids of claim 16.

* * * * *

SEQUENCE LISTING

```
<160> NUMBER OF SEQ ID NOS: 427

<210> SEQ ID NO 1
<211> LENGTH: 12
<212> TYPE: PRT
<213> ORGANISM: Homo sapiens

<400> SEQUENCE: 1

Lys Asn Asp Ser Thr Gly Ile Gln Asn Arg Ala Gly
1               5                   10


<210> SEQ ID NO 2
<211> LENGTH: 8
<212> TYPE: PRT
<213> ORGANISM: Homo sapiens

<400> SEQUENCE: 2

Leu Lys Pro Lys Ala Asp Ala Phe
1               5


<210> SEQ ID NO 3
<211> LENGTH: 74
<212> TYPE: PRT
<213> ORGANISM: Homo sapiens

<400> SEQUENCE: 3

Asn Leu Thr Thr Ile Ala Ser Trp Leu Ser Trp Leu Gln Tyr Phe Ser
1               5                   10                  15

Ile Pro Arg Tyr Gly Phe Thr Ala Leu Gln His Asn Glu Phe Leu Gly
            20                  25                  30

Gln Asn Phe Cys Pro Gly Leu Asn Ala Thr Gly Asn Asn Pro Cys Asn
        35                  40                  45

Tyr Ala Thr Cys Thr Gly Glu Glu Tyr Leu Val Lys Gln Gly Ile Asp
    50                  55                  60

Leu Ser Pro Trp Gly Leu Trp Lys Asn His
65                  70


<210> SEQ ID NO 4
<211> LENGTH: 119
<212> TYPE: PRT
```

<213> ORGANISM: Unknown
<220> FEATURE:
<223> OTHER INFORMATION: anti-ABCG2 antibody

<400> SEQUENCE: 4

Gln Val Gln Leu Gln Glu Ser Gly Pro Gly Leu Val Lys Pro Ser Gln
1 5 10 15

Ser Leu Ser Leu Thr Cys Thr Val Thr Gly Phe Ser Ile Thr Ser Asp
20 25 30

Tyr Ala Trp Asn Trp Ile Arg Gln Phe Pro Gly Lys Lys Leu Glu Trp
35 40 45

Met Gly Tyr Ile Asn Phe Asp Gly Gly Thr Thr Tyr Asn Pro Ser Leu
50 55 60

Arg Gly Arg Ile Ser Ile Thr Arg Asp Thr Ser Lys Asn Gln Phe Phe
65 70 75 80

Leu Gln Leu Arg Ser Val Thr Pro Glu Asp Thr Ala Thr Tyr Tyr Cys
85 90 95

Ala Thr Phe Tyr Gly Ala Lys Gly Thr Leu Asp Tyr Trp Gly Gln Gly
100 105 110

Thr Ser Val Thr Val Ser Ser
115

<210> SEQ ID NO 5
<211> LENGTH: 107
<212> TYPE: PRT
<213> ORGANISM: Unknown
<220> FEATURE:
<223> OTHER INFORMATION: anti-ABCG2 antibody

<400> SEQUENCE: 5

Asp Ile Val Leu Thr Gln Ser Pro Ser Ser Phe Ser Val Ser Leu Gly
1 5 10 15

Asp Arg Val Thr Ile Ser Cys Lys Ala Ser Gly Tyr Ile Leu Asn Arg
20 25 30

Leu Ala Trp Tyr Gln Gln Lys Pro Gly Asn Ala Pro Arg Leu Leu Ile
35 40 45

Ser Gly Ala Thr Ser Leu Glu Thr Gly Phe Pro Ser Arg Phe Ser Gly
50 55 60

Thr Gly Ser Gly Lys Asp Tyr Thr Leu Ser Ile Ser Ser Leu Gln Thr
65 70 75 80

Glu Asp Val Gly Thr Tyr Tyr Cys Gln Gln Tyr Trp Ser Thr Pro Trp
85 90 95

Thr Phe Gly Gly Gly Thr Lys Leu Glu Ile Lys
100 105

<210> SEQ ID NO 6
<211> LENGTH: 10
<212> TYPE: PRT
<213> ORGANISM: Unknown
<220> FEATURE:
<223> OTHER INFORMATION: anti-ABCG2 antibody

<400> SEQUENCE: 6

Gly Phe Ser Ile Thr Ser Asp Tyr Ala Trp
1 5 10

<210> SEQ ID NO 7
<211> LENGTH: 17
<212> TYPE: PRT
<213> ORGANISM: Unknown

<220> FEATURE:
<223> OTHER INFORMATION: anti-ABCG2 antibody

<400> SEQUENCE: 7

Gly Tyr Ile Asn Phe Asp Gly Gly Thr Thr Tyr Asn Pro Ser Leu Arg
1               5                   10                  15

Gly

<210> SEQ ID NO 8
<211> LENGTH: 12
<212> TYPE: PRT
<213> ORGANISM: Unknown
<220> FEATURE:
<223> OTHER INFORMATION: anti-ABCG2 antibody

<400> SEQUENCE: 8

Ala Thr Phe Tyr Gly Ala Lys Gly Thr Leu Asp Tyr
1               5                   10

<210> SEQ ID NO 9
<211> LENGTH: 11
<212> TYPE: PRT
<213> ORGANISM: Unknown
<220> FEATURE:
<223> OTHER INFORMATION: anti-ABCG2 antibody

<400> SEQUENCE: 9

Lys Ala Ser Gly Tyr Ile Leu Asn Arg Leu Ala
1               5                   10

<210> SEQ ID NO 10
<211> LENGTH: 7
<212> TYPE: PRT
<213> ORGANISM: Unknown
<220> FEATURE:
<223> OTHER INFORMATION: anti-ABCG2 antibody

<400> SEQUENCE: 10

Gly Ala Thr Ser Leu Glu Thr
1               5

<210> SEQ ID NO 11
<211> LENGTH: 9
<212> TYPE: PRT
<213> ORGANISM: Unknown
<220> FEATURE:
<223> OTHER INFORMATION: anti-ABCG2 antibody

<400> SEQUENCE: 11

Gln Gln Tyr Trp Ser Thr Pro Trp Thr
1               5

<210> SEQ ID NO 12
<211> LENGTH: 119
<212> TYPE: PRT
<213> ORGANISM: Mus musculus

<400> SEQUENCE: 12

Gln Val Gln Leu Gln Gln Pro Gly Ala Glu Leu Val Lys Pro Gly Ala
1               5                   10                  15

Ser Val Lys Leu Ser Cys Lys Thr Ser Gly Phe Thr Phe Ser Asn Ser
            20                  25                  30

Tyr Ile Ser Trp Leu Lys Gln Lys Pro Arg Gln Ser Leu Glu Trp Ile
        35                  40                  45

```
Ala Trp Ile Tyr Ala Gly Thr Gly Gly Thr Asn Tyr Asn Gln Lys Phe
    50                  55                  60

Thr Gly Lys Ala Gln Leu Thr Val Asp Thr Ser Ser Ser Thr Ala Tyr
65                  70                  75                  80

Met Gln Leu Ser Ser Leu Thr Ser Glu Asp Ser Ala Ile Tyr Tyr Cys
                85                  90                  95

Ala Thr Tyr Gly Asn Phe Leu Tyr Ala Met Asp Asn Trp Gly Gln Gly
            100                 105                 110

Thr Ser Val Thr Val Ser Ser
        115


<210> SEQ ID NO 13
<211> LENGTH: 120
<212> TYPE: PRT
<213> ORGANISM: Mus musculus

<400> SEQUENCE: 13

Glu Val Met Leu Val Glu Ser Gly Gly Ala Leu Val Lys Pro Gly Gly
1               5                   10                  15

Ser Leu Lys Leu Ser Cys Ala Ala Ser Gly Phe Thr Phe Ser Asn Asn
            20                  25                  30

Ala Met Ser Trp Val Arg Gln Thr Pro Glu Thr Arg Leu Glu Trp Val
        35                  40                  45

Ala Thr Ile Thr Gly Gly Gly Ser Tyr Thr Tyr Tyr Pro Asp Ser Val
    50                  55                  60

Lys Gly Arg Phe Thr Ile Ser Arg Asp Asn Ala Arg Asn Thr Leu Tyr
65                  70                  75                  80

Leu Gln Met Ser Ser Leu Arg Ser Glu Asp Thr Ala Thr Tyr Tyr Cys
                85                  90                  95

Ala Ser Pro Asp Gly Asn Tyr Glu Gly Val Leu Ala Tyr Trp Gly Gln
            100                 105                 110

Gly Thr Leu Val Thr Val Ser Ala
        115                 120


<210> SEQ ID NO 14
<211> LENGTH: 122
<212> TYPE: PRT
<213> ORGANISM: Mus musculus

<400> SEQUENCE: 14

Glu Val Gln Leu Gln Gln Ser Gly Pro Glu Leu Val Lys Pro Gly Ala
1               5                   10                  15

Ser Leu Lys Ile Ser Cys Lys Thr Phe Gly Tyr Ser Phe Thr Gly Tyr
            20                  25                  30

Tyr Met His Trp Val Lys Gln Ser Pro Glu Lys Ser Leu Glu Trp Ile
        35                  40                  45

Gly Lys Ile Val Pro Ser Thr Gly Gly Thr Thr Tyr Asn Gln Lys Phe
    50                  55                  60

Lys Ala Lys Ala Thr Leu Thr Val Asp Lys Ser Ser Phe Thr Ala Tyr
65                  70                  75                  80

Met Gln Leu Lys Ser Leu Thr Ser Glu Asp Ser Ala Val Tyr Tyr Cys
                85                  90                  95

Ala Arg Glu Lys Val Tyr Gly Tyr Asp Val Tyr Tyr Phe Asp Tyr Trp
            100                 105                 110

Gly Gln Gly Thr Thr Leu Thr Val Ser Ser
        115                 120
```

<210> SEQ ID NO 15
<211> LENGTH: 117
<212> TYPE: PRT
<213> ORGANISM: Mus musculus

<400> SEQUENCE: 15

```
Gln Gly Gln Met His Gln Ser Gly Ala Glu Leu Val Lys Pro Gly Ala
1               5                   10                  15

Ser Val Lys Leu Ser Cys Lys Thr Ser Gly Phe Thr Phe Asn Ser Gly
            20                  25                  30

Tyr Ile Ser Trp Leu Lys Gln Lys Pro Arg Gln Ser Leu Glu Trp Ile
        35                  40                  45

Ala Trp Ile Tyr Ala Gly Thr Gly Ile Ser Asn Phe Asn Gln Lys Phe
    50                  55                  60

Thr Gly Lys Ala Gln Leu Thr Val Asp Thr Ser Ser Ser Thr Ala Tyr
65                  70                  75                  80

Met Gln Leu Ser Ser Leu Thr Ser Ala Asp Ser Ala Ile Tyr Phe Cys
                85                  90                  95

Ala Ser Gly Ala Arg Lys Thr Leu Asp Phe Trp Gly Gln Gly Thr Ser
            100                 105                 110

Val Thr Val Ser Ser
        115
```

<210> SEQ ID NO 16
<211> LENGTH: 118
<212> TYPE: PRT
<213> ORGANISM: Mus musculus

<400> SEQUENCE: 16

```
Gln Val Gln Leu Gln Gln Ser Gly Ala Asp Leu Val Arg Pro Gly Ala
1               5                   10                  15

Ser Val Lys Leu Ser Cys Thr Ala Ser Gly Phe Asn Ile Lys Asp Asp
            20                  25                  30

Tyr Val His Trp Val Lys Gln Arg Pro Glu Gln Gly Leu Glu Trp Ile
        35                  40                  45

Gly Arg Ile Asp Pro Ala Asn Gly Asn Thr Arg Tyr Ala Pro Lys Phe
    50                  55                  60

Arg Gly Lys Ala Thr Met Thr Ala Asp Thr Ser Ser Asn Thr Ala Tyr
65                  70                  75                  80

Leu Gln Leu Ser Ser Leu Thr Ser Ala Asp Thr Ala Val Tyr Tyr Cys
                85                  90                  95

Ser Pro Pro Leu Trp Val Gly Gly Phe Ala Tyr Trp Gly Gln Gly Thr
            100                 105                 110

Leu Val Thr Val Ser Ser
        115
```

<210> SEQ ID NO 17
<211> LENGTH: 118
<212> TYPE: PRT
<213> ORGANISM: Artificial sequence
<220> FEATURE:
<223> OTHER INFORMATION: humanized sequence

<400> SEQUENCE: 17

```
Glu Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Asp
            20                  25                  30
```

Tyr Val His Trp Val Arg Gln Ala Pro Gly Gln Gly Leu Glu Trp Ile
35 40 45

Gly Arg Ile Asp Pro Ala Asn Gly Asn Thr Arg Tyr Ala Pro Lys Phe
50 55 60

Arg Gly Arg Ala Thr Met Thr Ala Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ser Pro Pro Leu Trp Val Gly Gly Phe Ala Tyr Trp Gly Gln Gly Thr
100 105 110

Leu Val Thr Val Ser Ser
115

<210> SEQ ID NO 18
<211> LENGTH: 118
<212> TYPE: PRT
<213> ORGANISM: Artificial sequence
<220> FEATURE:
<223> OTHER INFORMATION: humanized sequence

<400> SEQUENCE: 18

Glu Val Gln Leu Val Gln Ser Gly Ala Glu Val Lys Lys Pro Gly Ala
1 5 10 15

Ser Val Lys Val Ser Cys Lys Ala Ser Gly Phe Asn Ile Lys Asp Asp
20 25 30

Tyr Val His Trp Val Arg Gln Ala Pro Gly Gln Gly Leu Glu Trp Ile
35 40 45

Gly Arg Ile Asp Pro Ala Gln Gly Asn Thr Arg Tyr Ala Pro Lys Phe
50 55 60

Arg Gly Arg Ala Thr Met Thr Ala Asp Thr Ser Ile Ser Thr Ala Tyr
65 70 75 80

Met Glu Leu Ser Arg Leu Arg Ser Asp Asp Thr Ala Val Tyr Tyr Cys
85 90 95

Ser Pro Pro Leu Trp Val Gly Gly Phe Ala Tyr Trp Gly Gln Gly Thr
100 105 110

Leu Val Thr Val Ser Ser
115

<210> SEQ ID NO 19
<211> LENGTH: 118
<212> TYPE: PRT
<213> ORGANISM: Artificial sequence
<220> FEATURE:
<223> OTHER INFORMATION: humanized sequence

<400> SEQUENCE: 19

Glu Val Gln Leu Val Gln Ser Gly Ala Glu Val Lys Lys Pro Gly Ala
1 5 10 15

Ser Val Lys Val Ser Cys Lys Ala Ser Gly Phe Asn Ile Lys Asp Asp
20 25 30

Tyr Val His Trp Val Arg Gln Ala Pro Gly Gln Gly Leu Glu Trp Ile
35 40 45

Gly Arg Ile Asp Pro Ala Ser Gly Asn Thr Arg Tyr Ala Pro Lys Phe
50 55 60

Arg Gly Arg Ala Thr Met Thr Ala Asp Thr Ser Ile Ser Thr Ala Tyr
65 70 75 80

Met Glu Leu Ser Arg Leu Arg Ser Asp Asp Thr Ala Val Tyr Tyr Cys 85 90 95

Ser Pro Pro Leu Trp Val Gly Gly Phe Ala Tyr Trp Gly Gln Gly Thr
100 105 110

Leu Val Thr Val Ser Ser
115

<210> SEQ ID NO 20
<211> LENGTH: 118
<212> TYPE: PRT
<213> ORGANISM: Mus musculus

<400> SEQUENCE: 20

Gln Ile Gln Leu Gln Gln Ser Gly Pro Glu Leu Val Arg Pro Gly Ala
1 5 10 15

Ser Val Lys Ile Ser Cys Lys Ala Ser Gly Tyr Thr Phe Thr Asp Tyr
20 25 30

Tyr Ile Asn Trp Val Lys Gln Arg Pro Gly Gln Gly Leu Glu Trp Ile
35 40 45

Gly Trp Ile Tyr Pro Gly Asn Val Asn Val Lys Tyr Asn Glu Lys Phe
50 55 60

Lys Gly Lys Ala Thr Leu Thr Val Asp Thr Ser Ser Ser Thr Gly Tyr
65 70 75 80

Met Gln Leu Arg Ser Leu Thr Ser Glu Asp Ser Ala Val Tyr Phe Cys
85 90 95

Ala Arg Ser Ile Gly Leu Arg Tyr Phe Asp Asn Trp Gly Gln Gly Thr
100 105 110

Thr Leu Thr Val Ser Ser
115

<210> SEQ ID NO 21
<211> LENGTH: 118
<212> TYPE: PRT
<213> ORGANISM: Artificial sequence
<220> FEATURE:
<223> OTHER INFORMATION: humanized sequence

<400> SEQUENCE: 21

Glu Ile Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asp Tyr
20 25 30

Tyr Ile Asn Trp Val Arg Gln Ala Pro Gly Gln Arg Leu Glu Trp Ile
35 40 45

Gly Trp Ile Tyr Pro Gly Asn Val Asn Val Lys Tyr Asn Glu Lys Phe
50 55 60

Lys Gly Arg Ala Thr Leu Thr Val Asp Thr Ser Ala Ser Thr Gly Tyr
65 70 75 80

Met Glu Leu Ser Ser Leu Arg Ser Glu Asp Thr Ala Val Tyr Phe Cys
85 90 95

Ala Arg Ser Ile Gly Leu Arg Tyr Phe Asp Asn Trp Gly Gln Gly Thr
100 105 110

Leu Val Thr Val Ser Ser
115

<210> SEQ ID NO 22
<211> LENGTH: 119
<212> TYPE: PRT
<213> ORGANISM: Mus musculus

<400> SEQUENCE: 22

Glu Val Arg Leu Gln Gln Ser Gly Ala Glu Leu Val Lys Pro Gly Ala
1               5                   10                  15

Ser Val Lys Leu Ser Cys Lys Thr Ser Gly Phe Thr Phe Ser Asn Ser
            20                  25                  30

Tyr Ile Ser Trp Leu Lys Gln Lys Pro Arg Gln Ser Leu Glu Trp Ile
        35                  40                  45

Ala Trp Ile Tyr Ala Gly Thr Gly Gly Thr Asn Tyr Asn Gln Lys Phe
    50                  55                  60

Thr Gly Lys Ala Gln Leu Thr Val Asp Thr Ser Ser Ser Thr Ala Tyr
65                  70                  75                  80

Met Gln Leu Ser Ser Leu Thr Ser Glu Asp Ser Ala Ile Tyr Tyr Cys
                85                  90                  95

Ala Thr Tyr Gly Asn Phe Leu Tyr Ala Met Asp Asn Trp Gly Gln Gly
            100                 105                 110

Thr Ser Val Thr Val Ser Ser
        115

<210> SEQ ID NO 23
<211> LENGTH: 122
<212> TYPE: PRT
<213> ORGANISM: Mus musculus

<400> SEQUENCE: 23

Glu Val Gln Leu Gln Gln Ser Gly Pro Glu Leu Val Lys Pro Gly Ala
1               5                   10                  15

Ser Leu Lys Ile Ser Cys Lys Thr Phe Gly Tyr Ser Phe Thr Gly Tyr
            20                  25                  30

Tyr Met His Trp Val Lys Gln Ser Pro Glu Lys Ser Leu Glu Trp Ile
        35                  40                  45

Gly Lys Ile Val Pro Ser Thr Gly Gly Thr Thr Tyr Asn Gln Lys Phe
    50                  55                  60

Lys Ala Lys Ala Thr Leu Thr Val Asp Lys Ser Ser Phe Thr Ala Tyr
65                  70                  75                  80

Met Gln Leu Lys Ser Leu Thr Thr Glu Asp Ser Ala Val Tyr Tyr Cys
                85                  90                  95

Ala Arg Glu Lys Val Tyr Gly Tyr Asp Val Tyr Tyr Phe Asp Tyr Trp
            100                 105                 110

Gly Gln Gly Thr Thr Leu Thr Val Ser Ser
        115                 120

<210> SEQ ID NO 24
<211> LENGTH: 119
<212> TYPE: PRT
<213> ORGANISM: Mus musculus

<400> SEQUENCE: 24

Glu Val Gln Leu Gln Gln Ser Gly Ala Glu Leu Val Lys Pro Gly Ala
1               5                   10                  15

Ser Val Lys Leu Ser Cys Lys Thr Ser Gly Phe Thr Phe Ser Asn Ser
            20                  25                  30

Tyr Ile Ser Trp Leu Lys Gln Lys Pro Arg Gln Ser Leu Glu Trp Ile
        35                  40                  45

Ala Trp Ile Tyr Ala Gly Thr Gly Gly Thr Asn Tyr Asn Gln Lys Phe
    50                  55                  60

Thr Gly Lys Ala Gln Leu Thr Val Asp Thr Ser Ser Ser Thr Ala Tyr
65 70 75 80

Met Gln Leu Ser Ser Leu Thr Ser Glu Asp Ser Ala Ile Tyr Tyr Cys
85 90 95

Ala Thr Tyr Gly Asn Phe Leu Tyr Ala Met Asp Tyr Trp Gly Gln Gly
100 105 110

Thr Thr Leu Thr Val Ser Ser
115

<210> SEQ ID NO 25
<211> LENGTH: 118
<212> TYPE: PRT
<213> ORGANISM: Rattus norvegicus

<400> SEQUENCE: 25

Glu Val Lys Leu Leu Glu Ser Gly Pro Gly Leu Val Lys Pro Ser Gln
1 5 10 15

Ser Leu Ser Leu Thr Cys Ser Val Thr Gly Tyr Thr Ile Thr Ser Gly
20 25 30

Tyr Asp Trp Ser Trp Ile Arg Lys Phe Pro Gly Asn Lys Met Glu Trp
35 40 45

Met Gly Tyr Ile Ser Tyr Ser Gly Trp Thr Asn Tyr Asn Pro Ser Leu
50 55 60

Arg Ser Arg Ile Ser Ile Ser Arg Asp Thr Ser Lys Asn Gln Phe Phe
65 70 75 80

Leu Gln Leu Asn Ser Val Thr Thr Glu Asp Thr Ala Thr Tyr Tyr Cys
85 90 95

Ala Arg Val Arg Gly Tyr Asn Pro Phe Ala Tyr Trp Gly Gln Gly Thr
100 105 110

Leu Val Thr Val Ser Ser
115

<210> SEQ ID NO 26
<211> LENGTH: 118
<212> TYPE: PRT
<213> ORGANISM: Rattus norvegicus

<400> SEQUENCE: 26

Glu Val Gln Leu Glu Glu Ser Gly Pro Gly Leu Val Lys Pro Ser Gln
1 5 10 15

Ser Leu Ser Leu Thr Cys Ser Val Thr Gly Tyr Thr Ile Thr Ser Gly
20 25 30

Tyr Asp Trp Thr Trp Ile Arg Lys Phe Pro Gly Asn Lys Met Glu Trp
35 40 45

Met Gly Tyr Ile Ser Tyr Ser Gly Phe Thr Asn Tyr Asn Pro Ser Leu
50 55 60

Arg Ser Arg Ile Ser Ile Thr Arg Asp Thr Ser Lys Asn Gln Phe Phe
65 70 75 80

Leu Gln Leu Asn Ser Val Thr Thr Glu Asp Thr Ala Thr Tyr Tyr Cys
85 90 95

Thr Arg Thr Arg Gly Tyr Asn Pro Phe Ala Tyr Trp Gly Gln Gly Ala
100 105 110

Ser Val Ser Ser Ala Ser
115

<210> SEQ ID NO 27
<211> LENGTH: 118

<212> TYPE: PRT
<213> ORGANISM: Rattus norvegicus

<400> SEQUENCE: 27

Glu Ile Gln Leu Gln Glu Ser Gly Pro Gly Leu Val Lys Pro Ser Gln
1 5 10 15

Ser Leu Ser Leu Thr Cys Ser Val Thr Gly Tyr Thr Ile Thr Ser Gly
20 25 30

Tyr Asp Trp Thr Trp Leu Arg Lys Phe Pro Gly Asn Lys Met Glu Trp
35 40 45

Met Gly Tyr Ile Ser Tyr Ser Gly Phe Thr Asn Tyr Asn Pro Ser Leu
50 55 60

Arg Ser Arg Ile Ser Ile Ser Arg Asp Thr Ser Lys Asn Gln Phe Phe
65 70 75 80

Leu Gln Leu Asn Ser Val Thr Thr Glu Asp Thr Ala Thr Tyr Tyr Cys
85 90 95

Ala Arg Thr Arg Gly Tyr Asn Pro Phe Pro Tyr Trp Gly Gln Gly Thr
100 105 110

Leu Val Thr Val Ser Ser
115

<210> SEQ ID NO 28
<211> LENGTH: 121
<212> TYPE: PRT
<213> ORGANISM: Rattus norvegicus

<400> SEQUENCE: 28

Ser Val Gln Leu Lys Glu Ser Gly Pro Gly Leu Val Gln Pro Ser Gln
1 5 10 15

Thr Leu Ser Leu Thr Cys Thr Val Ser Gly Phe Ser Leu Thr Ser Asn
20 25 30

Gly Val Ser Trp Val Arg Gln Pro Pro Gly Lys Gly Leu Glu Trp Ile
35 40 45

Ala Ala Ile Ser Ser Gly Gly Ser Thr Tyr Tyr Asn Ser Val Leu Lys
50 55 60

Ser Arg Leu Ser Ile Ser Arg Asp Thr Ser Lys Ser Gln Val Phe Leu
65 70 75 80

Lys Met Asn Ser Leu Gln Thr Glu Asp Thr Ala Ile Tyr Phe Cys Thr
85 90 95

Arg Asp Thr Tyr Tyr Gly Tyr Asn Gln Ile Pro Phe Val Tyr Trp Gly
100 105 110

Gln Gly Thr Leu Val Thr Val Ser Ser
115 120

<210> SEQ ID NO 29
<211> LENGTH: 121
<212> TYPE: PRT
<213> ORGANISM: Rattus norvegicus

<400> SEQUENCE: 29

Ser Val Gln Trp Lys Glu Ser Gly Pro Gly Leu Val Gln Pro Ser Gln
1 5 10 15

Thr Leu Ser Leu Thr Cys Thr Val Ser Gly Phe Ser Leu Thr Ser Asn
20 25 30

Gly Val Ser Trp Val Arg Gln Pro Pro Gly Lys Gly Leu Glu Trp Ile
35 40 45

Ala Ala Ile Ser Ser Gly Gly Ser Thr Tyr Tyr Asn Ser Gly Leu Lys

```
    50                  55                  60

Ser Arg Leu Ser Ile Ser Arg Asp Thr Ser Lys Ser Gln Val Phe Leu
65                  70                  75                  80

Lys Met Asn Ser Leu Gln Thr Glu Asp Thr Ala Ile Tyr Phe Cys Thr
                85                  90                  95

Arg Ala Gly Tyr Tyr Gly Tyr Asn Pro Ile Trp Phe Thr Tyr Trp Gly
            100                 105                 110

Gln Gly Thr Leu Val Thr Val Ser Ser
        115                 120


<210> SEQ ID NO 30
<211> LENGTH: 121
<212> TYPE: PRT
<213> ORGANISM: Rattus norvegicus

<400> SEQUENCE: 30

Glu Val Gln Leu Val Glu Ser Gly Pro Gly Leu Met Gln Pro Ser Gln
1               5                   10                  15

Thr Leu Ser Leu Thr Cys Thr Val Ser Gly Phe Ser Leu Thr Ser Asn
            20                  25                  30

Gly Val Ser Trp Val Arg Gln Pro Pro Gly Lys Gly Leu Glu Trp Ile
        35                  40                  45

Ala Thr Ile Ser Ser Gly Gly Asn Thr Asn Tyr Asn Ser Ala Leu Lys
    50                  55                  60

Ser Arg Leu Ser Ile Ser Arg Asp Thr Ser Lys Ser Gln Val Phe Leu
65                  70                  75                  80

Lys Met Asn Ser Leu Gln Thr Glu Asp Thr Ala Ile Tyr Phe Cys Thr
                85                  90                  95

Arg Val Gly Tyr Tyr Gly Tyr Asn Pro Ile Trp Phe Ala Tyr Trp Gly
            100                 105                 110

Gln Gly Thr Leu Val Thr Val Ser Ser
        115                 120


<210> SEQ ID NO 31
<211> LENGTH: 117
<212> TYPE: PRT
<213> ORGANISM: Rattus norvegicus

<400> SEQUENCE: 31

Glu Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Asp Tyr
            20                  25                  30

Thr Ile Thr Trp Val Arg Gln Pro Pro Gly Lys Gly Leu Glu Trp Ile
        35                  40                  45

Ala Ala Thr Ser Val Gly Gly Ala Thr His Tyr Asn Ser Pro Leu Lys
    50                  55                  60

Ser Arg Leu Ser Ile Ser Gly Asp Thr Ser Lys Ser Gln Val Phe Leu
65                  70                  75                  80

Lys Met Asn Ser Leu Arg Thr Glu Asp Thr Ala Met Tyr Phe Cys Val
                85                  90                  95

Arg Ser Gly Tyr Tyr Ser Thr Tyr Met Asn Trp Gly Arg Gly Thr Met
            100                 105                 110

Val Thr Val Ser Ser
        115
```

<210> SEQ ID NO 32
<211> LENGTH: 117
<212> TYPE: PRT
<213> ORGANISM: Rattus norvegicus

<400> SEQUENCE: 32

Ser Val Gln Leu Met Glu Ser Gly Pro Gly Leu Val Gln Pro Ser Gln
1 5 10 15

Thr Leu Ser Leu Thr Cys Thr Val Ser Gly Phe Ser Leu Asn Ser Tyr
20 25 30

Asn Val Asn Trp Val Arg Gln Pro Pro Gly Lys Gly Leu Glu Trp Ile
35 40 45

Ala Ala Ile Ser Ser Gly Gly Ser Thr Tyr Tyr Asn Ser Val Leu Lys
50 55 60

Ser Arg Leu Ser Ile Thr Arg Asp Thr Ser Lys Ser Gln Val Phe Leu
65 70 75 80

Lys Met Asn Ser Leu Gln Thr Glu Asp Thr Ala Met Tyr Phe Cys Ala
85 90 95

Arg Ser Gly Tyr Tyr Ser Ser Tyr Met Asn Trp Gly Gln Gly Val Met
100 105 110

Val Thr Val Ser Ser
115

<210> SEQ ID NO 33
<211> LENGTH: 121
<212> TYPE: PRT
<213> ORGANISM: Rattus norvegicus

<400> SEQUENCE: 33

Glu Val Gln Leu Val Glu Ser Gly Gly Gly Leu Val Gln Pro Gly Arg
1 5 10 15

Ser Leu Lys Leu Ser Cys Ala Ala Ser Gly Phe Ile Phe Ser Arg Phe
20 25 30

Tyr Met Ala Trp Val Arg Gln Ala Pro Thr Lys Gly Leu Glu Trp Val
35 40 45

Ala Tyr Ile Asn Thr Gly Gly Gly Thr Thr Tyr Tyr Arg Asp Ser Val
50 55 60

Lys Gly Arg Phe Thr Ile Ser Arg Asp Asn Ala Lys Thr Thr Leu Tyr
65 70 75 80

Leu Gln Met Asp Ser Leu Arg Ser Glu Asp Thr Ala Thr Tyr Tyr Cys
85 90 95

Thr Thr Leu Ala Ala Pro Trp Asn Tyr Val Met Asp Ala Trp Gly Gln
100 105 110

Gly Ala Ser Val Thr Val Ser Ser Ala
115 120

<210> SEQ ID NO 34
<211> LENGTH: 118
<212> TYPE: PRT
<213> ORGANISM: Rattus norvegicus

<400> SEQUENCE: 34

Glu Val Gln Leu Val Glu Ser Gly Pro Gly Leu Val Lys Pro Ser Gln
1 5 10 15

Ser Leu Ser Leu Thr Cys Ser Val Thr Gly Tyr Thr Ile Thr Ser Gly
20 25 30

Tyr Asp Trp Thr Trp Ile Arg Lys Phe Pro Gly Asn Lys Met Glu Trp
35 40 45

Met Gly Tyr Ile Ser Tyr Ser Gly Phe Thr Asn Tyr Asn Pro Ser Leu
    50                  55                  60

Arg Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Thr Arg Thr Arg Gly Tyr Asn Pro Phe Ala Tyr Trp Gly Gln Gly Thr
            100                 105                 110

Leu Val Thr Val Ser Ser
        115

<210> SEQ ID NO 35
<211> LENGTH: 120
<212> TYPE: PRT
<213> ORGANISM: Rattus norvegicus

<400> SEQUENCE: 35

Glu Val Lys Leu Leu Glu Ser Gly Gly Gly Leu Val Gln Ser Gly Arg
1               5                   10                  15

Ser Leu Lys Leu Ser Cys Ala Ala Ser Gly Phe Ile Phe Ser Arg Phe
            20                  25                  30

Tyr Met Ala Trp Val Arg Gln Ala Pro Arg Lys Gly Leu Glu Trp Val
        35                  40                  45

Ala Tyr Ile Ser Asn Gly Ala Gly Ser Thr Tyr Tyr Arg Glu Ser Val
    50                  55                  60

Lys Gly Arg Phe Ile Ile Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Thr Thr Val Ala Ala Pro Trp Asn Tyr Val Met Asp Gly Trp Gly Gln
            100                 105                 110

Gly Ala Ser Val Thr Val Ser Ser
        115                 120

<210> SEQ ID NO 36
<211> LENGTH: 120
<212> TYPE: PRT
<213> ORGANISM: Rattus norvegicus

<400> SEQUENCE: 36

Glu Val Lys Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Arg Phe
            20                  25                  30

Tyr Met Ala Trp Val Arg Gln Ala Pro Thr Lys Gly Leu Glu Trp Val
        35                  40                  45

Ala His Ile Ser His Gly Gly Asp Thr Thr Tyr Tyr Arg Asp Ser Val
    50                  55                  60

Lys Gly Arg Phe Thr Ile Ser Arg Asp Asn Ala Lys Ser Thr Leu Phe
65                  70                  75                  80

Leu Gln Met Asp Ser Leu Arg Ser Glu Asp Thr Ala Thr Tyr Tyr Cys
                85                  90                  95

Thr Thr Ser Ala Ala Pro Trp Asn Tyr Val Met Asp Gly Trp Gly Leu
            100                 105                 110

Gly Ala Ser Val Thr Val Ser Ser
        115                 120

<210> SEQ ID NO 37
<211> LENGTH: 120
<212> TYPE: PRT
<213> ORGANISM: Rattus norvegicus

<400> SEQUENCE: 37

Glu Val Lys Leu Glu Glu Ser Gly Gly Gly Leu Val Gln Pro Gly Arg
1               5                   10                  15

Ser Leu Lys Leu Ser Cys Ala Ala Ser Gly Phe Thr Phe Ser Arg Phe
            20                  25                  30

Tyr Met Ala Trp Val Arg Gln Ala Pro Thr Lys Gly Leu Glu Trp Val
        35                  40                  45

Ala His Ile Ser His Gly Gly Asp Thr Thr Tyr Tyr Arg Asp Ser Val
    50                  55                  60

Lys Gly Arg Phe Thr Ile Ser Arg Asp Asn Ala Lys Ser Thr Leu Phe
65                  70                  75                  80

Leu Gln Met Asp Ser Leu Arg Ser Glu Asp Thr Ala Thr Tyr Tyr Cys
                85                  90                  95

Thr Thr Ser Ala Ala Pro Trp Asn Tyr Val Met Asp Gly Trp Gly Leu
            100                 105                 110

Gly Ala Ser Val Thr Val Ser Ser
        115                 120

<210> SEQ ID NO 38
<211> LENGTH: 120
<212> TYPE: PRT
<213> ORGANISM: Rattus norvegicus

<400> SEQUENCE: 38

Gln Ile Gln Leu Val Gln Ser Gly Ala Glu Leu Val Lys Pro Gly Ala
1               5                   10                  15

Ser Val Lys Leu Ser Cys Lys Thr Ser Gly Phe Thr Phe Ser Ser Asn
            20                  25                  30

Tyr Ile Ser Trp Leu Arg Gln Lys Pro Arg Gln Ser Leu Glu Trp Ile
        35                  40                  45

Ala Trp Ile Tyr Ser Gly Thr Gly Gly Thr Tyr Tyr Asn Gln Lys Phe
    50                  55                  60

Thr Gly Lys Ala Gln Leu Thr Ile Asp Thr Ser Ser Asn Thr Ala Tyr
65                  70                  75                  80

Met Gln Leu Ser Ser Leu Thr Ser Glu Asp Ser Ala Ile Tyr Tyr Cys
                85                  90                  95

Ala Arg His Val Gly Leu Arg Tyr Trp Tyr Phe Asp Val Trp Gly Ala
            100                 105                 110

Gly Thr Ser Val Thr Val Ser Ser
        115                 120

<210> SEQ ID NO 39
<211> LENGTH: 123
<212> TYPE: PRT
<213> ORGANISM: Rattus norvegicus

<400> SEQUENCE: 39

Glu Val Lys Leu Glu Glu Ser Gly Gly Gly Phe Val Gln Pro Gly Arg
1               5                   10                  15

Ser Leu Lys Leu Ser Cys Ala Ala Ser Gly Phe Thr Phe Arg Tyr Phe
            20                  25                  30

```
Tyr Met Ala Trp Val Arg Gln Ala Pro Thr Lys Gly Leu Glu Trp Val
        35                  40                  45

Ala Tyr Ile Ser Thr Gly Gly His Ser Thr Tyr Tyr Arg Glu Ser Val
    50                  55                  60

Lys Gly Arg Phe Thr Ile Ser Arg Asp Asp Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Thr Thr Val Ser Gly Asp Tyr Ser Ser Tyr Ile Tyr Val Met Asp Ala
            100                 105                 110

Trp Gly Gln Gly Thr Leu Val Thr Val Ser Ser
        115                 120


<210> SEQ ID NO 40
<211> LENGTH: 118
<212> TYPE: PRT
<213> ORGANISM: Rattus norvegicus

<400> SEQUENCE: 40

Glu Val Gln Leu Lys Glu Ser Gly Pro Gly Leu Val Lys Pro Ser Gln
1               5                   10                  15

Ser Leu Ser Leu Thr Cys Ser Val Thr Gly Tyr Thr Ile Thr Ser Gly
            20                  25                  30

Tyr Asp Trp Thr Trp Ile Arg Lys Phe Pro Gly Asn Lys Met Glu Trp
        35                  40                  45

Met Gly Tyr Ile Ser Tyr Ser Gly Phe Thr Asn Tyr Asn Pro Ser Leu
    50                  55                  60

Arg Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Thr Arg Thr Arg Gly Tyr Asn Pro Phe Ala Tyr Trp Gly Gln Gly Thr
            100                 105                 110

Leu Val Thr Val Ser Ser
        115


<210> SEQ ID NO 41
<211> LENGTH: 122
<212> TYPE: PRT
<213> ORGANISM: Rattus norvegicus

<400> SEQUENCE: 41

Glu Val Lys Leu Glu Glu Ser Gly Gly Ala Phe Val Gln Ser Gly Gly
1               5                   10                  15

Ser Leu Lys Val Ser Cys Ala Ala Ser Gly Phe Ile Phe Ser Asn Tyr
            20                  25                  30

Gly Met Ala Trp Val Arg Gln Ala Pro Thr Lys Gly Leu Glu Trp Val
        35                  40                  45

Ala Ser Ile Thr Asp Ser Gly Gly Asn Thr Tyr Tyr Arg Asp Ser Val
    50                  55                  60

Lys Gly Arg Phe Thr Ile Ser Arg Asp Asn Ala Lys Ser Thr Leu Tyr
65                  70                  75                  80

Leu Gln Met Asp Ser Leu Arg Ser Ala Asp Thr Ala Thr Tyr Tyr Cys
                85                  90                  95

Thr Thr Leu Gly Val Pro Met Gly Met Ile Asn Trp Phe Val Tyr Trp
            100                 105                 110
```

```
Gly Gln Gly Thr Leu Val Thr Val Ser Ser
        115                 120


<210> SEQ ID NO 42
<211> LENGTH: 113
<212> TYPE: PRT
<213> ORGANISM: Rattus norvegicus

<400> SEQUENCE: 42

Glu Ser Gly Pro Gly Leu Val Gln Pro Ser Gln Thr Leu Ser Leu Thr
1               5                   10                  15

Cys Thr Val Ser Gly Phe Ser Leu Thr Ser Asn Gly Val Thr Trp Ile
            20                  25                  30

Arg His Pro Pro Gly Lys Gly Leu Glu Trp Met Gly Val Ile Trp Ser
        35                  40                  45

Asn Gly Gly Thr Asp Tyr Asn Ser Ala Ile Lys Ser Arg Leu Gly Ile
    50                  55                  60

Ser Arg Asp Thr Ser Lys Ser Gln Val Phe Leu Lys Met Asn Ser Leu
65                  70                  75                  80

Gln Thr Glu Asp Thr Ala Ile Tyr Phe Cys Ala Arg Ala Ile Ala Ala
                85                  90                  95

Ser Tyr Val Met Asp Ala Trp Gly Pro Gly Ala Ser Val Thr Val Ser
            100                 105                 110

Ser


<210> SEQ ID NO 43
<211> LENGTH: 117
<212> TYPE: PRT
<213> ORGANISM: Rattus norvegicus

<400> SEQUENCE: 43

Val Gln Leu Lys Glu Ser Gly Pro Gly Leu Val Gln Pro Ser Gln Thr
1               5                   10                  15

Leu Ser Leu Thr Cys Thr Val Ser Gly Phe Ser Leu Thr Asp Thr Gly
            20                  25                  30

Val Ser Trp Val Arg Gln Pro Pro Gly Lys Gly Leu Glu Trp Ile Gly
        35                  40                  45

Ala Ile Trp Ser Gly Gly Val Thr Asp Tyr Asn Ser Ala Leu Lys Ser
    50                  55                  60

Arg Leu Ser Ile Ser Arg Asp Thr Ser Lys Ser Gln Val Leu Leu Lys
65                  70                  75                  80

Met Asn Ser Leu Gln Thr Glu Asp Thr Ala Met Tyr Phe Cys Ala Arg
                85                  90                  95

Thr Leu Ala Arg His Tyr Ile Met Asp Ala Trp Gly Gln Gly Val Met
            100                 105                 110

Val Thr Val Ser Ser
        115


<210> SEQ ID NO 44
<211> LENGTH: 118
<212> TYPE: PRT
<213> ORGANISM: Rattus norvegicus

<400> SEQUENCE: 44

Glu Val Gln Leu Val Glu Ser Gly Pro Gly Leu Val Gln Pro Ser Gln
1               5                   10                  15

Thr Leu Ser Leu Thr Cys Thr Val Ser Gly Leu Ser Leu Thr Ser Asn
            20                  25                  30
```

```
Gly Val Ser Trp Ile Arg Gln Pro Pro Gly Lys Gly Leu Glu Trp Leu
        35                  40                  45

Gly Val Ile Trp Ser Asp Gly Gly Thr Asp Tyr Asn Ser Ala Ile Arg
    50                  55                  60

Ser Arg Leu Thr Leu Ser Arg Asp Thr Ser Lys Ser Gln Val Phe Leu
65                  70                  75                  80

Lys Met Asn Ser Leu Gln Thr Glu Asp Thr Ala Met Tyr Phe Cys Ala
                85                  90                  95

Arg Ala Leu Ala Pro Ser Tyr Val Met Gly Pro Trp Gly Gln Gly Ala
            100                 105                 110

Ser Val Thr Val Ser Ser
        115
```

```
<210> SEQ ID NO 45
<211> LENGTH: 120
<212> TYPE: PRT
<213> ORGANISM: Rattus norvegicus

<400> SEQUENCE: 45

Glu Val Lys Leu Val Glu Ser Gly Gly Gly Leu Val Gln Pro Gly Asn
1               5                   10                  15

Ser Leu Thr Leu Ser Cys Val Ala Pro Gly Phe Thr Phe Ser Asn Tyr
            20                  25                  30

Gly Met His Trp Ile Arg Gln Ala Pro Lys Lys Gly Leu Glu Trp Ile
        35                  40                  45

Ala Met Ile Tyr Tyr Asp Ser Ser Lys Val Tyr Tyr Val Asp Thr Val
    50                  55                  60

Lys Gly Arg Phe Thr Ile Ser Arg Asp Asn Ser Lys Asn Thr Leu Tyr
65                  70                  75                  80

Leu Glu Met Asn Ser Leu Arg Ser Glu Asp Thr Ala Met Tyr Tyr Cys
                85                  90                  95

Ala Ala Pro Leu Ile Thr Ile Ala Ala Gly Phe Ala Tyr Trp Gly Gln
            100                 105                 110

Gly Thr Leu Val Thr Val Ser Ser
        115                 120
```

```
<210> SEQ ID NO 46
<211> LENGTH: 121
<212> TYPE: PRT
<213> ORGANISM: Rattus norvegicus

<400> SEQUENCE: 46

Glu Val Lys Leu Glu Glu Ser Gly Pro Gly Leu Val Gln Pro Ser Gln
1               5                   10                  15

Thr Leu Ser Leu Thr Cys Ser Val Ser Gly Phe Ser Leu Thr Ser Asp
            20                  25                  30

Gly Val Ser Trp Val Arg Gln Pro Pro Gly Lys Gly Leu Glu Trp Ile
        35                  40                  45

Ala Thr Ile Ser Ser Gly Gly Asn Thr Tyr Tyr Asn Ser Ala Leu Lys
    50                  55                  60

Ser Arg Leu Ser Ile Ser Arg Asp Thr Ser Lys Ser Gln Val Phe Leu
65                  70                  75                  80

Lys Met Asn Ser Leu Gln Thr Glu Asp Thr Ala Ile Tyr Phe Cys Ser
                85                  90                  95

Arg Gly Gly Tyr Tyr Gly Tyr Asn Pro Ile Trp Phe Val Tyr Trp Gly
            100                 105                 110
```

Gln Gly Thr Leu Val Thr Val Ser Ser
115 120

<210> SEQ ID NO 47
<211> LENGTH: 118
<212> TYPE: PRT
<213> ORGANISM: Rattus norvegicus
<220> FEATURE:
<221> NAME/KEY: SITE
<222> LOCATION: (13)..(13)
<223> OTHER INFORMATION: The amino acid at position 13 can be any naturally occuring amino acid
<220> FEATURE:
<221> NAME/KEY: SITE
<222> LOCATION: (59)..(59)
<223> OTHER INFORMATION: The amino acid at position 59 can be any naturally occuring amino acid

<400> SEQUENCE: 47

Glu Val Gln Leu Lys Glu Ser Gly Pro Gly Leu Val Xaa Pro Ser Lys
1 5 10 15

Thr Leu Ser Leu Thr Cys Thr Val Ser Gly Leu Ser Leu Thr Ser Asn
20 25 30

Ser Val Ser Trp Ile Arg Gln Pro Pro Gly Lys Gly Leu Arg Trp Met
35 40 45

Gly Val Ile Trp Ser Asn Gly Gly Thr Asp Xaa Asn Ser Ala Ile Lys
50 55 60

Ser Arg Leu Ile Ile Ser Lys Asp Thr Ser Asn Ser Gln Val Phe Leu
65 70 75 80

Lys Met Asn Ser Leu Gln Thr Glu Asp Thr Ala Leu Tyr Phe Cys Ala
85 90 95

Arg Ala Ile Ala Ser Ser Ser Val Val Asn Val Trp Gly Gln Gly Ser
100 105 110

Ser Val Ala Val Ser Ser
115

<210> SEQ ID NO 48
<211> LENGTH: 120
<212> TYPE: PRT
<213> ORGANISM: Rattus norvegicus

<400> SEQUENCE: 48

Glu Val Lys Leu Leu Glu Ser Gly Gly Gly Leu Val Gln Pro Gly Asn
1 5 10 15

Ser Leu Thr Leu Ser Cys Val Ala Ser Gly Phe Thr Phe Ser Asn Tyr
20 25 30

Gly Met His Trp Ile Arg Gln Ala Pro Lys Lys Gly Leu Glu Trp Ile
35 40 45

Ala Met Ile Tyr Tyr Asp Ser Ser Lys Met Tyr Phe Ala Asp Thr Leu
50 55 60

Lys Gly Arg Phe Thr Ile Ser Arg Asp Asn Ser Lys Asn Thr Leu Tyr
65 70 75 80

Leu Glu Met Asn Ser Leu Arg Ser Glu Asp Thr Ala Met Tyr Tyr Cys
85 90 95

Ala Ala Pro Leu Ile Thr Leu Ala Ala Gly Phe Thr Tyr Trp Gly Gln
100 105 110

Gly Thr Leu Val Thr Val Ser Ser
115 120

<210> SEQ ID NO 49
<211> LENGTH: 119
<212> TYPE: PRT
<213> ORGANISM: Rattus norvegicus

<400> SEQUENCE: 49

```
Gln Leu Gln Gln Ser Gly Ala Glu Val Ala Lys Pro Gly Ser Ser Val
1               5                   10                  15

Lys Ile Ser Cys Lys Ala Ser Gly Tyr Thr Phe Thr Ser Asn Thr Met
            20                  25                  30

His Trp Ile Lys Gln Thr Thr Gly Gln Ala Leu Glu Trp Thr Gly Tyr
        35                  40                  45

Ile Ser Pro Gly Ser Gly Gly Thr Met Tyr Asn Glu Lys Phe Lys Gly
    50                  55                  60

Lys Ala Thr Leu Thr Val Asp Lys Ser Ser Ser Thr Ala Tyr Met Gln
65                  70                  75                  80

Leu Ser Ser Leu Thr Pro Val Asp Thr Ala Val Tyr Tyr Cys Val Arg
                85                  90                  95

Glu Gly Tyr Tyr Tyr Ser Arg Tyr Ser Phe Ala Tyr Trp Gly Gln Gly
            100                 105                 110

Thr Leu Val Thr Val Ser Ser
        115
```

<210> SEQ ID NO 50
<211> LENGTH: 116
<212> TYPE: PRT
<213> ORGANISM: Rattus norvegicus

<400> SEQUENCE: 50

```
Val Lys Leu Glu Glu Ser Gly Pro Gly Leu Val Leu Pro Ser Gln Thr
1               5                   10                  15

Leu Ser Leu Ser Cys Thr Val Ser Gly Leu Ser Leu Ile Ser Asn Ser
            20                  25                  30

Ile Ser Trp Ile Arg Gln Pro Pro Gly Lys Gly Leu Glu Trp Met Gly
        35                  40                  45

Val Met Trp Asn Asn Gly Gly Thr Asp Tyr Asn Ser Ala Ile Lys Ser
    50                  55                  60

Arg Leu Ser Ile Ser Arg Asp Thr Ser Lys Ser Gln Val Phe Leu Lys
65                  70                  75                  80

Met Asn Ser Leu Gln Thr Glu Asp Thr Ala Met Tyr Phe Cys Ala Arg
                85                  90                  95

Gly Tyr Ser Ser Tyr Ile Phe Asp Tyr Trp Gly Gln Gly Ala Ser Val
            100                 105                 110

Thr Val Ser Ser
        115
```

<210> SEQ ID NO 51
<211> LENGTH: 118
<212> TYPE: PRT
<213> ORGANISM: Rattus norvegicus

<400> SEQUENCE: 51

```
Glu Val Gln Leu Thr Glu Ser Gly Pro Gly Leu Val Gln Pro Ser Gln
1               5                   10                  15

Thr Leu Ser Leu Thr Cys Thr Val Pro Gly Leu Ser Leu Thr Asn Thr
            20                  25                  30

Gly Val Ser Trp Ile Arg Gln Pro Pro Gly Lys Gly Leu Glu Trp Met
        35                  40                  45
```

Gly Val Ile Trp Ser Asp Gly Gly Thr Asp Tyr Asn Ser Ala Ile Lys
    50                  55                  60

Ser Arg Leu Ser Ile Ser Arg Asp Thr Ser Lys Ser Gln Val Phe Val
65                  70                  75                  80

Lys Met Asn Ser Leu Gln Thr Glu Asp Thr Ala Val Tyr Phe Cys Ala
                85                  90                  95

Arg Ala Leu Ala Pro Ser Tyr Val Met Glu Ala Trp Gly Gln Gly Ala
            100                 105                 110

Ser Val Thr Val Ser Ser
        115

<210> SEQ ID NO 52
<211> LENGTH: 117
<212> TYPE: PRT
<213> ORGANISM: Rattus norvegicus

<400> SEQUENCE: 52

Glu Val Gln Leu Lys Glu Ser Gly Pro Gly Leu Val Gln Pro Ser Gln
1               5                   10                  15

Thr Leu Ser Leu Thr Cys Thr Val Ser Gly Leu Ser Leu Thr Ser Asp
            20                  25                  30

Ser Val Ser Trp Ile Arg Gln Pro Pro Gly Lys Gly Leu Glu Trp Met
        35                  40                  45

Gly Val Ile Trp Ser Asn Gly Gly Thr Asp Tyr Asn Ser Ala Ile Lys
    50                  55                  60

Ser Arg Leu Ser Ile Ser Arg Asp Thr Ser Lys Ser Gln Val Phe Leu
65                  70                  75                  80

Lys Met Asn Ser Leu Gln Thr Glu Asp Thr Ala Met Tyr Phe Cys Ala
                85                  90                  95

Arg Thr Ile Pro Tyr Tyr Val Met Asp Ala Trp Gly Gln Gly Ala Ser
            100                 105                 110

Val Thr Val Ser Ser
        115

<210> SEQ ID NO 53
<211> LENGTH: 118
<212> TYPE: PRT
<213> ORGANISM: Rattus norvegicus

<400> SEQUENCE: 53

Gln Val Gln Leu Arg Glu Ser Gly Pro Gly Leu Val Gln Pro Ser Gln
1               5                   10                  15

Thr Leu Ser Leu Thr Cys Thr Val Ser Gly Leu Ser Leu Thr Ser Asn
            20                  25                  30

Ser Ile Ser Trp Ile Arg Gln Pro Pro Gly Lys Gly Leu Glu Trp Met
        35                  40                  45

Gly Val Ile Trp Ser Thr Gly Gly Thr Asp Tyr Asn Ser Ala Ile Lys
    50                  55                  60

Ser Arg Leu Ser Ile Ser Arg Asp Thr Ser Lys Ser Gln Val Phe Leu
65                  70                  75                  80

Lys Met Asn Ser Leu Gln Thr Glu Asp Thr Ala Met Tyr Phe Cys Ala
                85                  90                  95

Arg Ala Ile Ala Ala Ser Ala Val Met Asp Ala Trp Gly Gln Gly Ala
            100                 105                 110

Ser Val Thr Val Ser Ser
        115

<210> SEQ ID NO 54
<211> LENGTH: 117
<212> TYPE: PRT
<213> ORGANISM: Rattus norvegicus

<400> SEQUENCE: 54

```
Val Gln Leu Val Glu Ser Gly Pro Asp Leu Val Gln Pro Ser Gln Thr
1               5                   10                  15

Leu Ser Leu Thr Cys Thr Val Ser Gly Leu Ser Leu Thr Ser Thr Gly
            20                  25                  30

Val Ser Trp Ile Arg Gln Pro Pro Gly Arg Gly Leu Glu Trp Met Gly
        35                  40                  45

Val Ile Trp Ser Asn Gly Gly Thr Asp Tyr Asn Ser Ala Ile Arg Ser
    50                  55                  60

Arg Leu Ser Ile Ser Arg Asp Thr Ser Lys Ser Gln Val Phe Leu Lys
65                  70                  75                  80

Met Asn Ser Leu Gln Thr Glu Asp Thr Ala Met Tyr Phe Cys Ala Arg
                85                  90                  95

Ala Ile Ala Ala Ser Tyr Ile Met Asp Ala Trp Gly Gln Gly Ala Ser
            100                 105                 110

Val Thr Val Ser Ser
        115
```

<210> SEQ ID NO 55
<211> LENGTH: 122
<212> TYPE: PRT
<213> ORGANISM: Rattus norvegicus

<400> SEQUENCE: 55

```
Gln Val Thr Leu Lys Glu Ser Gly Pro Gly Ile Leu Gln Pro Ser His
1               5                   10                  15

Thr Leu Ser Leu Thr Cys Ser Phe Ser Gly Phe Ser Leu Ser Thr Tyr
            20                  25                  30

Gly Met Gly Val Ser Trp Val Arg Gln Pro Ser Gly Arg Gly Leu Glu
        35                  40                  45

Trp Leu Ala Thr Ile Trp Trp Asn Gly Asn Thr Tyr Asn Asn Pro Ser
    50                  55                  60

Leu Lys Ser Arg Leu Thr Val Ser Lys Gly Thr Ser Asn Asn Gln Ala
65                  70                  75                  80

Phe Leu Lys Val Thr Ser Val Asp Thr Ala Asp Thr Ala Thr Tyr Phe
                85                  90                  95

Cys Ala His Thr Leu Tyr Tyr Ser Thr Ser Ser Leu Phe Asp Tyr Trp
            100                 105                 110

Gly Gln Gly Val Val Val Thr Val Ser Ser
        115                 120
```

<210> SEQ ID NO 56
<211> LENGTH: 120
<212> TYPE: PRT
<213> ORGANISM: Rattus norvegicus

<400> SEQUENCE: 56

```
Val Gln Leu Lys Glu Ser Gly Pro Gly Leu Val Gln Pro Ser Gln Thr
1               5                   10                  15

Leu Ser Leu Thr Cys Thr Val Ser Gly Phe Ser Leu Thr Ser Asp Gly
            20                  25                  30
```

```
Val Ser Trp Val Arg Gln Pro Pro Gly Lys Gly Leu Glu Trp Ile Ala
        35                  40                  45

Ala Ile Ser Ser Gly Gly Ser Thr Tyr Tyr Asn Ser Ala Leu Lys Ser
    50                  55                  60

Arg Leu Ser Ile Ser Arg Asp Thr Ser Lys Ser Gln Val Phe Leu Lys
65                  70                  75                  80

Met Asn Ser Leu Gln Thr Glu Asp Thr Ala Ile Tyr Phe Cys Thr Arg
                85                  90                  95

Asp Thr Tyr Tyr Gly Tyr Asn Gln Ile Pro Phe Val Tyr Trp Gly Gln
            100                 105                 110

Gly Thr Leu Val Thr Val Ser Ser
        115                 120


<210> SEQ ID NO 57
<211> LENGTH: 121
<212> TYPE: PRT
<213> ORGANISM: Rattus norvegicus

<400> SEQUENCE: 57

Val Asn Leu Val Glu Ser Gly Pro Glu Leu Val Lys Pro Gly Thr Ser
1               5                   10                  15

Val Lys Ile Ser Cys Lys Ala Ser Gly Tyr Arg Phe Thr Ser Tyr Tyr
            20                  25                  30

Val His Trp Val Lys Gln Arg Pro Gly Gln Gly Leu Glu Trp Ile Gly
        35                  40                  45

Trp Ile Phe Pro Gly Ser Asp Asn Thr Lys Tyr Asn Glu Lys Phe Lys
    50                  55                  60

Gly Lys Ala Thr Leu Thr Ala Asp Thr Ser Ser Ser Thr Ala Tyr Met
65                  70                  75                  80

Gln Leu Ser Ser Leu Thr Ser Glu Asp Ser Ala Val Tyr Phe Cys Ala
                85                  90                  95

Ser Ile Tyr Tyr Gly Tyr Asp Gly Thr Leu Tyr Phe Asp Tyr Trp Gly
            100                 105                 110

Gln Gly Thr Ser Val Thr Val Ser Ser
        115                 120


<210> SEQ ID NO 58
<211> LENGTH: 117
<212> TYPE: PRT
<213> ORGANISM: Rattus norvegicus

<400> SEQUENCE: 58

Val Gln Leu Lys Glu Ser Gly Pro Gly Leu Val Gln Pro Ser Gln Thr
1               5                   10                  15

Leu Ser Leu Thr Cys Thr Val Ser Gly Leu Ser Leu Thr Ser Thr Gly
            20                  25                  30

Val Ser Trp Ile Arg Gln Pro Pro Gly Lys Gly Leu Glu Trp Met Gly
        35                  40                  45

Val Ile Trp Ser Asn Gly Gly Thr Asp Tyr Asn Ser Ala Ile Lys Ser
    50                  55                  60

Arg Leu Ser Ile Ser Arg Asp Thr Ser Lys Ser Gln Val Phe Leu Lys
65                  70                  75                  80

Met Asn Ser Leu Gln Thr Glu Asp Thr Ala Met Tyr Phe Cys Ala Arg
                85                  90                  95

Ala Ile Ala Pro Ser Tyr Ile Met Asp Ala Trp Gly Gln Gly Ala Ser
            100                 105                 110
```

Val Thr Val Ser Ser
115

<210> SEQ ID NO 59
<211> LENGTH: 121
<212> TYPE: PRT
<213> ORGANISM: Rattus norvegicus

<400> SEQUENCE: 59

Gln Val Gln Leu Gln Gln Ser Gly Ala Glu Val Ala Lys Pro Gly Ser
1 5 10 15

Ser Val Lys Ile Ser Cys Lys Ala Ser Gly Tyr Thr Phe Thr Ser Asn
20 25 30

Thr Met His Trp Ile Lys Gln Thr Thr Gly Gln Ala Leu Glu Trp Thr
35 40 45

Gly Tyr Ile Ser Pro Gly Ser Gly Gly Thr Met Tyr Asn Glu Lys Phe
50 55 60

Lys Gly Lys Ala Thr Leu Thr Val Asp Lys Ser Ser Ser Thr Ala Tyr
65 70 75 80

Met Gln Leu Ser Ser Leu Thr Pro Val Asp Thr Ala Val Tyr Tyr Cys
85 90 95

Val Arg Glu Gly Tyr Tyr Tyr Ser Arg Tyr Ser Phe Ala Tyr Trp Gly
100 105 110

Gln Gly Thr Leu Val Thr Val Ser Ser
115 120

<210> SEQ ID NO 60
<211> LENGTH: 121
<212> TYPE: PRT
<213> ORGANISM: Rattus norvegicus

<400> SEQUENCE: 60

Gln Val Ser Leu Lys Glu Ser Gly Pro Gly Met Leu Gln Pro Ser Lys
1 5 10 15

Thr Leu Ser Leu Thr Cys Ser Phe Ser Gly Phe Ser Leu Ser Thr Ser
20 25 30

Gly Met Val Val Asn Trp Ile Arg Gln Pro Ser Gly Lys Ser Leu Glu
35 40 45

Trp Leu Ala Ala Ile Asp Trp Asp Gly Asp Lys Tyr Tyr Asn Pro Ser
50 55 60

Leu Lys His Arg Leu Thr Val Ser Lys Asp Thr Ser Asn Thr Gln Val
65 70 75 80

Val Leu Lys Ile Thr Ser Val Asp Thr Ala Asp Thr Ala Thr Tyr Tyr
85 90 95

Cys Ala Arg Ser Ile Ala Pro Tyr Arg Gly Trp Phe Gly Tyr Trp Gly
100 105 110

Gln Gly Thr Leu Val Thr Val Ser Ser
115 120

<210> SEQ ID NO 61
<211> LENGTH: 119
<212> TYPE: PRT
<213> ORGANISM: Rattus norvegicus

<400> SEQUENCE: 61

Gln Val Thr Leu Lys Glu Ser Gly Pro Gly Ile Leu Arg Pro Ser His
1 5 10 15

Thr Leu Ser Leu Thr Cys Ser Phe Ser Gly Phe Ser Leu Thr Thr Tyr

```
            20                  25                  30

Gly Ile Cys Val Ser Trp Ile Arg Gln Pro Ser Gly Lys Gly Leu Glu
        35                  40                  45

Trp Leu Ala Asn Ile Cys Trp Glu Asp Ser Lys Ala Tyr Asn Pro Ser
    50                  55                  60

Leu Lys Asn Arg Leu Thr Ile Ser Lys Asp Thr Ser Asn Asn Gln Val
65                  70                  75                  80

Phe Leu Arg Ile Pro Ser Val Asp Thr Ala Asp Ser Ala Ile Tyr Tyr
                85                  90                  95

Cys Ala Arg Val Phe Asn Asn Tyr Pro Phe Pro Tyr Trp Gly Gln Gly
            100                 105                 110

Thr Leu Val Thr Val Ser Ser
        115


<210> SEQ ID NO 62
<211> LENGTH: 76
<212> TYPE: PRT
<213> ORGANISM: Rattus norvegicus

<400> SEQUENCE: 62

Gln Gly Thr Leu Lys Glu Ser Gly Pro Gly Ile Val Gln Ser Ser His
1               5                   10                  15

Thr Leu Ser Leu Thr Cys Ser Phe Ser Gly Phe Ser Leu Ser Thr Tyr
            20                  25                  30

Gly Met Gly Val Ser Trp Ile Arg Gln Pro Ser Gly Lys Gly Leu Glu
        35                  40                  45

Trp Leu Ala Ser Val Trp Trp Asn Gly Asp Thr Ser Asn Asn Pro Ser
    50                  55                  60

Leu Lys Ser Arg Leu Thr Val Ser Lys Asp Thr Ser
65                  70                  75


<210> SEQ ID NO 63
<211> LENGTH: 124
<212> TYPE: PRT
<213> ORGANISM: Rattus norvegicus

<400> SEQUENCE: 63

Glu Val Gln Leu Val Glu Ser Gly Gly Gly Leu Val Gln Pro Gly Arg
1               5                   10                  15

Ser Met Lys Leu Ser Cys Ala Ala Ser Gly Phe Thr Phe Ser Lys Ser
            20                  25                  30

Asp Met Ala Trp Val Arg Gln Ala Pro Thr Lys Gly Leu Lys Trp Val
        35                  40                  45

Ala Ser Ile Arg Tyr Asp Gly Gly Asn Thr Tyr Tyr Arg Asp Ser Val
    50                  55                  60

Arg Gly Arg Phe Thr Ile Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Ser Thr Ala Lys Ala Ala Ile Ser Thr Pro Ser Tyr Tyr Val Leu Asp
            100                 105                 110

Ala Trp Gly Gln Gly Ala Ser Val Thr Val Ser Ser
        115                 120


<210> SEQ ID NO 64
<211> LENGTH: 117
<212> TYPE: PRT
```

<213> ORGANISM: Rattus norvegicus

<400> SEQUENCE: 64

Gln Val Gln Leu Lys Glu Ser Gly Pro Gly Leu Val Gln Pro Ser Gln
1 5 10 15

Thr Leu Ser Leu Thr Cys Thr Val Ser Gly Leu Ser Leu Ser Ser Asn
20 25 30

Ser Val Ser Trp Ile Arg Gln Pro Pro Gly Lys Gly Leu Glu Trp Met
35 40 45

Gly Val Ile Trp Asn Asn Gly Gly Thr Asp Tyr Asn Ser Ala Ile Lys
50 55 60

Ser Arg Leu Ser Ile Ser Arg Asp Thr Ser Lys Ser Gln Val Phe Leu
65 70 75 80

Lys Leu Ser Ser Leu Gln Thr Glu Asp Thr Ala Met Tyr Phe Cys Ala
85 90 95

Arg Gly Tyr Ser Ser Tyr Ile Phe Asp Tyr Trp Gly Gln Gly Val Met
100 105 110

Val Thr Val Ser Ser
115

<210> SEQ ID NO 65
<211> LENGTH: 120
<212> TYPE: PRT
<213> ORGANISM: Artificial sequence
<220> FEATURE:
<223> OTHER INFORMATION: humanized sequence

<400> SEQUENCE: 65

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ile Phe Ser Arg Phe
20 25 30

Tyr Met Ala Trp Val Arg Gln Ala Pro Gly Lys Gly Leu Glu Trp Val
35 40 45

Ala Tyr Ile Asn Thr Gly Gly Gly Thr Thr Tyr Tyr Arg Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Thr Thr Leu Ala Ala Pro Trp Asn Tyr Val Met Asp Ala Trp Gly Gln
100 105 110

Gly Thr Leu Val Thr Val Ser Ser
115 120

<210> SEQ ID NO 66
<211> LENGTH: 120
<212> TYPE: PRT
<213> ORGANISM: Artificial sequence
<220> FEATURE:
<223> OTHER INFORMATION: humanized sequence

<400> SEQUENCE: 66

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Ile Phe Ser Arg Phe
20 25 30

Tyr Met Ala Trp Val Arg Gln Ala Pro Gly Lys Gly Leu Glu Trp Val

```
        35                  40                  45

Ala Tyr Ile Ser Asn Gly Ala Gly Ser Thr Tyr Tyr Arg Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Thr Val Ala Ala Pro Trp Asn Tyr Val Met Asp Gly Trp Gly Gln
            100                 105                 110

Gly Thr Leu Val Thr Val Ser Ser
        115                 120


<210> SEQ ID NO 67
<211> LENGTH: 120
<212> TYPE: PRT
<213> ORGANISM: Artificial sequence
<220> FEATURE:
<223> OTHER INFORMATION: humanized sequence

<400> SEQUENCE: 67

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Ser Arg Phe
            20                  25                  30

Tyr Met Ala Trp Val Arg Gln Ala Pro Gly Lys Gly Leu Glu Trp Val
        35                  40                  45

Ala Tyr Ile Ser Ser Gly Ala Gly Ser Thr Tyr Tyr Arg Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Thr Val Ala Ala Pro Trp Asn Tyr Val Met Asp Gly Trp Gly Gln
            100                 105                 110

Gly Thr Leu Val Thr Val Ser Ser
        115                 120


<210> SEQ ID NO 68
<211> LENGTH: 120
<212> TYPE: PRT
<213> ORGANISM: Artificial sequence
<220> FEATURE:
<223> OTHER INFORMATION: humanized sequence

<400> SEQUENCE: 68

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ile Phe Ser Arg Phe
            20                  25                  30

Tyr Met Ala Trp Val Arg Gln Ala Pro Gly Lys Gly Leu Glu Trp Val
        35                  40                  45

Ala Tyr Ile Ser Gln Gly Ala Gly Ser Thr Tyr Tyr Arg Glu Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Thr Thr Val Ala Ala Pro Trp Asn Tyr Val Met Asp Gly Trp Gly Gln
            100                 105                 110

Gly Thr Leu Val Thr Val Ser Ser
        115                 120


<210> SEQ ID NO 69
<211> LENGTH: 118
<212> TYPE: PRT
<213> ORGANISM: Artificial sequence
<220> FEATURE:
<223> OTHER INFORMATION: humanized sequence

<400> SEQUENCE: 69

Glu Val Gln Leu Gln Glu Ser Gly Pro Gly Leu Val Lys Pro Ser Glu
1               5                   10                  15

Thr Leu Ser Leu Thr Cys Ala Val Ser Gly Tyr Thr Ile Thr Ser Gly
            20                  25                  30

Tyr Asp Trp Thr Trp Ile Arg Lys Pro Pro Gly Lys Gly Met Glu Trp
        35                  40                  45

Met Gly Tyr Ile Ser Tyr Ser Gly Trp Thr Asn Tyr Asn Pro Ser Leu
    50                  55                  60

Arg Ser Arg Ile Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Val Arg Gly Tyr Asn Pro Phe Ala Tyr Trp Gly Gln Gly Thr
            100                 105                 110

Leu Val Thr Val Ser Ser
        115


<210> SEQ ID NO 70
<211> LENGTH: 121
<212> TYPE: PRT
<213> ORGANISM: Artificial sequence
<220> FEATURE:
<223> OTHER INFORMATION: humanized sequence

<400> SEQUENCE: 70

Glu Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Asn
            20                  25                  30

Gly Val Ser Trp Val Arg Gln Pro Pro Gly Lys Gly Leu Glu Trp Ile
        35                  40                  45

Ala Ala Ile Ser Ser Gly Gly Ser Thr Tyr Tyr Asn Ser Val Leu Lys
    50                  55                  60

Ser Arg Leu Thr Ile Ser Arg Asp Thr Ser Lys Asn Gln Val Ser Leu
65                  70                  75                  80

Lys Leu Ser Ser Val Thr Ala Ala Asp Thr Ala Val Tyr Phe Cys Thr
                85                  90                  95

Arg Asp Thr Tyr Tyr Gly Tyr Asn Gln Ile Pro Phe Val Tyr Trp Gly
            100                 105                 110

Gln Gly Thr Leu Val Thr Val Ser Ser
        115                 120


<210> SEQ ID NO 71
<211> LENGTH: 118
<212> TYPE: PRT
<213> ORGANISM: Artificial sequence
```

<220> FEATURE:
<223> OTHER INFORMATION: humanized sequence

<400> SEQUENCE: 71

Glu Ile Gln Leu Gln Glu Ser Gly Pro Gly Leu Val Lys Pro Ser Glu
1 5 10 15

Thr Leu Ser Leu Thr Cys Ala Val Ser Gly Tyr Thr Ile Thr Ser Gly
20 25 30

Tyr Asp Trp Thr Trp Leu Arg Lys Pro Pro Gly Lys Gly Met Glu Trp
35 40 45

Met Gly Tyr Ile Ser Tyr Ser Gly Phe Thr Asn Tyr Asn Pro Ser Leu
50 55 60

Arg Ser Arg Ile Thr Ile Ser Arg Asp Thr Ser Lys Asn Gln Phe Ser
65 70 75 80

Leu Lys Leu Ser Ser Val Thr Ala Ala Asp Thr Ala Val Tyr Tyr Cys
85 90 95

Ala Arg Thr Arg Gly Tyr Asn Pro Phe Pro Tyr Trp Gly Gln Gly Thr
100 105 110

Leu Val Thr Val Ser Ser
115

<210> SEQ ID NO 72
<211> LENGTH: 118
<212> TYPE: PRT
<213> ORGANISM: Artificial sequence
<220> FEATURE:
<223> OTHER INFORMATION: humanized sequence

<400> SEQUENCE: 72

Glu Val Gln Leu Gln Glu Ser Gly Pro Gly Leu Val Lys Pro Ser Glu
1 5 10 15

Thr Leu Ser Leu Thr Cys Ala Val Ser Gly Tyr Thr Ile Thr Ser Gly
20 25 30

Tyr Asp Trp Ser Trp Ile Arg Lys Pro Pro Gly Lys Gly Met Glu Trp
35 40 45

Met Gly Tyr Ile Ser Tyr Ser Gly Trp Thr Asn Tyr Asn Pro Ser Leu
50 55 60

Arg Ser Arg Ile Thr Ile Ser Arg Asp Thr Ser Lys Asn Gln Phe Ser
65 70 75 80

Leu Lys Leu Ser Ser Val Thr Ala Ala Asp Thr Ala Val Tyr Tyr Cys
85 90 95

Ala Arg Val Arg Gly Tyr Asn Pro Phe Ala Tyr Trp Gly Gln Gly Thr
100 105 110

Leu Val Thr Val Ser Ser
115

<210> SEQ ID NO 73
<211> LENGTH: 120
<212> TYPE: PRT
<213> ORGANISM: Artificial sequence
<220> FEATURE:
<223> OTHER INFORMATION: humanized sequence

<400> SEQUENCE: 73

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Arg Phe
20 25 30

```
Tyr Met Ala Trp Val Arg Gln Ala Pro Gly Lys Gly Leu Glu Trp Val
        35                  40                  45

Ala His Ile Ser His Gly Gly Asp Thr Thr Tyr Tyr Arg Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Thr Ser Ala Ala Pro Trp Asn Tyr Val Met Asp Gly Trp Gly Gln
            100                 105                 110

Gly Thr Leu Val Thr Val Ser Ser
        115                 120


<210> SEQ ID NO 74
<211> LENGTH: 120
<212> TYPE: PRT
<213> ORGANISM: Artificial sequence
<220> FEATURE:
<223> OTHER INFORMATION: humanized sequence

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Phe
            20                  25                  30

Tyr Met Ala Trp Val Arg Gln Ala Pro Gly Lys Gly Leu Glu Trp Val
        35                  40                  45

Ala His Ile Ser His Gly Gly Asp Thr Thr Tyr Tyr Arg Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Thr Ser Ala Ala Pro Trp Asn Tyr Val Met Asp Gly Trp Gly Gln
            100                 105                 110

Gly Ala Thr Val Thr Val Ser Ser
        115                 120


<210> SEQ ID NO 75
<211> LENGTH: 122
<212> TYPE: PRT
<213> ORGANISM: Artificial sequence
<220> FEATURE:
<223> OTHER INFORMATION: humanized sequence

<400> SEQUENCE: 75

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Thr Ser Tyr
            20                  25                  30

Tyr Val His Trp Val Arg Gln Ala Pro Gly Gln Arg Leu Glu Trp Ile
        35                  40                  45

Gly Trp Ile Phe Pro Gly Ser Asp Asn Thr Lys Tyr Asn Glu Lys Phe
    50                  55                  60

Lys Gly Arg Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95
```

```
Ala Ser Ile Tyr Tyr Gly Tyr Asp Gly Thr Leu Tyr Phe Asp Tyr Trp
            100                 105                 110

Gly Gln Gly Thr Leu Val Thr Val Ser Ser
        115                 120
```

<210> SEQ ID NO 76
<211> LENGTH: 120
<212> TYPE: PRT
<213> ORGANISM: Artificial sequence
<220> FEATURE:
<223> OTHER INFORMATION: humanized sequence

<400> SEQUENCE: 76

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Thr Ser Tyr
            20                  25                  30

Tyr Val His Trp Val Arg Gln Ala Pro Gly Gln Arg Leu Glu Trp Ile
        35                  40                  45

Gly Trp Ile Phe Pro Gly Ser Asp Asn Thr Lys Tyr Asn Glu Lys Phe
    50                  55                  60

Lys Gly Arg Ala Thr Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Ile Tyr Tyr Gly Tyr Asp Gly Thr Leu Tyr Phe Asp Tyr Trp
            100                 105                 110

Gly Gln Gly Thr Leu Val Thr Val
        115                 120
```

<210> SEQ ID NO 77
<211> LENGTH: 122
<212> TYPE: PRT
<213> ORGANISM: Artificial sequence
<220> FEATURE:
<223> OTHER INFORMATION: humanized sequence

<400> SEQUENCE: 77

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Arg Phe Thr Ser Tyr
            20                  25                  30

Tyr Val His Trp Val Arg Gln Ala Pro Gly Gln Gly Leu Glu Trp Met
        35                  40                  45

Gly Trp Ile Phe Pro Gly Ser Asp Asn Thr Lys Tyr Asn Glu Lys Phe
    50                  55                  60

Lys Gly Arg Val Thr Met Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Ile Tyr Tyr Gly Tyr Asp Gly Thr Leu Tyr Phe Asp Tyr Trp
            100                 105                 110

Gly Gln Gly Thr Thr Val Thr Val Ser Ser
        115                 120
```

<210> SEQ ID NO 78
<211> LENGTH: 122
<212> TYPE: PRT

<213> ORGANISM: Artificial sequence
<220> FEATURE:
<223> OTHER INFORMATION: humanized sequence

<400> SEQUENCE: 78

```
Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Arg Phe Thr Ser Tyr
            20                  25                  30

Tyr Val His Trp Val Arg Gln Ala Pro Gly Gln Gly Leu Glu Trp Ile
        35                  40                  45

Gly Trp Ile Phe Pro Gly Ser Asp Asn Thr Lys Tyr Asn Glu Lys Phe
    50                  55                  60

Lys Gly Arg Ala Thr Leu Thr Ala Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ser Ile Tyr Tyr Gly Tyr Asp Gly Thr Leu Tyr Phe Asp Tyr Trp
            100                 105                 110

Gly Gln Gly Thr Thr Val Thr Val Ser Ser
        115                 120
```

<210> SEQ ID NO 79
<211> LENGTH: 120
<212> TYPE: PRT
<213> ORGANISM: Artificial sequence
<220> FEATURE:
<223> OTHER INFORMATION: humanized sequence

<400> SEQUENCE: 79

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Phe
            20                  25                  30

Tyr Met Ala Trp Val Arg Gln Ala Pro Gly Lys Gly Leu Glu Trp Val
        35                  40                  45

Ala His Ile Ser His Gly Gly Asp Thr Thr Tyr Tyr Arg Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Thr Ser Ala Ala Pro Trp Asn Tyr Val Met Gln Gly Trp Gly Gln
            100                 105                 110

Gly Ala Thr Val Thr Val Ser Ser
        115                 120
```

<210> SEQ ID NO 80
<211> LENGTH: 120
<212> TYPE: PRT
<213> ORGANISM: Rattus norvegicus

<400> SEQUENCE: 80

```
Gln Gly Thr Leu Lys Glu Ser Gly Pro Gly Ile Val Gln Ser Ser His
1               5                   10                  15

Thr Leu Ser Leu Thr Cys Ser Phe Ser Gly Phe Ser Leu Ser Thr Tyr
            20                  25                  30

Gly Met Gly Val Ser Trp Ile Arg Gln Pro Ser Gly Lys Gly Leu Glu
```

```
        35                  40                  45

Trp Leu Ala Ser Val Trp Trp Asn Gly Asp Thr Ser Asn Asn Pro Ser
    50                  55                  60

Leu Lys Ser Arg Leu Thr Val Ser Lys Asp Thr Ser Asn Asn Gln Ala
65                  70                  75                  80

Phe Leu Lys Val Thr Ser Val Asp Thr Ala Asp Thr Ala Thr Tyr Tyr
                85                  90                  95

Cys Ala His Thr Leu Tyr Asn Asn Tyr Pro Phe Asp Tyr Trp Gly Gln
            100                 105                 110

Gly Val Met Val Thr Val Ser Ser
        115                 120


<210> SEQ ID NO 81
<211> LENGTH: 5
<212> TYPE: PRT
<213> ORGANISM: Mus musculus

<400> SEQUENCE: 81

Asn Ser Tyr Ile Ser
1               5


<210> SEQ ID NO 82
<211> LENGTH: 5
<212> TYPE: PRT
<213> ORGANISM: Mus musculus

<400> SEQUENCE: 82

Asn Asn Ala Met Ser
1               5


<210> SEQ ID NO 83
<211> LENGTH: 5
<212> TYPE: PRT
<213> ORGANISM: Mus musculus

<400> SEQUENCE: 83

Gly Tyr Tyr Met His
1               5


<210> SEQ ID NO 84
<211> LENGTH: 5
<212> TYPE: PRT
<213> ORGANISM: Mus musculus

<400> SEQUENCE: 84

Ser Gly Tyr Ile Ser
1               5


<210> SEQ ID NO 85
<211> LENGTH: 5
<212> TYPE: PRT
<213> ORGANISM: Mus musculus

<400> SEQUENCE: 85

Asp Asp Tyr Val His
1               5


<210> SEQ ID NO 86
<211> LENGTH: 5
<212> TYPE: PRT
<213> ORGANISM: Mus musculus

<400> SEQUENCE: 86
```

Asp Tyr Tyr Ile Asn
1 5

<210> SEQ ID NO 87
<211> LENGTH: 6
<212> TYPE: PRT
<213> ORGANISM: Rattus norvegicus

<400> SEQUENCE: 87

Ser Gly Tyr Asp Trp Ser
1 5

<210> SEQ ID NO 88
<211> LENGTH: 6
<212> TYPE: PRT
<213> ORGANISM: Rattus norvegicus

<400> SEQUENCE: 88

Ser Gly Tyr Asp Trp Thr
1 5

<210> SEQ ID NO 89
<211> LENGTH: 5
<212> TYPE: PRT
<213> ORGANISM: Rattus norvegicus

<400> SEQUENCE: 89

Ser Asn Gly Val Ser
1 5

<210> SEQ ID NO 90
<211> LENGTH: 5
<212> TYPE: PRT
<213> ORGANISM: Rattus norvegicus

<400> SEQUENCE: 90

Asp Tyr Thr Ile Thr
1 5

<210> SEQ ID NO 91
<211> LENGTH: 5
<212> TYPE: PRT
<213> ORGANISM: Rattus norvegicus

<400> SEQUENCE: 91

Ser Tyr Asn Val Asn
1 5

<210> SEQ ID NO 92
<211> LENGTH: 5
<212> TYPE: PRT
<213> ORGANISM: Rattus norvegicus

<400> SEQUENCE: 92

Arg Phe Tyr Met Ala
1 5

<210> SEQ ID NO 93
<211> LENGTH: 5
<212> TYPE: PRT
<213> ORGANISM: Rattus norvegicus

<400> SEQUENCE: 93

Ser Asn Tyr Ile Ser 1 5

<210> SEQ ID NO 94
<211> LENGTH: 5
<212> TYPE: PRT
<213> ORGANISM: Rattus norvegicus

<400> SEQUENCE: 94

Tyr Phe Tyr Met Ala
1 5

<210> SEQ ID NO 95
<211> LENGTH: 5
<212> TYPE: PRT
<213> ORGANISM: Rattus norvegicus

<400> SEQUENCE: 95

Asn Tyr Gly Met Ala
1 5

<210> SEQ ID NO 96
<211> LENGTH: 5
<212> TYPE: PRT
<213> ORGANISM: Rattus norvegicus

<400> SEQUENCE: 96

Ser Asn Gly Val Thr
1 5

<210> SEQ ID NO 97
<211> LENGTH: 5
<212> TYPE: PRT
<213> ORGANISM: Rattus norvegicus

<400> SEQUENCE: 97

Asp Thr Gly Val Ser
1 5

<210> SEQ ID NO 98
<211> LENGTH: 5
<212> TYPE: PRT
<213> ORGANISM: Rattus norvegicus

<400> SEQUENCE: 98

Asn Tyr Gly Met His
1 5

<210> SEQ ID NO 99
<211> LENGTH: 5
<212> TYPE: PRT
<213> ORGANISM: Rattus norvegicus

<400> SEQUENCE: 99

Ser Asp Gly Val Ser
1 5

<210> SEQ ID NO 100
<211> LENGTH: 5
<212> TYPE: PRT
<213> ORGANISM: Rattus norvegicus

<400> SEQUENCE: 100

Ser Asn Ser Val Ser
1 5

<210> SEQ ID NO 101
<211> LENGTH: 5
<212> TYPE: PRT
<213> ORGANISM: Rattus norvegicus

<400> SEQUENCE: 101

Ser Asn Thr Met His
1               5

<210> SEQ ID NO 102
<211> LENGTH: 5
<212> TYPE: PRT
<213> ORGANISM: Rattus norvegicus

<400> SEQUENCE: 102

Ser Asn Ser Ile Ser
1               5

<210> SEQ ID NO 103
<211> LENGTH: 5
<212> TYPE: PRT
<213> ORGANISM: Rattus norvegicus

<400> SEQUENCE: 103

Asn Thr Gly Val Ser
1               5

<210> SEQ ID NO 104
<211> LENGTH: 5
<212> TYPE: PRT
<213> ORGANISM: Rattus norvegicus

<400> SEQUENCE: 104

Ser Asp Ser Val Ser
1               5

<210> SEQ ID NO 105
<211> LENGTH: 5
<212> TYPE: PRT
<213> ORGANISM: Rattus norvegicus

<400> SEQUENCE: 105

Ser Thr Gly Val Ser
1               5

<210> SEQ ID NO 106
<211> LENGTH: 7
<212> TYPE: PRT
<213> ORGANISM: Rattus norvegicus

<400> SEQUENCE: 106

Thr Tyr Gly Met Gly Val Ser
1               5

<210> SEQ ID NO 107
<211> LENGTH: 5
<212> TYPE: PRT
<213> ORGANISM: Mus musculus

<400> SEQUENCE: 107

Ser Tyr Tyr Val His
1               5

<210> SEQ ID NO 108

<211> LENGTH: 7
<212> TYPE: PRT
<213> ORGANISM: Rattus norvegicus

<400> SEQUENCE: 108

Thr Ser Gly Met Val Val Asn
1 5

<210> SEQ ID NO 109
<211> LENGTH: 7
<212> TYPE: PRT
<213> ORGANISM: Rattus norvegicus

<400> SEQUENCE: 109

Thr Tyr Gly Ile Cys Val Ser
1 5

<210> SEQ ID NO 110
<211> LENGTH: 5
<212> TYPE: PRT
<213> ORGANISM: Rattus norvegicus

<400> SEQUENCE: 110

Lys Ser Asp Met Ala
1 5

<210> SEQ ID NO 111
<211> LENGTH: 17
<212> TYPE: PRT
<213> ORGANISM: Mus musculus

<400> SEQUENCE: 111

Trp Ile Tyr Ala Gly Thr Gly Gly Thr Asn Tyr Asn Gln Lys Phe Thr
1 5 10 15

Gly

<210> SEQ ID NO 112
<211> LENGTH: 17
<212> TYPE: PRT
<213> ORGANISM: Mus musculus

<400> SEQUENCE: 112

Thr Ile Thr Gly Gly Gly Ser Tyr Thr Tyr Tyr Pro Asp Ser Val Lys
1 5 10 15

Gly

<210> SEQ ID NO 113
<211> LENGTH: 17
<212> TYPE: PRT
<213> ORGANISM: Mus musculus

<400> SEQUENCE: 113

Lys Ile Val Pro Ser Thr Gly Gly Thr Thr Tyr Asn Gln Lys Phe Lys
1 5 10 15

Ala

<210> SEQ ID NO 114
<211> LENGTH: 17
<212> TYPE: PRT
<213> ORGANISM: Mus musculus

<400> SEQUENCE: 114

Trp Ile Tyr Ala Gly Thr Gly Ile Ser Asn Phe Asn Gln Lys Phe Thr 1 5 10 15

Gly

<210> SEQ ID NO 115
<211> LENGTH: 17
<212> TYPE: PRT
<213> ORGANISM: Mus musculus

<400> SEQUENCE: 115

Arg Ile Asp Pro Ala Asn Gly Asn Thr Arg Tyr Ala Pro Lys Phe Arg
1 5 10 15

Gly

<210> SEQ ID NO 116
<211> LENGTH: 17
<212> TYPE: PRT
<213> ORGANISM: Artificial sequence
<220> FEATURE:
<223> OTHER INFORMATION: humanized sequence

<400> SEQUENCE: 116

Arg Ile Asp Pro Ala Gln Gly Asn Thr Arg Tyr Ala Pro Lys Phe Arg
1 5 10 15

Gly

<210> SEQ ID NO 117
<211> LENGTH: 17
<212> TYPE: PRT
<213> ORGANISM: Artificial sequence
<220> FEATURE:
<223> OTHER INFORMATION: humanized sequence

<400> SEQUENCE: 117

Arg Ile Asp Pro Ala Ser Gly Asn Thr Arg Tyr Ala Pro Lys Phe Arg
1 5 10 15

Gly

<210> SEQ ID NO 118
<211> LENGTH: 17
<212> TYPE: PRT
<213> ORGANISM: Mus musculus

<400> SEQUENCE: 118

Trp Ile Tyr Pro Gly Asn Val Asn Val Lys Tyr Asn Glu Lys Phe Lys
1 5 10 15

Gly

<210> SEQ ID NO 119
<211> LENGTH: 16
<212> TYPE: PRT
<213> ORGANISM: Rattus norvegicus

<400> SEQUENCE: 119

Tyr Ile Ser Tyr Ser Gly Trp Thr Asn Tyr Asn Pro Ser Leu Arg Ser
1 5 10 15

<210> SEQ ID NO 120
<211> LENGTH: 16
<212> TYPE: PRT
<213> ORGANISM: Rattus norvegicus

<400> SEQUENCE: 120

Tyr Ile Ser Tyr Ser Gly Phe Thr Asn Tyr Asn Pro Ser Leu Arg Ser
1 5 10 15

<210> SEQ ID NO 121
<211> LENGTH: 16
<212> TYPE: PRT
<213> ORGANISM: Rattus norvegicus

<400> SEQUENCE: 121

Ala Ile Ser Ser Gly Gly Ser Thr Tyr Tyr Asn Ser Val Leu Lys Ser
1 5 10 15

<210> SEQ ID NO 122
<211> LENGTH: 16
<212> TYPE: PRT
<213> ORGANISM: Rattus norvegicus

<400> SEQUENCE: 122

Ala Ile Ser Ser Gly Gly Ser Thr Tyr Tyr Asn Ser Gly Leu Lys Ser
1 5 10 15

<210> SEQ ID NO 123
<211> LENGTH: 16
<212> TYPE: PRT
<213> ORGANISM: Rattus norvegicus

<400> SEQUENCE: 123

Thr Ile Ser Ser Gly Gly Asn Thr Asn Tyr Asn Ser Ala Leu Lys Ser
1 5 10 15

<210> SEQ ID NO 124
<211> LENGTH: 16
<212> TYPE: PRT
<213> ORGANISM: Rattus norvegicus

<400> SEQUENCE: 124

Ala Thr Ser Val Gly Gly Ala Thr His Tyr Asn Ser Pro Leu Lys Ser
1 5 10 15

<210> SEQ ID NO 125
<211> LENGTH: 17
<212> TYPE: PRT
<213> ORGANISM: Rattus norvegicus

<400> SEQUENCE: 125

Tyr Ile Asn Thr Gly Gly Gly Thr Thr Tyr Tyr Arg Asp Ser Val Lys
1 5 10 15

Gly

<210> SEQ ID NO 126
<211> LENGTH: 17
<212> TYPE: PRT
<213> ORGANISM: Rattus norvegicus

<400> SEQUENCE: 126

Tyr Ile Ser Asn Gly Ala Gly Ser Thr Tyr Tyr Arg Glu Ser Val Lys
1 5 10 15

Gly

<210> SEQ ID NO 127
<211> LENGTH: 17
<212> TYPE: PRT
<213> ORGANISM: Rattus norvegicus

<400> SEQUENCE: 127

His Ile Ser His Gly Gly Asp Thr Thr Tyr Tyr Arg Asp Ser Val Lys
1               5                   10                  15

Gly

<210> SEQ ID NO 128
<211> LENGTH: 17
<212> TYPE: PRT
<213> ORGANISM: Mus musculus

<400> SEQUENCE: 128

Trp Ile Tyr Ser Gly Thr Gly Gly Thr Tyr Tyr Asn Gln Lys Phe Thr
1               5                   10                  15

Gly

<210> SEQ ID NO 129
<211> LENGTH: 17
<212> TYPE: PRT
<213> ORGANISM: Rattus norvegicus

<400> SEQUENCE: 129

Tyr Ile Ser Thr Gly Gly His Ser Thr Tyr Tyr Arg Glu Ser Val Lys
1               5                   10                  15

Gly

<210> SEQ ID NO 130
<211> LENGTH: 17
<212> TYPE: PRT
<213> ORGANISM: Rattus norvegicus

<400> SEQUENCE: 130

Ser Ile Thr Asp Ser Gly Gly Asn Thr Tyr Tyr Arg Asp Ser Val Lys
1               5                   10                  15

Gly

<210> SEQ ID NO 131
<211> LENGTH: 16
<212> TYPE: PRT
<213> ORGANISM: Rattus norvegicus

<400> SEQUENCE: 131

Val Ile Trp Ser Asn Gly Gly Thr Asp Tyr Asn Ser Ala Ile Lys Ser
1               5                   10                  15

<210> SEQ ID NO 132
<211> LENGTH: 16
<212> TYPE: PRT
<213> ORGANISM: Rattus norvegicus

<400> SEQUENCE: 132

Ala Ile Trp Ser Gly Gly Val Thr Asp Tyr Asn Ser Ala Leu Lys Ser
1               5                   10                  15

<210> SEQ ID NO 133
<211> LENGTH: 16
<212> TYPE: PRT
<213> ORGANISM: Rattus norvegicus

<400> SEQUENCE: 133

Val Ile Trp Ser Asp Gly Gly Thr Asp Tyr Asn Ser Ala Ile Arg Ser
1               5                   10                  15

<210> SEQ ID NO 134
<211> LENGTH: 17
<212> TYPE: PRT
<213> ORGANISM: Rattus norvegicus

<400> SEQUENCE: 134

Met Ile Tyr Tyr Asp Ser Ser Lys Val Tyr Tyr Val Asp Thr Val Lys
1               5                   10                  15

Gly

<210> SEQ ID NO 135
<211> LENGTH: 16
<212> TYPE: PRT
<213> ORGANISM: Rattus norvegicus

<400> SEQUENCE: 135

Thr Ile Ser Ser Gly Gly Asn Thr Tyr Tyr Asn Ser Ala Leu Lys Ser
1               5                   10                  15

<210> SEQ ID NO 136
<211> LENGTH: 16
<212> TYPE: PRT
<213> ORGANISM: Rattus norvegicus
<220> FEATURE:
<221> NAME/KEY: SITE
<222> LOCATION: (10)..(10)
<223> OTHER INFORMATION: The amino acid at position 10 can be any naturally occuring amino acid

<400> SEQUENCE: 136

Val Ile Trp Ser Asn Gly Gly Thr Asp Xaa Asn Ser Ala Ile Lys Ser
1               5                   10                  15

<210> SEQ ID NO 137
<211> LENGTH: 17
<212> TYPE: PRT
<213> ORGANISM: Rattus norvegicus

<400> SEQUENCE: 137

Met Ile Tyr Tyr Asp Ser Ser Lys Met Tyr Phe Ala Asp Thr Leu Lys
1               5                   10                  15

Gly

<210> SEQ ID NO 138
<211> LENGTH: 17
<212> TYPE: PRT
<213> ORGANISM: Rattus norvegicus

<400> SEQUENCE: 138

Tyr Ile Ser Pro Gly Ser Gly Gly Thr Met Tyr Asn Glu Lys Phe Lys
1               5                   10                  15

Gly

<210> SEQ ID NO 139
<211> LENGTH: 16
<212> TYPE: PRT
<213> ORGANISM: Rattus norvegicus

<400> SEQUENCE: 139

Val Met Trp Asn Asn Gly Gly Thr Asp Tyr Asn Ser Ala Ile Lys Ser
1               5                   10                  15

<210> SEQ ID NO 140

<211> LENGTH: 16
<212> TYPE: PRT
<213> ORGANISM: Rattus norvegicus

<400> SEQUENCE: 140

Val Ile Trp Ser Asp Gly Gly Thr Asp Tyr Asn Ser Ala Ile Lys Ser
1 5 10 15

<210> SEQ ID NO 141
<211> LENGTH: 16
<212> TYPE: PRT
<213> ORGANISM: Rattus norvegicus

<400> SEQUENCE: 141

Val Ile Trp Ser Thr Gly Gly Thr Asp Tyr Asn Ser Ala Ile Lys Ser
1 5 10 15

<210> SEQ ID NO 142
<211> LENGTH: 16
<212> TYPE: PRT
<213> ORGANISM: Rattus norvegicus

<400> SEQUENCE: 142

Val Ile Trp Ser Asn Gly Gly Thr Asp Tyr Asn Ser Ala Ile Arg Ser
1 5 10 15

<210> SEQ ID NO 143
<211> LENGTH: 16
<212> TYPE: PRT
<213> ORGANISM: Rattus norvegicus

<400> SEQUENCE: 143

Thr Ile Trp Trp Asn Gly Asn Thr Tyr Asn Asn Pro Ser Leu Lys Ser
1 5 10 15

<210> SEQ ID NO 144
<211> LENGTH: 16
<212> TYPE: PRT
<213> ORGANISM: Rattus norvegicus

<400> SEQUENCE: 144

Ala Ile Ser Ser Gly Gly Ser Thr Tyr Tyr Asn Ser Ala Leu Lys Ser
1 5 10 15

<210> SEQ ID NO 145
<211> LENGTH: 17
<212> TYPE: PRT
<213> ORGANISM: Rattus norvegicus

<400> SEQUENCE: 145

Trp Ile Phe Pro Gly Ser Asp Asn Thr Lys Tyr Asn Glu Lys Phe Lys
1 5 10 15

Gly

<210> SEQ ID NO 146
<211> LENGTH: 16
<212> TYPE: PRT
<213> ORGANISM: Rattus norvegicus

<400> SEQUENCE: 146

Ala Ile Asp Trp Asp Gly Asp Lys Tyr Tyr Asn Pro Ser Leu Lys His
1 5 10 15

<210> SEQ ID NO 147

<211> LENGTH: 16
<212> TYPE: PRT
<213> ORGANISM: Rattus norvegicus

<400> SEQUENCE: 147

Asn Ile Cys Trp Glu Asp Ser Lys Ala Tyr Asn Pro Ser Leu Lys Asn
1 5 10 15

<210> SEQ ID NO 148
<211> LENGTH: 16
<212> TYPE: PRT
<213> ORGANISM: Rattus norvegicus

<400> SEQUENCE: 148

Ser Val Trp Trp Asn Gly Asp Thr Ser Asn Asn Pro Ser Leu Lys Ser
1 5 10 15

<210> SEQ ID NO 149
<211> LENGTH: 17
<212> TYPE: PRT
<213> ORGANISM: Rattus norvegicus

<400> SEQUENCE: 149

Ser Ile Arg Tyr Asp Gly Gly Asn Thr Tyr Tyr Arg Asp Ser Val Arg
1 5 10 15

Gly

<210> SEQ ID NO 150
<211> LENGTH: 16
<212> TYPE: PRT
<213> ORGANISM: Rattus norvegicus

<400> SEQUENCE: 150

Val Ile Trp Asn Asn Gly Gly Thr Asp Tyr Asn Ser Ala Ile Lys Ser
1 5 10 15

<210> SEQ ID NO 151
<211> LENGTH: 17
<212> TYPE: PRT
<213> ORGANISM: Artificial sequence
<220> FEATURE:
<223> OTHER INFORMATION: humanized sequence

<400> SEQUENCE: 151

Tyr Ile Ser Ser Gly Ala Gly Ser Thr Tyr Tyr Arg Glu Ser Val Lys
1 5 10 15

Gly

<210> SEQ ID NO 152
<211> LENGTH: 17
<212> TYPE: PRT
<213> ORGANISM: Artificial sequence
<220> FEATURE:
<223> OTHER INFORMATION: humanized sequence

<400> SEQUENCE: 152

Tyr Ile Ser Gln Gly Ala Gly Ser Thr Tyr Tyr Arg Glu Ser Val Lys
1 5 10 15

Gly

<210> SEQ ID NO 153
<211> LENGTH: 10
<212> TYPE: PRT
<213> ORGANISM: Mus musculus

<400> SEQUENCE: 153

Tyr Gly Asn Phe Leu Tyr Ala Met Asp Asn
1 5 10

<210> SEQ ID NO 154
<211> LENGTH: 11
<212> TYPE: PRT
<213> ORGANISM: Mus musculus

<400> SEQUENCE: 154

Pro Asp Gly Asn Tyr Glu Gly Val Leu Ala Tyr
1 5 10

<210> SEQ ID NO 155
<211> LENGTH: 13
<212> TYPE: PRT
<213> ORGANISM: Mus musculus

<400> SEQUENCE: 155

Glu Lys Val Tyr Gly Tyr Asp Val Tyr Tyr Phe Asp Tyr
1 5 10

<210> SEQ ID NO 156
<211> LENGTH: 8
<212> TYPE: PRT
<213> ORGANISM: Mus musculus

<400> SEQUENCE: 156

Gly Ala Arg Lys Thr Leu Asp Phe
1 5

<210> SEQ ID NO 157
<211> LENGTH: 9
<212> TYPE: PRT
<213> ORGANISM: Mus musculus

<400> SEQUENCE: 157

Pro Leu Trp Val Gly Gly Phe Ala Tyr
1 5

<210> SEQ ID NO 158
<211> LENGTH: 9
<212> TYPE: PRT
<213> ORGANISM: Mus musculus

<400> SEQUENCE: 158

Ser Ile Gly Leu Arg Tyr Phe Asp Asn
1 5

<210> SEQ ID NO 159
<211> LENGTH: 10
<212> TYPE: PRT
<213> ORGANISM: Mus musculus

<400> SEQUENCE: 159

Tyr Gly Asn Phe Leu Tyr Ala Met Asp Tyr
1 5 10

<210> SEQ ID NO 160
<211> LENGTH: 9
<212> TYPE: PRT
<213> ORGANISM: Rattus norvegicus

<400> SEQUENCE: 160

Val Arg Gly Tyr Asn Pro Phe Ala Tyr
1 5

<210> SEQ ID NO 161
<211> LENGTH: 9
<212> TYPE: PRT
<213> ORGANISM: Rattus norvegicus

<400> SEQUENCE: 161

Thr Arg Gly Tyr Asn Pro Phe Ala Tyr
1 5

<210> SEQ ID NO 162
<211> LENGTH: 9
<212> TYPE: PRT
<213> ORGANISM: Rattus norvegicus

<400> SEQUENCE: 162

Thr Arg Gly Tyr Asn Pro Phe Pro Tyr
1 5

<210> SEQ ID NO 163
<211> LENGTH: 13
<212> TYPE: PRT
<213> ORGANISM: Rattus norvegicus

<400> SEQUENCE: 163

Asp Thr Tyr Tyr Gly Tyr Asn Gln Ile Pro Phe Val Tyr
1 5 10

<210> SEQ ID NO 164
<211> LENGTH: 13
<212> TYPE: PRT
<213> ORGANISM: Rattus norvegicus

<400> SEQUENCE: 164

Ala Gly Tyr Tyr Gly Tyr Asn Pro Ile Trp Phe Thr Tyr
1 5 10

<210> SEQ ID NO 165
<211> LENGTH: 13
<212> TYPE: PRT
<213> ORGANISM: Rattus norvegicus

<400> SEQUENCE: 165

Val Gly Tyr Tyr Gly Tyr Asn Pro Ile Trp Phe Ala Tyr
1 5 10

<210> SEQ ID NO 166
<211> LENGTH: 9
<212> TYPE: PRT
<213> ORGANISM: Rattus norvegicus

<400> SEQUENCE: 166

Ser Gly Tyr Tyr Ser Thr Tyr Met Asn
1 5

<210> SEQ ID NO 167
<211> LENGTH: 9
<212> TYPE: PRT
<213> ORGANISM: Rattus norvegicus

<400> SEQUENCE: 167

Ser Gly Tyr Tyr Ser Ser Tyr Met Asn 1 5

<210> SEQ ID NO 168
<211> LENGTH: 11
<212> TYPE: PRT
<213> ORGANISM: Rattus norvegicus

<400> SEQUENCE: 168

Leu Ala Ala Pro Trp Asn Tyr Val Met Asp Ala
1 5 10

<210> SEQ ID NO 169
<211> LENGTH: 11
<212> TYPE: PRT
<213> ORGANISM: Rattus norvegicus

<400> SEQUENCE: 169

Val Ala Ala Pro Trp Asn Tyr Val Met Asp Gly
1 5 10

<210> SEQ ID NO 170
<211> LENGTH: 11
<212> TYPE: PRT
<213> ORGANISM: Rattus norvegicus

<400> SEQUENCE: 170

Ser Ala Ala Pro Trp Asn Tyr Val Met Asp Gly
1 5 10

<210> SEQ ID NO 171
<211> LENGTH: 11
<212> TYPE: PRT
<213> ORGANISM: Mus musculus

<400> SEQUENCE: 171

His Val Gly Leu Arg Tyr Trp Tyr Phe Asp Val
1 5 10

<210> SEQ ID NO 172
<211> LENGTH: 14
<212> TYPE: PRT
<213> ORGANISM: Rattus norvegicus

<400> SEQUENCE: 172

Val Ser Gly Asp Tyr Ser Ser Tyr Ile Tyr Val Met Asp Ala
1 5 10

<210> SEQ ID NO 173
<211> LENGTH: 13
<212> TYPE: PRT
<213> ORGANISM: Rattus norvegicus

<400> SEQUENCE: 173

Leu Gly Val Pro Met Gly Met Ile Asn Trp Phe Val Tyr
1 5 10

<210> SEQ ID NO 174
<211> LENGTH: 10
<212> TYPE: PRT
<213> ORGANISM: Rattus norvegicus

<400> SEQUENCE: 174

Ala Ile Ala Ala Ser Tyr Val Met Asp Ala
1 5 10

<210> SEQ ID NO 175
<211> LENGTH: 10
<212> TYPE: PRT
<213> ORGANISM: Rattus norvegicus

<400> SEQUENCE: 175

Thr Leu Ala Arg His Tyr Ile Met Asp Ala
1               5                   10

<210> SEQ ID NO 176
<211> LENGTH: 10
<212> TYPE: PRT
<213> ORGANISM: Rattus norvegicus

<400> SEQUENCE: 176

Ala Leu Ala Pro Ser Tyr Val Met Gly Pro
1               5                   10

<210> SEQ ID NO 177
<211> LENGTH: 11
<212> TYPE: PRT
<213> ORGANISM: Rattus norvegicus

<400> SEQUENCE: 177

Pro Leu Ile Thr Ile Ala Ala Gly Phe Ala Tyr
1               5                   10

<210> SEQ ID NO 178
<211> LENGTH: 13
<212> TYPE: PRT
<213> ORGANISM: Rattus norvegicus

<400> SEQUENCE: 178

Gly Gly Tyr Tyr Gly Tyr Asn Pro Ile Trp Phe Val Tyr
1               5                   10

<210> SEQ ID NO 179
<211> LENGTH: 10
<212> TYPE: PRT
<213> ORGANISM: Rattus norvegicus

<400> SEQUENCE: 179

Ala Ile Ala Ser Ser Ser Val Val Asn Val
1               5                   10

<210> SEQ ID NO 180
<211> LENGTH: 11
<212> TYPE: PRT
<213> ORGANISM: Rattus norvegicus

<400> SEQUENCE: 180

Pro Leu Ile Thr Leu Ala Ala Gly Phe Thr Tyr
1               5                   10

<210> SEQ ID NO 181
<211> LENGTH: 12
<212> TYPE: PRT
<213> ORGANISM: Rattus norvegicus

<400> SEQUENCE: 181

Glu Gly Tyr Tyr Tyr Ser Arg Tyr Ser Phe Ala Tyr
1               5                   10

<210> SEQ ID NO 182

<211> LENGTH: 9
<212> TYPE: PRT
<213> ORGANISM: Rattus norvegicus

<400> SEQUENCE: 182

Gly Tyr Ser Ser Tyr Ile Phe Asp Tyr
1               5

<210> SEQ ID NO 183
<211> LENGTH: 10
<212> TYPE: PRT
<213> ORGANISM: Rattus norvegicus

<400> SEQUENCE: 183

Ala Leu Ala Pro Ser Tyr Val Met Glu Ala
1               5                   10

<210> SEQ ID NO 184
<211> LENGTH: 7
<212> TYPE: PRT
<213> ORGANISM: Rattus norvegicus

<400> SEQUENCE: 184

Thr Ile Pro Tyr Tyr Val Met
1               5

<210> SEQ ID NO 185
<211> LENGTH: 10
<212> TYPE: PRT
<213> ORGANISM: Rattus norvegicus

<400> SEQUENCE: 185

Ala Ile Ala Ala Ser Ala Val Met Asp Ala
1               5                   10

<210> SEQ ID NO 186
<211> LENGTH: 10
<212> TYPE: PRT
<213> ORGANISM: Rattus norvegicus

<400> SEQUENCE: 186

Ala Ile Ala Ala Ser Tyr Ile Met Asp Ala
1               5                   10

<210> SEQ ID NO 187
<211> LENGTH: 12
<212> TYPE: PRT
<213> ORGANISM: Rattus norvegicus

<400> SEQUENCE: 187

Thr Leu Tyr Tyr Ser Thr Ser Ser Leu Phe Asp Tyr
1               5                   10

<210> SEQ ID NO 188
<211> LENGTH: 13
<212> TYPE: PRT
<213> ORGANISM: Mus musculus

<400> SEQUENCE: 188

Ile Tyr Tyr Gly Tyr Asp Gly Thr Leu Tyr Phe Asp Tyr
1               5                   10

<210> SEQ ID NO 189
<211> LENGTH: 10
<212> TYPE: PRT

<213> ORGANISM: Rattus norvegicus

<400> SEQUENCE: 189

Ala Ile Ala Pro Ser Tyr Ile Met Asp Ala
1 5 10

<210> SEQ ID NO 190
<211> LENGTH: 11
<212> TYPE: PRT
<213> ORGANISM: Rattus norvegicus

<400> SEQUENCE: 190

Ser Ile Ala Pro Tyr Arg Gly Trp Phe Gly Tyr
1 5 10

<210> SEQ ID NO 191
<211> LENGTH: 9
<212> TYPE: PRT
<213> ORGANISM: Rattus norvegicus

<400> SEQUENCE: 191

Val Phe Asn Asn Tyr Pro Phe Pro Tyr
1 5

<210> SEQ ID NO 192
<211> LENGTH: 10
<212> TYPE: PRT
<213> ORGANISM: Rattus norvegicus

<400> SEQUENCE: 192

Thr Leu Tyr Asn Asn Tyr Pro Phe Asp Tyr
1 5 10

<210> SEQ ID NO 193
<211> LENGTH: 15
<212> TYPE: PRT
<213> ORGANISM: Rattus norvegicus

<400> SEQUENCE: 193

Ala Lys Ala Ala Ile Ser Thr Pro Ser Tyr Tyr Val Leu Asp Ala
1 5 10 15

<210> SEQ ID NO 194
<211> LENGTH: 11
<212> TYPE: PRT
<213> ORGANISM: Artificial sequence
<220> FEATURE:
<223> OTHER INFORMATION: synthetic sequence

<400> SEQUENCE: 194

Ser Ala Ala Pro Trp Asn Tyr Val Met Gln Gly
1 5 10

<210> SEQ ID NO 195
<211> LENGTH: 107
<212> TYPE: PRT
<213> ORGANISM: Mus musculus

<400> SEQUENCE: 195

Asp Ile Gln Met Lys Gln Ser Pro Ala Ser Leu Ser Ala Ser Val Gly
1 5 10 15

Glu Thr Val Thr Ile Thr Cys Arg Ala Ser Gly Asn Ile His Asn Tyr
20 25 30

Leu Ala Trp Tyr Gln Gln Lys Gln Gly Lys Ser Pro Gln Leu Leu Val

```
        35                  40                  45

Tyr Asn Thr Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Trp
                85                  90                  95

Thr Phe Gly Gly Gly Thr Lys Leu Glu Ile Lys
            100                 105


<210> SEQ ID NO 196
<211> LENGTH: 107
<212> TYPE: PRT
<213> ORGANISM: Mus musculus

<400> SEQUENCE: 196

Asp Ile Gln Met Asn Gln Ser Pro Ser Ser Leu Ser Ala Ser Leu Gly
1               5                   10                  15

Asp Arg Val Thr Ile Ser Cys Ser Ala Ser Gln Gly Ile Ser Asn Tyr
            20                  25                  30

Leu Asn Trp Tyr Gln Gln Lys Pro Asp Gly Thr Ile Lys Leu Leu Ile
        35                  40                  45

Tyr Tyr Thr Ser Thr Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln His Tyr Ser Ser Leu Pro Trp
                85                  90                  95

Thr Phe Gly Gly Gly Thr Lys Leu Glu Ile Lys
            100                 105


<210> SEQ ID NO 197
<211> LENGTH: 107
<212> TYPE: PRT
<213> ORGANISM: Mus musculus

<400> SEQUENCE: 197

Asp Ile Val Met Ser Gln Ser Pro Ala Thr Leu Ser Val Thr Pro Gly
1               5                   10                  15

Asp Arg Val Ser Leu Ser Cys Arg Ala Ser Gln Ser Ile Ser Asp Tyr
            20                  25                  30

Leu His Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Ser Asp Phe Thr Leu Ser Ile Asn Ser Val Glu Pro
65                  70                  75                  80

Glu Asp Val Gly Val Tyr Tyr Cys Gln Asn Gly His Ser Phe Pro Trp
                85                  90                  95

Thr Phe Gly Gly Gly Thr Lys Leu Glu Ile Lys
            100                 105


<210> SEQ ID NO 198
<211> LENGTH: 107
<212> TYPE: PRT
<213> ORGANISM: Mus musculus

<400> SEQUENCE: 198
```

```
Asp Ile Gln Met Thr Gln Ser Ser Ser Tyr Leu Ser Val Ser Val Gly
1               5                   10                  15

Gly Arg Val Thr Ile Thr Cys Lys Ala Ser Asp Gln Ile Asn Tyr Trp
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Thr Ser Phe Gln Thr
65                  70                  75                  80

Glu Asp Val Ala Thr Tyr Tyr Cys Gln Gln Tyr Trp Thr Thr Pro Tyr
                85                  90                  95

Thr Phe Gly Gly Gly Thr Lys Val Glu Ile Lys
            100                 105


<210> SEQ ID NO 199
<211> LENGTH: 112
<212> TYPE: PRT
<213> ORGANISM: Mus musculus

<400> SEQUENCE: 199

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asp Val Asn Thr Tyr Leu His Trp Tyr Leu Gln Arg Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ser Glu Asp Leu Gly Ile Tyr Phe Cys Ser Gln Thr
                85                  90                  95

Thr His Val Pro Tyr Thr Phe Gly Gly Gly Thr Lys Leu Glu Ile Lys
            100                 105                 110


<210> SEQ ID NO 200
<211> LENGTH: 112
<212> TYPE: PRT
<213> ORGANISM: Artificial sequence
<220> FEATURE:
<223> OTHER INFORMATION: synthetic sequence

<400> SEQUENCE: 200

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asp Val Asn Thr Tyr Leu His Trp Tyr Gln Gln Arg Pro Gly Gln Ser
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Thr
                85                  90                  95
```

```
Thr His Val Pro Tyr Thr Phe Gly Gly Gly Thr Lys Leu Glu Ile Lys
            100                 105                 110


<210> SEQ ID NO 201
<211> LENGTH: 106
<212> TYPE: PRT
<213> ORGANISM: Mus musculus

<400> SEQUENCE: 201

Glu Lys Val Leu Thr Gln Ser Pro Ala Ile Met Ser Ala Ser Leu Gly
1               5                   10                  15

Glu Lys Val Thr Met Ser Cys Arg Ala Ser Ser Ser Val His Tyr Met
            20                  25                  30

Tyr Trp His Gln Gln Lys Ser Asp Ala Ser Pro Arg Leu Trp Ile Tyr
        35                  40                  45

Tyr Thr Ser Asn Leu Ala Pro Gly Val Pro Ala Arg Phe Ser Gly Ser
    50                  55                  60

Gly Ser Gly Asn Phe Tyr Ser Leu Thr Ile Ser Ser Val Glu Asp Glu
65                  70                  75                  80

Asp Gly Ala Thr Tyr Tyr Cys Gln Gln Phe Thr Thr Ser Thr Trp Thr
                85                  90                  95

Phe Gly Gly Gly Thr Lys Leu Glu Ile Lys
            100                 105


<210> SEQ ID NO 202
<211> LENGTH: 106
<212> TYPE: PRT
<213> ORGANISM: Artificial sequence
<220> FEATURE:
<223> OTHER INFORMATION: humanized sequence

<400> SEQUENCE: 202

Glu Lys Val Leu Thr Gln Ser Pro Ala Thr Leu Ser Leu Ser Pro Gly
1               5                   10                  15

Glu Arg Ala Thr Leu Ser Cys Arg Ala Ser Ser Ser Val His Tyr Met
            20                  25                  30

Tyr Trp His Gln Gln Lys Pro Gly Gln Ser Pro Arg Leu Trp Ile Tyr
        35                  40                  45

Tyr Thr Ser Asn Leu Ala Pro Gly Val Pro Ala Arg Phe Ser Gly Ser
    50                  55                  60

Gly Ser Gly Asn Asp Tyr Thr Leu Thr Ile Ser Ser Leu Glu Pro Glu
65                  70                  75                  80

Asp Phe Ala Val Tyr Tyr Cys Gln Gln Phe Thr Thr Ser Thr Trp Thr
                85                  90                  95

Phe Gly Gly Gly Thr Lys Leu Glu Ile Lys
            100                 105


<210> SEQ ID NO 203
<211> LENGTH: 107
<212> TYPE: PRT
<213> ORGANISM: Mus musculus

<400> SEQUENCE: 203

Asp Ile Val Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45
```

```
Tyr Asn Thr Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Trp
                85                  90                  95

Thr Phe Gly Gly Gly Thr Lys Leu Glu Ile Lys
            100                 105


<210> SEQ ID NO 204
<211> LENGTH: 107
<212> TYPE: PRT
<213> ORGANISM: Mus musculus

<400> SEQUENCE: 204

Asp Ile Gln Met Thr Gln Thr Pro Ser Ser Leu Ser Ala Ser Leu Gly
1               5                   10                  15

Asp Arg Val Thr Ile Thr Cys Ser Thr Ser Gln Gly Val Arg Ser Tyr
            20                  25                  30

Leu Asn Trp Tyr Gln Gln Lys Pro Asp Gly Ser Val Lys Leu Leu Ile
        35                  40                  45

Tyr Tyr Thr Ser Ser Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Leu Pro Tyr
                85                  90                  95

Thr Phe Gly Gly Gly Thr Lys Leu Glu Leu Lys
            100                 105


<210> SEQ ID NO 205
<211> LENGTH: 107
<212> TYPE: PRT
<213> ORGANISM: Mus musculus

<400> SEQUENCE: 205

Glu Ile Val Leu Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Trp
                85                  90                  95

Thr Phe Gly Gly Gly Thr Lys Leu Glu Ile Lys
            100                 105


<210> SEQ ID NO 206
<211> LENGTH: 106
<212> TYPE: PRT
<213> ORGANISM: Rattus norvegicus

<400> SEQUENCE: 206
```

```
Asp Ile Val Met Thr Gln Ser Pro Ser Leu Leu Ser Ala Ser Val Gly
1               5                   10                  15

Asp Arg Val Thr Leu Ser Cys Lys Ala Gly Gln Asn Ile Asn Asn Tyr
            20                  25                  30

Leu Ala Trp Tyr Gln Gln Lys Leu Gly Glu Ala Pro Lys Leu Leu Ile
        35                  40                  45

Tyr Asn Ala Asn Ser Leu Gln Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Gln Gln Tyr Asn Ser Trp Thr Thr
                85                  90                  95

Phe Gly Ser Gly Thr Lys Leu Glu Ile Lys
            100                 105


<210> SEQ ID NO 207
<211> LENGTH: 106
<212> TYPE: PRT
<213> ORGANISM: Rattus norvegicus

<400> SEQUENCE: 207

Asp Ile Val Met Thr Gln Ser Pro Ser Leu Leu Ser Ala Ser Val Gly
1               5                   10                  15

Asp Arg Val Thr Leu Ser Cys Lys Ala Gly Arg Asn Ile Asn Asn Tyr
            20                  25                  30

Leu Ala Trp Tyr Gln Gln Lys Leu Gly Lys Ala Pro Lys Leu Leu Ile
        35                  40                  45

Tyr Asn Thr Asn Ser Leu Gln Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Gln Gln Tyr Asn Ser Trp Thr Thr
                85                  90                  95

Phe Gly Ser Gly Thr Lys Leu Glu Ile Lys
            100                 105


<210> SEQ ID NO 208
<211> LENGTH: 106
<212> TYPE: PRT
<213> ORGANISM: Rattus norvegicus

<400> SEQUENCE: 208

Asp Ile Gln Met Thr Gln Ser Pro Ser Leu Leu Ser Ala Ser Val Gly
1               5                   10                  15

Asp Arg Val Ser Leu Ser Cys Lys Ala Gly Arg Asn Val Asn Asn Tyr
            20                  25                  30

Leu Ala Trp Tyr Gln Gln Lys Leu Gly Lys Pro Pro Lys Leu Leu Ile
        35                  40                  45

Tyr Asn Ser Asn Ser Leu Gln Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Gln Gln Tyr Asn Ser Trp Thr Thr
                85                  90                  95

Phe Gly Ser Gly Thr Lys Leu Glu Ile Lys
            100                 105
```

<210> SEQ ID NO 209
<211> LENGTH: 112
<212> TYPE: PRT
<213> ORGANISM: Rattus norvegicus

<400> SEQUENCE: 209

```
Asp Val Val Leu Ala Gln Thr Pro Pro Thr Leu Ser Ala Thr Ile Gly
1               5                   10                  15

Gln Ser Val Ser Ile Ser Cys Arg Ser Ser Gln Ser Leu Leu His Ser
            20                  25                  30

Ser Gly Asn Thr Tyr Leu Asn Trp Leu Leu Gln Arg Pro Gly Gln Pro
        35                  40                  45

Pro Gln Leu Leu Ile Tyr Leu Val Ser Arg Leu Glu Ser Arg Val Pro
    50                  55                  60

Asn Arg Phe Ser Gly Ser Gly Ser Gly Thr Asp Phe Thr Leu Lys Ile
65                  70                  75                  80

Ser Gly Val Glu Ala Glu Asp Leu Gly Val Tyr Tyr Cys Val Gln Ser
                85                  90                  95

Thr His Ala Pro Arg Thr Phe Gly Gly Gly Thr Lys Leu Glu Leu Lys
            100                 105                 110
```

<210> SEQ ID NO 210
<211> LENGTH: 112
<212> TYPE: PRT
<213> ORGANISM: Rattus norvegicus

<400> SEQUENCE: 210

```
Asp Val Val Met Thr Gln Thr Pro Pro Thr Leu Ser Ala Thr Ile Gly
1               5                   10                  15

Gln Ser Val Ser Ile Ser Cys Arg Ser Ser Gln Ser Leu Leu His Gly
            20                  25                  30

Ser Gly Asn Thr Tyr Leu Asn Trp Leu Leu Gln Arg Pro Gly Gln Pro
        35                  40                  45

Pro Gln Ile Leu Ile Tyr Leu Val Ser Arg Leu Glu Ser Arg Val Pro
    50                  55                  60

Lys Arg Phe Ser Gly Ser Gly Ser Gly Thr Asp Phe Thr Leu Lys Ile
65                  70                  75                  80

Ser Gly Val Glu Ala Asp Asp Leu Gly Val Tyr Tyr Cys Val Gln Ser
                85                  90                  95

Thr His Ala Pro Phe Thr Phe Gly Ser Gly Thr Lys Leu Glu Leu Lys
            100                 105                 110
```

<210> SEQ ID NO 211
<211> LENGTH: 112
<212> TYPE: PRT
<213> ORGANISM: Rattus norvegicus

<400> SEQUENCE: 211

```
Asp Val Val Met Thr Gln Thr Pro Pro Thr Leu Ser Ala Thr Ile Gly
1               5                   10                  15

His Ser Val Ser Ile Ser Cys Arg Ser Ser Gln Ser Leu Phe His Ser
            20                  25                  30

Ser Gly Asn Thr Tyr Leu Ser Trp Phe Leu Gln Arg Pro Gly Gln Pro
        35                  40                  45

Pro Gln Leu Leu Ile Tyr Leu Val Ser Arg Leu Glu Ser Arg Val Pro
    50                  55                  60

Asn Arg Phe Ser Gly Ser Gly Ser Gly Thr Asp Phe Thr Leu Lys Ile
```

```
65                  70                  75                  80

Ser Val Leu Glu Ala Glu Asp Leu Gly Val Tyr Tyr Cys Val Gln Thr
                85                  90                  95

Thr His Ala Pro Phe Thr Phe Gly Ser Gly Thr Lys Leu Glu Ile Lys
            100                 105                 110


<210> SEQ ID NO 212
<211> LENGTH: 112
<212> TYPE: PRT
<213> ORGANISM: Rattus norvegicus

<400> SEQUENCE: 212

Asp Val Val Met Thr Gln Thr Pro Pro Thr Phe Ser Ala Thr Ile Gly
1               5                   10                  15

Gln Ser Val Ser Ile Ser Cys Arg Ser Ser Gln Ser Leu Leu His Ser
            20                  25                  30

Ser Gly Asn Thr Phe Leu Ser Trp Leu Leu Gln Arg Pro Gly Gln Pro
        35                  40                  45

Pro Gln Leu Leu Ile Tyr Leu Val Ser Arg Leu Glu Phe Gly Val Pro
    50                  55                  60

Asn Arg Phe Ser Gly Ser Gly Ser Gly Thr Asp Phe Thr Leu Lys Ile
65                  70                  75                  80

Ser Gly Val Glu Ala Glu Asp Leu Gly Val Tyr Tyr Cys Val Gln Ser
                85                  90                  95

Thr His Val Met Asn Thr Phe Gly Ala Gly Thr Lys Leu Glu Ile Lys
            100                 105                 110


<210> SEQ ID NO 213
<211> LENGTH: 112
<212> TYPE: PRT
<213> ORGANISM: Rattus norvegicus

<400> SEQUENCE: 213

Asp Val Val Met Thr Gln Thr Pro Pro Thr Leu Ser Ala Thr Ile Gly
1               5                   10                  15

Gln Ser Val Ser Ile Ser Cys Arg Ser Ser Gln Ser Leu Leu His Ser
            20                  25                  30

Thr Gly Asn Thr Tyr Leu Asn Trp Leu Leu Gln Arg Pro Gly Gln Pro
        35                  40                  45

Pro Gln Leu Leu Ile Tyr Leu Val Ser Arg Leu Glu Tyr Gly Val Pro
    50                  55                  60

Asn Arg Phe Ser Gly Ser Gly Ser Gly Thr Asp Phe Thr Leu Lys Ile
65                  70                  75                  80

Ser Gly Val Glu Ala Glu Asp Leu Gly Val Tyr Tyr Cys Ala Gln Ser
                85                  90                  95

Thr His Ala Leu Asn Thr Phe Gly Ala Gly Thr Lys Leu Glu Leu Lys
            100                 105                 110


<210> SEQ ID NO 214
<211> LENGTH: 106
<212> TYPE: PRT
<213> ORGANISM: Rattus norvegicus

<400> SEQUENCE: 214

Asp Val Val Met Thr Gln Ser Pro Ser Leu Leu Ser Ala Ser Val Gly
1               5                   10                  15

Asp Arg Val Thr Leu Thr Cys Lys Gly Ser Gln Asn Ile Asn Asn Phe
            20                  25                  30
```

```
Leu Ala Trp Tyr Gln Gln Lys Leu Gly Glu Ala Pro Lys Leu Leu Thr
        35                  40                  45

Tyr Lys Thr Asn Ser Leu His Thr Gly Ile Pro Ser Arg Phe Ser Gly
    50                  55                  60

Ser Gly Ser Gly Thr Asp Tyr Thr Leu Thr Ile Ser Ser Leu His Ser
65                  70                  75                  80

Glu Asp Leu Ala Thr Tyr Tyr Cys Tyr Gln Tyr Asn Asn Gly Tyr Thr
                85                  90                  95

Phe Gly Pro Gly Thr Lys Leu Glu Leu Lys
            100                 105


<210> SEQ ID NO 215
<211> LENGTH: 106
<212> TYPE: PRT
<213> ORGANISM: Rattus norvegicus

<400> SEQUENCE: 215

Asp Val Val Met Thr Gln Ser Pro Ser Leu Leu Ser Ala Ser Val Gly
1               5                   10                  15

Asp Arg Val Thr Leu Ser Cys Lys Ala Gly Arg Asn Ile Asn Asn Tyr
            20                  25                  30

Leu Ala Trp Tyr Gln Gln Lys Leu Gly Lys Ala Pro Lys Leu Leu Ile
        35                  40                  45

Tyr Asn Thr Asn Ser Leu Gln Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Cys Gln Gln Tyr Asn Ser Trp Thr Thr
                85                  90                  95

Phe Gly Ser Gly Thr Lys Leu Glu Ile Lys
            100                 105


<210> SEQ ID NO 216
<211> LENGTH: 106
<212> TYPE: PRT
<213> ORGANISM: Rattus norvegicus

<400> SEQUENCE: 216

Asn Ile Gln Ile Thr Gln Ser Pro Ser Leu Leu Ser Ala Ser Val Gly
1               5                   10                  15

Asp Arg Val Thr Leu Ser Cys Lys Gly Ser Gln Asn Ile Asn Asn Tyr
            20                  25                  30

Leu Ala Trp Tyr Gln Gln Lys Leu Gly Glu Ala Pro Lys Leu Leu Ile
        35                  40                  45

Tyr Lys Thr Asn Ser Leu His Thr Gly Ile Pro Ser Arg Phe Ser Gly
    50                  55                  60

Ser Gly Ser Gly Thr Asp Tyr Thr Leu Thr Ile Ser Ser Leu His Ser
65                  70                  75                  80

Glu Asp Leu Ala Thr Tyr Tyr Cys Tyr Gln Tyr Asn Asn Gly Tyr Thr
                85                  90                  95

Phe Gly Ala Gly Thr Lys Leu Glu Leu Lys
            100                 105


<210> SEQ ID NO 217
<211> LENGTH: 106
<212> TYPE: PRT
<213> ORGANISM: Rattus norvegicus
```

<400> SEQUENCE: 217

Asp Ile Val Met Thr Gln Ser Pro Ser Leu Leu Ser Ala Ser Val Gly
1               5                   10                  15

Asp Arg Val Thr Leu Thr Cys Lys Gly Ser Gln Asn Ile Asn Asn Phe
            20                  25                  30

Leu Ala Trp Tyr Gln Gln Lys Leu Gly Glu Ala Pro Lys Leu Leu Ile
        35                  40                  45

Tyr Lys Thr Asn Ser Leu His Thr Gly Ile Pro Ser Arg Phe Ser Gly
    50                  55                  60

Ser Gly Ser Gly Thr Asp Tyr Thr Leu Thr Ile Ser Ser Leu His Ser
65                  70                  75                  80

Glu Asp Leu Ala Thr Tyr Tyr Cys Tyr Gln Tyr Asn Asn Gly Tyr Thr
                85                  90                  95

Phe Gly Ala Gly Thr Lys Leu Glu Leu Lys
            100                 105

<210> SEQ ID NO 218
<211> LENGTH: 106
<212> TYPE: PRT
<213> ORGANISM: Rattus norvegicus

<400> SEQUENCE: 218

Asp Ile Gln Met Thr Gln Ser Pro Ser Leu Leu Ser Ala Ser Val Gly
1               5                   10                  15

Asp Arg Val Thr Leu Thr Cys Lys Gly Ser Gln Asn Ile Asn Asn Phe
            20                  25                  30

Leu Ala Trp Tyr Gln Gln Lys Leu Gly Glu Ala Pro Lys Leu Leu Ile
        35                  40                  45

Tyr Lys Thr Asn Ser Leu His Thr Gly Ile Pro Ser Arg Phe Ser Gly
    50                  55                  60

Ser Gly Ser Gly Thr Asp Tyr Thr Leu Thr Ile Ser Ser Leu His Ser
65                  70                  75                  80

Glu Asp Leu Ala Thr Tyr Tyr Cys Tyr Gln Tyr Asn Asn Gly Tyr Thr
                85                  90                  95

Phe Gly Ala Gly Thr Lys Leu Glu Leu Lys
            100                 105

<210> SEQ ID NO 219
<211> LENGTH: 114
<212> TYPE: PRT
<213> ORGANISM: Rattus norvegicus

<400> SEQUENCE: 219

Asp Ile Val Leu Thr Gln Ser Pro Ala Ser Leu Thr Val Ser Leu Gly
1               5                   10                  15

Gln Arg Ala Thr Ile Ser Cys Arg Ala Ser Glu Ser Val Asp Ser Asn
            20                  25                  30

Gly Asn Ser Phe Met His Trp Tyr Gln Gln Lys Pro Gly Gln Ser Pro
        35                  40                  45

Lys Val Leu Ile Tyr Arg Ala Ser Asn Leu Glu Ser Gly Val Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Asn
                85                  90                  95

```
Glu Asp Pro Trp Thr Phe Gly Gly Gly Thr Lys Leu Glu Ile Lys Arg
            100                 105                 110

Glu Phe


<210> SEQ ID NO 220
<211> LENGTH: 108
<212> TYPE: PRT
<213> ORGANISM: Rattus norvegicus

<400> SEQUENCE: 220

Val Met Thr Gln Ser Pro Val Leu Ala Val Ser Leu Gly Gln Arg Ala
1               5                   10                  15

Thr Leu Ser Cys Arg Ala Ser Gln Ser Val Thr Ile Ser Gly Ile Asn
            20                  25                  30

Leu Met His Trp Tyr Gln Gln Lys Pro Gly Gln Gln Pro Arg Leu Leu
        35                  40                  45

Val Tyr Arg Ala Ser Asn Leu Ala Ser Gly Ile Pro Ala Arg Phe Ser
    50                  55                  60

Gly Ser Gly Ser Gly Thr Asp Phe Thr Leu Thr Ile Asp Pro Val Gln
65                  70                  75                  80

Ala Ala Asp Ile Ala Ala Tyr Tyr Cys Gln Gln Thr Arg Val Ser Pro
                85                  90                  95

Trp Thr Phe Gly Gly Gly Thr Lys Leu Glu Ile Lys
            100                 105


<210> SEQ ID NO 221
<211> LENGTH: 103
<212> TYPE: PRT
<213> ORGANISM: Rattus norvegicus

<400> SEQUENCE: 221

Val Thr Gln Ser Pro Ser Leu Leu Ser Ala Ser Val Gly Asp Arg Val
1               5                   10                  15

Thr Leu Ser Cys Lys Ala Gly Arg Asn Ile Asn Asn Tyr Leu Ala Trp
            20                  25                  30

Tyr Gln Gln Lys Leu Gly Lys Ala Pro Lys Leu Leu Ile Tyr Asn Thr
        35                  40                  45

Asn Ser Leu Gln Thr Gly Ile Pro Ser Arg Phe Ser Gly Ser Gly Ser
    50                  55                  60

Gly Thr Asp Phe Thr Leu Thr Ile Ser Ser Leu Gln Pro Glu Asp Val
65                  70                  75                  80

Ala Thr Tyr Phe Cys Gln Gln Tyr Asn Ser Trp Thr Thr Phe Gly Ser
                85                  90                  95

Gly Thr Lys Leu Glu Leu Lys
            100


<210> SEQ ID NO 222
<211> LENGTH: 103
<212> TYPE: PRT
<213> ORGANISM: Rattus norvegicus

<400> SEQUENCE: 222

Thr Gln Ser Pro Pro Ser Leu Ser Ala Ser Leu Gly Asp Lys Val Thr
1               5                   10                  15

Ile Thr Cys Gln Ala Ser Gln Tyr Ile Tyr Lys Tyr Leu Ala Trp Tyr
            20                  25                  30

His Gln Lys Pro Gly Lys Ala Pro Arg Leu Leu Ile Arg Tyr Thr Ser
        35                  40                  45
```

Thr Leu Glu Ser Gly Thr Pro Ser Arg Phe Ser Gly Ser Gly Ser Gly
    50                  55                  60

Arg Asp Tyr Ser Phe Ser Ile Ser Asn Val Glu Ser Gly Asp Phe Ala
65                  70                  75                  80

Thr Tyr Tyr Cys Leu Gln Tyr Val Asn Leu Pro Phe Thr Phe Gly Ala
                85                  90                  95

Gly Thr Lys Leu Glu Leu Lys
            100

<210> SEQ ID NO 223
<211> LENGTH: 103
<212> TYPE: PRT
<213> ORGANISM: Rattus norvegicus

<400> SEQUENCE: 223

Met Ile Gln Ser Pro Pro Ser Leu Ser Ala Ser Leu Gly Asp Lys Val
1               5                   10                  15

Thr Ile Thr Cys Gln Ala Ser His Asn Ile Tyr Lys Tyr Val Ala Trp
            20                  25                  30

Phe Gln Leu Lys Pro Gly Arg Ala Pro Arg Leu Leu Ile Arg Tyr Thr
        35                  40                  45

Ser Thr Leu Gln Ser Gly Thr Pro Ser Arg Phe Ser Gly Ser Gly Ser
    50                  55                  60

Gly Arg Asp Tyr Ser Phe Ser Ile Ser Asn Val Glu Ser Glu Asp Phe
65                  70                  75                  80

Ala Ser Tyr Phe Cys Leu Gln Tyr Val Asn Leu Trp Thr Phe Gly Gly
                85                  90                  95

Gly Thr Lys Leu Glu Leu Lys
            100

<210> SEQ ID NO 224
<211> LENGTH: 107
<212> TYPE: PRT
<213> ORGANISM: Rattus norvegicus

<400> SEQUENCE: 224

Asp Ile Leu Met Thr Lys Ser Pro Pro Ser Leu Ser Ala Ser Leu Gly
1               5                   10                  15

Asp Lys Val Thr Ile Thr Cys Gln Ala Ser Gln His Ile Asn Asn Tyr
            20                  25                  30

Ile Ala Trp Tyr Gln Gln Lys Pro Arg Lys Ala Pro Arg Leu Leu Ile
        35                  40                  45

Arg Tyr Ala Ser Thr Leu Gln Ser Gly Thr Pro Ser Arg Phe Ser Gly
    50                  55                  60

Ser Gly Ser Gly Arg Thr Tyr Ser Phe Ser Ile Ser Asn Val Arg Ser
65                  70                  75                  80

Glu Asp Ile Ala Ser Tyr Tyr Cys Leu Gln Tyr Val Asn Leu Pro Tyr
                85                  90                  95

Thr Phe Gly Ala Gly Thr Lys Leu Glu Leu Lys
            100                 105

<210> SEQ ID NO 225
<211> LENGTH: 110
<212> TYPE: PRT
<213> ORGANISM: Mus musculus

<400> SEQUENCE: 225

```
Ile Val Leu Thr Gln Ser Pro Ala Ser Leu Thr Val Ser Leu Gly Gln
1               5                   10                  15

Arg Ala Thr Ile Ser Cys Arg Ala Ser Glu Ser Val Asp Ser Asn Gly
            20                  25                  30

Asn Ser Phe Met His Trp Tyr Gln Gln Lys Pro Gly Gln Ser Pro Lys
        35                  40                  45

Val Leu Ile Tyr Arg Ala Ser Asn Leu Glu Ser Gly Val Pro Ala Arg
    50                  55                  60

Phe Ser Gly Ser Gly Ser Arg Thr Asp Phe Thr Leu Thr Ile Asn Pro
65                  70                  75                  80

Val Glu Ala Asp Asp Val Ala Thr Tyr Tyr Cys Gln Gln Ser Asn Glu
                85                  90                  95

Asp Pro Trp Thr Phe Gly Gly Gly Thr Lys Leu Glu Ile Lys
            100                 105                 110


<210> SEQ ID NO 226
<211> LENGTH: 106
<212> TYPE: PRT
<213> ORGANISM: Rattus norvegicus

<400> SEQUENCE: 226

Asp Ile Glu Met Thr Gln Ser Pro Pro Ser Leu Ser Ala Ser Leu Gly
1               5                   10                  15

Asp Lys Val Thr Ile Thr Cys Gln Ala Ser Gln Asn Ile His Lys Tyr
            20                  25                  30

Ile Ala Trp Tyr Gln Gln Lys Pro Gly Lys Ala Pro Arg Leu Leu Leu
        35                  40                  45

Arg Tyr Thr Ser Thr Leu Glu Ser Gly Thr Pro Ser Arg Phe Ser Gly
    50                  55                  60

Ser Gly Ser Gly Arg Asp Tyr Ser Phe Ser Ile Ser Asn Val Glu Ser
65                  70                  75                  80

Glu Asp Phe Ala Ser Tyr Tyr Cys Leu Gln Tyr Val Asn Leu Trp Thr
                85                  90                  95

Phe Gly Gly Gly Thr Lys Leu Glu Ile Lys
            100                 105


<210> SEQ ID NO 227
<211> LENGTH: 115
<212> TYPE: PRT
<213> ORGANISM: Rattus norvegicus

<400> SEQUENCE: 227

Asp Ile Val Met Thr Gln Ser Pro Ser Ser Leu Ala Val Ser Ala Gly
1               5                   10                  15

Glu Thr Val Thr Ile Asn Cys Lys Ser Ser Gln Ser Leu Phe Trp Ser
            20                  25                  30

Gly Ser Gln Met Asn Tyr Leu Ala Trp Tyr Gln Gln Lys Pro Gly Gln
        35                  40                  45

Ser Pro Lys Leu Leu Ile Tyr Tyr Ala Ser Thr Ala Gln Ser Gly Val
    50                  55                  60

Pro Asp Arg Phe Ile Gly Ser Gly Ser Gly Thr Asp Phe Thr Leu Thr
65                  70                  75                  80

Ile Ser Gly Val Gln Ala Glu Asp Leu Ala Val Tyr Tyr Cys Gln His
                85                  90                  95

His Tyr Asp Ser Leu Pro Pro Tyr Thr Phe Gly Ala Gly Thr Lys Leu
            100                 105                 110
```

```
Glu Ile Lys
        115


<210> SEQ ID NO 228
<211> LENGTH: 112
<212> TYPE: PRT
<213> ORGANISM: Rattus norvegicus

<400> SEQUENCE: 228

Asp Val Val Met Thr Gln Thr Pro Pro Thr Leu Ser Ala Thr Ile Gly
1               5                   10                  15

Gln Ser Val Ser Ile Ser Cys Arg Ser Ser Gln Ser Leu Leu His Ser
            20                  25                  30

Ser Gly Asn Thr Tyr Leu His Trp Leu Leu Gln Arg Pro Gly Gln Pro
        35                  40                  45

Pro Gln Leu Leu Val Tyr Leu Val Ser Arg Leu Glu Ser Gly Val Pro
    50                  55                  60

Asn Arg Phe Ser Gly Ser Gly Ser Gly Thr Asp Phe Thr Leu Arg Ile
65                  70                  75                  80

Ser Gly Ile Glu Ala Glu Asp Leu Gly Val Tyr Tyr Cys Val Gln Ser
                85                  90                  95

Thr His Ala Pro Phe Thr Phe Gly Ser Gly Thr Lys Leu Glu Ile Lys
            100                 105                 110


<210> SEQ ID NO 229
<211> LENGTH: 106
<212> TYPE: PRT
<213> ORGANISM: Rattus norvegicus

<400> SEQUENCE: 229

Asp Ile Gln Met Thr Gln Ser Pro Pro Ser Leu Ser Ala Ser Leu Gly
1               5                   10                  15

Asp Lys Val Thr Ile Thr Cys Gln Ala Ser Gln Asn Ile His Lys Tyr
            20                  25                  30

Ile Gly Trp Tyr Gln Gln Lys Pro Gly Lys Ala Pro Arg Leu Leu Ile
        35                  40                  45

Arg Tyr Thr Ser Thr Leu Glu Ser Gly Thr Pro Ser Arg Phe Ser Gly
    50                  55                  60

Ser Gly Ser Gly Arg Tyr Tyr Ser Phe Ser Ile Ser Asn Val Glu Ser
65                  70                  75                  80

Glu Asp Ile Ala Ser Tyr Tyr Cys Leu Gln Tyr Val Asn Leu Trp Thr
                85                  90                  95

Phe Gly Gly Gly Thr Lys Leu Glu Leu Lys
            100                 105


<210> SEQ ID NO 230
<211> LENGTH: 111
<212> TYPE: PRT
<213> ORGANISM: Rattus norvegicus

<400> SEQUENCE: 230

Thr Gln Ser Pro Ser Ser Leu Ala Val Ser Thr Gly Glu Thr Val Thr
1               5                   10                  15

Ile Asn Cys Lys Ser Ser Gln Ser Leu Phe Trp Ser Gly Ser Gln Met
            20                  25                  30

Asn Tyr Leu Ala Trp Tyr Gln Gln Lys Pro Gly Gln Ser Pro Lys Leu
        35                  40                  45

Leu Ile Tyr Tyr Thr Ser Thr Arg Gln Ser Gly Val Pro Asp Arg Phe
```

```
    50                  55                  60

Ile Gly Ser Gly Ser Gly Thr Asp Phe Thr Leu Thr Ile Ser Gly Val
65                  70                  75                  80

Gln Ala Glu Asp Leu Ala Val Tyr Tyr Cys Gln His His Tyr Asp Ser
                85                  90                  95

Leu Pro Pro Tyr Thr Phe Gly Ala Gly Thr Lys Leu Glu Leu Lys
            100                 105                 110


<210> SEQ ID NO 231
<211> LENGTH: 107
<212> TYPE: PRT
<213> ORGANISM: Rattus norvegicus

<400> SEQUENCE: 231

Asp Val Val Leu Thr Gln Ser Pro Ala Ser Leu Ser Ala Ser Leu Glu
1               5                   10                  15

Glu Ile Val Thr Ile Thr Cys Gln Ala Ser Gln Asp Ile Gly Ile Trp
            20                  25                  30

Leu Ala Trp Tyr Gln Gln Lys Pro Gly Lys Ser Pro Gln Leu Leu Ile
        35                  40                  45

Phe Gly Ala Thr Ser Leu Ala Asp Gly Val Pro Ser Arg Phe Ser Gly
    50                  55                  60

Ser Arg Ser Gly Thr Gln Tyr Ser Leu Lys Ile Ser Arg Leu Gln Leu
65                  70                  75                  80

Glu Asp Ile Gly Ile Tyr Tyr Cys Gln Gln Ala Ser Ser Ala Pro Trp
                85                  90                  95

Thr Phe Gly Gly Gly Thr Lys Leu Glu Leu Lys
            100                 105


<210> SEQ ID NO 232
<211> LENGTH: 106
<212> TYPE: PRT
<213> ORGANISM: Rattus norvegicus

<400> SEQUENCE: 232

Asp Ile Leu Met Thr Gln Ser Pro Pro Ser Leu Ser Ala Ser Leu Gly
1               5                   10                  15

Asp Lys Val Thr Ile Thr Cys Gln Ala Ser Gln Asn Ile His Gly Tyr
            20                  25                  30

Ile Ala Trp Tyr Gln Gln Lys Pro Gly Arg Leu Pro Arg Leu Leu Ile
        35                  40                  45

Arg Leu Thr Ser Thr Leu Glu Ser Gly Thr Pro Ser Arg Phe Ser Gly
    50                  55                  60

Ser Gly Ser Gly Arg Asp Tyr Ser Phe Ser Ile Ser Asn Val Glu Ser
65                  70                  75                  80

Glu Asp Leu Ala Ser Tyr Tyr Cys Leu Gln Tyr Val Asn Leu Trp Thr
                85                  90                  95

Phe Gly Gly Gly Thr Lys Leu Glu Leu Lys
            100                 105


<210> SEQ ID NO 233
<211> LENGTH: 106
<212> TYPE: PRT
<213> ORGANISM: Rattus norvegicus

<400> SEQUENCE: 233

Asp Ile Gln Met Thr Gln Ser Pro Pro Ser Leu Ser Ala Ser Leu Gly
1               5                   10                  15
```

```
Asp Lys Val Thr Ile Thr Cys Gln Ala Ser Gln Asn Ile His Lys Tyr
            20                  25                  30

Ile Ala Trp Tyr Gln Gln Lys Pro Gly Lys Ala Pro Arg Leu Leu Ile
        35                  40                  45

Arg Tyr Thr Ser Thr Leu Gln Ser Gly Thr Pro Ser Arg Phe Ser Gly
    50                  55                  60

Ser Gly Ser Gly Arg Asp Tyr Ser Phe Ser Ile Ser Asn Val Glu Ser
65                  70                  75                  80

Glu Asp Ile Ala Ser Tyr Tyr Cys Leu Gln Tyr Val Asn Leu Trp Thr
                85                  90                  95

Phe Gly Gly Gly Thr Lys Leu Glu Leu Lys
            100                 105


<210> SEQ ID NO 234
<211> LENGTH: 106
<212> TYPE: PRT
<213> ORGANISM: Rattus norvegicus

<400> SEQUENCE: 234

Asp Ile Gln Met Thr Gln Ser Pro Pro Ser Leu Ser Ala Ser Leu Gly
1               5                   10                  15

Asp Lys Val Thr Ile Thr Cys Gln Ala Ser His Asn Ile Asn Lys Tyr
            20                  25                  30

Ile Ala Trp Tyr Gln Gln Lys Pro Arg Lys Ala Pro Arg Leu Leu Ile
        35                  40                  45

Arg Tyr Thr Ser Thr Leu Gln Ser Gly Thr Pro Ser Arg Phe Ser Gly
    50                  55                  60

Ser Gly Ser Gly Arg Asp Tyr Ser Phe Ser Ile Ser Asn Val Glu Ser
65                  70                  75                  80

Glu Asp Ile Ala Ser Tyr Tyr Cys Leu Gln Tyr Val Asn Leu Trp Thr
                85                  90                  95

Phe Gly Gly Gly Thr Lys Leu Glu Leu Lys
            100                 105


<210> SEQ ID NO 235
<211> LENGTH: 106
<212> TYPE: PRT
<213> ORGANISM: Rattus norvegicus

<400> SEQUENCE: 235

Asp Ile Gln Met Thr Gln Ser Pro Pro Ser Leu Ser Ala Ser Leu Gly
1               5                   10                  15

Asp Lys Val Thr Ile Thr Cys Gln Ala Ser Gln Asn Ile His Lys Tyr
            20                  25                  30

Ile Ala Trp Tyr Arg His Lys Pro Gly Lys Pro Pro Arg Leu Leu Ile
        35                  40                  45

Arg Tyr Thr Ser Thr Leu Gln Ser Gly Thr Pro Ser Arg Phe Ser Gly
    50                  55                  60

Ser Gly Ser Gly Arg Asp Tyr Ser Phe Ser Ile Ser Asn Val Glu Ser
65                  70                  75                  80

Glu Asp Ile Ala Ser Tyr Tyr Cys Leu Gln Tyr Val Asn Leu Trp Thr
                85                  90                  95

Phe Gly Gly Gly Thr Lys Leu Glu Leu Lys
            100                 105


<210> SEQ ID NO 236
```

<211> LENGTH: 103
<212> TYPE: PRT
<213> ORGANISM: Rattus norvegicus

<400> SEQUENCE: 236

Met Ile Gln Ser Pro Pro Ser Leu Ser Ala Ser Leu Gly Asp Lys Val
1 5 10 15

Thr Ile Thr Cys Gln Ala Ser Gln Asn Ile His Thr Tyr Leu Ala Trp
20 25 30

Tyr Gln Gln Lys Pro Gly Lys Ala Pro Arg Leu Leu Ile Arg Tyr Thr
35 40 45

Ser Thr Leu Glu Ser Gly Thr Pro Ser Arg Phe Ser Gly Gly Gly Ser
50 55 60

Gly Arg His Tyr Ser Phe Ser Ile Ser Asn Val Glu Ser Glu Asp Val
65 70 75 80

Ala Ser Tyr Tyr Cys Leu Gln Tyr Val Asn Leu Pro Thr Phe Gly Gly
85 90 95

Gly Thr Lys Leu Glu Leu Lys
100

<210> SEQ ID NO 237
<211> LENGTH: 106
<212> TYPE: PRT
<213> ORGANISM: Rattus norvegicus

<400> SEQUENCE: 237

Asn Ile Gln Leu Thr Gln Ser Pro Ser Leu Leu Ser Ala Ser Val Gly
1 5 10 15

Asp Arg Val Thr Leu Ser Cys Lys Gly Ser Gln Asn Ile Asn Asn Tyr
20 25 30

Leu Ala Trp Tyr Gln Gln Lys Leu Gly Glu Ala Pro Lys Leu Leu Ile
35 40 45

Tyr Lys Thr Asn Ser Leu His Thr Gly Ile Pro Ser Arg Phe Ser Gly
50 55 60

Ser Gly Ser Gly Thr Asp Tyr Thr Leu Thr Ile Ser Ser Leu His Ser
65 70 75 80

Glu Asp Leu Ala Thr Tyr Tyr Cys Tyr Gln Tyr Asn Asn Gly Tyr Thr
85 90 95

Phe Gly Ala Gly Thr Asn Leu Glu Leu Lys
100 105

<210> SEQ ID NO 238
<211> LENGTH: 112
<212> TYPE: PRT
<213> ORGANISM: Rattus norvegicus

<400> SEQUENCE: 238

Asp Val Val Leu Thr Gln Thr Pro Pro Thr Leu Ser Ala Thr Ile Gly
1 5 10 15

Gln Ser Val Ser Ile Ser Cys Arg Ser Ser Gln Ser Leu Leu His Ser
20 25 30

Ser Gly Asn Thr Tyr Leu Asn Trp Leu Leu Gln Arg Pro Gly Gln Pro
35 40 45

Pro Gln Phe Leu Ile Tyr Leu Val Ser Arg Leu Glu Ser Arg Val Pro
50 55 60

Asn Arg Phe Ser Gly Ser Gly Ser Gly Thr Asp Phe Thr Leu Lys Ile
65 70 75 80

```
Ser Gly Val Glu Ala Glu Asp Leu Gly Val Tyr Tyr Cys Val Gln Ser
                85                  90                  95

Thr Pro Ala Pro Arg Thr Phe Gly Gly Gly Thr Lys Leu Glu Leu Lys
            100                 105                 110


<210> SEQ ID NO 239
<211> LENGTH: 107
<212> TYPE: PRT
<213> ORGANISM: Mus musculus

<400> SEQUENCE: 239

Asp Ile Val Met Thr Gln Ser His Thr Phe Met Ser Thr Ser Val Gly
1               5                   10                  15

Asp Arg Val Ser Val Thr Cys Lys Ala Ser Gln Asn Val Gly Asn Asn
            20                  25                  30

Val Ala Trp Tyr Gln Gln Lys Pro Gly Gln Ser Pro Asn Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asp Arg Tyr Pro Leu
                85                  90                  95

Thr Phe Gly Gly Gly Thr Lys Leu Glu Ile Lys
            100                 105


<210> SEQ ID NO 240
<211> LENGTH: 106
<212> TYPE: PRT
<213> ORGANISM: Rattus norvegicus

<400> SEQUENCE: 240

Asp Ile Gln Met Thr Gln Ser Pro Pro Ser Leu Ser Ala Ser Leu Gly
1               5                   10                  15

Asp Lys Val Thr Ile Thr Cys Gln Ala Ser Gln Asn Ile His Lys Tyr
            20                  25                  30

Ile Ala Trp Tyr Arg Gln Lys Pro Gly Lys Pro Pro Arg Leu Leu Ile
        35                  40                  45

Arg Tyr Thr Ser Thr Leu Gln Ser Gly Thr Pro Ser Arg Phe Ser Gly
    50                  55                  60

Ser Gly Ser Gly Arg Asp Tyr Ser Phe Ser Ile Ser Asn Val Glu Ser
65                  70                  75                  80

Glu Asp Ile Ala Ser Tyr Tyr Cys Leu Gln Tyr Val Asn Leu Trp Thr
                85                  90                  95

Phe Gly Gly Gly Thr Lys Leu Glu Leu Lys
            100                 105


<210> SEQ ID NO 241
<211> LENGTH: 107
<212> TYPE: PRT
<213> ORGANISM: Rattus norvegicus

<400> SEQUENCE: 241

Glu Ile Val Leu Ile Gln Ser Pro Ser Ser Leu Pro Ala Ser Leu Gly
1               5                   10                  15

Glu Arg Val Thr Ile Ile Cys Arg Ala Ser Gln Asp Ile Gly Asn Asn
            20                  25                  30

Leu Asn Trp Tyr Gln Gln Lys Pro Asp Gly Thr Ile Lys Pro Leu Ile
```

```
        35                  40                  45

Tyr Phe Thr Ser Asn Phe Gln Ser Gly Val Pro Ser Ser Phe Ser Gly
    50                  55                  60

Ser Arg Ser Gly Thr Asp Phe Ser Leu Thr Ile Ser Ser Leu Glu Ala
65                  70                  75                  80

Glu Asp Phe Ala Met Tyr Tyr Cys Gln Gln Asp Ala Ser Leu Pro Trp
                85                  90                  95

Thr Phe Gly Gly Gly Thr Lys Leu Glu Ile Lys
            100                 105


<210> SEQ ID NO 242
<211> LENGTH: 102
<212> TYPE: PRT
<213> ORGANISM: Rattus norvegicus

<400> SEQUENCE: 242

Thr Gln Ser Pro Pro Ser Leu Ser Ala Ser Leu Gly Asp Lys Val Thr
1               5                   10                  15

Ile Thr Cys Gln Ala Ser Gln Asn Ile Asn Lys Tyr Val Ala Trp Tyr
            20                  25                  30

Gln Gln Lys Pro Gly Lys Ala Pro Arg Leu Leu Ile Arg Tyr Thr Ser
        35                  40                  45

Thr Leu Glu Ser Gly Thr Pro Ser Arg Phe Ser Gly Ser Gly Ser Trp
    50                  55                  60

Arg Asp Tyr Ser Phe Ser Ile Ser Asn Val Glu Ser Glu Asp Ile Ala
65                  70                  75                  80

Asp Tyr Tyr Cys Leu Gln Tyr Val Asn Leu Trp Thr Phe Gly Gly Gly
                85                  90                  95

Thr Lys Leu Glu Leu Lys
            100


<210> SEQ ID NO 243
<211> LENGTH: 107
<212> TYPE: PRT
<213> ORGANISM: Rattus norvegicus

<400> SEQUENCE: 243

Asp Ile Gln Met Thr Gln Ser Pro Pro Ser Leu Ser Ala Ser Leu Gly
1               5                   10                  15

Asp Lys Val Thr Ile Thr Cys Gln Ala Ser Gln Asn Ile Tyr Lys Tyr
            20                  25                  30

Ile Ala Trp Tyr Gln Gln Lys Pro Gly Lys Ala Pro Arg Leu Leu Ile
        35                  40                  45

Arg Tyr Thr Ser Thr Leu His Phe Gly Thr Pro Ser Arg Phe Ser Gly
    50                  55                  60

Ser Gly Ser Gly Arg Asp Tyr Ser Phe Ser Ile Ser Asn Val Glu Ser
65                  70                  75                  80

Glu Asp Ile Ala Arg Tyr Tyr Cys Gln Gln Tyr Val Lys Phe Pro Asn
                85                  90                  95

Thr Phe Gly Ala Gly Thr Ile Leu Glu Leu Lys
            100                 105


<210> SEQ ID NO 244
<211> LENGTH: 107
<212> TYPE: PRT
<213> ORGANISM: Rattus norvegicus

<400> SEQUENCE: 244
```

```
Asp Ile Gly Met Thr Gln Ser Pro Thr Ser Met Ser Lys Ser Val Gly
1               5                   10                  15

Asp Arg Val Thr Met Asn Cys Lys Ala Ser Gln Asn Val Gly Ser Asn
            20                  25                  30

Val Asp Trp Phe Gln Gln Lys Thr Gly Gln Ser Pro Lys Leu Leu Ile
        35                  40                  45

Tyr Lys Ser Ser Asn Arg Tyr Thr Gly Val Pro Ala Arg Phe Thr Gly
    50                  55                  60

Ser Gly Ser Gly Thr Asp Phe Thr Phe Thr Ile Ser Asn Met Gln Ala
65                  70                  75                  80

Glu Asp Leu Ala Val Tyr Tyr Cys Met Gln Ser Asn Ser Tyr Pro Pro
                85                  90                  95

Thr Phe Gly Gly Gly Thr Lys Leu Glu Leu Lys
            100                 105


<210> SEQ ID NO 245
<211> LENGTH: 106
<212> TYPE: PRT
<213> ORGANISM: Rattus norvegicus

<400> SEQUENCE: 245

Asp Ile Gln Met Thr Gln Ser Pro Pro Ser Leu Ser Ala Ser Leu Gly
1               5                   10                  15

Asp Lys Val Thr Ile Thr Cys Gln Ser Ser Gln Asn Ile Asn Asn Tyr
            20                  25                  30

Ile Ala Trp Tyr Gln Gln Lys Pro Gly Glu Ala Pro Arg Val Leu Ile
        35                  40                  45

Arg Tyr Thr Ser Thr Leu Gln Ser Gly Ala Pro Ser Arg Phe Ser Gly
    50                  55                  60

Ser Gly Ser Trp Arg Asp Tyr Ser Phe Thr Ile Ser Asn Val Glu Ser
65                  70                  75                  80

Glu Asp Ile Ala Asp Tyr Tyr Cys Leu Gln Tyr Val Asn Leu Trp Thr
                85                  90                  95

Phe Gly Gly Gly Thr Lys Leu Glu Ile Lys
            100                 105


<210> SEQ ID NO 246
<211> LENGTH: 106
<212> TYPE: PRT
<213> ORGANISM: Artificial sequence
<220> FEATURE:
<223> OTHER INFORMATION: humanized sequence

<400> SEQUENCE: 246

Asp Ile Gln Met Thr Gln Ser Pro Ser Ser Leu Ser Ala Ser Val Gly
1               5                   10                  15

Asp Arg Val Thr Ile Thr Cys Lys Gly Ser Gln Asn Ile Asn Asn Phe
            20                  25                  30

Leu Ala Trp Tyr Gln Gln Lys Pro Gly Lys Ala Pro Lys Ser Leu Ile
        35                  40                  45

Tyr Lys Thr Asn Ser Leu His Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Tyr Gln Tyr Asn Ser Gly Tyr Thr
                85                  90                  95
```

```
Phe Gly Gln Gly Thr Lys Leu Glu Ile Lys
            100                 105


<210> SEQ ID NO 247
<211> LENGTH: 106
<212> TYPE: PRT
<213> ORGANISM: Artificial sequence
<220> FEATURE:
<223> OTHER INFORMATION: humanized sequence

<400> SEQUENCE: 247

Asp Ile Gln Met Thr Gln Ser Pro Ser Ser Leu Ser Ala Ser Val Gly
1               5                   10                  15

Asp Arg Val Thr Ile Thr Cys Lys Gly Ser Gln Asn Ile Asn Asn Phe
            20                  25                  30

Leu Ala Trp Tyr Gln Gln Lys Pro Gly Lys Ala Pro Lys Ser Leu Ile
        35                  40                  45

Tyr Lys Thr Asn Ser Leu His Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Tyr Gln Tyr Asn Asp Gly Tyr Thr
                85                  90                  95

Phe Gly Gln Gly Thr Lys Leu Glu Ile Lys
            100                 105


<210> SEQ ID NO 248
<211> LENGTH: 106
<212> TYPE: PRT
<213> ORGANISM: Artificial sequence
<220> FEATURE:
<223> OTHER INFORMATION: humanized sequence

<400> SEQUENCE: 248

Asp Ile Gln Met Thr Gln Ser Pro Ser Ser Leu Ser Ala Ser Val Gly
1               5                   10                  15

Asp Arg Val Thr Ile Thr Cys Lys Gly Ser Gln Asn Ile Asn Asn Phe
            20                  25                  30

Leu Ala Trp Tyr Gln Gln Lys Pro Gly Lys Ala Pro Lys Ser Leu Ile
        35                  40                  45

Tyr Lys Thr Asn Ser Leu His Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Tyr Gln Tyr Asn Gln Gly Tyr Thr
                85                  90                  95

Phe Gly Gln Gly Thr Lys Leu Glu Ile Lys
            100                 105


<210> SEQ ID NO 249
<211> LENGTH: 106
<212> TYPE: PRT
<213> ORGANISM: Artificial sequence
<220> FEATURE:
<223> OTHER INFORMATION: humanized sequence

<400> SEQUENCE: 249

Asp Ile Gln Met Thr Gln Ser Pro Ser Ser Leu Ser Ala Ser Val Gly
1               5                   10                  15

Asp Arg Val Thr Ile Thr Cys Lys Gly Ser Gln Asn Ile Asn Asn Phe
```

```
            20                  25                  30

Leu Ala Trp Tyr Gln Gln Lys Pro Gly Lys Ala Pro Lys Ser Leu Ile
        35                  40                  45

Tyr Lys Thr Asn Ser Leu His Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Tyr Gln Tyr Asn Asn Gly Tyr Thr
                85                  90                  95

Phe Gly Gln Gly Thr Lys Leu Glu Ile Lys
            100                 105


<210> SEQ ID NO 250
<211> LENGTH: 107
<212> TYPE: PRT
<213> ORGANISM: Artificial sequence
<220> FEATURE:
<223> OTHER INFORMATION: humanized sequence

<400> SEQUENCE: 250

Asp Ile Gln Met Thr Gln Ser Pro Ser Ser Leu Ser Ala Ser Val Gly
1               5                   10                  15

Asp Arg Val Thr Ile Thr Cys Lys Ala Gly Arg Asn Val Asn Asn Tyr
            20                  25                  30

Leu Ala Trp Tyr Gln Gln Lys Pro Gly Lys Pro Pro Lys Leu Leu Ile
        35                  40                  45

Tyr Asn Ser Asn Ser Leu Gln Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Phe Tyr Cys Gln Gln Tyr Asn Ser Trp Thr
                85                  90                  95

Thr Phe Gly Gln Gly Thr Lys Leu Glu Ile Lys
            100                 105


<210> SEQ ID NO 251
<211> LENGTH: 112
<212> TYPE: PRT
<213> ORGANISM: Artificial sequence
<220> FEATURE:
<223> OTHER INFORMATION: humanized sequence

<400> SEQUENCE: 251

Asp Val Val Leu Thr Gln Thr Pro Leu Ser Leu Ser Val Thr Pro Gly
1               5                   10                  15

Gln Pro Ala Ser Ile Ser Cys Arg Ser Ser Gln Ser Leu Leu His Ser
            20                  25                  30

Ser Gly Asn Thr Tyr Leu Asn Trp Leu Leu Gln Lys Pro Gly Gln Pro
        35                  40                  45

Pro Gln Leu Leu Ile Tyr Leu Val Ser Arg Leu Glu Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Ser
                85                  90                  95

Thr His Ala Pro Arg Thr Phe Gly Gly Gly Thr Lys Leu Glu Ile Lys
            100                 105                 110
```

<210> SEQ ID NO 252
<211> LENGTH: 106
<212> TYPE: PRT
<213> ORGANISM: Artificial sequence
<220> FEATURE:
<223> OTHER INFORMATION: humanized sequence

<400> SEQUENCE: 252

```
Ala Ile Gln Leu Thr Gln Ser Pro Ser Ser Leu Ser Ala Ser Val Gly
1               5                   10                  15

Asp Arg Val Thr Ile Thr Cys Lys Gly Ser Gln Asn Ile Asn Asn Phe
            20                  25                  30

Leu Ala Trp Tyr Gln Gln Lys Pro Gly Lys Ala Pro Lys Leu Leu Ile
        35                  40                  45

Tyr Lys Thr Asn Ser Leu His Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Tyr Gln Tyr Asn Asn Gly Tyr Thr
                85                  90                  95

Phe Gly Gln Gly Thr Lys Leu Glu Ile Lys
            100                 105
```

<210> SEQ ID NO 253
<211> LENGTH: 106
<212> TYPE: PRT
<213> ORGANISM: Artificial sequence
<220> FEATURE:
<223> OTHER INFORMATION: humanized sequence

<400> SEQUENCE: 253

```
Asp Ile Gln Ile Thr Gln Ser Pro Ser Ser Leu Ser Ala Ser Val Gly
1               5                   10                  15

Asp Arg Val Thr Ile Thr Cys Lys Gly Ser Gln Asn Ile Asn Asn Tyr
            20                  25                  30

Leu Ala Trp Tyr Gln Gln Lys Pro Gly Lys Ala Pro Lys Leu Leu Ile
        35                  40                  45

Tyr Lys Thr Asn Ser Leu His Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Tyr Gln Tyr Asn Asn Gly Tyr Thr
                85                  90                  95

Phe Gly Gln Gly Thr Lys Leu Glu Ile Lys
            100                 105
```

<210> SEQ ID NO 254
<211> LENGTH: 106
<212> TYPE: PRT
<213> ORGANISM: Artificial sequence
<220> FEATURE:
<223> OTHER INFORMATION: humanized sequence

<400> SEQUENCE: 254

```
Asp Ile Gln Met Thr Gln Ser Pro Ser Ser Leu Ser Ala Ser Val Gly
1               5                   10                  15

Asp Arg Val Thr Ile Thr Cys Lys Ala Gly Arg Asn Val Asn Asn Tyr
            20                  25                  30

Leu Ala Trp Tyr Gln Gln Lys Pro Gly Lys Pro Pro Lys Leu Leu Ile
```

```
        35                  40                  45

Tyr Asn Ser Asn Ser Leu Gln Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Asn Ser Trp Thr Thr
                85                  90                  95

Phe Gly Gln Gly Thr Lys Leu Glu Ile Lys
            100                 105


<210> SEQ ID NO 255
<211> LENGTH: 106
<212> TYPE: PRT
<213> ORGANISM: Artificial sequence
<220> FEATURE:
<223> OTHER INFORMATION: humanized sequence

<400> SEQUENCE: 255

Asp Ile Gln Met Thr Gln Ser Pro Ser Ser Leu Ser Ala Ser Val Gly
1               5                   10                  15

Asp Arg Val Thr Ile Thr Cys Lys Ala Gly Gln Asn Ile Asn Asn Tyr
            20                  25                  30

Leu Ala Trp Tyr Gln Gln Lys Pro Gly Lys Ala Pro Lys Leu Leu Ile
        35                  40                  45

Tyr Asn Ala Asn Ser Leu Gln Thr Gly Ile Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Trp Thr Thr
                85                  90                  95

Phe Gly Gln Gly Thr Lys Leu Glu Ile Lys
            100                 105


<210> SEQ ID NO 256
<211> LENGTH: 106
<212> TYPE: PRT
<213> ORGANISM: Artificial sequence
<220> FEATURE:
<223> OTHER INFORMATION: humanized sequence

<400> SEQUENCE: 256

Asp Ile Gln Leu Thr Gln Ser Pro Ser Ser Leu Ser Ala Ser Val Gly
1               5                   10                  15

Asp Arg Val Thr Leu Thr Cys Lys Gly Ser Gln Asn Ile Asn Asn Phe
            20                  25                  30

Leu Ala Trp Tyr Gln Gln Lys Pro Gly Lys Ala Pro Lys Leu Leu Ile
        35                  40                  45

Tyr Lys Thr Asn Ser Leu His Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Tyr Gln Tyr Asn Asn Gly Tyr Thr
                85                  90                  95

Phe Gly Gln Gly Thr Lys Leu Glu Ile Lys
            100                 105


<210> SEQ ID NO 257
<211> LENGTH: 107
```

<212> TYPE: PRT
<213> ORGANISM: Artificial sequence
<220> FEATURE:
<223> OTHER INFORMATION: humanized sequence

<400> SEQUENCE: 257

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Asn Asn
            20                  25                  30

Val Ala Trp Tyr Gln Gln Lys Pro Gly Lys Ser Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Asp Arg Tyr Pro Leu
                85                  90                  95

Thr Phe Gly Gly Gly Thr Lys Leu Glu Ile Lys
            100                 105
```

<210> SEQ ID NO 258
<211> LENGTH: 107
<212> TYPE: PRT
<213> ORGANISM: Artificial sequence
<220> FEATURE:
<223> OTHER INFORMATION: humanized sequence

<400> SEQUENCE: 258

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Asn Asn
            20                  25                  30

Val Ala Trp Tyr Gln Gln Lys Pro Gly Lys Ser Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Arg Tyr Pro Leu
                85                  90                  95

Thr Phe Gly Gly Gly Thr Lys Leu Glu Ile Lys
            100                 105
```

<210> SEQ ID NO 259
<211> LENGTH: 107
<212> TYPE: PRT
<213> ORGANISM: Artificial sequence
<220> FEATURE:
<223> OTHER INFORMATION: humanized sequence

<400> SEQUENCE: 259

```
Glu Ile Val Met Thr Gln Ser Pro Ala Thr Leu Ser Val Ser Pro Gly
1               5                   10                  15

Glu Arg Ala Thr Leu Ser Cys Lys Ala Ser Gln Asn Val Gly Asn Asn
            20                  25                  30

Val Ala Trp Tyr Gln Gln Lys Pro Gly Gln Ser Pro Arg Ala Leu Ile
        35                  40                  45

Tyr Ser Ala Ser Tyr Arg Tyr Ser Gly Val Pro Ala Arg Phe Ser Gly
```

```
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Arg Tyr Pro Leu
                85                  90                  95

Thr Phe Gly Gly Gly Thr Lys Leu Glu Ile Lys
            100                 105


<210> SEQ ID NO 260
<211> LENGTH: 107
<212> TYPE: PRT
<213> ORGANISM: Artificial sequence
<220> FEATURE:
<223> OTHER INFORMATION: humanized sequence

<400> SEQUENCE: 260

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Asn Asn
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Arg Tyr Pro Leu
                85                  90                  95

Thr Phe Gly Gln Gly Thr Lys Leu Glu Ile Lys
            100                 105


<210> SEQ ID NO 261
<211> LENGTH: 107
<212> TYPE: PRT
<213> ORGANISM: Artificial sequence
<220> FEATURE:
<223> OTHER INFORMATION: humanized sequence

<400> SEQUENCE: 261

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Asn Asn
            20                  25                  30

Val Ala Trp Tyr Gln Gln Lys Pro Gly Lys Ala Pro Lys Ala Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asp Arg Tyr Pro Leu
                85                  90                  95

Thr Phe Gly Gln Gly Thr Lys Leu Glu Ile Lys
            100                 105


<210> SEQ ID NO 262
<211> LENGTH: 107
<212> TYPE: PRT
<213> ORGANISM: Artificial sequence
<220> FEATURE:
```

<223> OTHER INFORMATION: humanized sequence

<400> SEQUENCE: 262

Asp Ile Gln Met Thr Gln Ser Pro Ser Ser Leu Ser Ala Ser Val Gly
1 5 10 15

Asp Arg Val Thr Val Thr Cys Lys Ala Ser Gln Asn Val Gly Asn Asn
20 25 30

Val Ala Trp Tyr Gln Gln Lys Pro Gly Lys Ala Pro Lys Ala Leu Ile
35 40 45

Tyr Ser Ala Ser Tyr Arg Tyr Ser Gly Val Pro Ser Arg Phe Ser Gly
50 55 60

Ser Gly Ser Gly Thr Asp Phe Thr Leu Thr Ile Ser Ser Val Gln Pro
65 70 75 80

Glu Asp Phe Ala Thr Tyr Tyr Cys Gln Gln Tyr Asp Arg Tyr Pro Leu
85 90 95

Thr Phe Gly Gln Gly Thr Lys Leu Glu Ile Lys
100 105

<210> SEQ ID NO 263
<211> LENGTH: 106
<212> TYPE: PRT
<213> ORGANISM: Artificial sequence
<220> FEATURE:
<223> OTHER INFORMATION: humanized sequence

<400> SEQUENCE: 263

Asp Ile Gln Leu Thr Gln Ser Pro Ser Ser Leu Ser Ala Ser Val Gly
1 5 10 15

Asp Arg Val Thr Leu Thr Cys Lys Gly Ser Gln Asn Ile Asn Asn Phe
20 25 30

Leu Ala Trp Tyr Gln Gln Lys Pro Gly Lys Ala Pro Lys Leu Leu Ile
35 40 45

Tyr Lys Thr Asn Ser Leu His Thr Gly Ile Pro Ser Arg Phe Ser Gly
50 55 60

Ser Gly Ser Gly Thr Asp Tyr Thr Leu Thr Ile Ser Ser Leu Gln Pro
65 70 75 80

Glu Asp Phe Ala Thr Tyr Tyr Cys Tyr Gln Tyr Asn Gln Gly Tyr Thr
85 90 95

Phe Gly Gln Gly Thr Lys Leu Glu Ile Lys
100 105

<210> SEQ ID NO 264
<211> LENGTH: 106
<212> TYPE: PRT
<213> ORGANISM: Artificial sequence
<220> FEATURE:
<223> OTHER INFORMATION: humanized sequence

<400> SEQUENCE: 264

Asp Ile Gln Leu Thr Gln Ser Pro Ser Ser Leu Ser Ala Ser Val Gly
1 5 10 15

Asp Arg Val Thr Leu Thr Cys Lys Gly Ser Gln Asn Ile Asn Asn Phe
20 25 30

Leu Ala Trp Tyr Gln Gln Lys Pro Gly Lys Ala Pro Lys Leu Leu Ile
35 40 45

Tyr Lys Thr Asn Ser Leu His Thr Gly Ile Pro Ser Arg Phe Ser Gly
50 55 60

Ser Gly Ser Gly Thr Asp Tyr Thr Leu Thr Ile Ser Ser Leu Gln Pro

```
65                  70                  75                  80

Glu Asp Phe Ala Thr Tyr Tyr Cys Tyr Gln Tyr Asn Ser Gly Tyr Thr
                85                  90                  95

Phe Gly Gln Gly Thr Lys Leu Glu Ile Lys
            100                 105


<210> SEQ ID NO 265
<211> LENGTH: 107
<212> TYPE: PRT
<213> ORGANISM: Rattus norvegicus

<400> SEQUENCE: 265

Asp Ile Gln Met Thr Gln Ser Pro Pro Ser Leu Ser Ala Ser Leu Gly
1               5                   10                  15

Asp Lys Val Thr Ile Thr Cys Gln Ala Ser Gln Asn Ile Tyr Lys Tyr
            20                  25                  30

Ile Ala Trp Tyr Gln Gln Lys Pro Gly Lys Ala Pro Arg Leu Leu Ile
        35                  40                  45

Arg Tyr Thr Ser Thr Leu Asp Ser Gly Thr Pro Ser Arg Phe Ser Gly
    50                  55                  60

Ser Gly Ser Gly Arg Asp Tyr Ser Phe Ser Ile Ser Asn Val Glu Ser
65                  70                  75                  80

Glu Asp Ile Ala Ser Tyr Tyr Cys Gln Gln Tyr Val Asn Phe Pro Asn
                85                  90                  95

Thr Phe Gly Ala Gly Thr Asn Leu Glu Leu Lys
            100                 105


<210> SEQ ID NO 266
<211> LENGTH: 11
<212> TYPE: PRT
<213> ORGANISM: Mus musculus

<400> SEQUENCE: 266

Arg Ala Ser Gly Asn Ile His Asn Tyr Leu Ala
1               5                   10


<210> SEQ ID NO 267
<211> LENGTH: 11
<212> TYPE: PRT
<213> ORGANISM: Mus musculus

<400> SEQUENCE: 267

Ser Ala Ser Gln Gly Ile Ser Asn Tyr Leu Asn
1               5                   10


<210> SEQ ID NO 268
<211> LENGTH: 11
<212> TYPE: PRT
<213> ORGANISM: Mus musculus

<400> SEQUENCE: 268

Arg Ala Ser Gln Ser Ile Ser Asp Tyr Leu His
1               5                   10


<210> SEQ ID NO 269
<211> LENGTH: 11
<212> TYPE: PRT
<213> ORGANISM: Mus musculus

<400> SEQUENCE: 269

Lys Ala Ser Asp Gln Ile Asn Tyr Trp Leu Ala
```

1 5 10

<210> SEQ ID NO 270
<211> LENGTH: 16
<212> TYPE: PRT
<213> ORGANISM: Mus musculus

<400> SEQUENCE: 270

Arg Ser Ser Gln Ser Leu Val His Ser Asp Val Asn Thr Tyr Leu His
1 5 10 15

<210> SEQ ID NO 271
<211> LENGTH: 10
<212> TYPE: PRT
<213> ORGANISM: Mus musculus

<400> SEQUENCE: 271

Arg Ala Ser Ser Ser Val His Tyr Met Tyr
1 5 10

<210> SEQ ID NO 272
<211> LENGTH: 11
<212> TYPE: PRT
<213> ORGANISM: Mus musculus

<400> SEQUENCE: 272

Ser Thr Ser Gln Gly Val Arg Ser Tyr Leu Asn
1 5 10

<210> SEQ ID NO 273
<211> LENGTH: 11
<212> TYPE: PRT
<213> ORGANISM: Rattus norvegicus

<400> SEQUENCE: 273

Lys Ala Gly Gln Asn Ile Asn Asn Tyr Leu Ala
1 5 10

<210> SEQ ID NO 274
<211> LENGTH: 11
<212> TYPE: PRT
<213> ORGANISM: Rattus norvegicus

<400> SEQUENCE: 274

Lys Ala Gly Arg Asn Ile Asn Asn Tyr Leu Ala
1 5 10

<210> SEQ ID NO 275
<211> LENGTH: 11
<212> TYPE: PRT
<213> ORGANISM: Rattus norvegicus

<400> SEQUENCE: 275

Lys Ala Gly Arg Asn Val Asn Asn Tyr Leu Ala
1 5 10

<210> SEQ ID NO 276
<211> LENGTH: 16
<212> TYPE: PRT
<213> ORGANISM: Rattus norvegicus

<400> SEQUENCE: 276

Arg Ser Ser Gln Ser Leu Leu His Ser Ser Gly Asn Thr Tyr Leu Asn
1 5 10 15

<210> SEQ ID NO 277
<211> LENGTH: 16
<212> TYPE: PRT
<213> ORGANISM: Rattus norvegicus

<400> SEQUENCE: 277

Arg Ser Ser Gln Ser Leu Leu His Gly Ser Gly Asn Thr Tyr Leu Asn
1 5 10 15

<210> SEQ ID NO 278
<211> LENGTH: 16
<212> TYPE: PRT
<213> ORGANISM: Rattus norvegicus

<400> SEQUENCE: 278

Arg Ser Ser Gln Ser Leu Phe His Ser Ser Gly Asn Thr Tyr Leu Ser
1 5 10 15

<210> SEQ ID NO 279
<211> LENGTH: 16
<212> TYPE: PRT
<213> ORGANISM: Rattus norvegicus

<400> SEQUENCE: 279

Arg Ser Ser Gln Ser Leu Leu His Ser Ser Gly Asn Thr Phe Leu Ser
1 5 10 15

<210> SEQ ID NO 280
<211> LENGTH: 16
<212> TYPE: PRT
<213> ORGANISM: Rattus norvegicus

<400> SEQUENCE: 280

Arg Ser Ser Gln Ser Leu Leu His Ser Thr Gly Asn Thr Tyr Leu Asn
1 5 10 15

<210> SEQ ID NO 281
<211> LENGTH: 11
<212> TYPE: PRT
<213> ORGANISM: Rattus norvegicus

<400> SEQUENCE: 281

Lys Gly Ser Gln Asn Ile Asn Asn Phe Leu Ala
1 5 10

<210> SEQ ID NO 282
<211> LENGTH: 11
<212> TYPE: PRT
<213> ORGANISM: Rattus norvegicus

<400> SEQUENCE: 282

Lys Gly Ser Gln Asn Ile Asn Asn Tyr Leu Ala
1 5 10

<210> SEQ ID NO 283
<211> LENGTH: 15
<212> TYPE: PRT
<213> ORGANISM: Rattus norvegicus

<400> SEQUENCE: 283

Arg Ala Ser Glu Ser Val Asp Ser Asn Gly Asn Ser Phe Met His
1 5 10 15

<210> SEQ ID NO 284

<211> LENGTH: 15
<212> TYPE: PRT
<213> ORGANISM: Rattus norvegicus

<400> SEQUENCE: 284

Arg Ala Ser Gln Ser Val Thr Ile Ser Gly Ile Asn Leu Met His
1 5 10 15

<210> SEQ ID NO 285
<211> LENGTH: 11
<212> TYPE: PRT
<213> ORGANISM: Rattus norvegicus

<400> SEQUENCE: 285

Gln Ala Ser Gln Tyr Ile Tyr Lys Tyr Leu Ala
1 5 10

<210> SEQ ID NO 286
<211> LENGTH: 11
<212> TYPE: PRT
<213> ORGANISM: Rattus norvegicus

<400> SEQUENCE: 286

Gln Ala Ser His Asn Ile Tyr Lys Tyr Val Ala
1 5 10

<210> SEQ ID NO 287
<211> LENGTH: 11
<212> TYPE: PRT
<213> ORGANISM: Rattus norvegicus

<400> SEQUENCE: 287

Gln Ala Ser Gln His Ile Asn Asn Tyr Ile Ala
1 5 10

<210> SEQ ID NO 288
<211> LENGTH: 11
<212> TYPE: PRT
<213> ORGANISM: Rattus norvegicus

<400> SEQUENCE: 288

Gln Ala Ser Gln Asn Ile His Lys Tyr Ile Ala
1 5 10

<210> SEQ ID NO 289
<211> LENGTH: 17
<212> TYPE: PRT
<213> ORGANISM: Rattus norvegicus

<400> SEQUENCE: 289

Lys Ser Ser Gln Ser Leu Phe Trp Ser Gly Ser Gln Met Asn Tyr Leu
1 5 10 15

Ala

<210> SEQ ID NO 290
<211> LENGTH: 16
<212> TYPE: PRT
<213> ORGANISM: Rattus norvegicus

<400> SEQUENCE: 290

Arg Ser Ser Gln Ser Leu Leu His Ser Ser Gly Asn Thr Tyr Leu His
1 5 10 15

<210> SEQ ID NO 291

<211> LENGTH: 11
<212> TYPE: PRT
<213> ORGANISM: Rattus norvegicus

<400> SEQUENCE: 291

Gln Ala Ser Gln Asn Ile His Lys Tyr Ile Gly
1 5 10

<210> SEQ ID NO 292
<211> LENGTH: 11
<212> TYPE: PRT
<213> ORGANISM: Rattus norvegicus

<400> SEQUENCE: 292

Gln Ala Ser Gln Asp Ile Gly Ile Trp Leu Ala
1 5 10

<210> SEQ ID NO 293
<211> LENGTH: 11
<212> TYPE: PRT
<213> ORGANISM: Rattus norvegicus

<400> SEQUENCE: 293

Gln Ala Ser Gln Asn Ile His Gly Tyr Ile Ala
1 5 10

<210> SEQ ID NO 294
<211> LENGTH: 11
<212> TYPE: PRT
<213> ORGANISM: Rattus norvegicus

<400> SEQUENCE: 294

Gln Ala Ser His Asn Ile Asn Lys Tyr Ile Ala
1 5 10

<210> SEQ ID NO 295
<211> LENGTH: 11
<212> TYPE: PRT
<213> ORGANISM: Rattus norvegicus

<400> SEQUENCE: 295

Gln Ala Ser Gln Asn Ile His Thr Tyr Leu Ala
1 5 10

<210> SEQ ID NO 296
<211> LENGTH: 11
<212> TYPE: PRT
<213> ORGANISM: Mus musculus

<400> SEQUENCE: 296

Lys Ala Ser Gln Asn Val Gly Asn Asn Val Ala
1 5 10

<210> SEQ ID NO 297
<211> LENGTH: 11
<212> TYPE: PRT
<213> ORGANISM: Rattus norvegicus

<400> SEQUENCE: 297

Arg Ala Ser Gln Asp Ile Gly Asn Asn Leu Asn
1 5 10

<210> SEQ ID NO 298
<211> LENGTH: 11
<212> TYPE: PRT

<213> ORGANISM: Rattus norvegicus

<400> SEQUENCE: 298

Gln Ala Ser Gln Asn Ile Asn Lys Tyr Val Ala
1               5                   10

<210> SEQ ID NO 299
<211> LENGTH: 11
<212> TYPE: PRT
<213> ORGANISM: Rattus norvegicus

<400> SEQUENCE: 299

Gln Ala Ser Gln Asn Ile Tyr Lys Tyr Ile Ala
1               5                   10

<210> SEQ ID NO 300
<211> LENGTH: 11
<212> TYPE: PRT
<213> ORGANISM: Rattus norvegicus

<400> SEQUENCE: 300

Lys Ala Ser Gln Asn Val Gly Ser Asn Val Asp
1               5                   10

<210> SEQ ID NO 301
<211> LENGTH: 11
<212> TYPE: PRT
<213> ORGANISM: Rattus norvegicus

<400> SEQUENCE: 301

Gln Ser Ser Gln Asn Ile Asn Asn Tyr Ile Ala
1               5                   10

<210> SEQ ID NO 302
<211> LENGTH: 7
<212> TYPE: PRT
<213> ORGANISM: Mus musculus

<400> SEQUENCE: 302

Asn Thr Lys Thr Leu Ala Asp
1               5

<210> SEQ ID NO 303
<211> LENGTH: 7
<212> TYPE: PRT
<213> ORGANISM: Mus musculus

<400> SEQUENCE: 303

Tyr Thr Ser Thr Leu His Ser
1               5

<210> SEQ ID NO 304
<211> LENGTH: 7
<212> TYPE: PRT
<213> ORGANISM: Mus musculus

<400> SEQUENCE: 304

Tyr Ala Ser Gln Ser Ile Ser
1               5

<210> SEQ ID NO 305
<211> LENGTH: 7
<212> TYPE: PRT
<213> ORGANISM: Mus musculus

<400> SEQUENCE: 305

Lys Val Ser Asn Arg Phe Ser
1 5

<210> SEQ ID NO 306
<211> LENGTH: 7
<212> TYPE: PRT
<213> ORGANISM: Mus musculus

<400> SEQUENCE: 306

Tyr Thr Ser Asn Leu Ala Pro
1 5

<210> SEQ ID NO 307
<211> LENGTH: 7
<212> TYPE: PRT
<213> ORGANISM: Mus musculus

<400> SEQUENCE: 307

Tyr Thr Ser Ser Leu His Ser
1 5

<210> SEQ ID NO 308
<211> LENGTH: 7
<212> TYPE: PRT
<213> ORGANISM: Mus musculus

<400> SEQUENCE: 308

Asn Ala Lys Thr Leu Ala Asp
1 5

<210> SEQ ID NO 309
<211> LENGTH: 7
<212> TYPE: PRT
<213> ORGANISM: Rattus norvegicus

<400> SEQUENCE: 309

Asn Ala Asn Ser Leu Gln Thr
1 5

<210> SEQ ID NO 310
<211> LENGTH: 7
<212> TYPE: PRT
<213> ORGANISM: Rattus norvegicus

<400> SEQUENCE: 310

Asn Thr Asn Ser Leu Gln Thr
1 5

<210> SEQ ID NO 311
<211> LENGTH: 7
<212> TYPE: PRT
<213> ORGANISM: Rattus norvegicus

<400> SEQUENCE: 311

Asn Ser Asn Ser Leu Gln Thr
1 5

<210> SEQ ID NO 312
<211> LENGTH: 7
<212> TYPE: PRT
<213> ORGANISM: Rattus norvegicus

<400> SEQUENCE: 312

Leu Val Ser Arg Leu Glu Ser
1 5

<210> SEQ ID NO 313
<211> LENGTH: 7
<212> TYPE: PRT
<213> ORGANISM: Rattus norvegicus

<400> SEQUENCE: 313

Leu Val Ser Arg Leu Glu Phe
1 5

<210> SEQ ID NO 314
<211> LENGTH: 7
<212> TYPE: PRT
<213> ORGANISM: Rattus norvegicus

<400> SEQUENCE: 314

Leu Val Ser Arg Leu Glu Tyr
1 5

<210> SEQ ID NO 315
<211> LENGTH: 7
<212> TYPE: PRT
<213> ORGANISM: Rattus norvegicus

<400> SEQUENCE: 315

Lys Thr Asn Ser Leu His Thr
1 5

<210> SEQ ID NO 316
<211> LENGTH: 7
<212> TYPE: PRT
<213> ORGANISM: Rattus norvegicus

<400> SEQUENCE: 316

Arg Ala Ser Asn Leu Glu Ser
1 5

<210> SEQ ID NO 317
<211> LENGTH: 7
<212> TYPE: PRT
<213> ORGANISM: Rattus norvegicus

<400> SEQUENCE: 317

Arg Ala Ser Asn Leu Ala Ser
1 5

<210> SEQ ID NO 318
<211> LENGTH: 7
<212> TYPE: PRT
<213> ORGANISM: Rattus norvegicus

<400> SEQUENCE: 318

Tyr Thr Ser Thr Leu Glu Ser
1 5

<210> SEQ ID NO 319
<211> LENGTH: 7
<212> TYPE: PRT
<213> ORGANISM: Rattus norvegicus

<400> SEQUENCE: 319

Tyr Thr Ser Thr Leu Gln Ser
1 5

<210> SEQ ID NO 320
<211> LENGTH: 7
<212> TYPE: PRT
<213> ORGANISM: Rattus norvegicus

<400> SEQUENCE: 320

Tyr Ala Ser Thr Leu Gln Ser
1 5

<210> SEQ ID NO 321
<211> LENGTH: 7
<212> TYPE: PRT
<213> ORGANISM: Rattus norvegicus

<400> SEQUENCE: 321

Tyr Ala Ser Thr Ala Gln Ser
1 5

<210> SEQ ID NO 322
<211> LENGTH: 7
<212> TYPE: PRT
<213> ORGANISM: Rattus norvegicus

<400> SEQUENCE: 322

Tyr Thr Ser Thr Arg Gln Ser
1 5

<210> SEQ ID NO 323
<211> LENGTH: 7
<212> TYPE: PRT
<213> ORGANISM: Rattus norvegicus

<400> SEQUENCE: 323

Gly Ala Thr Ser Leu Ala Asp
1 5

<210> SEQ ID NO 324
<211> LENGTH: 7
<212> TYPE: PRT
<213> ORGANISM: Rattus norvegicus

<400> SEQUENCE: 324

Leu Thr Ser Thr Leu Glu Ser
1 5

<210> SEQ ID NO 325
<211> LENGTH: 7
<212> TYPE: PRT
<213> ORGANISM: Mus musculus

<400> SEQUENCE: 325

Ser Ala Ser Tyr Arg Tyr Ser
1 5

<210> SEQ ID NO 326
<211> LENGTH: 7
<212> TYPE: PRT
<213> ORGANISM: Rattus norvegicus

<400> SEQUENCE: 326

Phe Thr Ser Asn Phe Gln Ser
1 5

<210> SEQ ID NO 327
<211> LENGTH: 7
<212> TYPE: PRT
<213> ORGANISM: Rattus norvegicus

<400> SEQUENCE: 327

Tyr Thr Ser Thr Leu His Phe
1               5

<210> SEQ ID NO 328
<211> LENGTH: 7
<212> TYPE: PRT
<213> ORGANISM: Rattus norvegicus

<400> SEQUENCE: 328

Lys Ser Ser Asn Arg Tyr Thr
1               5

<210> SEQ ID NO 329
<211> LENGTH: 7
<212> TYPE: PRT
<213> ORGANISM: Rattus norvegicus

<400> SEQUENCE: 329

Tyr Thr Ser Thr Leu Asp Ser
1               5

<210> SEQ ID NO 330
<211> LENGTH: 9
<212> TYPE: PRT
<213> ORGANISM: Mus musculus

<400> SEQUENCE: 330

Gln His Phe Trp Ser Thr Pro Trp Thr
1               5

<210> SEQ ID NO 331
<211> LENGTH: 9
<212> TYPE: PRT
<213> ORGANISM: Mus musculus

<400> SEQUENCE: 331

Gln His Tyr Ser Ser Leu Pro Trp Thr
1               5

<210> SEQ ID NO 332
<211> LENGTH: 9
<212> TYPE: PRT
<213> ORGANISM: Mus musculus

<400> SEQUENCE: 332

Gln Asn Gly His Ser Phe Pro Trp Thr
1               5

<210> SEQ ID NO 333
<211> LENGTH: 9
<212> TYPE: PRT
<213> ORGANISM: Mus musculus

<400> SEQUENCE: 333

Gln Gln Tyr Trp Thr Thr Pro Tyr Thr
1               5

<210> SEQ ID NO 334
<211> LENGTH: 9

<212> TYPE: PRT
<213> ORGANISM: Mus musculus

<400> SEQUENCE: 334

Ser Gln Thr Thr His Val Pro Tyr Thr
1 5

<210> SEQ ID NO 335
<211> LENGTH: 9
<212> TYPE: PRT
<213> ORGANISM: Mus musculus

<400> SEQUENCE: 335

Gln Gln Phe Thr Thr Ser Thr Trp Thr
1 5

<210> SEQ ID NO 336
<211> LENGTH: 9
<212> TYPE: PRT
<213> ORGANISM: Mus musculus

<400> SEQUENCE: 336

Gln Gln Tyr Ser Lys Leu Pro Tyr Thr
1 5

<210> SEQ ID NO 337
<211> LENGTH: 8
<212> TYPE: PRT
<213> ORGANISM: Rattus norvegicus

<400> SEQUENCE: 337

Gln Gln Tyr Asn Ser Trp Thr Thr
1 5

<210> SEQ ID NO 338
<211> LENGTH: 9
<212> TYPE: PRT
<213> ORGANISM: Rattus norvegicus

<400> SEQUENCE: 338

Val Gln Ser Thr His Ala Pro Arg Thr
1 5

<210> SEQ ID NO 339
<211> LENGTH: 9
<212> TYPE: PRT
<213> ORGANISM: Rattus norvegicus

<400> SEQUENCE: 339

Val Gln Ser Thr His Ala Pro Phe Thr
1 5

<210> SEQ ID NO 340
<211> LENGTH: 9
<212> TYPE: PRT
<213> ORGANISM: Rattus norvegicus

<400> SEQUENCE: 340

Val Gln Thr Thr His Ala Pro Phe Thr
1 5

<210> SEQ ID NO 341
<211> LENGTH: 9
<212> TYPE: PRT
<213> ORGANISM: Rattus norvegicus

<400> SEQUENCE: 341

Val Gln Ser Thr His Val Met Asn Thr
1 5

<210> SEQ ID NO 342
<211> LENGTH: 9
<212> TYPE: PRT
<213> ORGANISM: Rattus norvegicus

<400> SEQUENCE: 342

Ala Gln Ser Thr His Ala Leu Asn Thr
1 5

<210> SEQ ID NO 343
<211> LENGTH: 8
<212> TYPE: PRT
<213> ORGANISM: Rattus norvegicus

<400> SEQUENCE: 343

Tyr Gln Tyr Asn Asn Gly Tyr Thr
1 5

<210> SEQ ID NO 344
<211> LENGTH: 9
<212> TYPE: PRT
<213> ORGANISM: Unknown
<220> FEATURE:
<223> OTHER INFORMATION: Rattus norvegicus or Mus musculus

<400> SEQUENCE: 344

Gln Gln Ser Asn Glu Asp Pro Trp Thr
1 5

<210> SEQ ID NO 345
<211> LENGTH: 9
<212> TYPE: PRT
<213> ORGANISM: Rattus norvegicus

<400> SEQUENCE: 345

Gln Gln Thr Arg Val Ser Pro Trp Thr
1 5

<210> SEQ ID NO 346
<211> LENGTH: 9
<212> TYPE: PRT
<213> ORGANISM: Rattus norvegicus

<400> SEQUENCE: 346

Leu Gln Tyr Val Asn Leu Pro Phe Thr
1 5

<210> SEQ ID NO 347
<211> LENGTH: 8
<212> TYPE: PRT
<213> ORGANISM: Rattus norvegicus

<400> SEQUENCE: 347

Leu Gln Tyr Val Asn Leu Trp Thr
1 5

<210> SEQ ID NO 348
<211> LENGTH: 9
<212> TYPE: PRT
<213> ORGANISM: Rattus norvegicus

<400> SEQUENCE: 348

Leu Gln Tyr Val Asn Leu Pro Tyr Thr
1 5

<210> SEQ ID NO 349
<211> LENGTH: 11
<212> TYPE: PRT
<213> ORGANISM: Rattus norvegicus

<400> SEQUENCE: 349

Gln His His Tyr Asp Ser Leu Pro Pro Tyr Thr
1 5 10

<210> SEQ ID NO 350
<211> LENGTH: 9
<212> TYPE: PRT
<213> ORGANISM: Rattus norvegicus

<400> SEQUENCE: 350

Gln Gln Ala Ser Ser Ala Pro Trp Thr
1 5

<210> SEQ ID NO 351
<211> LENGTH: 8
<212> TYPE: PRT
<213> ORGANISM: Rattus norvegicus

<400> SEQUENCE: 351

Leu Gln Tyr Val Asn Leu Pro Thr
1 5

<210> SEQ ID NO 352
<211> LENGTH: 9
<212> TYPE: PRT
<213> ORGANISM: Rattus norvegicus

<400> SEQUENCE: 352

Val Gln Ser Thr Pro Ala Pro Arg Thr
1 5

<210> SEQ ID NO 353
<211> LENGTH: 9
<212> TYPE: PRT
<213> ORGANISM: Rattus norvegicus

<400> SEQUENCE: 353

Gln Gln Tyr Asp Arg Tyr Pro Leu Thr
1 5

<210> SEQ ID NO 354
<211> LENGTH: 9
<212> TYPE: PRT
<213> ORGANISM: Rattus norvegicus

<400> SEQUENCE: 354

Gln Gln Asp Ala Ser Leu Pro Trp Thr
1 5

<210> SEQ ID NO 355
<211> LENGTH: 9
<212> TYPE: PRT
<213> ORGANISM: Rattus norvegicus

<400> SEQUENCE: 355

Gln Gln Tyr Val Lys Phe Pro Asn Thr
1 5

<210> SEQ ID NO 356
<211> LENGTH: 9
<212> TYPE: PRT
<213> ORGANISM: Rattus norvegicus

<400> SEQUENCE: 356

Met Gln Ser Asn Ser Tyr Pro Pro Thr
1 5

<210> SEQ ID NO 357
<211> LENGTH: 8
<212> TYPE: PRT
<213> ORGANISM: Artificial sequence
<220> FEATURE:
<223> OTHER INFORMATION: humanized sequence

<400> SEQUENCE: 357

Tyr Gln Tyr Asn Ser Gly Tyr Thr
1 5

<210> SEQ ID NO 358
<211> LENGTH: 8
<212> TYPE: PRT
<213> ORGANISM: Artificial sequence
<220> FEATURE:
<223> OTHER INFORMATION: humanized sequence

<400> SEQUENCE: 358

Tyr Gln Tyr Asn Asp Gly Tyr Thr
1 5

<210> SEQ ID NO 359
<211> LENGTH: 8
<212> TYPE: PRT
<213> ORGANISM: Artificial sequence
<220> FEATURE:
<223> OTHER INFORMATION: humanized sequence

<400> SEQUENCE: 359

Tyr Gln Tyr Asn Gln Gly Tyr Thr
1 5

<210> SEQ ID NO 360
<211> LENGTH: 9
<212> TYPE: PRT
<213> ORGANISM: Artificial sequence
<220> FEATURE:
<223> OTHER INFORMATION: humanized sequence

<400> SEQUENCE: 360

Cys Gln Gln Tyr Asn Ser Trp Thr Thr
1 5

<210> SEQ ID NO 361
<211> LENGTH: 9
<212> TYPE: PRT
<213> ORGANISM: Rattus norvegicus

<400> SEQUENCE: 361

Gln Gln Tyr Val Asn Phe Pro Asn Thr
1 5

<210> SEQ ID NO 362
<211> LENGTH: 19
<212> TYPE: PRT
<213> ORGANISM: Artificial sequence
<220> FEATURE:
<223> OTHER INFORMATION: synthetic sequence

<400> SEQUENCE: 362

Val Ala Thr Ile Ser Ser Gly Gly Gly Asn Thr Tyr Tyr Pro Asp Ser
1 5 10 15

Val Lys Gly

<210> SEQ ID NO 363
<211> LENGTH: 19
<212> TYPE: PRT
<213> ORGANISM: Artificial sequence
<220> FEATURE:
<223> OTHER INFORMATION: synthetic sequence

<400> SEQUENCE: 363

Val Ala Thr Ile Ser Ser Gly Gly Gly Gln Thr Tyr Tyr Pro Asp Ser
1 5 10 15

Val Lys Gly

<210> SEQ ID NO 364
<211> LENGTH: 19
<212> TYPE: PRT
<213> ORGANISM: Artificial sequence
<220> FEATURE:
<223> OTHER INFORMATION: humanized sequence

<400> SEQUENCE: 364

Val Ala Thr Ile Ser Ser Gly Gly Gly Ser Thr Tyr Tyr Pro Asp Ser
1 5 10 15

Val Lys Gly

<210> SEQ ID NO 365
<211> LENGTH: 12
<212> TYPE: PRT
<213> ORGANISM: Artificial sequence
<220> FEATURE:
<223> OTHER INFORMATION: synthetic sequence

<400> SEQUENCE: 365

Ala Arg Tyr Gly Ala Gly Asp Ala Trp Phe Ala Tyr
1 5 10

<210> SEQ ID NO 366
<211> LENGTH: 119
<212> TYPE: PRT
<213> ORGANISM: Artificial sequence
<220> FEATURE:
<223> OTHER INFORMATION: synthetic sequence

<400> SEQUENCE: 366

Glu Val Met Leu Val Glu Ser Gly Gly Ala Leu Val Lys Pro Gly Gly
1 5 10 15

Ser Leu Lys Leu Ser Cys Ala Ala Ser Gly Phe Thr Phe Ser Asn Asn
20 25 30

Ala Met Ser Trp Val Arg Gln Thr Pro Glu Thr Arg Leu Glu Trp Val
35 40 45

Ala Thr Ile Thr Gly Gly Gly Ser Tyr Thr Tyr Tyr Pro Asp Ser Val
50 55 60

```
Lys Gly Arg Phe Thr Ile Ser Arg Asp Asn Ala Arg Asn Thr Leu Tyr
65                  70                  75                  80

Leu Gln Met Ser Ser Leu Arg Ser Glu Asp Thr Ala Thr Tyr Tyr Cys
                85                  90                  95

Ala Ser Pro Asp Gly Asn Tyr Glu Gly Val Leu Ala Tyr Trp Gly Gln
            100                 105                 110

Gly Thr Leu Val Thr Val Ser
        115
```

<210> SEQ ID NO 367
<211> LENGTH: 112
<212> TYPE: PRT
<213> ORGANISM: Artificial sequence
<220> FEATURE:
<223> OTHER INFORMATION: synthetic sequence

<400> SEQUENCE: 367

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Thr Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Leu Glu Ala Glu Asp Leu Gly Val Tyr Tyr Cys Phe Gln Gly
                85                  90                  95

Ser His Phe Pro Arg Thr Phe Gly Gly Gly Thr Arg Leu Glu Ile Lys
            100                 105                 110
```

<210> SEQ ID NO 368
<211> LENGTH: 16
<212> TYPE: PRT
<213> ORGANISM: Artificial sequence
<220> FEATURE:
<223> OTHER INFORMATION: synthetic sequence

<400> SEQUENCE: 368

```
Arg Ser Ser Gln Ser Ile Val His Ser Thr Gly Asn Thr Tyr Leu Glu
1               5                   10                  15
```

<210> SEQ ID NO 369
<211> LENGTH: 8
<212> TYPE: PRT
<213> ORGANISM: Artificial sequence
<220> FEATURE:
<223> OTHER INFORMATION: synthetic sequence

<400> SEQUENCE: 369

```
Gln Gly Ser His Phe Pro Arg Thr
1               5
```

<210> SEQ ID NO 370
<211> LENGTH: 112
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (35)..(35)

<223> OTHER INFORMATION: The amino acid at position 35 is Asn, Gln or
      Ser

<400> SEQUENCE: 370

Asp Val Leu Met Thr Gln Thr Pro Val Ser Leu Ser Val Ser Leu Gly
1               5                   10                  15

Asp Gln Ala Ser Ile Ser Cys Arg Ser Ser Gln Ser Ile Val His Ser
            20                  25                  30

Thr Gly Xaa Thr Tyr Leu Glu Trp Tyr Leu Gln Lys Pro Gly Gln Ser
        35                  40                  45

Pro Lys Leu Leu Ile Tyr Lys Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Ala
                85                  90                  95

Ser His Phe Pro Arg Thr Phe Gly Gly Gly Thr Lys Leu Glu Ile Lys
            100                 105                 110

<210> SEQ ID NO 371
<211> LENGTH: 16
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (12)..(12)
<223> OTHER INFORMATION: The amino acid at position 12 is Asn, Gln or
      Ser

<400> SEQUENCE: 371

Arg Ser Ser Gln Ser Ile Val His Ser Thr Gly Xaa Thr Tyr Leu Glu
1               5                   10                  15

<210> SEQ ID NO 372
<211> LENGTH: 7
<212> TYPE: PRT
<213> ORGANISM: Artificial sequence
<220> FEATURE:
<223> OTHER INFORMATION: synthetic sequence

<400> SEQUENCE: 372

Lys Ile Ser Asn Arg Phe Ser
1               5

<210> SEQ ID NO 373
<211> LENGTH: 9
<212> TYPE: PRT
<213> ORGANISM: Artificial sequence
<220> FEATURE:
<223> OTHER INFORMATION: synthetic sequence

<400> SEQUENCE: 373

Phe Gln Ala Ser His Phe Pro Arg Thr
1               5

<210> SEQ ID NO 374
<211> LENGTH: 112
<212> TYPE: PRT
<213> ORGANISM: Artificial sequence
<220> FEATURE:
<223> OTHER INFORMATION: synthetic sequence

<400> SEQUENCE: 374

```
Asp Val Leu Met Thr Gln Thr Pro Val Ser Leu Ser Val Ser Leu Gly
1               5                   10                  15

Asp Gln Ala Ser Ile Ser Cys Arg Ser Ser Gln Ser Ile Val His Ser
            20                  25                  30

Thr Gly Asn Thr Tyr Leu Glu Trp Tyr Leu Gln Lys Pro Gly Gln Ser
        35                  40                  45

Pro Lys Leu Leu Ile Tyr Lys Ile Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Ala
                85                  90                  95

Ser His Phe Pro Arg Thr Phe Gly Gly Gly Thr Lys Leu Glu Ile Lys
            100                 105                 110


<210> SEQ ID NO 375
<211> LENGTH: 113
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (35)..(35)
<223> OTHER INFORMATION: The amino acid at position 35 is Asn, Gln or
      Ser

<400> SEQUENCE: 375

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Ile Val His Ser
            20                  25                  30

Thr Gly Xaa Thr Tyr Leu Glu Trp Tyr Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Ser His Phe Pro Arg Thr Phe Gly Gly Gly Thr Lys Leu Glu Ile Lys
            100                 105                 110

Arg


<210> SEQ ID NO 376
<211> LENGTH: 17
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (12)..(12)
<223> OTHER INFORMATION: The amino acid at position 12 is Asn, Gln or
      Ser

<400> SEQUENCE: 376

Arg Ser Ser Gln Ser Ile Val His Ser Thr Gly Xaa Thr Tyr Leu Glu
1               5                   10                  15

Trp
```

<210> SEQ ID NO 377
<211> LENGTH: 8
<212> TYPE: PRT
<213> ORGANISM: Artificial sequence
<220> FEATURE:
<223> OTHER INFORMATION: synthetic sequence

<400> SEQUENCE: 377

```
Lys Ile Ser Asn Arg Phe Ser Gly
1               5
```

<210> SEQ ID NO 378
<211> LENGTH: 10
<212> TYPE: PRT
<213> ORGANISM: Artificial sequence
<220> FEATURE:
<223> OTHER INFORMATION: synthetic sequence

<400> SEQUENCE: 378

```
Phe Gln Ala Ser His Phe Pro Arg Thr Phe
1               5                   10
```

<210> SEQ ID NO 379
<211> LENGTH: 119
<212> TYPE: PRT
<213> ORGANISM: Artificial sequence
<220> FEATURE:
<223> OTHER INFORMATION: synthetic sequence

<400> SEQUENCE: 379

```
Glu Val Ile Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Thr Ile Ser Ser Gly Gly Gly Asn Thr Tyr Tyr Pro Asp Ser Val
    50                  55                  60

Lys Gly Arg Phe Thr Ile Ser Arg Asp Asn Ala Lys Asn Asn Leu Tyr
65                  70                  75                  80

Leu Gln Met Ser Ser Leu Arg Ser Glu Asp Thr Ala Leu Tyr Tyr Cys
                85                  90                  95

Ala Arg Tyr Tyr Arg Tyr Glu Ala Trp Phe Ala Ser Trp Gly Gln Gly
            100                 105                 110

Thr Leu Val Thr Val Ser Ala
        115
```

<210> SEQ ID NO 380
<211> LENGTH: 119
<212> TYPE: PRT
<213> ORGANISM: Artificial sequence
<220> FEATURE:
<223> OTHER INFORMATION: synthetic sequence

<400> SEQUENCE: 380

```
Glu Val Lys Val Val Glu Ser Gly Gly Val Leu Val Arg Pro Gly Gly
1               5                   10                  15

Ser Leu Lys Leu Ser Cys Ala Ala Ser Gly Phe Thr Phe Ser Arg Tyr
            20                  25                  30

Thr Met Ser Trp Val Arg Gln Thr Pro Glu Lys Arg Leu Glu Trp Val
        35                  40                  45
```

Ala Thr Ile Ser Ser Gly Gly Gly Asn Thr Tyr Tyr Pro Asp Ser Val
    50                  55                  60

Lys Gly Arg Phe Thr Val Ser Arg Asp Asn Ala Met Ser Ser Leu Tyr
65                  70                  75                  80

Leu Gln Met Ser Ser Leu Arg Ser Glu Asp Thr Ala Leu Tyr Tyr Cys
                85                  90                  95

Ala Arg Tyr Gly Ala Gly Asp Ala Trp Phe Ala Tyr Trp Gly Gln Gly
            100                 105                 110

Thr Leu Val Thr Val Ser Ser
        115

<210> SEQ ID NO 381
<211> LENGTH: 120
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (57)..(57)
<223> OTHER INFORMATION: The amino acid at position 57 is Asn, Gln or
      Ser

<400> SEQUENCE: 381

Glu Val Gln Leu Val Glu Ser Gly Gly Val Val Val Gln Pro Gly Gly
1               5                   10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
        35                  40                  45

Ala Thr Ile Ser Ser Gly Gly Gly Xaa Thr Tyr Tyr Pro Asp Ser Val
    50                  55                  60

Lys Gly Arg Phe Thr Val Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Arg Tyr Gly Ala Gly Asp Ala Trp Phe Ala Tyr Trp Gly Gln Gly
            100                 105                 110

Thr Leu Val Thr Val Ser Ser Ala
        115                 120

<210> SEQ ID NO 382
<211> LENGTH: 5
<212> TYPE: PRT
<213> ORGANISM: Artificial sequence
<220> FEATURE:
<223> OTHER INFORMATION: synthetic sequence

<400> SEQUENCE: 382

Arg Tyr Thr Met Ser
1               5

<210> SEQ ID NO 383
<211> LENGTH: 17
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (8)..(8)
<223> OTHER INFORMATION: The amino acid at position 8 is Asn, Gln or Ser

<400> SEQUENCE: 383

Thr Ile Ser Ser Gly Gly Gly Xaa Thr Tyr Tyr Pro Asp Ser Val Lys
1 5 10 15

Gly

<210> SEQ ID NO 384
<211> LENGTH: 10
<212> TYPE: PRT
<213> ORGANISM: Artificial sequence
<220> FEATURE:
<223> OTHER INFORMATION: synthetic sequence

<400> SEQUENCE: 384

Tyr Gly Ala Gly Asp Ala Trp Phe Ala Tyr
1 5 10

<210> SEQ ID NO 385
<211> LENGTH: 119
<212> TYPE: PRT
<213> ORGANISM: Artificial sequence
<220> FEATURE:
<223> OTHER INFORMATION: synthetic sequence

<400> SEQUENCE: 385

Glu Val Gln Leu Val Glu Ser Gly Gly Val Val Val Gln Pro Gly Gly
1 5 10 15

Ser Leu Arg Leu Ser Cys Ala Ala Ser Gly Phe Thr Phe Ser Arg Tyr
20 25 30

Thr Met Ser Trp Val Arg Gln Ala Pro Gly Lys Gly Leu Glu Trp Val
35 40 45

Ala Thr Ile Ser Ser Gly Gly Gly Asn Thr Tyr Tyr Pro Asp Ser Val
50 55 60

Lys Gly Arg Phe Thr Val Ser Arg Asp Asn Ser Lys Asn Ser Leu Tyr
65 70 75 80

Leu Gln Met Asn Ser Leu Arg Thr Glu Asp Thr Ala Leu Tyr Tyr Cys
85 90 95

Ala Arg Tyr Gly Ala Gly Asp Ala Trp Phe Ala Tyr Trp Gly Gln Gly
100 105 110

Thr Leu Val Thr Val Ser Ser
115

<210> SEQ ID NO 386
<211> LENGTH: 119
<212> TYPE: PRT
<213> ORGANISM: Artificial sequence
<220> FEATURE:
<223> OTHER INFORMATION: synthetic sequence

<400> SEQUENCE: 386

Glu Val Gln Leu Val Glu Ser Gly Gly Val Val Val Gln Pro Gly Gly
1 5 10 15

Ser Leu Arg Leu Ser Cys Ala Ala Ser Gly Phe Thr Phe Ser Arg Tyr
20 25 30

Thr Met Ser Trp Val Arg Gln Ala Pro Gly Lys Gly Leu Glu Trp Val
35 40 45

Ala Thr Ile Ser Ser Gly Gly Gly Gln Thr Tyr Tyr Pro Asp Ser Val
50 55 60

Lys Gly Arg Phe Thr Val Ser Arg Asp Asn Ser Lys Asn Ser Leu Tyr
65 70 75 80

```
Leu Gln Met Asn Ser Leu Arg Thr Glu Asp Thr Ala Leu Tyr Tyr Cys
                85                  90                  95

Ala Arg Tyr Gly Ala Gly Asp Ala Trp Phe Ala Tyr Trp Gly Gln Gly
            100                 105                 110

Thr Leu Val Thr Val Ser Ser
        115


<210> SEQ ID NO 387
<211> LENGTH: 119
<212> TYPE: PRT
<213> ORGANISM: Artificial sequence
<220> FEATURE:
<223> OTHER INFORMATION: synthetic sequence

<400> SEQUENCE: 387

Glu Val Gln Leu Val Glu Ser Gly Gly Val Val Val Gln Pro Gly Gly
1               5                   10                  15

Ser Leu Arg Leu Ser Cys Ala Ala Ser Gly Phe Thr Phe Ser Arg Tyr
            20                  25                  30

Thr Met Ser Trp Val Arg Gln Ala Pro Gly Lys Gly Leu Glu Trp Val
        35                  40                  45

Ala Thr Ile Ser Ser Gly Gly Gly Ser Thr Tyr Tyr Pro Asp Ser Val
    50                  55                  60

Lys Gly Arg Phe Thr Val Ser Arg Asp Asn Ser Lys Asn Ser Leu Tyr
65                  70                  75                  80

Leu Gln Met Asn Ser Leu Arg Thr Glu Asp Thr Ala Leu Tyr Tyr Cys
                85                  90                  95

Ala Arg Tyr Gly Ala Gly Asp Ala Trp Phe Ala Tyr Trp Gly Gln Gly
            100                 105                 110

Thr Leu Val Thr Val Ser Ser
        115


<210> SEQ ID NO 388
<211> LENGTH: 121
<212> TYPE: PRT
<213> ORGANISM: Artificial sequence
<220> FEATURE:
<223> OTHER INFORMATION: synthetic sequence

<400> SEQUENCE: 388

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asp Tyr Asn Pro Ser
    50                  55                  60

Leu Lys Ser Arg Val Thr Met Ser Val Asp Thr Ser Lys Asn Gln Phe
65                  70                  75                  80

Ser Leu Lys Val Asn Ser Val Thr Ala Ala Asp Thr Ala Val Tyr Tyr
                85                  90                  95

Cys Ala Arg Val Ser Ile Phe Gly Val Gly Thr Phe Asp Tyr Trp Gly
            100                 105                 110

Gln Gly Thr Leu Val Thr Val Ser Ser
        115                 120
```

<210> SEQ ID NO 389
<211> LENGTH: 450
<212> TYPE: PRT
<213> ORGANISM: Artificial sequence
<220> FEATURE:
<223> OTHER INFORMATION: synthetic sequence

<400> SEQUENCE: 389

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
```

```
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 390
<211> LENGTH: 451
<212> TYPE: PRT
<213> ORGANISM: Artificial sequence
<220> FEATURE:
<223> OTHER INFORMATION: synthetic sequence

<400> SEQUENCE: 390

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asp Tyr Asn Pro Ser
    50                  55                  60

Leu Lys Ser Arg Val Thr Met Ser Val Asp Thr Ser Lys Asn Gln Phe
65                  70                  75                  80

Ser Leu Lys Val Asn Ser Val Thr Ala Ala Asp Thr Ala Val Tyr Tyr
                85                  90                  95

Cys Ala Arg Val Ser Ile Phe Gly Val Gly Thr Phe Asp Tyr Trp Gly
            100                 105                 110

Gln Gly Thr Leu Val Thr Val Ser Ser Ala Ser Thr Lys Gly Pro Ser
        115                 120                 125

Val Leu Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
```

```
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 391
<211> LENGTH: 448
<212> TYPE: PRT
<213> ORGANISM: Artificial sequence
<220> FEATURE:
<223> OTHER INFORMATION: synthetic sequence

<400> SEQUENCE: 391

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
```

180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr Cys Pro Pro Cys Pro Ala Pro Glu Leu Leu Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Ala Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Glu Glu Met Thr Lys Asn Gln Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Lys Leu Thr Val Asp Lys Ser
405 410 415

Arg Trp Gln Gln Gly Asn Val Phe Ser Cys Ser Val Met His Glu Ala
420 425 430

Leu His Asn His Tyr Thr Gln Lys Ser Leu Ser Leu Ser Pro Gly Lys
435 440 445

<210> SEQ ID NO 392
<211> LENGTH: 117
<212> TYPE: PRT
<213> ORGANISM: Artificial sequence
<220> FEATURE:
<223> OTHER INFORMATION: synthetic sequence

<400> SEQUENCE: 392

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Asn Tyr
20 25 30

Asn Met His Trp Val Arg Gln Ala Pro Gly Gln Arg Leu Glu Trp Met
35 40 45

Gly Thr Ile Tyr Pro Gly Asn Asp Asp Thr Ser Tyr Asn Gln Lys Phe
50 55 60

Lys Asp Arg Val Thr Ile Thr Ala Asp Thr Ser Ala Ser Thr Ala Tyr
65 70 75 80

Met Glu Leu Ser Ser Leu Arg Ser Glu Asp Thr Ala Val Tyr Tyr Cys
85 90 95

Ala Arg Gly Gly Tyr Arg Ala Met Asp Tyr Trp Gly Gln Gly Thr Leu

```
            100                 105                 110

Val Thr Val Ser Ser
        115


<210> SEQ ID NO 393
<211> LENGTH: 655
<212> TYPE: PRT
<213> ORGANISM: Homo sapiens

<400> SEQUENCE: 393

Met Ser Ser Ser Asn Val Glu Val Phe Ile Pro Val Ser Gln Gly Asn
1               5                   10                  15

Thr Asn Gly Phe Pro Ala Thr Ala Ser Asn Asp Leu Lys Ala Phe Thr
            20                  25                  30

Glu Gly Ala Val Leu Ser Phe His Asn Ile Cys Tyr Arg Val Lys Leu
        35                  40                  45

Lys Ser Gly Phe Leu Pro Cys Arg Lys Pro Val Glu Lys Glu Ile Leu
    50                  55                  60

Ser Asn Ile Asn Gly Ile Met Lys Pro Gly Leu Asn Ala Ile Leu Gly
65                  70                  75                  80

Pro Thr Gly Gly Gly Lys Ser Ser Leu Leu Asp Val Leu Ala Ala Arg
                85                  90                  95

Lys Asp Pro Ser Gly Leu Ser Gly Asp Val Leu Ile Asn Gly Ala Pro
            100                 105                 110

Arg Pro Ala Asn Phe Lys Cys Asn Ser Gly Tyr Val Val Gln Asp Asp
        115                 120                 125

Val Val Met Gly Thr Leu Thr Val Arg Glu Asn Leu Gln Phe Ser Ala
    130                 135                 140

Ala Leu Arg Leu Ala Thr Thr Met Thr Asn His Glu Lys Asn Glu Arg
145                 150                 155                 160

Ile Asn Arg Val Ile Gln Glu Leu Gly Leu Asp Lys Val Ala Asp Ser
                165                 170                 175

Lys Val Gly Thr Gln Phe Ile Arg Gly Val Ser Gly Gly Glu Arg Lys
            180                 185                 190

Arg Thr Ser Ile Gly Met Glu Leu Ile Thr Asp Pro Ser Ile Leu Phe
        195                 200                 205

Leu Asp Glu Pro Thr Thr Gly Leu Asp Ser Ser Thr Ala Asn Ala Val
    210                 215                 220

Leu Leu Leu Leu Lys Arg Met Ser Lys Gln Gly Arg Thr Ile Ile Phe
225                 230                 235                 240

Ser Ile His Gln Pro Arg Tyr Ser Ile Phe Lys Leu Phe Asp Ser Leu
                245                 250                 255

Thr Leu Leu Ala Ser Gly Arg Leu Met Phe His Gly Pro Ala Gln Glu
            260                 265                 270

Ala Leu Gly Tyr Phe Glu Ser Ala Gly Tyr His Cys Glu Ala Tyr Asn
        275                 280                 285

Asn Pro Ala Asp Phe Phe Leu Asp Ile Ile Asn Gly Asp Ser Thr Ala
    290                 295                 300

Val Ala Leu Asn Arg Glu Glu Asp Phe Lys Ala Thr Glu Ile Ile Glu
305                 310                 315                 320

Pro Ser Lys Gln Asp Lys Pro Leu Ile Glu Lys Leu Ala Glu Ile Tyr
                325                 330                 335

Val Asn Ser Ser Phe Tyr Lys Glu Thr Lys Ala Glu Leu His Gln Leu
            340                 345                 350
```

```
Ser Gly Gly Glu Lys Lys Lys Lys Ile Thr Val Phe Lys Glu Ile Ser
        355                 360                 365

Tyr Thr Thr Ser Phe Cys His Gln Leu Arg Trp Val Ser Lys Arg Ser
    370                 375                 380

Phe Lys Asn Leu Leu Gly Asn Pro Gln Ala Ser Ile Ala Gln Ile Ile
385                 390                 395                 400

Val Thr Val Val Leu Gly Leu Val Ile Gly Ala Ile Tyr Phe Gly Leu
                405                 410                 415

Lys Asn Asp Ser Thr Gly Ile Gln Asn Arg Ala Gly Val Leu Phe Phe
            420                 425                 430

Leu Thr Thr Asn Gln Cys Phe Ser Ser Val Ser Ala Val Glu Leu Phe
        435                 440                 445

Val Val Glu Lys Lys Leu Phe Ile His Glu Tyr Ile Ser Gly Tyr Tyr
    450                 455                 460

Arg Val Ser Ser Tyr Phe Leu Gly Lys Leu Leu Ser Asp Leu Leu Pro
465                 470                 475                 480

Met Arg Met Leu Pro Ser Ile Ile Phe Thr Cys Ile Val Tyr Phe Met
                485                 490                 495

Leu Gly Leu Lys Pro Lys Ala Asp Ala Phe Phe Val Met Met Phe Thr
            500                 505                 510

Leu Met Met Val Ala Tyr Ser Ala Ser Ser Met Ala Leu Ala Ile Ala
        515                 520                 525

Ala Gly Gln Ser Val Val Ser Val Ala Thr Leu Leu Met Thr Ile Cys
    530                 535                 540

Phe Val Phe Met Met Ile Phe Ser Gly Leu Leu Val Asn Leu Thr Thr
545                 550                 555                 560

Ile Ala Ser Trp Leu Ser Trp Leu Gln Tyr Phe Ser Ile Pro Arg Tyr
                565                 570                 575

Gly Phe Thr Ala Leu Gln His Asn Glu Phe Leu Gly Gln Asn Phe Cys
            580                 585                 590

Pro Gly Leu Asn Ala Thr Gly Asn Asn Pro Cys Asn Tyr Ala Thr Cys
        595                 600                 605

Thr Gly Glu Glu Tyr Leu Val Lys Gln Gly Ile Asp Leu Ser Pro Trp
    610                 615                 620

Gly Leu Trp Lys Asn His Val Ala Leu Ala Cys Met Ile Val Ile Phe
625                 630                 635                 640

Leu Thr Ile Ala Tyr Leu Lys Leu Leu Phe Leu Lys Lys Tyr Ser
                645                 650                 655
```

<210> SEQ ID NO 394
<211> LENGTH: 657
<212> TYPE: PRT
<213> ORGANISM: Mus musculus

<400> SEQUENCE: 394

```
Met Ser Ser Ser Asn Asp His Val Leu Val Pro Met Ser Gln Arg Asn
1               5                   10                  15

Asn Asn Gly Leu Pro Arg Thr Asn Ser Arg Ala Val Arg Thr Leu Ala
            20                  25                  30

Glu Gly Asp Val Leu Ser Phe His His Ile Thr Tyr Arg Val Lys Val
        35                  40                  45

Lys Ser Gly Phe Leu Val Arg Lys Thr Val Glu Lys Glu Ile Leu Ser
    50                  55                  60

Asp Ile Asn Gly Ile Met Lys Pro Gly Leu Asn Ala Ile Leu Gly Pro
65                  70                  75                  80
```

```
Thr Gly Gly Gly Lys Ser Ser Leu Leu Asp Val Leu Ala Ala Arg Lys
                85                  90                  95

Asp Pro Lys Gly Leu Ser Gly Asp Val Leu Ile Asn Gly Ala Pro Gln
            100                 105                 110

Pro Ala His Phe Lys Cys Cys Ser Gly Tyr Val Val Gln Asp Asp Val
        115                 120                 125

Val Met Gly Thr Leu Thr Val Arg Glu Asn Leu Gln Phe Ser Ala Ala
    130                 135                 140

Leu Arg Leu Pro Thr Thr Met Lys Asn His Glu Lys Asn Glu Arg Ile
145                 150                 155                 160

Asn Thr Ile Ile Lys Glu Leu Gly Leu Glu Lys Val Ala Asp Ser Lys
                165                 170                 175

Val Gly Thr Gln Phe Ile Arg Gly Ile Ser Gly Gly Glu Arg Lys Arg
            180                 185                 190

Thr Ser Ile Gly Met Glu Leu Ile Thr Asp Pro Ser Ile Leu Phe Leu
        195                 200                 205

Asp Glu Pro Thr Thr Gly Leu Asp Ser Ser Thr Ala Asn Ala Val Leu
    210                 215                 220

Leu Leu Leu Lys Arg Met Ser Lys Gln Gly Arg Thr Ile Ile Phe Ser
225                 230                 235                 240

Ile His Gln Pro Arg Tyr Ser Ile Phe Lys Leu Phe Asp Ser Leu Thr
                245                 250                 255

Leu Leu Ala Ser Gly Lys Leu Val Phe His Gly Pro Ala Gln Lys Ala
            260                 265                 270

Leu Glu Tyr Phe Ala Ser Ala Gly Tyr His Cys Glu Pro Tyr Asn Asn
        275                 280                 285

Pro Ala Asp Phe Phe Leu Asp Val Ile Asn Gly Asp Ser Ser Ala Val
    290                 295                 300

Met Leu Asn Arg Glu Glu Gln Asp Asn Glu Ala Asn Lys Thr Glu Glu
305                 310                 315                 320

Pro Ser Lys Gly Glu Lys Pro Val Ile Glu Asn Leu Ser Glu Phe Tyr
                325                 330                 335

Ile Asn Ser Ala Ile Tyr Gly Glu Thr Lys Ala Glu Leu Asp Gln Leu
            340                 345                 350

Pro Gly Ala Gln Glu Lys Lys Gly Thr Ser Ala Phe Lys Glu Pro Val
        355                 360                 365

Tyr Val Thr Ser Phe Cys His Gln Leu Arg Trp Ile Ala Arg Arg Ser
    370                 375                 380

Phe Lys Asn Leu Leu Gly Asn Pro Gln Ala Ser Val Ala Gln Leu Ile
385                 390                 395                 400

Val Thr Val Ile Leu Gly Leu Ile Ile Gly Ala Ile Tyr Phe Asp Leu
                405                 410                 415

Lys Tyr Asp Ala Ala Gly Met Gln Asn Arg Ala Gly Val Leu Phe Phe
            420                 425                 430

Leu Thr Thr Asn Gln Cys Phe Ser Ser Val Ser Ala Val Glu Leu Phe
        435                 440                 445

Val Val Glu Lys Lys Leu Phe Ile His Glu Tyr Ile Ser Gly Tyr Tyr
    450                 455                 460

Arg Val Ser Ser Tyr Phe Phe Gly Lys Val Met Ser Asp Leu Leu Pro
465                 470                 475                 480

Met Arg Phe Leu Pro Ser Val Ile Phe Thr Cys Val Leu Tyr Phe Met
                485                 490                 495
```

```
Leu Gly Leu Lys Lys Thr Val Asp Ala Phe Phe Ile Met Met Phe Thr
            500                 505                 510

Leu Ile Met Val Ala Tyr Thr Ala Ser Ser Met Ala Leu Ala Ile Ala
        515                 520                 525

Thr Gly Gln Ser Val Val Ser Val Ala Thr Leu Leu Met Thr Ile Ala
    530                 535                 540

Phe Val Phe Met Met Leu Phe Ser Gly Leu Leu Val Asn Leu Arg Thr
545                 550                 555                 560

Ile Gly Pro Trp Leu Ser Trp Leu Gln Tyr Phe Ser Ile Pro Arg Tyr
                565                 570                 575

Gly Phe Thr Ala Leu Gln Tyr Asn Glu Phe Leu Gly Gln Glu Phe Cys
            580                 585                 590

Pro Gly Phe Asn Val Thr Asp Asn Ser Thr Cys Val Asn Ser Tyr Ala
        595                 600                 605

Ile Cys Thr Gly Asn Glu Tyr Leu Ile Asn Gln Gly Ile Glu Leu Ser
    610                 615                 620

Pro Trp Gly Leu Trp Lys Asn His Val Ala Leu Ala Cys Met Ile Ile
625                 630                 635                 640

Ile Phe Leu Thr Ile Ala Tyr Leu Lys Leu Leu Phe Leu Lys Lys Tyr
                645                 650                 655

Ser


<210> SEQ ID NO 395
<211> LENGTH: 14
<212> TYPE: PRT
<213> ORGANISM: Mus musculus

<400> SEQUENCE: 395

Asp Leu Lys Tyr Asp Ala Ala Gly Met Gln Asn Arg Ala Gly
1               5                   10


<210> SEQ ID NO 396
<211> LENGTH: 8
<212> TYPE: PRT
<213> ORGANISM: Mus musculus

<400> SEQUENCE: 396

Leu Lys Lys Thr Val Asp Ala Phe
1               5


<210> SEQ ID NO 397
<211> LENGTH: 76
<212> TYPE: PRT
<213> ORGANISM: Mus musculus

<400> SEQUENCE: 397

Asn Leu Arg Thr Ile Gly Pro Trp Leu Ser Trp Leu Gln Tyr Phe Ser
1               5                   10                  15

Ile Pro Arg Tyr Gly Phe Thr Ala Leu Gln Tyr Asn Glu Phe Leu Gly
            20                  25                  30

Gln Glu Phe Cys Pro Gly Phe Asn Val Thr Asp Asn Ser Thr Cys Val
        35                  40                  45

Asn Ser Tyr Ala Ile Cys Thr Gly Asn Glu Tyr Leu Ile Asn Gln Gly
    50                  55                  60

Ile Glu Leu Ser Pro Trp Gly Leu Trp Lys Asn His
65                  70                  75


<210> SEQ ID NO 398
```

<211> LENGTH: 655
<212> TYPE: PRT
<213> ORGANISM: Macaca fascicularis

<400> SEQUENCE: 398

Met Ser Ser Ser Asn Val Glu Val Phe Ile Pro Met Ser Gln Glu Asn
1 5 10 15

Thr Asn Gly Phe Pro Thr Thr Thr Ser Asn Asp Arg Lys Ala Phe Thr
20 25 30

Glu Gly Ala Val Leu Ser Phe His Asn Ile Cys Tyr Arg Val Lys Val
35 40 45

Lys Ser Gly Phe Leu Pro Gly Arg Lys Pro Val Glu Lys Glu Ile Leu
50 55 60

Ser Asn Ile Asn Gly Ile Met Lys Pro Gly Leu Asn Ala Ile Leu Gly
65 70 75 80

Pro Thr Gly Gly Gly Lys Ser Ser Leu Leu Asp Val Leu Ala Ala Arg
85 90 95

Lys Asp Pro Ser Gly Leu Ser Gly Asp Val Leu Ile Asn Gly Ala Leu
100 105 110

Arg Pro Thr Asn Phe Lys Cys Asn Ser Gly Tyr Val Val Gln Asp Asp
115 120 125

Val Val Met Gly Thr Leu Thr Val Arg Glu Asn Leu Gln Phe Ser Ala
130 135 140

Ala Leu Arg Leu Pro Thr Thr Met Thr Asn His Glu Lys Asn Glu Arg
145 150 155 160

Ile Asn Arg Val Ile Gln Glu Leu Gly Leu Asp Lys Val Ala Asp Ser
165 170 175

Lys Val Gly Thr Gln Phe Ile Arg Gly Val Ser Gly Gly Glu Arg Lys
180 185 190

Arg Thr Ser Ile Gly Met Glu Leu Ile Thr Asp Pro Ser Ile Leu Phe
195 200 205

Leu Asp Glu Pro Thr Thr Gly Leu Asp Ser Ser Thr Ala Asn Ala Val
210 215 220

Leu Leu Leu Leu Lys Arg Met Ser Lys Gln Gly Arg Thr Ile Ile Phe
225 230 235 240

Ser Ile His Gln Pro Arg Tyr Ser Ile Phe Lys Leu Phe Asp Ser Leu
245 250 255

Thr Leu Leu Ala Ser Gly Arg Leu Met Phe His Gly Pro Ala Gln Glu
260 265 270

Ala Leu Gly Tyr Phe Glu Ser Ala Gly Tyr His Cys Glu Ala Tyr Asn
275 280 285

Asn Pro Ala Asp Phe Phe Leu Asp Ile Ile Asn Gly Asp Ser Thr Ala
290 295 300

Val Ala Leu Asn Arg Glu Glu Asp Phe Lys Ala Thr Glu Ile Ile Glu
305 310 315 320

Pro Ser Lys Arg Asp Lys Pro Leu Val Glu Lys Leu Ala Glu Ile Tyr
325 330 335

Val Asp Ser Ser Phe Tyr Lys Glu Thr Lys Ala Glu Leu His Gln Leu
340 345 350

Ser Gly Gly Glu Lys Lys Lys Lys Ile Thr Val Phe Lys Glu Ile Ser
355 360 365

Tyr Thr Thr Ser Phe Cys His Gln Leu Arg Trp Val Ser Lys Arg Ser
370 375 380

Phe Lys Asn Leu Leu Gly Asn Pro Gln Ala Ser Ile Ala Gln Ile Ile

```
385                 390                 395                 400

Val Thr Val Ile Leu Gly Leu Val Ile Gly Ala Ile Tyr Phe Gly Leu
                405                 410                 415

Asn Asn Asp Ser Thr Gly Ile Gln Asn Arg Ala Gly Val Leu Phe Phe
            420                 425                 430

Leu Thr Thr Asn Gln Cys Phe Ser Ser Val Ser Ala Val Glu Leu Phe
        435                 440                 445

Val Val Glu Lys Lys Leu Phe Ile His Glu Tyr Ile Ser Gly Tyr Tyr
    450                 455                 460

Arg Val Ser Ser Tyr Phe Phe Gly Lys Leu Leu Ser Asp Leu Leu Pro
465                 470                 475                 480

Met Arg Met Leu Pro Ser Ile Ile Phe Thr Cys Ile Val Tyr Phe Met
                485                 490                 495

Leu Gly Leu Lys Pro Thr Ala Asp Ala Phe Phe Ile Met Met Phe Thr
            500                 505                 510

Leu Met Met Val Ala Tyr Ser Ala Ser Ser Met Ala Leu Ala Ile Ala
        515                 520                 525

Ala Gly Gln Ser Val Val Ser Val Ala Thr Leu Leu Met Thr Ile Cys
    530                 535                 540

Phe Val Phe Met Met Ile Phe Ser Gly Leu Leu Val Asn Leu Thr Thr
545                 550                 555                 560

Ile Ala Ser Trp Leu Ser Trp Leu Gln Tyr Phe Ser Ile Pro Arg Tyr
                565                 570                 575

Gly Phe Thr Ala Leu Gln His Asn Glu Phe Leu Gly Gln Asn Phe Cys
            580                 585                 590

Pro Gly Leu Asn Ala Thr Val Asn Asn Thr Cys Asn Tyr Ala Thr Cys
        595                 600                 605

Thr Gly Glu Glu Tyr Leu Thr Lys Gln Gly Ile Asp Leu Ser Pro Trp
    610                 615                 620

Gly Leu Trp Lys Asn His Val Ala Leu Ala Cys Met Ile Val Ile Phe
625                 630                 635                 640

Leu Thr Ile Ala Tyr Leu Lys Leu Leu Phe Leu Lys Lys Tyr Ser
                645                 650                 655


<210> SEQ ID NO 399
<211> LENGTH: 12
<212> TYPE: PRT
<213> ORGANISM: Macaca fascicularis

<400> SEQUENCE: 399

Asn Asn Asp Ser Thr Gly Ile Gln Asn Arg Ala Gly
1               5                   10


<210> SEQ ID NO 400
<211> LENGTH: 8
<212> TYPE: PRT
<213> ORGANISM: Macaca fascicularis

<400> SEQUENCE: 400

Leu Lys Pro Thr Ala Asp Ala Phe
1               5


<210> SEQ ID NO 401
<211> LENGTH: 74
<212> TYPE: PRT
<213> ORGANISM: Macaca fascicularis

<400> SEQUENCE: 401
```

```
Asn Leu Thr Thr Ile Ala Ser Trp Leu Ser Trp Leu Gln Tyr Phe Ser
1               5                   10                  15

Ile Pro Arg Tyr Gly Phe Thr Ala Leu Gln His Asn Glu Phe Leu Gly
            20                  25                  30

Gln Asn Phe Cys Pro Gly Leu Asn Ala Thr Val Asn Asn Thr Cys Asn
        35                  40                  45

Tyr Ala Thr Cys Thr Gly Glu Glu Tyr Leu Thr Lys Gln Gly Ile Asp
    50                  55                  60

Leu Ser Pro Trp Gly Leu Trp Lys Asn His
65                  70


<210> SEQ ID NO 402
<211> LENGTH: 655
<212> TYPE: PRT
<213> ORGANISM: Pan troglodytes

<400> SEQUENCE: 402

Met Ser Ser Ser Asn Val Glu Val Phe Ile Pro Met Ser Gln Gly Asn
1               5                   10                  15

Thr Asn Gly Phe Pro Ala Thr Thr Ser Asn Asp Leu Lys Ala Phe Thr
            20                  25                  30

Glu Gly Ala Val Leu Ser Phe His Asn Ile Cys Tyr Arg Val Lys Leu
        35                  40                  45

Lys Ser Gly Phe Leu Pro Cys Arg Lys Pro Val Glu Lys Glu Ile Leu
    50                  55                  60

Ser Asn Ile Asn Gly Ile Met Lys Pro Gly Leu Asn Ala Ile Leu Gly
65                  70                  75                  80

Pro Thr Gly Gly Gly Lys Ser Ser Leu Leu Asp Val Leu Ala Ala Arg
                85                  90                  95

Lys Asp Pro Ser Gly Leu Ser Gly Asp Val Leu Ile Asn Gly Ala Pro
            100                 105                 110

Arg Pro Ala Asn Phe Lys Cys Asn Ser Gly Tyr Val Val Gln Asp Asp
        115                 120                 125

Val Val Met Gly Thr Leu Thr Val Arg Glu Asn Leu Gln Phe Ser Ala
    130                 135                 140

Ala Leu Arg Leu Pro Thr Thr Met Thr Asn His Glu Lys Asn Glu Arg
145                 150                 155                 160

Ile Asn Arg Val Ile Gln Glu Leu Gly Leu Asp Lys Val Ala Asp Ser
                165                 170                 175

Lys Val Gly Thr Gln Phe Ile Arg Gly Val Ser Gly Gly Glu Arg Lys
            180                 185                 190

Arg Thr Ser Ile Gly Met Glu Leu Ile Thr Asp Pro Ser Ile Leu Phe
        195                 200                 205

Leu Asp Glu Pro Thr Thr Gly Leu Asp Ser Ser Thr Ala Asn Ala Val
    210                 215                 220

Leu Leu Leu Leu Lys Arg Met Ser Lys Gln Gly Arg Thr Ile Ile Phe
225                 230                 235                 240

Ser Ile His Gln Pro Arg Tyr Ser Ile Phe Lys Leu Phe Asp Ser Leu
                245                 250                 255

Thr Leu Leu Ala Ser Gly Arg Leu Met Phe His Gly Pro Ala Gln Glu
            260                 265                 270

Ala Leu Gly Tyr Phe Glu Ser Ala Gly Tyr His Cys Glu Ala Tyr Asn
        275                 280                 285

Asn Pro Ala Asp Phe Phe Leu Asp Ile Ile Asn Gly Asp Ser Thr Ala
```

```
    290                 295                 300

Val Ala Leu Asn Arg Glu Glu Asp Phe Lys Ala Thr Glu Ile Ile Glu
305                 310                 315                 320

Pro Ser Lys Gln Asp Lys Pro Leu Ile Glu Lys Leu Ala Glu Ile Tyr
                325                 330                 335

Val Asn Ser Ser Phe Tyr Lys Glu Thr Lys Ala Glu Leu His Gln Leu
            340                 345                 350

Ser Gly Gly Glu Lys Lys Lys Lys Ile Thr Val Phe Lys Glu Ile Ser
        355                 360                 365

Tyr Thr Thr Ser Phe Cys His Gln Leu Arg Trp Val Ser Lys Arg Ser
    370                 375                 380

Phe Lys Asn Leu Leu Gly Asn Pro Gln Ala Ser Ile Ala Gln Ile Ile
385                 390                 395                 400

Val Thr Val Ile Leu Gly Leu Val Ile Gly Ala Ile Tyr Phe Gly Leu
                405                 410                 415

Lys Asn Asp Ser Thr Gly Ile Gln Asn Arg Ala Gly Val Leu Phe Phe
            420                 425                 430

Leu Thr Thr Asn Gln Cys Phe Ser Ser Val Ser Ala Val Glu Leu Phe
        435                 440                 445

Val Val Glu Lys Lys Leu Phe Ile His Glu Tyr Ile Ser Gly Tyr Tyr
    450                 455                 460

Arg Val Ser Ser Tyr Phe Leu Gly Lys Leu Leu Ser Asp Leu Leu Pro
465                 470                 475                 480

Met Arg Met Leu Pro Ser Ile Ile Phe Thr Cys Ile Val Tyr Phe Met
                485                 490                 495

Leu Gly Leu Lys Pro Lys Ala Asp Ala Phe Phe Val Met Met Phe Thr
            500                 505                 510

Leu Met Met Val Ala Tyr Ser Ala Ser Ser Met Ala Leu Ala Ile Ala
        515                 520                 525

Ala Gly Gln Ser Val Val Ser Val Ala Thr Leu Leu Met Thr Ile Cys
    530                 535                 540

Phe Val Phe Met Met Ile Phe Ser Gly Leu Leu Val Asn Leu Thr Thr
545                 550                 555                 560

Ile Ala Ser Trp Leu Ser Trp Leu Gln Tyr Phe Ser Ile Pro Arg Tyr
                565                 570                 575

Gly Phe Thr Ala Leu Gln His Asn Glu Phe Leu Gly Gln Asn Phe Cys
            580                 585                 590

Pro Gly Leu Asn Ala Thr Gly Asn Asn Pro Cys Asn Tyr Ala Thr Cys
        595                 600                 605

Thr Gly Glu Glu Tyr Leu Val Lys Gln Gly Ile Asp Leu Ser Pro Trp
    610                 615                 620

Gly Leu Trp Lys Asn His Val Ala Leu Ala Cys Met Ile Val Ile Phe
625                 630                 635                 640

Leu Thr Ile Ala Tyr Leu Lys Leu Leu Phe Leu Lys Lys Tyr Ser
                645                 650                 655


<210> SEQ ID NO 403
<211> LENGTH: 655
<212> TYPE: PRT
<213> ORGANISM: Homo sapiens

<400> SEQUENCE: 403

Met Ser Ser Ser Asn Val Glu Val Phe Ile Pro Val Ser Gln Gly Asn
1               5                   10                  15
```

```
Thr Asn Gly Phe Pro Ala Thr Ala Ser Asn Asp Leu Lys Ala Phe Thr
            20                  25                  30

Glu Gly Ala Val Leu Ser Phe His Asn Ile Cys Tyr Arg Val Lys Leu
        35                  40                  45

Lys Ser Gly Phe Leu Pro Cys Arg Lys Pro Val Glu Lys Glu Ile Leu
    50                  55                  60

Ser Asn Ile Asn Gly Ile Met Lys Pro Gly Leu Asn Ala Ile Leu Gly
65                  70                  75                  80

Pro Thr Gly Gly Gly Lys Ser Ser Leu Leu Asp Val Leu Ala Ala Arg
                85                  90                  95

Lys Asp Pro Ser Gly Leu Ser Gly Asp Val Leu Ile Asn Gly Ala Pro
            100                 105                 110

Arg Pro Ala Asn Phe Lys Cys Asn Ser Gly Tyr Val Val Gln Asp Asp
        115                 120                 125

Val Val Met Gly Thr Leu Thr Val Arg Glu Asn Leu Gln Phe Ser Ala
    130                 135                 140

Ala Leu Arg Leu Ala Thr Thr Met Thr Asn His Glu Lys Asn Glu Arg
145                 150                 155                 160

Ile Asn Arg Val Ile Gln Glu Leu Gly Leu Asp Lys Val Ala Asp Ser
                165                 170                 175

Lys Val Gly Thr Gln Phe Ile Arg Gly Val Ser Gly Gly Glu Arg Lys
            180                 185                 190

Arg Thr Ser Ile Gly Met Glu Leu Ile Thr Asp Pro Ser Ile Leu Phe
        195                 200                 205

Leu Asp Gln Pro Thr Thr Gly Leu Asp Ser Ser Thr Ala Asn Ala Val
    210                 215                 220

Leu Leu Leu Leu Lys Arg Met Ser Lys Gln Gly Arg Thr Ile Ile Phe
225                 230                 235                 240

Ser Ile His Gln Pro Arg Tyr Ser Ile Phe Lys Leu Phe Asp Ser Leu
                245                 250                 255

Thr Leu Leu Ala Ser Gly Arg Leu Met Phe His Gly Pro Ala Gln Glu
            260                 265                 270

Ala Leu Gly Tyr Phe Glu Ser Ala Gly Tyr His Cys Glu Ala Tyr Asn
        275                 280                 285

Asn Pro Ala Asp Phe Phe Leu Asp Ile Ile Asn Gly Asp Ser Thr Ala
    290                 295                 300

Val Ala Leu Asn Arg Glu Glu Asp Phe Lys Ala Thr Glu Ile Ile Glu
305                 310                 315                 320

Pro Ser Lys Gln Asp Lys Pro Leu Ile Glu Lys Leu Ala Glu Ile Tyr
                325                 330                 335

Val Asn Ser Ser Phe Tyr Lys Glu Thr Lys Ala Glu Leu His Gln Leu
            340                 345                 350

Ser Gly Gly Glu Lys Lys Lys Lys Ile Thr Val Phe Lys Glu Ile Ser
        355                 360                 365

Tyr Thr Thr Ser Phe Cys His Gln Leu Arg Trp Val Ser Lys Arg Ser
    370                 375                 380

Phe Lys Asn Leu Leu Gly Asn Pro Gln Ala Ser Ile Ala Gln Ile Ile
385                 390                 395                 400

Val Thr Val Val Leu Gly Leu Val Ile Gly Ala Ile Tyr Phe Gly Leu
                405                 410                 415

Lys Asn Asp Ser Thr Gly Ile Gln Asn Arg Ala Gly Val Leu Phe Phe
            420                 425                 430

Leu Thr Thr Asn Gln Cys Phe Ser Ser Val Ser Ala Val Glu Leu Phe
```

```
        435                 440                 445

Val Val Glu Lys Lys Leu Phe Ile His Glu Tyr Ile Ser Gly Tyr Tyr
    450                 455                 460

Arg Val Ser Ser Tyr Phe Leu Gly Lys Leu Leu Ser Asp Leu Leu Pro
465                 470                 475                 480

Met Arg Met Leu Pro Ser Ile Ile Phe Thr Cys Ile Val Tyr Phe Met
                485                 490                 495

Leu Gly Leu Lys Pro Lys Ala Asp Ala Phe Phe Val Met Met Phe Thr
            500                 505                 510

Leu Met Met Val Ala Tyr Ser Ala Ser Ser Met Ala Leu Ala Ile Ala
        515                 520                 525

Ala Gly Gln Ser Val Val Ser Val Ala Thr Leu Leu Met Thr Ile Cys
    530                 535                 540

Phe Val Phe Met Met Ile Phe Ser Gly Leu Leu Val Asn Leu Thr Thr
545                 550                 555                 560

Ile Ala Ser Trp Leu Ser Trp Leu Gln Tyr Phe Ser Ile Pro Arg Tyr
                565                 570                 575

Gly Phe Thr Ala Leu Gln His Asn Glu Phe Leu Gly Gln Asn Phe Cys
            580                 585                 590

Pro Gly Leu Asn Ala Thr Gly Asn Asn Pro Cys Asn Tyr Ala Thr Cys
        595                 600                 605

Thr Gly Glu Glu Tyr Leu Val Lys Gln Gly Ile Asp Leu Ser Pro Trp
    610                 615                 620

Gly Leu Trp Lys Asn His Val Ala Leu Ala Cys Met Ile Val Ile Phe
625                 630                 635                 640

Leu Thr Ile Ala Tyr Leu Lys Leu Leu Phe Leu Lys Lys Tyr Ser
                645                 650                 655


<210> SEQ ID NO 404
<211> LENGTH: 655
<212> TYPE: PRT
<213> ORGANISM: Homo sapiens

<400> SEQUENCE: 404

Met Ser Ser Ser Asn Val Glu Val Phe Ile Pro Val Ser Gln Gly Asn
1               5                   10                  15

Thr Asn Gly Phe Pro Ala Thr Ala Ser Asn Asp Leu Lys Ala Phe Thr
            20                  25                  30

Glu Gly Ala Val Leu Ser Phe His Asn Ile Cys Tyr Arg Val Lys Leu
        35                  40                  45

Lys Ser Gly Phe Leu Pro Cys Arg Lys Pro Val Glu Lys Glu Ile Leu
    50                  55                  60

Ser Asn Ile Asn Gly Ile Met Lys Pro Gly Leu Asn Ala Ile Leu Gly
65                  70                  75                  80

Pro Thr Gly Gly Gly Met Ala Ser Leu Leu Asp Val Leu Ala Ala Arg
                85                  90                  95

Lys Asp Pro Ser Gly Leu Ser Gly Asp Val Leu Ile Asn Gly Ala Pro
            100                 105                 110

Arg Pro Ala Asn Phe Lys Cys Asn Ser Gly Tyr Val Val Gln Asp Asp
        115                 120                 125

Val Val Met Gly Thr Leu Thr Val Arg Glu Asn Leu Gln Phe Ser Ala
    130                 135                 140

Ala Leu Arg Leu Ala Thr Thr Met Thr Asn His Glu Lys Asn Glu Arg
145                 150                 155                 160
```

```
Ile Asn Arg Val Ile Gln Glu Leu Gly Leu Asp Lys Val Ala Asp Ser
                165                 170                 175

Lys Val Gly Thr Gln Phe Ile Arg Gly Val Ser Gly Gly Glu Arg Lys
            180                 185                 190

Arg Thr Ser Ile Gly Met Glu Leu Ile Thr Asp Pro Ser Ile Leu Phe
        195                 200                 205

Leu Asp Glu Pro Thr Thr Gly Leu Asp Ser Ser Thr Ala Asn Ala Val
    210                 215                 220

Leu Leu Leu Leu Lys Arg Met Ser Lys Gln Gly Arg Thr Ile Ile Phe
225                 230                 235                 240

Ser Ile His Gln Pro Arg Tyr Ser Ile Phe Lys Leu Phe Asp Ser Leu
                245                 250                 255

Thr Leu Leu Ala Ser Gly Arg Leu Met Phe His Gly Pro Ala Gln Glu
            260                 265                 270

Ala Leu Gly Tyr Phe Glu Ser Ala Gly Tyr His Cys Glu Ala Tyr Asn
        275                 280                 285

Asn Pro Ala Asp Phe Phe Leu Asp Ile Ile Asn Gly Asp Ser Thr Ala
    290                 295                 300

Val Ala Leu Asn Arg Glu Glu Asp Phe Lys Ala Thr Glu Ile Ile Glu
305                 310                 315                 320

Pro Ser Lys Gln Asp Lys Pro Leu Ile Glu Lys Leu Ala Glu Ile Tyr
                325                 330                 335

Val Asn Ser Ser Phe Tyr Lys Glu Thr Lys Ala Glu Leu His Gln Leu
            340                 345                 350

Ser Gly Gly Glu Lys Lys Lys Lys Ile Thr Val Phe Lys Glu Ile Ser
        355                 360                 365

Tyr Thr Thr Ser Phe Cys His Gln Leu Arg Trp Val Ser Lys Arg Ser
    370                 375                 380

Phe Lys Asn Leu Leu Gly Asn Pro Gln Ala Ser Ile Ala Gln Ile Ile
385                 390                 395                 400

Val Thr Val Val Leu Gly Leu Val Ile Gly Ala Ile Tyr Phe Gly Leu
                405                 410                 415

Lys Asn Asp Ser Thr Gly Ile Gln Asn Arg Ala Gly Val Leu Phe Phe
            420                 425                 430

Leu Thr Thr Asn Gln Cys Phe Ser Ser Val Ser Ala Val Glu Leu Phe
        435                 440                 445

Val Val Glu Lys Lys Leu Phe Ile His Glu Tyr Ile Ser Gly Tyr Tyr
    450                 455                 460

Arg Val Ser Ser Tyr Phe Leu Gly Lys Leu Leu Ser Asp Leu Leu Pro
465                 470                 475                 480

Met Arg Met Leu Pro Ser Ile Ile Phe Thr Cys Ile Val Tyr Phe Met
                485                 490                 495

Leu Gly Leu Lys Pro Lys Ala Asp Ala Phe Phe Val Met Met Phe Thr
            500                 505                 510

Leu Met Met Val Ala Tyr Ser Ala Ser Ser Met Ala Leu Ala Ile Ala
        515                 520                 525

Ala Gly Gln Ser Val Val Ser Val Ala Thr Leu Leu Met Thr Ile Cys
    530                 535                 540

Phe Val Phe Met Met Ile Phe Ser Gly Leu Leu Val Asn Leu Thr Thr
545                 550                 555                 560

Ile Ala Ser Trp Leu Ser Trp Leu Gln Tyr Phe Ser Ile Pro Arg Tyr
                565                 570                 575

Gly Phe Thr Ala Leu Gln His Asn Glu Phe Leu Gly Gln Asn Phe Cys
```

580 585 590

Pro Gly Leu Asn Ala Thr Gly Asn Asn Pro Cys Asn Tyr Ala Thr Cys
595 600 605

Thr Gly Glu Glu Tyr Leu Val Lys Gln Gly Ile Asp Leu Ser Pro Trp
610 615 620

Gly Leu Trp Lys Asn His Val Ala Leu Ala Cys Met Ile Val Ile Phe
625 630 635 640

Leu Thr Ile Ala Tyr Leu Lys Leu Leu Phe Leu Lys Lys Tyr Ser
645 650 655

<210> SEQ ID NO 405
<211> LENGTH: 655
<212> TYPE: PRT
<213> ORGANISM: Homo sapiens

<400> SEQUENCE: 405

Met Ser Ser Ser Asn Val Glu Val Phe Ile Pro Val Ser Gln Gly Asn
1 5 10 15

Thr Asn Gly Phe Pro Ala Thr Ala Ser Asn Asp Leu Lys Ala Phe Thr
20 25 30

Glu Gly Ala Val Leu Ser Phe His Asn Ile Cys Tyr Arg Val Lys Leu
35 40 45

Lys Ser Gly Phe Leu Pro Cys Arg Lys Pro Val Glu Lys Glu Ile Leu
50 55 60

Ser Asn Ile Asn Gly Ile Met Lys Pro Gly Leu Asn Ala Ile Leu Gly
65 70 75 80

Pro Thr Gly Gly Gly Met Ala Ser Leu Leu Asp Val Leu Ala Ala Arg
85 90 95

Lys Asp Pro Ser Gly Leu Ser Gly Asp Val Leu Ile Asn Gly Ala Pro
100 105 110

Arg Pro Ala Asn Phe Lys Cys Asn Ser Gly Tyr Val Val Ala Asp Asp
115 120 125

Val Val Met Gly Thr Leu Thr Val Arg Glu Asn Leu Gln Phe Ser Ala
130 135 140

Ala Leu Arg Leu Ala Thr Thr Met Thr Asn His Glu Lys Asn Glu Arg
145 150 155 160

Ile Asn Arg Val Ile Gln Glu Leu Gly Leu Asp Lys Val Ala Asp Ser
165 170 175

Lys Val Gly Thr Gln Phe Ile Arg Gly Val Ser Gly Gly Glu Arg Lys
180 185 190

Arg Thr Ser Ile Gly Met Glu Leu Ile Thr Asp Pro Ser Ile Leu Phe
195 200 205

Leu Asp Glu Pro Thr Thr Gly Leu Asp Ser Ser Thr Ala Asn Ala Val
210 215 220

Leu Leu Leu Leu Lys Arg Met Ser Lys Gln Gly Arg Thr Ile Ile Phe
225 230 235 240

Ser Ile His Gln Pro Arg Tyr Ser Ile Phe Lys Leu Phe Asp Ser Leu
245 250 255

Thr Leu Leu Ala Ser Gly Arg Leu Met Phe His Gly Pro Ala Gln Glu
260 265 270

Ala Leu Gly Tyr Phe Glu Ser Ala Gly Tyr His Cys Glu Ala Tyr Asn
275 280 285

Asn Pro Ala Asp Phe Phe Leu Asp Ile Ile Asn Gly Asp Ser Thr Ala
290 295 300

```
Val Ala Leu Asn Arg Glu Glu Asp Phe Lys Ala Thr Glu Ile Ile Glu
305                 310                 315                 320

Pro Ser Lys Gln Asp Lys Pro Leu Ile Glu Lys Leu Ala Glu Ile Tyr
                325                 330                 335

Val Asn Ser Ser Phe Tyr Lys Glu Thr Lys Ala Glu Leu His Gln Leu
            340                 345                 350

Ser Gly Gly Glu Lys Lys Lys Lys Ile Thr Val Phe Lys Glu Ile Ser
        355                 360                 365

Tyr Thr Thr Ser Phe Cys His Gln Leu Arg Trp Val Ser Lys Arg Ser
    370                 375                 380

Phe Lys Asn Leu Leu Gly Asn Pro Gln Ala Ser Ile Ala Gln Ile Ile
385                 390                 395                 400

Val Thr Val Val Leu Gly Leu Val Ile Gly Ala Ile Tyr Phe Gly Leu
                405                 410                 415

Lys Asn Asp Ser Thr Gly Ile Gln Asn Arg Ala Gly Val Leu Phe Phe
            420                 425                 430

Leu Thr Thr Asn Gln Cys Phe Ser Ser Val Ser Ala Val Glu Leu Phe
        435                 440                 445

Val Val Glu Lys Lys Leu Phe Ile His Glu Tyr Ile Ser Gly Tyr Tyr
    450                 455                 460

Arg Val Ser Ser Tyr Phe Leu Gly Lys Leu Leu Ser Asp Leu Leu Pro
465                 470                 475                 480

Met Arg Met Leu Pro Ser Ile Ile Phe Thr Cys Ile Val Tyr Phe Met
                485                 490                 495

Leu Gly Leu Lys Pro Lys Ala Asp Ala Phe Phe Val Met Met Phe Thr
            500                 505                 510

Leu Met Met Val Ala Tyr Ser Ala Ser Ser Met Ala Leu Ala Ile Ala
        515                 520                 525

Ala Gly Gln Ser Val Val Ser Val Ala Thr Leu Leu Met Thr Ile Cys
    530                 535                 540

Phe Val Phe Met Met Ile Phe Ser Gly Leu Leu Val Asn Leu Thr Thr
545                 550                 555                 560

Ile Ala Ser Trp Leu Ser Trp Leu Gln Tyr Phe Ser Ile Pro Arg Tyr
                565                 570                 575

Gly Phe Thr Ala Leu Gln His Asn Glu Phe Leu Gly Gln Asn Phe Cys
            580                 585                 590

Pro Gly Leu Asn Ala Thr Gly Asn Asn Pro Cys Asn Tyr Ala Thr Cys
        595                 600                 605

Thr Gly Glu Glu Tyr Leu Val Lys Gln Gly Ile Asp Leu Ser Pro Trp
    610                 615                 620

Gly Leu Trp Lys Asn His Val Ala Leu Ala Cys Met Ile Val Ile Phe
625                 630                 635                 640

Leu Thr Ile Ala Tyr Leu Lys Leu Leu Phe Leu Lys Lys Tyr Ser
                645                 650                 655


<210> SEQ ID NO 406
<211> LENGTH: 655
<212> TYPE: PRT
<213> ORGANISM: Homo sapiens

<400> SEQUENCE: 406

Met Ser Ser Ser Asn Val Glu Val Phe Ile Pro Val Ser Gln Gly Asn
1               5                   10                  15

Thr Asn Gly Phe Pro Ala Thr Ala Ser Asn Asp Leu Lys Ala Phe Thr
            20                  25                  30
```

```
Glu Gly Ala Val Leu Ser Phe His Asn Ile Cys Tyr Arg Val Lys Leu
        35                  40                  45

Lys Ser Gly Phe Leu Pro Cys Arg Lys Pro Val Glu Lys Glu Ile Leu
    50                  55                  60

Ser Asn Ile Asn Gly Ile Met Lys Pro Gly Leu Asn Ala Ile Leu Gly
65                  70                  75                  80

Pro Thr Gly Gly Gly Met Ala Ser Leu Leu Asp Val Leu Ala Ala Arg
                85                  90                  95

Lys Asp Pro Ser Gly Leu Ser Gly Asp Val Leu Ile Asn Gly Ala Pro
            100                 105                 110

Arg Pro Ala Asn Phe Lys Cys Asn Ser Gly Tyr Val Val Ala Asp Asp
        115                 120                 125

Val Val Met Gly Thr Leu Thr Val Arg Glu Asn Leu Gln Phe Ser Ala
    130                 135                 140

Ala Leu Arg Leu Ala Thr Thr Met Thr Asn His Glu Lys Asn Glu Arg
145                 150                 155                 160

Ile Asn Arg Val Ile Gln Glu Leu Gly Leu Asp Lys Val Ala Asp Ser
                165                 170                 175

Lys Val Gly Thr Gln Phe Ile Arg Gly Val Ser Gly Gly Glu Arg Lys
            180                 185                 190

Arg Thr Ser Ile Gly Met Glu Leu Ile Thr Asp Pro Ser Ile Leu Phe
        195                 200                 205

Leu Asp Glu Pro Thr Thr Gly Leu Asp Ser Ser Thr Ala Asn Ala Val
    210                 215                 220

Leu Leu Leu Leu Lys Arg Met Ser Lys Gln Gly Arg Thr Ile Ile Phe
225                 230                 235                 240

Ser Ile His Gln Pro Glu Tyr Ser Ile Phe Lys Leu Phe Asp Ser Leu
                245                 250                 255

Thr Leu Leu Ala Ser Gly Arg Leu Met Phe His Gly Pro Ala Gln Glu
            260                 265                 270

Ala Leu Gly Tyr Phe Glu Ser Ala Gly Tyr His Cys Glu Ala Tyr Asn
        275                 280                 285

Asn Pro Ala Asp Phe Phe Leu Asp Ile Ile Asn Gly Asp Ser Thr Ala
    290                 295                 300

Val Ala Leu Asn Arg Glu Glu Asp Phe Lys Ala Thr Glu Ile Ile Glu
305                 310                 315                 320

Pro Ser Lys Gln Asp Lys Pro Leu Ile Glu Lys Leu Ala Glu Ile Tyr
                325                 330                 335

Val Asn Ser Ser Phe Tyr Lys Glu Thr Lys Ala Glu Leu His Gln Leu
            340                 345                 350

Ser Gly Gly Glu Lys Lys Lys Lys Ile Thr Val Phe Lys Glu Ile Ser
        355                 360                 365

Tyr Thr Thr Ser Phe Cys His Gln Leu Arg Trp Val Ser Lys Arg Ser
    370                 375                 380

Phe Lys Asn Leu Leu Gly Asn Pro Gln Ala Ser Ile Ala Gln Ile Ile
385                 390                 395                 400

Val Thr Val Val Leu Gly Leu Val Ile Gly Ala Ile Tyr Phe Gly Leu
                405                 410                 415

Lys Asn Asp Ser Thr Gly Ile Gln Asn Arg Ala Gly Val Leu Phe Phe
            420                 425                 430

Leu Thr Thr Asn Gln Cys Phe Ser Ser Val Ser Ala Val Glu Leu Phe
        435                 440                 445
```

Val Val Glu Lys Lys Leu Phe Ile His Glu Tyr Ile Ser Gly Tyr Tyr
    450                 455                 460

Arg Val Ser Ser Tyr Phe Leu Gly Lys Leu Leu Ser Asp Leu Leu Pro
465                 470                 475                 480

Met Arg Met Leu Pro Ser Ile Ile Phe Thr Cys Ile Val Tyr Phe Met
                485                 490                 495

Leu Gly Leu Lys Pro Lys Ala Asp Ala Phe Phe Val Met Met Phe Thr
            500                 505                 510

Leu Met Met Val Ala Tyr Ser Ala Ser Ser Met Ala Leu Ala Ile Ala
        515                 520                 525

Ala Gly Gln Ser Val Val Ser Val Ala Thr Leu Leu Met Thr Ile Cys
    530                 535                 540

Phe Val Phe Met Met Ile Phe Ser Gly Leu Leu Val Asn Leu Thr Thr
545                 550                 555                 560

Ile Ala Ser Trp Leu Ser Trp Leu Gln Tyr Phe Ser Ile Pro Arg Tyr
                565                 570                 575

Gly Phe Thr Ala Leu Gln His Asn Glu Phe Leu Gly Gln Asn Phe Cys
            580                 585                 590

Pro Gly Leu Asn Ala Thr Gly Asn Asn Pro Cys Asn Tyr Ala Thr Cys
        595                 600                 605

Thr Gly Glu Glu Tyr Leu Val Lys Gln Gly Ile Asp Leu Ser Pro Trp
    610                 615                 620

Gly Leu Trp Lys Asn His Val Ala Leu Ala Cys Met Ile Val Ile Phe
625                 630                 635                 640

Leu Thr Ile Ala Tyr Leu Lys Leu Leu Phe Leu Lys Lys Tyr Ser
                645                 650                 655

<210> SEQ ID NO 407
<211> LENGTH: 5
<212> TYPE: PRT
<213> ORGANISM: Artificial sequence
<220> FEATURE:
<223> OTHER INFORMATION: synthetic sequence
<220> FEATURE:
<221> NAME/KEY: REPEAT
<222> LOCATION: (1)..(5)
<223> OTHER INFORMATION: The sequence may be repeated n times, where n
      is an integer of at least one

<400> SEQUENCE: 407

Gly Ser Gly Gly Ser
1               5

<210> SEQ ID NO 408
<211> LENGTH: 4
<212> TYPE: PRT
<213> ORGANISM: Artificial sequence
<220> FEATURE:
<223> OTHER INFORMATION: synthetic sequence
<220> FEATURE:
<221> NAME/KEY: REPEAT
<222> LOCATION: (1)..(4)
<223> OTHER INFORMATION: The sequence may be repeated n times, where n
      is an integer of at least one

<400> SEQUENCE: 408

Gly Gly Gly Ser
1

<210> SEQ ID NO 409
<211> LENGTH: 4
<212> TYPE: PRT

<213> ORGANISM: Artificial sequence
<220> FEATURE:
<223> OTHER INFORMATION: synthetic sequence

<400> SEQUENCE: 409

Gly Gly Ser Gly
1

<210> SEQ ID NO 410
<211> LENGTH: 5
<212> TYPE: PRT
<213> ORGANISM: Artificial sequence
<220> FEATURE:
<223> OTHER INFORMATION: synthetic sequence

<400> SEQUENCE: 410

Gly Gly Ser Gly Gly
1 5

<210> SEQ ID NO 411
<211> LENGTH: 5
<212> TYPE: PRT
<213> ORGANISM: Artificial sequence
<220> FEATURE:
<223> OTHER INFORMATION: synthetic sequence

<400> SEQUENCE: 411

Gly Ser Gly Ser Gly
1 5

<210> SEQ ID NO 412
<211> LENGTH: 5
<212> TYPE: PRT
<213> ORGANISM: Artificial sequence
<220> FEATURE:
<223> OTHER INFORMATION: synthetic sequence

<400> SEQUENCE: 412

Gly Ser Gly Gly Gly
1 5

<210> SEQ ID NO 413
<211> LENGTH: 5
<212> TYPE: PRT
<213> ORGANISM: Artificial sequence
<220> FEATURE:
<223> OTHER INFORMATION: synthetic sequence

<400> SEQUENCE: 413

Gly Gly Gly Ser Gly
1 5

<210> SEQ ID NO 414
<211> LENGTH: 5
<212> TYPE: PRT
<213> ORGANISM: Artificial sequence
<220> FEATURE:
<223> OTHER INFORMATION: synthetic sequence

<400> SEQUENCE: 414

Gly Ser Ser Ser Gly
1 5

<210> SEQ ID NO 415
<211> LENGTH: 121
<212> TYPE: PRT
<213> ORGANISM: Rattus norvegicus

<400> SEQUENCE: 415

Glu Val Lys Leu Glu Glu Ser Gly Pro Gly Leu Val Gln Pro Ser Gln
1 5 10 15

Thr Leu Ser Leu Thr Cys Thr Val Ser Gly Phe Ser Leu Thr Ser Asp
20 25 30

Gly Val Ser Trp Val Arg Gln Pro Pro Gly Lys Gly Leu Glu Trp Ile
35 40 45

Ala Ala Ile Ser Ser Gly Gly Ser Thr Tyr Tyr Asn Ser Ala Leu Lys
50 55 60

Ser Arg Leu Ser Ile Ser Arg Asp Thr Ser Lys Ser Gln Val Phe Leu
65 70 75 80

Lys Met Asn Ser Leu Gln Thr Glu Asp Thr Ala Ile Tyr Phe Cys Thr
85 90 95

Arg Asp Thr Tyr Tyr Gly Tyr Asn Gln Ile Pro Phe Val Tyr Trp Gly
100 105 110

Gln Gly Thr Leu Val Thr Val Ser Ser
115 120

<210> SEQ ID NO 416
<211> LENGTH: 106
<212> TYPE: PRT
<213> ORGANISM: Rattus norvegicus

<400> SEQUENCE: 416

Asp Ile Val Ile Ile Gln Ser Pro Pro Ser Leu Ser Ala Ser Leu Gly
1 5 10 15

Asp Lys Val Thr Ile Ser Cys Gln Ala Ser Gln Asn Ile His Arg Tyr
20 25 30

Ile Ala Trp Tyr Gln Gln Lys Pro Gly Lys Ala Pro Arg Leu Leu Ile
35 40 45

Arg Tyr Thr Ser Thr Leu Glu Ser Gly Thr Pro Ser Arg Phe Ser Gly
50 55 60

Ser Gly Ser Gly Arg Asp Tyr Ser Phe Ser Ile Ser Asn Val Glu Ser
65 70 75 80

Glu Asp Ile Ala Ser Tyr Tyr Cys Leu Gln Tyr Val Asn Leu Trp Thr
85 90 95

Phe Gly Gly Gly Thr Lys Leu Glu Leu Lys
100 105

<210> SEQ ID NO 417
<211> LENGTH: 107
<212> TYPE: PRT
<213> ORGANISM: Artificial sequence
<220> FEATURE:
<223> OTHER INFORMATION: synthetic sequence

<400> SEQUENCE: 417

Glu Ile Val Met Thr Gln Ser Pro Ala Thr Leu Ser Leu Ser Pro Gly
1 5 10 15

Glu Arg Ala Thr Leu Ser Cys Arg Ala Ser Gln Ser Val Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro 65 70 75 80

Glu Asp Phe Ala Val Tyr Tyr Cys His Gln Tyr Gly Ser Thr Pro Leu
85 90 95

Thr Phe Gly Gly Gly Thr Lys Ala Glu Ile Lys
100 105

<210> SEQ ID NO 418
<211> LENGTH: 118
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (57)..(57)
<223> OTHER INFORMATION: The amino acid at position 57 is Asn, Gln or Ser

<400> SEQUENCE: 418

Glu Val Lys Val Val Glu Ser Gly Gly Val Leu Val Arg Pro Gly Gly
1 5 10 15

Ser Leu Lys Leu Ser Cys Ala Ala Ser Gly Phe Thr Phe Ser Arg Tyr
20 25 30

Thr Met Ser Trp Val Arg Gln Thr Pro Glu Lys Arg Leu Glu Trp Val
35 40 45

Ala Thr Ile Ser Ser Gly Gly Gly Xaa Thr Tyr Tyr Pro Asp Ser Val
50 55 60

Lys Gly Arg Phe Thr Val Ser Arg Asp Asn Ala Met Ser Ser Leu Tyr
65 70 75 80

Leu Gln Met Ser Ser Leu Arg Ser Glu Asp Thr Ala Leu Tyr Tyr Cys
85 90 95

Ala Arg Tyr Gly Ala Gly Asp Ala Trp Phe Ala Tyr Trp Gly Gln Gly
100 105 110

Thr Leu Val Thr Val Ser
115

<210> SEQ ID NO 419
<211> LENGTH: 10
<212> TYPE: PRT
<213> ORGANISM: Artificial sequence
<220> FEATURE:
<223> OTHER INFORMATION: synthetic sequence

<400> SEQUENCE: 419

Gly Phe Thr Phe Ser Arg Tyr Thr Met Ser
1 5 10

<210> SEQ ID NO 420
<211> LENGTH: 10
<212> TYPE: PRT
<213> ORGANISM: Artificial sequence
<220> FEATURE:
<223> OTHER INFORMATION: synthetic sequence
<220> FEATURE:
<221> NAME/KEY: SITE
<222> LOCATION: (3)..(10)
<223> OTHER INFORMATION: The amino acids at positions 3 to 10 may independently either be present or absent

<400> SEQUENCE: 420

Gly Gly Gly Gly Gly Gly Gly Gly Gly Gly
1 5 10

<210> SEQ ID NO 421
<211> LENGTH: 9
<212> TYPE: PRT
<213> ORGANISM: Artificial sequence
<220> FEATURE:
<223> OTHER INFORMATION: synthetic sequence

<400> SEQUENCE: 421

Gly Gly Ser Ile Ser Ser Gly Asp Tyr
1 5

<210> SEQ ID NO 422
<211> LENGTH: 5
<212> TYPE: PRT
<213> ORGANISM: Artificial sequence
<220> FEATURE:
<223> OTHER INFORMATION: synthetic sequence

<400> SEQUENCE: 422

Tyr Tyr Ser Gly Ser
1 5

<210> SEQ ID NO 423
<211> LENGTH: 11
<212> TYPE: PRT
<213> ORGANISM: Artificial sequence
<220> FEATURE:
<223> OTHER INFORMATION: synthetic sequence

<400> SEQUENCE: 423

Val Ser Ile Phe Gly Val Gly Thr Phe Asp Tyr
1 5 10

<210> SEQ ID NO 424
<211> LENGTH: 7
<212> TYPE: PRT
<213> ORGANISM: Artificial sequence
<220> FEATURE:
<223> OTHER INFORMATION: synthetic sequence

<400> SEQUENCE: 424

Gly Phe Thr Phe Ser Asp Ser
1 5

<210> SEQ ID NO 425
<211> LENGTH: 6
<212> TYPE: PRT
<213> ORGANISM: Artificial sequence
<220> FEATURE:
<223> OTHER INFORMATION: synthetic sequence

<400> SEQUENCE: 425

Ser Pro Tyr Gly Gly Ser
1 5

<210> SEQ ID NO 426
<211> LENGTH: 9
<212> TYPE: PRT
<213> ORGANISM: Artificial sequence
<220> FEATURE:
<223> OTHER INFORMATION: synthetic sequence

<400> SEQUENCE: 426

Arg His Trp Pro Gly Gly Phe Asp Tyr
1 5

<210> SEQ ID NO 427

-continued

```
<211> LENGTH: 118
<212> TYPE: PRT
<213> ORGANISM: Homo sapiens

<400> SEQUENCE: 427

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser
        115
```